(12) United States Patent
Hopper et al.

(10) Patent No.: US 7,723,348 B2
(45) Date of Patent: May 25, 2010

(54) PHOSPHODIESTERASE 4 INHIBITORS

(75) Inventors: Allen Hopper, Glen Rock, NJ (US); Robert F. Dunn, Towaco, NJ (US); Erik Mikal Kuester, Rochester, MN (US); Richard D. Conticello, Ossining, NY (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 0 days.

(21) Appl. No.: 12/108,833

(22) Filed: Apr. 24, 2008

(65) Prior Publication Data
US 2008/0207660 A1 Aug. 28, 2008

Related U.S. Application Data

(62) Division of application No. 11/249,769, filed on Oct. 14, 2005, now Pat. No. 7,432,266.

(60) Provisional application No. 60/618,725, filed on Oct. 15, 2004.

(51) Int. Cl.
A61K 31/506 (2006.01)
A61K 31/437 (2006.01)
A61K 31/454 (2006.01)
A61K 31/4155 (2006.01)

(52) U.S. Cl. .................. 514/275; 514/303; 514/322; 514/406

(58) Field of Classification Search .................. 514/275, 514/406, 407, 303, 341
See application file for complete search history.

(56) References Cited

U.S. PATENT DOCUMENTS

| | | | |
|---|---|---|---|
| 4,012,495 A | 3/1977 | Schmiechen et al. | |
| 4,193,926 A | 3/1980 | Schmiechen et al. | |
| 4,219,551 A | 8/1980 | Seidelmann et al. | |
| 5,539,111 A | 7/1996 | Petzoldt et al. | |
| 5,814,651 A | 9/1998 | Duplantier et al. | |
| 5,846,514 A | 12/1998 | Foster et al. | |
| 5,869,516 A | 2/1999 | Christadler et al. | |
| 5,935,978 A | 8/1999 | Fenton et al. | |
| 6,136,821 A | 10/2000 | Hersperger | |
| 6,235,736 B1 | 5/2001 | Ina et al. | |
| 6,258,833 B1 | 7/2001 | Martins et al. | |
| 6,334,997 B1 | 1/2002 | Foster et al. | |
| 6,372,777 B1 | 4/2002 | Martins et al. | |
| 6,403,597 B1 | 6/2002 | Wilson et al. | |
| 6,423,710 B1 | 7/2002 | Martins et al. | |
| 6,495,154 B1 | 12/2002 | Tam et al. | |
| 7,226,930 B2 | 6/2007 | Hopper, et al. | |
| 2007/0254913 A1* | 11/2007 | Dunn et al. | 514/303 |

FOREIGN PATENT DOCUMENTS

| | | |
|---|---|---|
| EP | 1 251 126 | 10/2002 |
| EP | 1251126 | 10/2002 |
| JP | 1072415 | 3/1998 |
| WO | WO 92/19594 | 11/1992 |
| WO | WO 93/07141 | 4/1993 |
| WO | WO 93/25517 | 12/1993 |
| WO | WO 94/14742 | 7/1994 |
| WO | WO 95/28926 | 11/1995 |
| WO | WO 95/35282 | 12/1995 |
| WO | WO 97/12884 A1 * | 4/1997 |
| WO | WO 97/25312 | 7/1997 |
| WO | WO 97/49702 | 12/1997 |
| WO | WO 98/58901 | 12/1998 |
| WO | WO 00/66562 | 11/2000 |
| WO | WO 01/40216 | 6/2001 |
| WO | WO 01 40216 | 6/2001 |
| WO | WO 01/58895 | 8/2001 |
| WO | WO 01/68600 | 9/2001 |
| WO | WO 02/45749 | 6/2002 |
| WO | WO 03/087062 | 10/2003 |
| WO | WO 04/007463 | 1/2004 |
| WO | WO 2004/007463 | 1/2004 |
| WO | WO 2004/094411 | 11/2004 |

OTHER PUBLICATIONS

Vippagunta, et al., Crystalline solids, 2001, Advanced Drug Delivery Reviews, 48, pp. 3 and 18.*
Barad et al. Proc. Natl. Acad. Sci., USA, Dec. 1998 vol. 95, pp. 15020-15025.
Christensen et al. J.Med. Chem, 1998, vol. 41, pp. 821-835.
Crossland, Drugs of the Future, 1998, vol. 13, No. 1.
Database Caplus, XP002294352, Journal of the Chemical Society, Perkins Transactions 1, 1997, vol. 12, pp. 1477-1500 Accession No. 1978-6818.
Database Caplus, XP002294353, Synthetic Communication, 1996, vol. 26, No. 14, pp. 2603-2611.
Database Beilstein, XP002294354, 1996, Acta Crystallographica Sect. B., vol. 52, No. 4, pp. 746-752.

(Continued)

Primary Examiner—Kamal A Saeed
Assistant Examiner—Kristin Bianchi
(74) Attorney, Agent, or Firm—Millen, White, Zelano, Branigan, P.C.

(57) ABSTRACT

Selective PDE4 inhibition is achieved by aryl and heteroaryl pyrazole compounds. The compounds exhibit improved PDE4 inhibition as compared to compounds such as rolipram and show selectivity with regard to inhibition of other classes of PDEs.

61 Claims, No Drawings

OTHER PUBLICATIONS

Demnitz et al. Molecules, 1998, vol. 3 pp. 107-119.
Egawa et al Jpn. J Pharmacol, 1997, Nov. 75, (3) pp. 275-281.
Halrow et al. Polyhedron, 1997, vol. 16, No. 24, pp. 4257-4264.
Houslay et al. 1998, Advance in Pharmacology, 1998, vol. 44, pp. 225-342.
Japanese Patent Abstract No. 2001-039954, (Feb. 13, 2001).
Keller et al. Chem. Pharm. Bull, 2001, 49 (8) 1009-1017.
Krause et al Xenobiotica, 1998, vol. 18, No. 5, pp. 561-571.
Kusters et al. Journal of Chromatopgraphy, 1996, vol. 737, pp. 333-337.
Langlois et al., 1997, Synthetic Communicaitons, 27 (18), pp. 3133-3144.
Lourenco et al. Nuclear Medicine & Biology, 2001, vol. 28, pp. 347-358.
Marivet et al. J. Med. Chem. 1989, 32, pp. 1450-1457.
Martin, Idrugs, 2001, 4(3), pp. 312-338.
Meyers et al. J. Org. Chem., 1993, vol. 58, pp. 36-42.
Accession No. 1993:531492 Caplus; Comparison of the effect of isobutylmethylxanthine and phosphodiesterase-selective inhibitors on cAMP levels in SH-SY5Y neuroblastoma cells; Anthony J. Morgan et al.
Nagakura et al. British Journal of Pharmacology, 2002, 135, pp. 1783-1793.
Osby et al. Tetrahedron Letters, 1985, vol. 26, No. 52, pp. 6413-6416.
Patent Abstracts of Japan, vol. 2000, No. 19, Jun. 5, 2001 & JP 2001 039954 A (Tomono Agrica Co.,Ltd.), Feb. 13, 2001 p. 123.
Robichaud et al. Neuropharmacology, 1999, 38, pp. 289-297.
Schmiechen et al. Psychopharmacology, 1990, 102 (1) pp. 17-20.
Wang et al. Biochemical & Biophysical Research Communciations, 1997, pp. 234,320-324.
Int'l Search Report and the Written Opinion of the Int'l Searching Authority, issued Feb. 27, 2006 in PCT Application No. PCT/US2005/036801.
Database Caplus, XP-002294354, Copyright 1988-2001.
Malcolm A. Halcrow, et al. "Metal complexes of sterically hindered pyrazolylpyridines . . . ", Polyhedron, vol. 16, No. 124, pp. 4257-4264, 1997.
Database Caplus, XP-002367781, Copyright 1988-2005.
Cancer and Metastasis Reviews (1998), 17 (1), 91-106.
A. Maureen Rouhi, Chemical & Engineering News, Feb. 24, 2003, pp. 32-35.
US Pharmacopia #23, national formulary #18, pp. 1843-1844 (1995).
Zhang et al. Neuropsychopharmacology, 2000, 23, pp. 198-204.
Zhang et al. Psychopharmacology DOI, 2000, 10.

* cited by examiner

PHOSPHODIESTERASE 4 INHIBITORS

This application is a divisional of U.S. patent application Ser. No. 11/249,769, filed Oct. 14, 2005 now U.S. Pat. No. 7,432,266, which is incorporated by reference herein.

This application claims the benefit of U.S. Provisional Application Ser. No. 60/618,725, filed Oct. 15, 2004, the entire disclosure of which is hereby incorporated by reference.

This application is related to copending U.S. application Ser. No. 10/825,611, filed Apr. 16, 2004, which claims the benefit of U.S. Provisional Application Ser. No. 60/463,725, filed Apr. 18, 2003, the entire disclosures of each of which are hereby incorporated by reference.

FIELD OF THE INVENTION

The present invention relates generally to the field of phosphodiesterase 4 (PDE4) enzyme inhibition. More specifically, this invention relates to selective PDE4 inhibition by novel compounds, e.g., aryl and heteroaryl substituted pyrazole compounds, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE1 is stimulated by $Ca^{2+}$/calmodulin. PDE2 is cGMP-dependent, and is found in the heart and adrenals. PDE3 is cGMP-inhibited, and inhibition of this enzyme creates positive inotropic activity. PDE4 is cAMP specific, and its inhibition causes airway relaxation, anti-inflammatory and antidepressant activity. PDE5 appears to be important in regulating cGMP content in vascular smooth muscle, and therefore PDE5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [Wang et al., Expression, Purification, and Characterization of Human cAMP-Specific Phosphodiesterase (PDE4) Subtypes A, B, C, and D, *Biochem. Biophys. Res. Comm.*, 234, 320-324 (1997)]. In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful anti-inflammatory agents and therefore may be useful in treating diseases where inflammation is problematic such as asthma or arthritis. Further, rolipram improves the cognitive performance of rats and mice in learning paradigms.

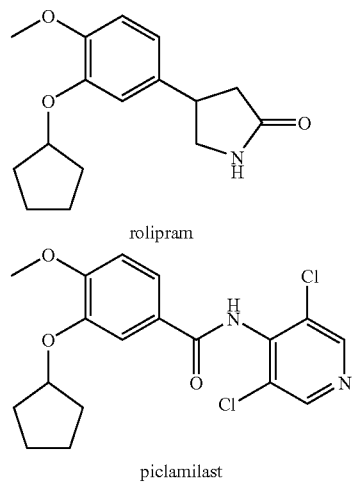

rolipram piclamilast

In addition to such compounds as rolipram, xanthine derivatives such as pentoxifylline, denbufylline, and theophylline inhibit PDE4 and have received attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an antidepressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799-807 for a general review]. Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion, and stomach erosion. In humans, the primary side effect is nausea and emesis. Thus, there is a continuing need to develop selective PDE4 inhibitors with improved side effect profiles (e.g., are relatively non-emetic) while retaining therapeutic utility.

SUMMARY OF THE INVENTION

The present invention relates to novel compounds that inhibit, preferably selectively, PDE4 enzymes, and especially have improved side effect profiles, e.g., are relatively non-emetic (e.g., as compared to the previously discussed prior art compounds). In particular, the present invention relates to aryl and heteroaryl substituted pyrazole compounds. The compounds of this invention at the same time facilitate entry into cells, especially cells of the nervous system.

Still further, the present invention provides methods for synthesizing compounds with such activity and selectivity, as well as methods of and corresponding pharmaceutical compositions for treating a patient, e.g., mammals, including humans, in need of PDE inhibition. Treatment is preferably for a disease state that involves elevated intracellular PDE4 levels or decreased cAMP levels, e.g., involving neurological syndromes, especially those states associated with depression and/or memory impairment, most especially major depression and/or long term memory impairment. In particular, such depression and/or memory impairment is due at least in part to catabolism of intracellular cAMP levels by PDE4 enzymes or where such an impaired condition can be improved by increasing cAMP levels. In a preferred aspect, the compounds of the inventions improve such diseases by inhibiting PDE4 enzymes at doses that do not induce emesis or other side effects.

DETAILED DESCRIPTION OF THE INVENTION

The present invention relates to selective PDE4 inhibition by novel compounds, e.g., aryl and heteroaryl substituted pyrazole compounds, methods of preparing such compounds, compositions containing such compounds, and methods of use thereof.

The present invention includes compounds selected from Formulas I, II, III, IV, V, VI, VII, VIII, IX or X:

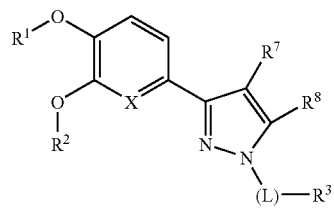

I

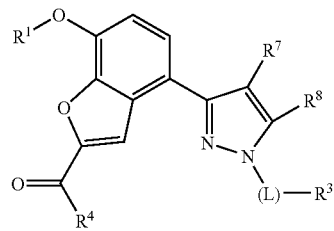

II

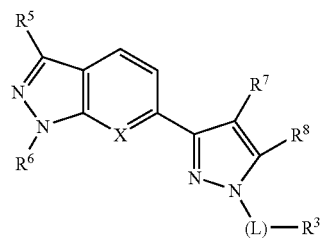

III

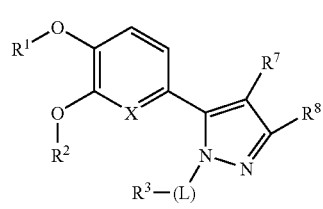

IV

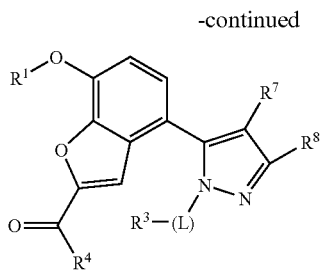

V

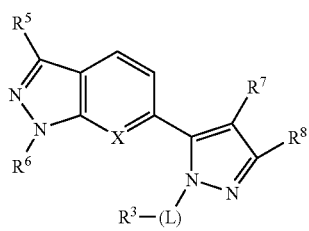

VI

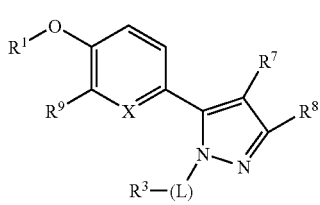

VII

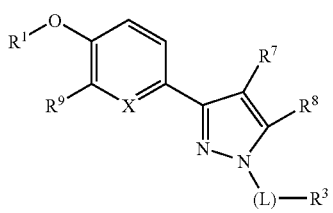

VIII

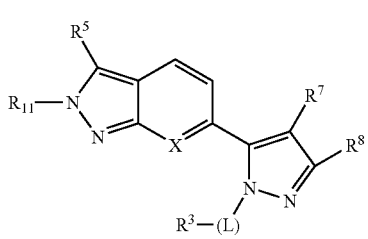

IX

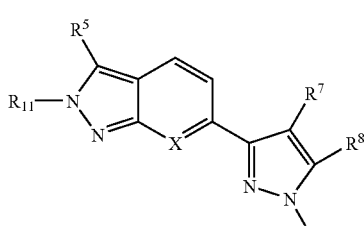

X wherein

X is CH or N;

L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_n$CONH; $(CH_2)_n$OCONH; $(CH_2)_n$CON($C_{1-6}$-alkyl); $(CH_2)_n$NHCO;

(CH$_2$)$_n$CONHSO$_2$; (CH$_2$)$_n$SO$_2$NH; (CH$_2$)$_n$SO$_2$; or (CH$_2$)$_n$CO$_2$ (e.g., a bond, CH$_2$CONH, SO$_2$, CH$_2$CO$_2$, CH$_2$CO);

n is 0 to 3;

R$^1$ is alkyl having 1 to 4 carbon atoms, which is unsubstituted or substituted one or more times by halogen (e.g., CH$_3$, CHF$_2$);

R$^2$ is H,
- alkyl having 1 to 8 carbon atoms, which is unsubstituted or substituted one or more times by halogen, oxo or combinations thereof wherein optionally one or more —CH$_2$CH$_2$— groups are replaced in each case by —CH=CH— or —C≡C— groups (e.g., CH$_3$, CHF$_2$),
- cycloalkyl having 3 to 8 carbon atoms, which is unsubstituted or substituted one or more times by halogen, oxo, alkyl having 1 to 4 carbon atoms or combinations thereof (e.g., cyclopentyl),
- a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, amino, alkylamino, dialkylamino, or combinations thereof (e.g., tetrahydrofuranyl),
- aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof,
- arylalkyl having 7 to 16 carbon atoms, which is unsubstituted or substituted, preferably in the aryl portion, one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof (e.g., benzyl, difluorobenzyl),
- a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof,
- arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof,
- a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or
- cycloalkylalkyl having 4 to 16 carbon atoms (e.g., cyclopentylethyl and cyclopropylmethyl), which is unsubstituted or substituted one or more times by halogen, oxo, alkyl or combinations thereof;

R$^3$ is H,
- alkyl having 1 to 8 carbon atoms, which is unsubstituted or substituted one or more times, by halogen, oxo, or combinations thereof wherein optionally one or more —CH$_2$CH$_2$— groups are replaced in each case by —CH=CH— or —C≡C— groups (e.g., C$_2$H$_5$, CH(CH$_3$)$_2$, n-propyl, n-butyl, t-butyl),
- cycloalkyl having 3 to 8 carbon atoms, which is unsubstituted or substituted one or more times by halogen, oxo, alkyl, or combinations thereof (e.g., cyclopentyl, cyclohexyl),
- aryl having 6 to 14 carbon atoms, which is unsubstituted or substituted one or more times by halogen, alkyl, hydroxy, alkoxy, halogenated alkyl, halogenated alkoxy (e.g., OCF$_3$), nitro, methylenedioxy, ethylenedioxy, amino, alkylamino, dialkylamino, —CO—N(R$^{10}$)$_2$, —SO$_2$—N(R$^{10}$)$_2$, hydroxyalkyl, hydroxyalkoxy (e.g., —OCH$_2$HC$_2$OH), alkoxyalkoxy (e.g., methoxyethoxy (CH$_3$OCH$_2$CH$_2$O—), alkoxyalkoxyalkyl (e.g., CH$_3$OCH$_2$CH$_2$OCH$_2$—), carboxy, cyano, acyl, alkoxycarbonyl, alkylthio, alkylsulfinyl, alkylsulfonyl, arylsulfinyl, arylsulfonyl, aminosulfonyl, phenyl, halogenated phenyl, phenoxy, benzyloxy, acyloxy (e.g., acetoxy), acylamido (e.g., acetamido), furanyl which is unsubstituted or substituted by halogen, C$_{1-4}$-alkyl, C$_{1-4}$-alkoxy, C$_{2-8}$-alkoxycarbonyl, and/or benzyl, pyrrolyl which is unsubstituted or substituted by halogen, C$_{1-4}$-alkyl, C$_{1-4}$-alkoxy, C$_{2-8}$-alkoxycarbonyl, and/or benzyl, pyrazolyl which is unsubstituted or substituted by halogen, C$_{1-4}$-alkyl, C$_{1-4}$-alkoxy, C$_{2-8}$-alkoxycarbonyl, and/or benzyl, isoxazolyl which is unsubstituted or substituted by halogen, C$_{1-4}$-alkyl, C$_{1-4}$alkoxy, C$_{2-8}$-alkoxycarbonyl, and/or benzyl, imidazolyl which is unsubstituted or substituted by halogen, C$_{1-4}$-alkyl, C$_{1-4}$-alkoxy, C$_{2-8}$-alkoxycarbonyl, and/or benzyl, pyridinyl which is unsubstituted or substituted by halogen, C$_{1-4}$-alkyl, C$_{1-4}$-alkoxy, C$_{2-8}$-alkoxycarbonyl, and/or benzyl, pyrimidinyl which is unsubstituted or substituted by halogen, C$_{1-4}$-alkyl, C$_{1-4}$-alkoxy, C$_{2-8}$-alkoxycarbonyl, and/or benzyl, morpholinyl which is unsubstituted or substituted by C$_{1-4}$-alkyl, C$_{2-8}$-alkoxycarbonyl, and/or benzyl, piperadinyl which is unsubstituted or substituted by C$_{1-4}$-alkyl, C$_{2-8}$-alkoxycarbonyl, and/or benzyl, piperazinyl which is unsubstituted or substituted by C$_{1-4}$-alkyl, C$_{2-8}$-alkoxycarbonyl, and/or benzyl, tetrazolyl which is unsubstituted or substituted by C$_{1-4}$-alkyl, C$_{2-8}$-alkoxycarbonyl, and/or benzyl, alkylsulphonimide (e.g., CH$_3$SO$_2$—NHCO—), arylsulphonimide (e.g., C$_6$H$_5$SO$_2$—NHCO—) wherein the aryl portion is optionally substituted by halogen, C$_{1-4}$-alkyl, C$_{1-4}$-alkoxy, or combinations thereof (e.g., phenyl, bromophenyl, cyanophenyl, nitrophenyl, fluorophenyl, difluorophenyl, trifluoromethoxyphenyl, methylphenyl, dimethylphenyl, methoxyphenyl, biphenyl substituted by —CONH$_2$, and phenyl substituted by biphenyl or —CONH$_2$),
- heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, acylamido (e.g., acetamido), or combinations thereof (e.g., pyridyl, methylpyridyl, benzothiazolyl), arylalkyl having 7 to 16 carbon atoms, which is unsubstituted or substituted, preferably in the aryl portion, one or more times by halogen, alkyl, hydroxy, alkoxy, halogenated alkyl (e.g. $CF_3$), halogenated alkoxy (e.g. $OCF_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy (e.g., acetoxy), acylamido (e.g., acetamido), tetrazolyl, alkylsulphonimide, arylsulphonimide thereof and/or substituted in the alkyl portion by halogen, oxo, cyano, or combinations thereof (e.g., benzyl, methylbenzyl, t.-butylbenzyl, methoxybenzyl, dimethoxybenzyl, fluorobenzyl, difluorobenzyl, trifluoromethylbenzyl, trifluoromethoxybenzyl, chlorobenzyl, aminobenzyl, nitrobenzyl, methoxycarbonylbenzyl, methylsulfonylbenzyl, phenethyl, phenpropyl), a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof (e.g., pyridylmethyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, or alkoxyalkyl having 3 to 8 carbon atoms;

$R^4$ is alkyl having, 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$);

$R^5$ is H, or alkyl having 1 to 6 carbon atoms, which is unsubstituted or substituted one or more times by halogen wherein optionally one or more —$CH_2CH_2$— groups are replaced in each case by —CH=CH— or —C≡C— groups (e.g., $CH_3$, $C_2H_5$);

$R^6$ is H, alkyl having 1 to 6 carbon atoms, which is unsubstituted or substituted one or more times by halogen, oxo, hydroxy or combinations thereof wherein optionally one or more —$CH_2CH_2$— groups are replaced in each case by —CH=CH— or —C≡C— groups, alkoxyalkyl having 2 to 6 carbon atoms (e.g., methoxyethyl ($CH_2CH_2OCH_3$), ethoxymethyl ($CH_2OCH_2CH_3$)), which is unsubstituted or substituted one or more times by halogen, oxo, or combinations thereof;

alkoxycarbonyl (—C(=O)O-alkyl) having 2 to 6 carbon atoms (e.g., —C(=O)OCH($CH_3$)$_2$);

—CO—$N^5R^{12}$;

cycloalkyl having 3 to 8 carbon atoms, which is unsubstituted or substituted one or more times by halogen, oxo, alkyl, or combinations thereof (e.g., cyclopentyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl, 2-pyrimidinyl, 4-tetrahydropyranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated; partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl (e.g., $CH_3$, $C_2H_5$, $CF_3$, hydroxymethyl, 2-(2-hydroxy)propyl, hydroxymethyl), carboxy, alkoxycarbonyl having 2 to 6 carbon atoms (e.g., ethoxycarbonyl), —CO-alkyl having 2 to 6 carbon atoms (e.g., $CH_3CO$), or phenyl;

$R^9$ is halogen (e.g., F); and $R^{10}$ is H.

alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups (e.g., $CH_3$, $CHF_2$), or alkoxy having 2 to 8 carbon atoms, which is unsubstituted or substituted one or more times by halogen;

$R^{11}$ is H, alkyl having 1 to 6 carbon atoms (e.g., methyl, ethylpropyl), which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$, $C_2H_5$), or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof (e.g., tetrahydro-2H-pyranylmethyl, pyrollidinylethyl;

$R^{12}$ is H, alkyl having 1 to 6 carbon atoms (e.g., methyl, ethylpropyl), which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$, $C_2H_5$), cycloalkyl having, 3 to 8 carbon atoms, which is unsubstituted or substituted one or more times by halogen, oxo, alkyl, or combinations thereof (e.g., cyclopentyl), or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof (e.g., furylmethyl);

and pharmaceutically acceptable salts or solvates (e.g., hydrates) thereof, or solvates of pharmaceutically acceptable salts thereof.

According to a further compound aspect of the invention, the compounds are of formulas I, II, III, IV, V, VI, VII or VIII, wherein L is $(CH_2)_n$OCONH, particularly compounds of formula IV wherein L is $(CH_2)_n$OCONH.

According to a further compound aspect of the invention, the compounds are of formulas I, II, III, IV, V, VI, VII or VIII, particularly IV and VI, wherein $R^3$ is aryl having 6 to 14 carbon atoms (particularly phenyl or biphenyl), which is substituted by at least one substituent selected from —CO—N$(R^{10})_2$ (wherein $R^{10}$ is preferably, H, alkyl or alkoxy), aminosulfonyl, furanyl which is unsubstituted or substituted by halogen, $C_{1-4}$-alkyl, $C_{1-4}$-alkoxy, $C_{2-3}$-alkoxycarbonyl and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is substituted by halogen, $C_{1-4}$-alkyl, $C_{1-4}$-alkoxy, $C_{2-8}$-alkoxycarbonyl, and/or benzyl, isoxazolyl which is unsubstituted or substituted by halogen, $C_{1-4}$-alkyl, $C_{1-4}$-alkoxy, $C_{2-8}$-alkoxycarbonyl, and/or benzyl, imidazolyl which is substituted by halogen, $C_{1-4}$-alkyl, $C_{1-4}$-alkoxy, $C_{2-8}$-alkoxycarbonyl, and/or benzyl, pyridinyl which is substituted by halogen, $C_{1-4}$-alkyl, $C_{1-4}$-alkoxy, $C_{2-8}$-alkoxycarbonyl, and/or benzyl, pyrimidinyl which is unsubstituted or substituted by halogen, $C_{1-4}$-alkyl, $C_{1-4}$-alkoxy, $C_{2-8}$-alkoxycarbonyl, and/or benzyl, morpholinyl which is substituted by $C_{1-4}$-alkyl, $C_{2-8}$alkoxycarbonyl, and/or benzyl, piperadinyl which is substituted by $C_{1-4}$-alkyl, $C_{2-8}$-alkoxycarbonyl, and/or benzyl, piperazinyl which is substituted by $C_{1-4}$-alkyl, $C_{2-8}$-alkoxycarbonyl, and/or benzyl, tetrazolyl which is unsubstituted or substituted by $C_{1-4}$-alkyl, $C_{2-8}$-alkoxycarbonyl, and/or benzyl, or arylsulphonimide (e.g., $C_6H_5SO_2$—NHCO—) wherein the aryl portion is substituted by halogen or $C_{1-4}$-alkoxy.

According to a further compound aspect of the invention, the compounds are of Formula IX or X, e.g., Formula IX.

According to a further compound aspect of the invention, the compounds are of formulas I, II, III, IV, V, VI, VII or VIII, particularly IV and VI, wherein $R^3$ is aryl substituted at least once by —$SO_2$—$N(R^{10})_2$, alkoxyalkoxy (e.g., methoxyethoxy), alkoxyalkoxyalkyl (e.g., $CH_3OCH_2CH_2OCH_2$—) or benzyloxy.

According to a further compound aspect of the invention, the compounds are of formulas III or VI, wherein $R^6$ is alkyl having 1 to 6 carbon atoms which is substituted at least once by hydroxy; alkoxyalkyl having 2 to 6 carbon atoms (e.g., methoxyethyl, ethoxymethyl), which is unsubstituted or substituted one or more times by halogen, oxo, or combinations thereof, alkoxycarbonyl (—C(=O)O-alkyl) having 2 to 6 carbon atoms (e.g., —C(=O)OCH$(CH_3)_2$; or —CO—NR$^5$R$^{12}$.

In accordance with the method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound selected from Formulas I, II, III, IV, V, VI, VII, VIII, IX or X:

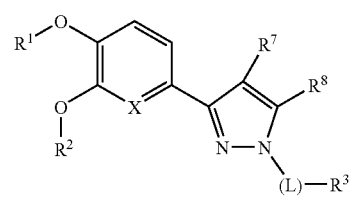

I

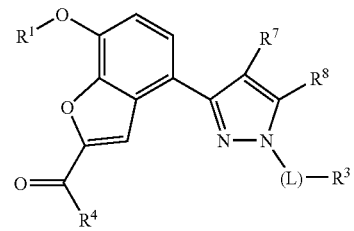

II

-continued

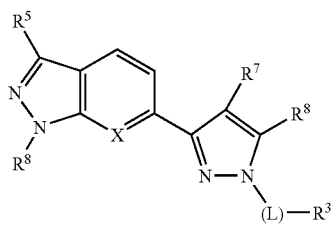

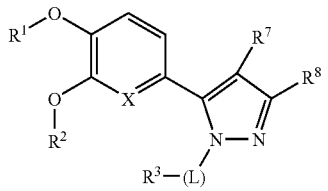

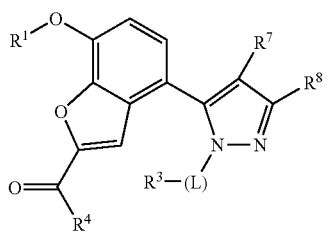

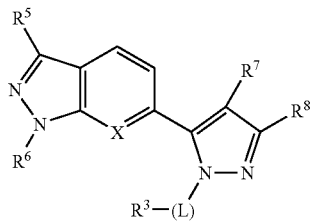

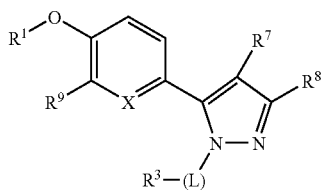

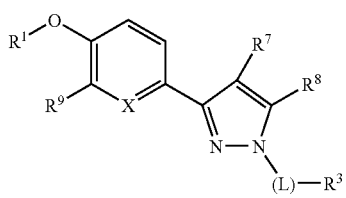

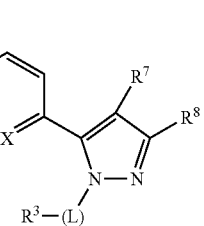

-continued

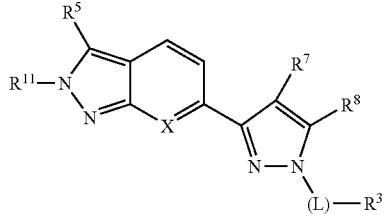

wherein
X is CH or N;
L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen (preferably F), hydroxy, cyano or combinations thereof; $(CH_2)_nCONH$; $(CH_2)_nOCONH$; $(CH_2)_nCON(C_{1-6}$-alkyl); $(CH_2)_nNHCO$; $(CH_2)_nCONHSO_2$; $(CH_2)_nSO_2NH$; $(CH_2)_nSO_2$; or $(CH_2)_nCO_2$ (e.g., a bond, $CH_2CONH$, $SO_2$, $CH_2CO_2$, $CH_2CO$);
n is 0 to 3;
$R^1$ is alkyl having 1 to 4 carbon atoms, which is unsubstituted or substituted one or more times by halogen (e.g., $CH_3$, $CHF_2$);
$R^2$ is H,
alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups (e.g., $CH_3$, $CHF_2$),
cycloalkyl having 3 to 8 carbon atoms, which is unsubstituted or substituted one or more times by halogen, oxo, alkyl having 1 to 4 carbon atoms or combinations thereof (e.g., cyclopentyl),
a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl), which is unsubstituted or substituted one or more times by halogen, aryl, alkyl, alkoxy, cyano, halogenated alkyl (e.g., trifluoromethyl), nitro, oxo, ammo, alkylamino, dialkylamino, or combinations thereof (e.g., tetrahydrofuranyl),
aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof,
arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof (e.g., benzyl, difluorobenzyl), a partially unsaturated carbocyclic group having 5 to 14 carbon atoms, (e.g., cyclohexenyl, cyclohexadienyl, indanyl, and tetrahydronaphthenyl), which is unsubstituted or substituted one or more times by halogen, alkyl, alkoxy, nitro, cyano, oxo, or combinations thereof, arylalkenyl having 8 to 16 carbon atoms, wherein the alkenyl portion has up to 5 carbon atoms, which is unsubstituted or substituted, preferably in the aryl portion, one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof, or cycloalkylalkyl having 4 to 16 carbon atoms (e.g., cyclopentylethyl and cyclopropylmethyl), which is unsubstituted or substituted one or more times by halogen, oxo, alkyl or combinations thereof;

$R^3$ is H, alkyl having 1 to 8 carbon atoms, which is unsubstituted or substituted one or more times by halogen, oxo; or combinations thereof wherein optionally one or more —$CH_2CH_2$— groups are replaced in each case by —CH=CH— or —C≡C— groups (e.g., $C_2H_5$, $CH(CH_3)_2$, n-propyl, n-butyl, t.-butyl), cycloalkyl having 3 to 8 carbon atoms, which is unsubstituted or substituted one or more times by halogen, oxo, alkyl, or combinations thereof (e.g., cyclopentyl, cyclohexyl), aryl having 6 to 14 carbon atoms, which is unsubstituted or substituted one or more times by halogen, alkyl, hydroxy, alkoxy, halogenated alkyl, halogenated alkoxy (e.g., $OCF_3$), nitro, methylenedioxy, ethylenedioxy, amino, alkylamino, dialkylamino, —CO—N($R^{10}$)$_2$, —$SO_2$—N($R^{10}$)$_2$, hydroxyalkyl, hydroxyalkoxy (e.g., —$OCH_2HC_2OH$), alkoxyalkoxy (e.g., methoxyethoxy ($CH_3OCH_2CH_2O$—), alkoxyalkoxyalkyl (e.g., $CH_3OCH_2CH_2OCH_2$—), carboxy, cyano, acyl, alkoxycarbonyl, alkylthio, alkylsulfinyl, alkylsulfonyl, arylsulfinyl, arylsulfonyl, aminosulfonyl, phenyl, halogenated phenyl, phenoxy, benzyloxy, acyloxy (e.g., acetoxy), acylamido (e.g., acetamido), furanyl which is unsubstituted or substituted by halogen, $C_{1-4}$-alkyl, $C_{1-4}$-alkoxy, $C_{2-8}$-alkoxycarbonyl, and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is unsubstituted or substituted by halogen, $C_{1-4}$-alkyl, $C_{1-4}$alkoxy, $C_{2-8}$ alkoxycarbonyl, and/or benzyl, isoxazolyl which is unsubstituted or substituted by halogen, $C_{1-4}$-alkyl, $C_{1-4}$-alkoxy, $C_{2-8}$-alkoxycarbonyl, and/or benzyl, imidazolyl which is unsubstituted or substituted by halogen, $C_{1-4}$-alkyl, $C_{1-4}$-alkoxy, $C_{2-8}$-alkoxycarbonyl, and/or benzyl, pyridinyl which is unsubstituted or substituted by halogen, $C_{1-4}$alkyl, $C_{1-4}$-alkoxy, $C_{2-8}$-alkoxycarbonyl, and/or benzyl, pyridinyl which is unsubstituted or substituted by halo-en, $C_{1-4}$-alkyl, $C_{1-4}$-alkoxy, $C_{2-8}$-alkoxycarbonyl, and/or benzyl, morpholinyl which is unsubstituted or substituted by $C_{1-4}$-alkyl, $C_{2-8}$-alkoxycarbonyl, and/or benzyl, piperadinyl which is unsubstituted or substituted by $C_{1-4}$-alkyl, $C_{2-8}$-alkoxycarbonyl, and/or benzyl, piperazinyl which is unsubstituted or substituted by $C_{1-4}$-alkyl, $C_{2-8}$-alkoxycarbonyl, and/or benzyl, tetrazolyl which is unsubstituted or substituted by $C_{1-4}$-alkyl, $C_{2-8}$-alkoxycarbonyl, and/or benzyl, alkylsulphonimide (e.g., $CH_3SO_2$—NHCO—), arylsulphonimide (e.g., $C_6H_5SO_2$—NHCO—) wherein the aryl portion is optionally substituted by halogen, $C_{1-4}$-alkyl, $C_{1-4}$-alkoxy, or combinations thereof (e.g., phenyl, bromophenyl, cyanophenyl, nitrophenyl, fluorophenyl, difluorophenyl, trifluoromethoxyphenyl, methylphenyl, dimethylphenyl, methoxyphenyl, biphenyl substituted by —$CONH_2$, and phenyl substituted by biphenyl or —$CONH_2$), heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, acylamido (e.g., acetamido), or combinations thereof (e.g., pyridyl, methylpyridyl, benzothiazolyl), arylalkyl having 7 to 16 carbon atoms, which is unsubstituted or substituted, preferably in the aryl portion, one or more times by halogen, alkyl, hydroxy, alkoxy, halogenated alkyl (e.g. $CF_3$), halogenated alkoxy (e.g. $OCF_3$), nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfanyl, arylsulfinyl, arylsulfonyl, phenyl, halogenated phenyl, phenoxy, acyloxy (e.g., acetoxy), acylamido (e.g., acetamido), tetrazolyl, alkylsulphonimide, arylsulphonimide, or combinations thereof and/or substituted in the alkyl portion by halogen, oxo, cyano, or combinations thereof (e.g., benzyl, methylbenzyl, t.-butylbenzyl, methoxybenzyl, dimethoxybenzyl, fluorobenzyl, difluorobenzyl, trifluoromethylbenzyl, trifluoromethoxybenzyl, chlorobenzyl, aminobenzyl, nitrobenzyl, methoxycarbonylbenzyl, methylsulfonylbenzyl, phenethyl, phenpropyl), a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl (e.g., trifluoromethyl), halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof (e.g., pyridylmethyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, or alkoxyalkyl having 3 to 8 carbon atoms;

$R^4$ is alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups (e.g., $CH_3$);

$R^5$ is H, or alkyl having 1 to 6 carbon atoms, which is unsubstituted or substituted one or more times by halogen wherein optionally one or more —$CH_2CH_2$— groups are replaced in each case by —CH=CH— or —C≡C— groups (e.g., $CH_3$, $C_2H_5$);

$R^6$ is H, alkyl having 1 to 6 carbon atoms, which is unsubstituted or substituted one or more times by halogen, oxo, hydroxy or combinations thereof wherein optionally one or more —$CH_2CH_2$— groups are replaced in each case by —CH=CH— or —C≡C— groups, alkoxyalkyl having 2 to 6 carbon atoms (e.g., methoxyethyl ($CH_2CH_2OCH_3$), ethoxymethyl ($CH_2OCH_2CH_3$)), which is unsubstituted or substituted one or more times by halogen, oxo, or combinations thereof;

alkoxycarbonyl (—C(=O)O-alkyl) having 2 to 6 carbon atoms (e.g., —C(=O)OCH$(CH_3)_2$);

—CO—NR$^5$R$^{12}$;

cycloalkyl having 3 to 8 carbon atoms, which is unsubstituted or substituted one or more times by halogen, oxo, alkyl, or combinations thereof (e.g., cyclopentyl), cycloalkylalkyl having 4 to 16 carbon atoms (e.g., cyclopentylethyl and cyclopropylmethyl), which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof, arylalkyl having 7 to 16 carbon atoms, which is unsubstituted or substituted, preferably in the aryl portion, one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido (e.g., acetamido), and acyloxy (e.g., acetoxy), or combinations thereof, a heterocyclic group, which is saturated, partially saturated or fully unsaturated, having 5 to 10 ring atoms in which at least 1 ring atom is an N, O or S atom (e.g., 3-thienyl, 2-thienyl, 3-tetrahydrofuranyl, 2-pyrimidinyl, 4-tetrahydropyranyl), which is unsubstituted or substituted one or more times by halogen, aryl, alkyl, alkoxy, alkoxycarbonyl, cyano, halogenated alkyl (e.g., trifluoromethyl), nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl (e.g., $CH_3$, $C_2H_5$, $CF_3$, hydroxymethyl, 2-(2-hydroxy)propyl, hydroxymethyl), carboxy, alkoxycarbonyl having 2 to 6 carbon atoms (e.g., ethoxycarbonyl), —CO-alkyl having 2 to 6 carbon atoms (e.g., $CH_3CO$), or phenyl;

$R^9$ is halogen (e.g., F); and $R^{10}$ is H, alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups (e.g., $CH_3$, $CHF_2$), or alkoxy having 2 to 8 carbon atoms, which is unsubstituted or substituted one or more times by halogen;

$R^{11}$ is H, alkyl having 1 to 6 carbon atoms (e.g., methyl, ethylpropyl), which is unsubstituted or substituted one or more times by halogen, oxo, or combinations thereof wherein optionally one or more —$CH_2CH_2$— groups are replaced in each case by =CH=CH— or —C≡C— groups (e.g., $CH_3$, $C_2H_5$), or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof (e.g., tetrahydro-2H-pyranylmethyl, pyrollidinylethyl;

$R^{12}$ is H, alkyl having 1 to 6 carbon atoms (e.g., methyl, ethylpropyl), which is unsubstituted or substituted one or more times by halogen, oxo, or combinations thereof wherein optionally one or more —$CH_2CH_2$— groups are replaced in each case by —CH=CH— or <C≡C— groups (e.g., $CH_3$, $C_2H_5$), cycloalkyl having 3 to 8 carbon atoms, which is unsubstituted or substituted one or more times by halogen, oxo, alkyl, or combinations thereof (e.g., cyclopentyl), or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl (e.g., trifluoromethyl), nitro, oxo, amino, alkylamino, dialkylamino, carboxy or combinations thereof and/or substituted in the alkyl portion by halogen, oxo, cyano, or combinations thereof (e.g., furylmethyl);

and pharmaceutically acceptable salts or solvates (e.g., hydrates) thereof, or solvates of pharmaceutically acceptable salts thereof.

According to a further method aspect of the invention, the compounds are of formulas I, II, III, IV, V, VI, VII or VII, wherein L is $(CH_2)_n$OCONH, particularly compounds of formula IV wherein L is $(CH_2)_n$OCONH.

According to a further method aspect of the invention, the compounds are of formulas I, II, III, IV, V, VI, VII or VIII, particularly IV and VI, wherein $R^3$ is aryl having 6 to 14 carbon atoms (particularly phenyl or biphenyl), which is substituted by at least one substituent selected from —CO—N$(R^{10})_2$ (wherein $R^{10}$ is preferably, H, alkyl or alkoxy), aminosulfonyl, furanyl which is unsubstituted or substituted by halogen, $C_{1-4}$-alkyl, $C_{1-4}$-alkoxy, $C_{2-8}$-alkoxycarbonyl and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is substituted by halogen, $C_{1-4}$-alkyl, $C_{1-4}$-alkoxy, $C_{2-8}$-alkoxycarbonyl, and/or benzyl, isoxazolyl which is unsubstituted or substituted by halogen, $C_{1-4}$-alkyl, $C_{1-4}$-alkoxy, $C_{2-8}$-alkoxycarbonyl, and/or benzyl, imidazolyl which is substituted by halogen, $C_{1-4}$-alkyl, $C_{1-4}$-alkoxy, $C_{2-8}$-alkoxycarbonyl, and/or benzyl, pyridinyl which is substituted by halogen, $C_{1-4}$-alkyl, $C_{1-4}$-alkoxy, $C_{2-8}$-alkoxycarbonyl, and/or benzyl, pyrimidinyl which is unsubstituted or substituted by halogen, $C_{1-4}$-alkyl, $C_{1-4}$-alkoxy, $C_{2-8}$-alkoxycarbonyl, and/or benzyl, morpholinyl which is substituted by $C_{1-4}$-alkyl, $C_{2-8}$-alkoxycarbonyl, and/or benzyl, piperadinyl which is substituted by $C_{1-4}$-alkyl, $C_{2-8}$-alkoxycarbonyl, and/or benzyl, piperazinyl which is substituted by $C_{1-4}$-alkyl, $C_{2-8}$-alkoxycarbonyl, and/or benzyl, tetrazolyl which is unsubstituted or substituted by $C_{1-4}$-alkyl, $C_{2-8}$-alkoxycarbonyl, and/or benzyl, or arylsulphonimide (e.g., $C_6H_5SO_2$—NHCO—) wherein the aryl portion is substituted by halogen or $C_{1-4}$-alkoxy.

According to a further method aspect of the invention, the compounds are of Formula IX or X, e.g., Formula IX.

According to a further method aspect of the invention, the compounds are of formulas I, II, III, IV, V, VI, VII or VIII, particularly IV and VI, wherein $R^3$ is aryl substituted at least once by —$SO_2$—N$(R^{10})_2$, alkoxyalkoxy (e.g., methoxyethoxy), alkoxyalkoxyalkyl (e.g., $CH_3OCH_2CH_2OCH_2$—) or benzyloxy.

According to a further method aspect of the invention, the compounds are of formulas III or VI, wherein $R^6$ is alkyl having 1 to 6 carbon atoms which is substituted at least once by hydroxy; alkoxyalkyl having 2 to 6 carbon atoms (e.g., methoxyethyl, ethoxymethyl), which is unsubstituted or substituted one or more times by halogen, oxo, or combinations thereof; alkoxycarbonyl (—C(=O)O-alkyl) having 2 to 6 carbon atoms (e.g., —C(=O)OCH$(CH_3)_2$); or —CONR$^5$—R$^{12}$.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes, but is not limited to, inflammatory diseases. These compounds may also function as antidepressants, or be useful in treating cognitive and negative symptoms of schizophrenia.

Assays for determining PDE4 inhibiting activity, selectivity of PDE4 inhibiting activity, and selectivity of inhibiting PDE4 isoenzymes are known within the art. See, e.g., U.S. Pat. No. 6,136,821, the disclosure of which is incorporated herein by reference.

Halogen herein refers to F, Cl, Br, and I. Preferred halogens are F and Cl.

Alkyl means a straight-chain or branched-chain aliphatic hydrocarbon radical. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

These alkyl radicals can optionally have one or more —$CH_2CH_2$— groups replaced in each case by —CH=CH— or —C≡C— groups. Suitable alkenyl or alkynyl groups are 1-propenyl, 2-propenyl, 1-propynyl, 1-butenyl, 2-butenyl, 3-butenyl, 1-butynyl, 1,3-butadienyl, and 3-methyl-2-butenyl.

In the arylalkyl groups, heterocyclic-alkenyl groups, cycloalkyl-alkyl groups and alkoxyalkyl groups, "alkyl" refers to a divalent alkylene group having in general up to about 13 carbon atoms. In the case of the arylalkyl group, the "alkyl" portion has, for example, up to 10 carbon atoms, preferably 1 to 6 carbon atoms. In the heterocyclic-alkyl groups, the "alkyl" portion has, for example, 1 to 12 carbon atoms, preferably 1 to 4 carbon atoms. In the alkoxyalkyl groups, the "alkyl" portion preferably has 2 to 7 carbon atoms. In the cycloalkylalkyl groups, the "alkyl" portion has, for example, 1 to 13 carbon atoms, preferably 1 to 4 carbon atoms.

In the cases where alkyl is a substituent (e.g., alkyl substituents on aryl and heterocyclic groups) or is part of a substituent (e.g., in the alkylamino, dialkylamino, hydroxyalkyl, hydroxyalkoxy, alkylthio, alkylsulfinyl, and alkylsulfonyl substituents for aryl), the alkyl portion preferably has 1 to 12 carbon atoms, especially 1 to 8 carbon atoms, in particular 1 to 4 carbon atoms.

Alkoxy means alkyl-O— groups in which the alkyl portion has 1 to 8 carbon atoms, and which can be substituted, for example, by halogens. Suitable alkoxy groups include methoxy, ethoxy, propoxy, isopropoxy, isobutoxy, sec-butoxy, pentoxy, hexoxy, heptoxy, octoxy, and trifluoromethoxy. Preferred alkoxy groups are methoxy, ethoxy and difluoromethoxy.

Similarly, alkokycarbonyl means an alkyl-O—CO— group in which the alkyl portion has 1 to 8 carbon atoms, e.g., 2 to 6 carbon atoms.

Alkoxyalkoxy means alkyl-O-alkyl-O— groups in which each of the alkyl portions have 1 to 8 carbon atoms (e.g., 1 to 4 carbon atoms), and which can be substituted, for example, by halogens. Suitable alkoxyalkoxy groups include methoxyethoxy, ethoxymethoxy, propoxymethoxy, and isopropoxymethoxy.

Alkoxyalkoxyalkyl means alkyl-O-alkyl-O-alkyl- groups in which each of the alkyl portions have 1 to 8 carbon atoms (e.g., 1 to 4 carbon atoms), and which can be substituted, for example, by halogens. Suitable alkylalkoxyalkoxy groups include $CH_3OCH_2CH_2OCH_2$—.

Alkenyl refers to straight-chain or branched-chain aliphatic radicals containing 2 to 12 carbon atoms in which one or more —$CH_2$—$CH_2$— structures is replaced by —CH=CH—. Suitable alkenyl groups are ethenyl, 1-propenyl, 2-methylethenyl, 1-butene, 2-butene, 1-pentenyl, and 2-pentenyl. In the arylalkenyl groups, alkenyl refers to an alkyenylene group having preferably 2 to 5 carbon atoms.

Cycloalkyl means a monocyclic, bicyclic or tricyclic saturated hydrocarbon radical having 3 to 8 carbon atoms, preferably 4 to 6 carbon atoms, more preferably 5 carbon atoms. Suitable cycloalkyl groups include cyclopropyl, cyclobutyl, cyclopentyl, cyclohexyl, cycloheptyl, cyclooctyl, and norbornyl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, and bicyclo[4.2.0]octyl.

The cycloalkyl group can be substituted by halogens, oxo and/or alkyl.

Cycloalkylalkyl refers to a cycloalkyl-alkyl-radical in which the cycloalkyl and alkyl portions are in accordance with the previous descriptions. Suitable examples include cyclopentylethyl and cyclopropylmethyl.

Aryl, as a group or substituent per se or as part of a group or substituent, refers to an aromatic carbocyclic radical containing 6 to 14 carbon atoms, preferably 6 to 12 carbon atoms. Suitable aryl groups include phenyl, naphthyl and biphenyl. Substituted aryl groups include, but are not limited to, the above-described aryl groups which are substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, and acyloxy (e.g., acetoxy).

Arylalkyl refers to an aryl-alkyl-radical in which the aryl and alkyl portions are in accordance with the previous descriptions. Suitable examples include 1-phenethyl, 2-phenethyl, phenpropyl, phenbutyl, phenpentyl, and naphthylenemethyl.

Arylalkenyl refers to an aryl-alkenyl-radical in which the aryl and alkenyl portions are in accordance with the previous descriptions of aryl and alkenyl. Suitable examples include 3-aryl-2-propenyl.

Heterocyclic groups refer to saturated, partially saturated and fully unsaturated heterocyclic groups having one or two rings and a total number of 5 to 10 ring atoms wherein at least one of the ring atoms is an N, O or S atom. Preferably, the heterocyclic group contains 1 to 3, especially 1 or 2, hetero-ring atoms selected from N, O and S. Suitable saturated and partially saturated heterocyclic groups include, but are not limited to tetrahydrofuranyl, tetrahydrothienyl, pyrrolidinyl, isoxazolinyl, thiazolyl and the like. Suitable heteroaryl groups include but are not limited to furyl, thienyl, pyrrolyl, pyrazolyl, imidazolyl, pyridyl, pyrimidinyl, indolyl, quinolinyl, naphthylidinyl, azaindolyl (e.g., 7-azaindolyl), 1,2,3,4,-tetrahydroisoquinolyl, and the like. Preferred heterocyclic and heteroaryl groups include terahydrofuranyl, tetrahydropyranyl, 2-thienyl, 3-thienyl, 2-, 3- or 4-pyridyl, 2-, 3-, 4-, 5-, 6-, 7- or 8-quinolinyl, 7-azaindolyl, and 1-, 3-, 4-, 5-, 6-, 7- or 8-isoquinolinyl.

Substituted heterocyclic groups refer to the heterocyclic groups described above which are substituted in one or more places by, for example, halogen, aryl, alkyl, alkoxy, cyano, halogenated alkyl (e.g., trifluoromethyl), nitro, oxo, amino, alkylamino, and dialkylamino.

Heterocyclic-alkyl refers to a heterocyclic-alkyl-group wherein the heterocyclic and alkyl portions are in accordance with the previous discussions. Suitable examples are pyridylmethyl, thienylmethyl, pyrimidinylmethyl, pyrazinylmethyl, isoquinolinylmethyl, pyridylethyl and thienylethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C=C bond. Suitable examples are cyclopentenyl, cyclohexenyl, tetrahydronaphthenyl and indan-2-yl.

Acyl refers to alkanoyl radicals having 1 to 13 carbon atoms in which the alkyl portion can be substituted by halogen, hydroxy, carboxy, alkyl, aryl and/or alkoxy; or aroyl radicals having 7 to 15 carbon atoms in which the aryl portion can be substituted by halogen, alkyl, alkoxy, nitro, carboxy and/or hydroxy. Suitable acyl groups include formyl, acetyl, propionyl, butanoyl and benzoyl.

Substituted radicals preferably have 1 to 3 substituents, especially 1 or 2 substituents.

In each case, X is preferably CH and L is preferably a single bond.

$R^1$ is preferably alkyl having 1 to 2 carbon atoms, which is unsubstituted or substituted, and more preferably 1 carbon atom. For $R^1$, the substituted alkyl groups are preferably substituted one or more times by halogen, especially F and Cl. More preferably, $R^1$ is $CH_3$ or $CF_2H$.

$R^2$ is preferably alkyl having 1 to 4 carbon atoms. For $R^2$, the substituted alkyl groups are preferably substituted one or more times by halogen, especially F and Cl. Preferably, $R^2$ is alkyl having 1 to 4 carbons which is unsubstituted or substituted with one or more F atoms.

$R^2$ can also be preferably cycloalkylalkyl group, wherein the "alkyl" portion preferably has 1 to 2 carbon atoms. $R^2$ is also preferably a cycloalkyl, which has 4 to 7 atoms. $R^2$ is also preferably a saturated heterocyclic group with 5 to 7 atoms and containing 1 or 2 hetero-ring atoms selected from O and S. More preferably, $R^2$ is a saturated heterocyclic group with 5 ring atoms containing 1 hetero-ring atom selected from O and S.

In particular, $R^2$ is preferably alkyl, halogenated alkyl, cycloalkyl which is substituted or unsubstituted, cycloalkylalkyl which is substituted or unsubstituted, tetrahydrofuranyl, or arylalkyl which is substituted or unsubstituted. More preferably, $R_2$ is $CH_3$, $C_2H_5$, isopropyl, $CF_2H$, cyclobutyl, cyclopentyl, cyclopropylmethyl, or 3-tetrahydrofuranyl.

$R^3$ is preferably aryl preferably having 6 to 14 carbon atoms (particularly phenyl or biphenyl) which is unsubstituted or substituted with one or more halogen (preferably fluorine), cyano, nitro, amino, alkyl (preferably methyl), alkoxy (preferably methoxy) or carboxy (e.g., phenyl, bromophenyl, nitrophenyl, fluorophenyl, methoxyphenyl, carboxyphenyl, trifluoromethoxyphenyl, dimethylphenyl, 4-carboxyphenyl, 2,3-difluorophenyl, 4-methylphenyl, 4-tert.-butylphenyl, 4-methoxyphenyl, 3,4-difluorophenyl, or 4-fluorophenyl). $R^3$ is also preferably an aryl having 6 to 14 carbon atoms (particularly phenyl or biphenyl), which is substituted by at least one substituent selected from —CO—N($R^{10}$)$_2$ (wherein $R^{10}$ is preferably, H, alkyl or alkoxy), aminosulfonyl, furanyl which is unsubstituted or substituted by halogen, $C_{1-4}$-alkyl, $C_{1-4}$-alkoxy, $C_{2-8}$-alkoxycarbonyl and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is substituted by halogen, $C_{1-4}$-alkyl, $C_{1-4}$-alkoxy, $C_{2-8}$-alkoxycarbonyl, and/or benzyl, isoxazolyl which is unsubstituted or substituted by halogen, $C_{1-4}$-alkyl, $C_{1-4}$-alkoxy, $C_{2-8}$-alkoxycarbonyl, and/or benzyl, imidazolyl which is substituted by halogen, $C_{1-4}$-alkyl, $C_{1-4}$-alkoxy, $C_{2-8}$-alkoxycarbonyl, and/or benzyl, pyridinyl which is substituted by halogen, $C_{1-4}$-alkyl, $C_{1-4}$-alkoxy, $C_{2-8}$- alkoxycarbonyl, and/or benzyl, pyrimidinyl which is unsubstituted or substituted by halogen, $C_{1-4}$-alkyl, $C_{1-4}$-alkoxy, $C_{2-8}$-alkoxycarbonyl, and/or benzyl, morpholinyl which is substituted by $C_{1-4}$-alkyl, $C_{2-8}$-alkoxycarbonyl, and/or benzyl, piperadinyl which is substituted by $C_{1-4}$-alkyl, $C_{2-8}$-alkoxycarbonyl, and/or benzyl, piperazinyl which is substituted by $C_{1-4}$-alkyl, $C_{2-8}$-alkoxycarbonyl, and/or benzyl, tetrazolyl which is unsubstituted or substituted by $C_{1-4}$alkyl, $C_{2-8}$-alkoxycarbonyl, and/or benzyl, or arylsulphonimide (e.g., $C_6H_5SO_2$—NHCO—) wherein the aryl portion is substituted by halogen or $C_{1-4}$-alkoxy.

$R^3$ can also preferably be a cycloalkyl group, and more preferably cyclohexyl or cyclopentyl. $R^3$ can also preferably be an alkyl group, more preferably ethyl, $CH(CH_3)_2$, n-propyl, n-butyl, or t-butyl.

$R^3$ is also preferably a heterocyclic group, more preferably thiazolyl, pyridyl or benzothiazolyl, which in each case is substituted or unsubstituted.

In accordance with a further preference, $R^3$ is arylalkyl such as benzyl or phenethyl, which in each case is substituted or unsubstituted. In particular, $R^3$ is an arylalkyl selected from benzyl, methylbenzyl, t.-butylbenzyl, methoxybenzyl, dimethoxybenzyl, carboxybenzyl, fluorobenzyl, difluorobenzyl, trifluoromethylbenzyl, trifluoromethoxybenzyl, chlorobenzyl, nitrobenzyl, methoxycarbonylbenzyl, and phenethyl.

In accordance with a further preference, $R^3$ is a heterocyclic-alkyl group, which is saturated, partially saturated or fully unsaturated, having 5 to 10 ring atoms in which at least 1 ring atom is an N, O or S atom, and which is optionally substituted one or more times in the heterocyclic portion by, for example, halogen, alkyl, hydroxy, alkoxy, halogenated alkyl (e.g., trifluoromethyl), halogenated alkoxy, nitro, amino, alkylamino, dialkylamino, hydroxyalkyl, hydroxyalkoxy, carboxy, cyano, or combinations thereof and/or optionally substituted in the alkyl portion by halogen, oxo, cyano, or combinations thereof (e.g., pyridylmethyl).

Overall, for each formula, $R^3$ is preferably ethyl, aryl (e.g., phenyl) or heteroaryl, and L is preferably a single bond.

$R^4$ is preferably alkyl having 1 to 3 carbon atoms, and more preferably $R^4$ is $CH_3$. $R^4$ is preferably a substituted alkyl group having 1 to 3 carbon atoms and is preferably substituted one or more times by halogen, especially F and Cl.

When $R^5$ is a substituent on the indazole or pyrazolopyridine ring (see formulas III, VI and IX), then it is preferably alkyl having 1 to 3 carbon atoms. More preferably, $R^5$ is $CH_3$ or $CH_2CH_3$.

When $R^5$ is part of the —$COR^5R^{12}$ group (see the definition of $R^6$), then it is preferably H.

$R^6$ is preferably other than H. For example, $R^6$ is preferably cycloalkyl having 4 to 7 carbon atoms, and more preferably is cyclopropyl or cyclopentyl.

$R^7$ and $R^8$ are each preferably H. $R^8$ can also preferably be alkyl, fluorinated alkyl, hydroxyalkyl, carboxy, alkoxycarbonyl having 2 to 6 carbon atoms (e.g., ethoxycarbonyl), —CO-alkyl having 2 to 6 carbon atoms (e.g., $CH_3CO$), or phenyl. For example, $R^8$ can be H, $CH_3$, $C_2H_5$, $CF_3$, hydroxymethyl, 2-(2-hydroxy)propyl), carboxy, ethoxycarbonyl, $CH_3CO$, or phenyl.

$R^9$ preferably is F.

$R^{10}$ preferably is H or alkyl having 1 to 8 carbon atoms (e.g., 1 to 4 carbon atoms), such as methyl, ethyl, isopropyl.

$R^{11}$ preferably is alkyl having 1 to 6 carbon atoms (e.g., methyl, ethyl, ethylpropyl) or heterocyclic-alkyl group (e.g., tetrahydro-2H-pyranylmethyl, pyrrolidinylethyl).

$R^{12}$ preferably is alkyl having 1 to 6 carbon atoms (e.g., methyl, ethyl, ethylpropyl) or heterocyclic-alkyl group (e.g., furylmethyl).

X is preferably CH.

L is preferably a bond, $CH_2$, $CH_2CH_2$, $CH_2CO$, $CH_2CO_2$, or $CH_2CONH$. L is also preferably $(CH_2)_nOCONH$.

The subscript n is preferably 0 or 2.

Preferred compounds of the invention are those of Formulas III, IV, and VI, particularly those of Formulas IV and VI, especially those of Formula VI.

In addition, preferred PDE4 inhibitors in accordance with the invention are compounds described by subformulas Ia-Im, IIIa-IIIy, IVa-IVm, Va-Vh, VIa-VIy, VIIa-VIIe, VIIIa-VIIIe, IXa-IXf and Xa-Xf which correspond to Formulas I, II, III, IV, V, VI, VII, VIII, IX or X but exhibit the following preferred groups:

Ia or IVa
  $R^1$ is $CH_3$ or $CF_2H$.

Ib or IVb
  $R^1$ is $CH_3$ or $CF_2H$; and
  $R^2$ is alkyl, cycloalkyl, cycloalkylalkyl, or a heterocyclic group, which in each case is substituted or unsubstituted.

Ic or IVc
  $R^1$ is $CH_3$ or $CF_2H$; and
  $R^2$ is $CF_2H$, cyclopropylmethyl, or 3-tetrahydrofuranyl (preferably 3-(3R)-tetrahydrofuranyl).

Id or IVd
  $R^1$ is $CH_3$ or $CF_2H$; and
  $R^3$ is alkyl, cycloalkyl, aryl, arylalkyl, heterocyclic group, or heterocyclic-alkyl group, which in each case is substituted or unsubstituted.

Ie or IVe
  $R^1$ is $CH_3$ or $CF_2H$;
  $R^3$ is alkyl, cycloalkyl, aryl, arylalkyl, heterocyclic group, or heterocyclic-alkyl group; and
  L is a bond, $CH_2$, $CH_2CH_2$, or $(CH_2)_nOCONH$ (e.g., $CH_2CH_2OCONH$).

If or IVf
  $R^1$ is $CH_3$ or $CF_2H$;
  $R^2$ is alkyl, cycloalkyl, cycloalkylalkyl, or a heterocyclic group, which in each case is substituted or unsubstituted;
  $R^3$ is alkyl, cycloalkyl, aryl, arylalkyl, heterocyclic group, or heterocyclic-alkyl group, which in each case is substituted or unsubstituted; and
  L is a bond, $CH_2$, or $(CH_2)_nOCONH$ (e.g., $CH_2CH_2OCONH$).

Ig or IVg
  $R^1$ is $CH_3$ or $CF_2H$;
  $R^2$ is $CF_2H$, cyclopropylmethyl, or 3-tetrahydrofuranyl (preferably 3-(3R)-tetrahydrofuranyl);
  $R^3$ is alkyl, cycloalkyl, aryl, arylalkyl, heterocyclic group, or heterocyclic-alkyl group, which in each case is substituted or unsubstituted; and
  L is a bond, $CH_2$, $CH_2CH_2$, or $(CH_2)_nOCONH$ (e.g., $CH_2CH_2OCONH$).

Ih or IVh
  $R^3$ is aryl (e.g., phenyl or biphenyl), arylalkyl (e.g., benzyl), or heterocyclic group (e.g., pyridinyl, thiazinyl, or piperidinyl), which in each case is substituted or unsubstituted; and
  L is a bond.

Ii or IVi $R^3$ is phenyl, biphenyl, or benzyl which is unsubstituted or substituted by at least one substituent selected from alkyl, alkoxy, halogenated alkoxy, halogen (e.g., F), carboxy, amino, cyano, alkylsulfonyl, acyl (e.g., acetyl), aminosulfonyl, —CO—N($R^{10}$)$_2$, acylamido (e.g., acetamido), alkylsulphonimide, arylsulphonimide (e.g., $C_6H_5SO_2$—NHCO—) wherein the aryl portion is optionally substituted by halogen or $C_{1-4}$-alkoxy, furanyl which is unsubstituted or substituted by halogen, $C_{1-4}$-alkyl, $C_{1-4}$-alkoxy, $C_{2-8}$-alkoxycarbonyl and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is substituted by halogen, $C_{1-4}$-alkyl, $C_{1-4}$-alkoxy, $C_{2-8}$-alkoxycarbonyl, and/or benzyl, isoxazolyl which is unsubstituted or substituted by halogen, $C_{1-4}$alkyl, $C_{1-4}$-alkoxy, $C_{2-8}$-alkoxycarbonyl, and/or benzyl, imidazolyl which is substituted by halogen, $C_{1-4}$-alkyl, $C_{1-4}$-alkoxy, $C_{2-8}$-alkoxycarbonyl, and/or benzyl, pyridinyl which is substituted by halogen, $C_{1-4}$-alkyl, $C_{1-4}$-alkoxy, $C_{2-8}$-alkoxycarbonyl, and/or benzyl, pyrimidinyl which is unsubstituted or substituted by halogen, $C_{1-4}$-alkyl, $C_{1-4}$-alkoxy, $C_{2-8}$-alkoxycarbonyl, and/or benzyl, morpholinyl which is substituted by $C_{1-4}$alkyl, $C_{2-8}$-alkoxycarbonyl, and/or benzyl, piperadinyl which is substituted by $C_{1-4}$-alkyl, $C_{2-8}$-alkoxycarbonyl, and/or benzyl, piperazinyl which is substituted by $C_{1-4}$-alkyl, $C_{2-8}$-alkoxycarbonyl, and/or benzyl, tetrazolyl which is unsubstituted or substituted by $C_{1-4}$-alkyl, $C_{2-8}$-alkoxycarbonyl, and/or benzyl; and L is a bond.

Ij or IVj
$R^3$ is alkyl, cycloalkyl, aryl (e.g., phenyl), arylalkyl (e.g., benzyl), heterocyclic group, or heterocyclic-alkyl group (e.g., thienyl), which in each case is substituted or unsubstituted; and
L is $(CH_2)_n$OCONH.

Ik or IVk
$R^3$ is alkyl, cyclopentyl, phenyl which is unsubstituted or substituted by alkyl, alkoxy, halogen, or cyano), benzyl), thienyl, isoxazolyl which is unsubstituted or substituted by alkyl (e.g., dimethylisoxazolyl), furanylmethyl, or heterocyclic-alkyl group (e.g., pyridinyl, thiazinyl, Or piperidinyl), which in each case is substituted or unsubstituted; and
L is $(CH_2)_n$OCONH.

Im or IVm
$R^1$ is methyl or difluoromethyl;
$R^2$ is difluoromethyl, methyl, ethyl, teratrydrofuranyl, cyclopentyl, or cyclopropyl; and
$R^7$ and $R^8$ are each H.

IIIa or VIa $R^5$ is alkyl having 1 to 3 carbon atoms (e.g., ethyl).

IIIb or VIb $R^6$ is cycloalkyl having 4 to 7 carbon atoms (e.g., cyclopentyl).

IIIc or VIc $R^6$ is cycloalkyl having 3 to 7 carbon atoms (e.g., cyclopropyl or cyclopentyl).

IIId or VId $R^6$ is cycloalkyl having 3 to 7 carbon atoms (e.g., cyclopropyl or cyclopentyl), alkyl having 1 to 6 carbon atoms (e.g., isopropyl), or a heterocyclic group (e.g., 4-tetrahydropyranyl, 2-pyrimidinyl, or 3-tetrahydrofuranyl).

IIIe or VIe $R^3$ is aryl (e.g., phenyl), arylalkyl (e.g., benzyl), or hetetoaryl group (e.g., pyridinyl, pyrimidinyl, pyrazolyl, or pyrrolyl), which in each case is substituted or unsubstituted.

IIIf or VIf $R^5$ is ethyl; and
6 is isopropyl, cyclopropyl, cyclopentyl, 4-tetrahydropyranyl, or 2-pyrimidinyl.

IIIg or VIg $R^5$ is alkyl having 1 to 3 carbon atoms (e.g., ethyl);
$R^6$ is cycloalkyl having 4 to 7 carbon atoms (e.g., cyclopentyl); and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted.

IIIh or VIh $R^5$ is alkyl having 1 to 3 carbon atoms (e.g., ethyl);
$R^6$ is cycloalkyl having 3 to 7 carbon atoms (e.g., cyclopropyl or cyclopentyl); and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted.

IIIi or VIi $R^5$ is alkyl having 1 to 3 carbon atoms (e.g., ethyl);
$R^6$ is cycloalkyl having 3 to 7 carbon atoms (e.g., cyclopropyl or cyclopentyl), alkyl having 1 to 6 carbon atoms (e.g., isopropyl), or a heterocyclic group (e.g., 4-tetrahydropyranyl, 2-pyrimidinyl, or 3-tetrahydrofuranyl); and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted.

IIIj or VIj $R^5$ is alkyl having 1 to 3 carbon atoms (e.g., ethyl);
$R^6$ is cycloalkyl having 3 to 7 carbon atoms (e.g., cyclopropyl or cyclopentyl), alkyl having 1 to 6 carbon atoms (e.g., isopropyl), or a heterocyclic group (e.g., 4-tetrahydropyranyl, 2-pyrimidinyl, or 3-tetrahydrofuranyl); and
$R^3$ is aryl (e.g., phenyl, 4-methylsulfonylpenyl), alkyl (e.g., ethyl), or heteroaryl group (e.g., pyridinyl, pyrimidinyl, pyrazolyl, or pyrrolyl), which in each case is substituted or unsubstituted.

IIIk or VIk L is a single bond.

IIIm or VIm $R^5$ is alkyl having 1 to 3 carbon atoms (e.g., ethyl);
$R^6$ is cycloalkyl having 3 to 7 carbon atoms (e.g., cyclopropyl or cyclopentyl);
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted; and
L is a single bond.

IIIn or VIn $R^5$ is $CH_2CH_3$;
$R^6$ is cyclopentyl; and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted.

IIIo or VIo $R^5$ is $CH_2CH_3$;
$R^6$ is cyclopentyl;
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted; and
L is a single bond.

IIIp or VIp $R^5$ is $CH_2CH_3$;
$R^6$ is cyclopentyl; and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy.

IIIq or VIq $R^5$ is $CH_2CH_3$;
$R^6$ is cyclopentyl;
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy; and
L is a single bond.

IIIr or VIr $R^5$ is $CH_2CH_3$;
$R^6$ is cyclopropyl, isopropyl, tetrahydropyranyl, or pyrimidinyl; and
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted.

IIIs or VIs $R^5$ is $CH_2CH_3$;
$R^6$ is cyclopropyl, isopropyl, tetrahydropyranyl, or pyrimidinyl;
$R^3$ is aryl (e.g., phenyl), arylalkyl (e.g., benzyl), or heteroaryl group (e.g., pyridinyl, pyrimidinyl, pyrazolyl, or pyrrolyl), which in each case is substituted or unsubstituted; and
L is a single bond.

IIIt or VIt $R^5$ is $CH_2CH_3$;
$R^6$ is cyclopropyl, isopropyl, tetrahydropyranyl, or pyrimidinyl; and
$R^3$ is aryl (e.g., phenyl), arylalkyl (e.g., benzyl), or heteroaryl group (e.g., pyridinyl, piperidinyl, pyrimidinyl, pyrazolyl, or pyrrolyl), which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy.

IIIu or VIu $R^5$ is $CH_2CH_3$;
$R^6$ is cyclopropyl, isopropyl, tetrahydropyranyl, or pyrimidinyl;
$R^3$ is aryl (e.g., phenyl), arylalkyl (e.g., benzyl), or heteroaryl group (e.g., pyridinyl, piperidinyl, pyrimidinyl, pyrazolyl, or pyrrolyl), which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy; and
L is a single bond.

IIIv or VIv $R^5$ is $CH_2CH_3$;
$R^6$ is cyclopropyl, cyclopentyl, isopropyl, tetrahydropyranyl, or pyrimidinyl; and
$R^3$ is phenyl which is substituted or unsubstituted.

IIIw or VIw $R^5$ is $CH_2CH_3$;
$R^6$ is cyclopropyl, cyclopentyl, isopropyl, tetrahydropyranyl, or pyrimidinyl;
$R^3$ is phenyl which is substituted or unsubstituted; and
L is a single bond.

IIIx or VIx $R^5$ is $CH_2CH_3$;
$R^6$ is cyclopropyl, cyclopentyl, isopropyl, tetrahydropyranyl, or pyrimidinyl; and
$R^3$ is phenyl which is substituted or unsubstituted.

IIIy or VIy $R^5$ is $CH_2CH_3$;
$R^6$ is cyclopropyl, cyclopentyl, isopropyl, tetrahydropyranyl, or pyrmidinyl;
$R^3$ is phenyl which is substituted or unsubstituted; and
L is a single bond.

VIIa or VIIIa $R^1$ is $CH_3$;
$R^2$ is F or Br; and
$R^3$ is substituted or unsubstituted aryl or arylalkyl.

VIIb or VIIIb $R^1$ is $CH_3$;
$R^2$ is F or Br;
$R^3$ is substituted or unsubstituted aryl or arylalkyl; and
L is a bond.

VIIc or VIIIc $R^1$ is $CH_3$;
X is CH;
$R^2$ is F or Br;
$R^3$ is substituted or unsubstituted aryl or arylalkyl;
L is a bond; and
$R^7$ and $R^8$ are each H.

VIId or VIIId $R^1$ is $CH_3$;
X is CH;
$R^2$ is F or Br;
$R^3$ is substituted or unsubstituted phenyl or benzyl;
L is a bond; and
$R^7$ and $R^8$ are each H.

VIIe or VIIIe $R^1$ is $CH_3$;
X is CH;
$R^2$ is F or Br;
$R^3$ is substituted or unsubstituted phenyl or benzyl;
L is a bond;
$R^7$ and $R^8$ are each H; and
X is CH.

IXa or Xa $R^5$ is alkyl having 1 to 3 carbon atoms (e.g., ethyl).

IXb or Xb $R^{11}$ is alkyl having 1 to 6 carbon atoms, tetrahydro-2H-pyranylmethyl or pyrrolidinylethyl.

IXc or Xc $R^3$ is aryl (e.g., phenyl), arylalkyl (e.g., benzyl), or heterocyclic group (e.g., pyridinyl, piperidinyl, pyrimidinyl, pyrazolyl, or pyrrolyl), which in each case is substituted or unsubstituted.

IXd or Xd L is a single bond.

IXe or Xe $R^5$ is alkyl having 1 to 3 carbon atoms (e.g., ethyl);
$R^{11}$ is alkyl having 1 to 6 carbon atoms, tetrahydro-2H-pyranylmethyl or pyrrolidinylethyl;
$R^3$ is aryl (e.g., phenyl), arylalkyl (e.g., benzyl), or heterocyclic group (e.g., pyridinyl, piperidinyl, pyrimidinyl, pyrazolyl, or pyrrolyl), which in each case is substituted or unsubstituted; and
L is a single bond.

IXf or Xf $R^5$ is $CH_2CH_3$;
$R^{11}$ is methyl, tetrahydro-2H-pyranylmethyl or pyrrolidinylethyl;
$R^3$ is phenyl which in each case is substituted or unsubstituted; and
L is a single bond.

According to preferred compounds of the invention, 5-aryl-1-substituted pyrazoles and 5-heteroaryl-1-substituted pyrazoles (e.g. Formulas IV, V, and VI) are generally preferred over 3-aryl-1-substituted pyrazoles and 3-heteroaryl-1-substituted pyrazoles (e.g. Formulas I, II, and III).

According to a further preferred compound and/or method aspect of the invention, the compounds of Formulas I, II, III, IV, V, VI, VII and VIII are selected from:
1) 1-cyclopentyl-3-ethyl-6-[1-(4-methoxyphenyl)-1H-pyrazol-5-yl]-1H-indazole,
2) 4-[5-(1-cyclopentyl-3-ethyl-1H-indazol-6-yl)-1H-pyrazol-1-yl]benzoic acid, 3) 1-cyclopentyl-3-ethyl-6-(1-pyridin-2-yl-1H-pyrazol-5-yl)-1H-indazole,
4) 1-cyclopentyl-6-[1-(3,4-difluorophenyl)-1H-pyrazol-5-yl]-3-ethyl-1H-indazole,
5) 6-(1-benzyl-1H-pyrazol-5-yl)-1-cyclopentyl-3-ethyl-1H-indazole,
6) 1-cyclopentyl-3-ethyl-6-(1-pyridin-4-yl-1H-pyrazol-5-yl)-1H-indazole,
7) 1-cyclopentyl-3-ethyl-6-(1-piperidin-4-yl-1H-pyrazol-5-yl)-1H-indazole,
8) 1-cyclopentyl-3-ethyl-6-[1-(4-pyrimidin-5-ylphenyl)-1H-pyrazol-5-yl]-1H-indazole,
9) 1-cyclopentyl-3-ethyl-6-{1-[4-(1H-pyrazol-4-yl)phenyl]-1H-pyrazol-5-yl}-1H-indazole,
10) 1-cyclopentyl-3-ethyl-6-{1-[4-(1H-pyrrol-2-yl)phenyl]-1H-pyrazol-5-yl}-1H-indazole,
11) 1-cyclopentyl-3-ethyl-6-[1-(4-pyridin-3-yl)phenyl]-1H-pyrazol-5-yl]-1H-indazole,
12) 4-[5-(1-cyclopentyl-3-ethyl-1H-indazol-6-yl)-1H-pyrazol-1-yl]benzamide,
13) 1-cyclopentyl-3-ethyl-6-{1-[4-(trifluoromethoxy)phenyl]-1H-pyrazol-5-yl}-1H-indazole,
14) 1-cyclopentyl-3-ethyl-6-[1-(4-fluorophenyl)-1H-pyrazol-5-yl]-1H-indazole,
15) 4-[5-(1-cyclopentyl-3-ethyl-1H-indazol-6-yl)-1H-pyrazol-1-yl]benzonitrile,
16) 6-[1-(4-chlorophenyl)-1H-pyrazol-5-yl]-1-cyclopentyl-3-ethyl-1H-indazole,
17) 1-cyclopentyl-3-ethyl-6-[1-(4-methylphenyl)-1H-pyrazol-5-yl]-1H-indazole,
18) 4-[5-(1-cyclopentyl-3-ethyl-1H-indazol-6-yl)-1H-pyrazol-1-yl]benzenesulfonamide,
19) 4-[5-(1-cyclopentyl-3-ethyl-1H-indazol-6-yl)-1H-pyrazol-1-yl]-N-(methylsulfonyl)benzamide,
20) 4-[5-(1-cyclopentyl-3-ethyl-1H-indazol-6-yl)-1H-pyrazol-1-yl]-N-(ethylsulfonyl)benzamide,
21) 1-cyclopentyl-3-ethyl-6-{1-[4-(1H-tetrazol-5-yl)phenyl]-1H-pyrazol-5-yl}-1H-indazole,
22) 1-cyclopentyl-3-ethyl-6-{1-[4-(methylsulfonyl)phenyl]-1H-pyrazol-5-yl}-1H-indazole,
23) 4-[5-(1-cyclopentyl-3-ethyl-1H-indazol-6-yl)-1H-pyrazol-1-yl]-N-methoxy-N-methylbenzamide,
24) 1-{4-[5-(1-cyclopentyl-3-ethyl-1H-indazol-6-yl)-1H-pyrazol-1-yl]phenyl}ethanone,
25) 4-[5-(1-cyclopentyl-3-ethyl-1H-indazol-6-yl)-1H-pyrazol-1-yl]-N,N-diethylbenzamide,
26) 1-cyclopentyl-6-{1-[4-(difluoromethoxy)phenyl]-1H-pyrazol-5-yl}-3-ethyl-1H-indazole,
27) 4-[4-(5-{4-methoxy-3-[(3R)-tetrahydrofuran-3-yloxy]phenyl}-1H-pyrazol-1-yl)phenyl]morpholine,
28) 4-{[5-(3-fluoro-4-methoxyphenyl)-1H-pyrazol-1-yl]methyl}benzoic acid,
29) 4-(5-{4-methoxy-3-[(3R)-tetrahydrofuran-3-yloxy]phenyl}-1H-pyrazol-1-yl)benzoic acid,
30) 5-{4-methoxy-3-[(3R)-tetrahydrofuran-3-yloxy]phenyl}-1-[4-(methylsulfonyl)phenyl]-1H-pyrazole,
31) 2-(5-{4-methoxy-3-[(3R)-tetrahydrofuran-3-yloxy]phenyl}-1H-pyrazol-1-yl)-1,3-thiazole,
32) 1-benzyl-5-(3,4-dimethoxyphenyl)-1H-pyrazole,
33) 2-(5-{4-methoxy-3-[(3R)-tetrahydrofuran-3-yloxy]phenyl}-1H-pyrazol-1-yl)benzoic acid,
34) 3-(5-{4-methoxy-3-[(3R)-tetrahydrofuran-3-yloxy]phenyl}-1H-pyrazol-1-yl)benzoic acid,
35) 1-[4-(3-furyl)phenyl]-5-{4-methoxy-3-[(3R)-tetrahydrofuran-3-yloxy]phenyl}-1H-pyrazole,
36) 4-[(5-{4-methoxy-3-[(3R)-tetrahydrofuran-3-yloxy]phenyl}-1H-pyrazol-1-yl)methyl]-N-(phenylsulfonyl)benzamide,
37) N-[(4-methoxyphenyl)sulfonyl]-4-[(5-{4-methoxy-3-[(3R)-tetrahydrofuran-3-yloxy]phenyl}-1H-pyrazol-1-yl)methyl]benzamide,
38) N-[(4-fluorophenyl)sulfonyl]-4-[(5-{4-methoxy-3-[(3R)-tetrahydrofuran-3-yloxy]phenyl}-1H-pyrazol-1-yl)methyl]benzamide,
39) tert-butyl 4-[4-(5-{4-methoxy-3-[(3R)-tetrahydrofuran-3-yloxy]phenyl}-1H-pyrazol-1-yl)phenyl]piperazine-1-carboxylate,
40) 4-[5-(3,4-dimethoxyphenyl)-1H-pyrazol-1-yl]pyridine,
41) 4-(5-{4-methoxy-3-[(3R)-tetrahydrofuran-3-yloxy]phenyl}-1H-pyrazol-1-yl)pyridine,
42) 4-(5-{4-methoxy-3-[(3R)-tetrahydrofuran-3-yloxy]phenyl}-1H-pyrazol-1-yl)piperidine,
43) 1-[4-(5-{4-methoxy-3-[(3R)-tetrahydrofuran-3-yloxy]phenyl}-1H-pyrazol-1-yl)phenyl]piperazine,
44) 1-(4-fluorobenzyl)-5-{4-methoxy-3-[(3R)-tetrahydrofuran-3-yloxy]phenyl}-4-methyl-1H-pyrazole,
45) 5-(3-Bromo-4-methoxyphenyl)-1-(4-methoxyphenyl)-1H-pyrazole,
46) 5-{4-methoxy-3-[(3R)-tetrahydrofuran-3-yloxy]phenyl}-1-[4-(1H-pyrrol-2-yl)phenyl]-1H-pyrazole,
47) 3-[4-(5-{4-methoxy-3-[(3R)-tetrahydrofuran-3-yloxy]phenyl}-1H-pyrazol-1-yl)phenyl]pyridine,
48) 2-(5-{4-Methoxy-3-[(3R)-tetrahydrofuran-3-yloxy]phenyl}-1H-pyrazol-1-yl)ethyl (4-fluorophenyl)carbamate,
49) 2-(5-{4-Methoxy-3-[(3R)-tetrahydrofuran-3-yloxy]phenyl}-1H-pyrazol-1-yl)ethyl benzylcarbamate,
50) 2-(5-{4-Methoxy-3-[(3R)-tetrahydrofuran-3-yloxy]phenyl}-1H-pyrazol-1-yl)ethyl 1-methylpropylcarbamate,
51) 1-Isobutyl-5-(4-methoxy-3-[(3R)-tetrahydrofuran-3-yloxy]phenyl)-1H-pyrazole,
52) 5-[3,4-bis(difluoromethoxy)phenyl]-1-(4-methoxyphenyl)-1H-pyrazole,
53) 2-(5-{4-Methoxy-3-[(3R)-tetrahydrofuran-3-yloxy]phenyl}-1H-pyrazol-1-yl)ethyl phenylcarbamate,
54) 2-(5-{4-Methoxy-3-[(3R)-tetrahydrofuran-3-yloxy]phenyl}-1H-pyrazol-1-yl)ethyl propylcarbamate,
55) 2-(5-{4-Methoxy-3-[(3R)-tetrahydrofuran-3-yloxy]phenyl}-1H-pyrazol-1-yl)ethyl (2-fluorophenyl)carbamate,
56) 5-[4-(difluoromethoxy)-3-methoxyphenyl]-1-(4-methoxyphenyl)-1H-pyrazole,
57) 2-(5-{4-Methoxy-3-[(3R)-tetrahydrofuran-3-yloxy]phenyl}-1H-pyrazol-1-yl)ethyl (4-methoxyphenyl)carbamate,
58) 2-(5-{4-Methoxy-3-[(3R)-tetrahydrofuran-3-yloxy]phenyl}-1H-pyrazol-1-yl)ethyl (3-fluorophenyl)carbamate,
59) 2-(5-{4-Methoxy-3-[(3R)-tetrahydrofuran-3-yloxy]phenyl}-1H-pyrazol-1-yl)ethyl (4-chlorophenyl)carbamate,
60) 1-benzyl-4-[4-(5-{4-methoxy-3-[(3R)-tetrahydrofuran-3-yloxy]phenyl}-1H-pyrazol-1-yl)phenyl]-1H-pyrazole,
61) 2-fluoro-5-[4-(5-{4-methoxy-3-[(3R)-tetrahydrofuran-3-yloxy]phenyl}-1H-pyrazol-1-yl)phenyl]pyridine,
62) 5-[4-(5-{4-methoxy-3-[(3R)-tetrahydrofuran-3-yloxy]phenyl}-1H-pyrazol-1-yl)phenyl]pyrimidine,
63) N-[4'-(5-{4-methoxy-3-[(3R)-tetrahydrofuran-3-yloxy]phenyl}-1H-pyrazol-1-yl)biphenyl-2-yl]acetamide,
64) 4'-(5-{4-methoxy-3-[(3R)-tetrahydrofuran-3-yloxy]phenyl}-1H-pyrazol-1-yl)biphenyl-2-carboxamide,
65) N-[4'-(5-{4-methoxy-3-[(3R)-tetrahydrofuran-3-yloxy]phenyl}-1H-pyrazol-1-yl)biphenyl-3-yl]acetamide,
66) 3-fluoro-4-[4-(5-{4-methoxy-3-[(3R)-tetrahydrofuran-3-yloxy]phenyl}-1H-pyrazol-1-yl)phenyl]pyridine, 67) 2-methoxy-5-[4-(5-{4-methoxy-3-[(3R)-tetrahydrofuran-3-yloxy]phenyl}-1H-pyrazol-1-yl)phenyl]pyridine,
68) 4-[4-(5-{4-methoxy-3-[(3R)-tetrahydrofuran-3-yloxy]phenyl}-1H-pyrazol-1-yl)phenyl]-3,5-dimethylisoxazole,
69) 2-(5-{4-methoxy-3-[(3R)-tetrahydrofuran-3-yloxy]phenyl}-1H-pyrazol-1-yl)ethyl (2-furylmethyl)carbamate,
70) 2-(5-{4-Methoxy-3-[(3R)-tetrahydrofuran-3-yloxy]phenyl}-1H-pyrazol-1-yl)ethyl (4-methylphenyl)carbamate,
71) 4-(5-{4-methoxy-3-[(3R)-tetrahydrofuran-3-yloxy]phenyl}-1H-pyrazol-1-yl)benzenesulfonamide,
72) 4-(5-{4-methoxy-3-[(3R)-tetrahydrofuran-3-yloxy]phenyl}-1H-pyrazol-1-yl)benzonitrile,
73) 2-(5-{4-Methoxy-3-[(3R)-tetrahydrofuran-3-yloxy]phenyl}-1H-pyrazol-1-yl)ethyl (cyclopentyl)carbamate,
74) 4-(5-{4-methoxy-3-[(3R)-tetrahydrofuran-3-yloxy]phenyl}-1H-pyrazol-1-yl)aniline,
75) 2-(5-{4-Methoxy-3-[(3R)-tetrahydrofuran-3-yloxy]phenyl}-1H-pyrazol-1-yl)ethyl 2-thienylcarbamate,
76) 5-[4-(5-{4-methoxy-3-[(3R)-tetrahydrofuran-3-yloxy]phenyl}-1H-pyrazol-1-yl)phenyl]-1H-tetrazole,
77) 2-(5-{4-Methoxy-3-[(3R)-tetrahydrofuran-3-yloxy]phenyl}-1H-pyrazol-1-yl)ethyl (4-cyanophenyl)carbamate,
78) 2-(5-{4-Methoxy-3-[(3R)-tetrahydrofuran-3-yloxy]phenyl}-1H-pyrazol-1-yl)ethyl [2-(2-thienyl)ethyl]carbamate,
79) 2-(5-{4-Methoxy-3-[(3R)-tetrahydrofuran-3-yloxy]phenyl}-1H-pyrazol-1-yl)ethyl (3,5-dimethylisoxazol-4-yl)carbamate,
80) 2-(5-{4-Methoxy-3-[(3R)-tetrahydrofuran-3-yloxy]phenyl}-1H-pyrazol-1-yl)ethyl 3-thienylcarbamate,
81) 5-[1-(4-fluorophenyl)-1H-pyrazol-5-yl]-2-methoxyphenol,
82) 5-[3-(benzyloxy)-4-methoxyphenyl]-1-(4-fluorophenyl)-1H-pyrazole,
83) 2-(5-{4-Methoxy-3-[(3R)-tetrahydrofuran-3-yloxy]phenyl}-1H-pyrazol-1-yl)ethyl (3,4-dichlorophenyl)carbamate,
84) 2-(5-{4-Methoxy-3-[(3R)-tetrahydrofuran-3-yloxy]phenyl}-1H-pyrazol-1-yl)ethyl (3,4-difluorophenyl)carbamate,
85) 5-(3,4-dimethoxyphenyl)-1-(4-fluorophenyl)-1H-pyrazole,
86) 5-(3-ethoxy-4-methoxyphenyl)-1-(4-fluorophenyl)-1H-pyrazole,
87) 5-[3-(cyclopropylmethoxy)-4-methoxyphenyl]-1-(4-fluorophenyl)-1H-pyrazole,
88) 5-[3-(cyclopentyloxy)-4-methoxyphenyl]-1-(4-fluorophenyl)-1H-pyrazole,
89) 5-[3,4-bis(difluoromethoxy)phenyl]-1-[4-(difluoromethoxy)phenyl]-1H-pyrazole, and physiologically acceptable salts thereof,
wherein a compound listed above (in either a free base form or in the form of a pharmaceutically acceptable salt thereof) can also be in the form of a solvate (such as a hydrate),
wherein a compound listed above (in a free base form or solvate thereof, or in the form of a pharmaceutically acceptable salt or solvate thereof) can also be in the form of a polymorph, and
wherein if the compound exhibits chirality it can be in the form of a mixture of enantiomers such as a racemate or a mixture of diastereomers, or can be in the form of a single enantiomer or a single diastereomer.

According to a further preferred compound and/or method aspect of the invention, the compounds of Formulas I, I, III, IV, V, VI, VII and VIII are selected from:

1) 1-cyclopentyl-3-ethyl-6-[1-(4-methoxyphenyl)-1H-pyrazol-5-yl]-1H-indazole,
2) 4-[5-(1-cyclopentyl-3-ethyl-1H-indazol-6-yl)-1H-pyrazol-1-yl]benzoic acid,
3) 1-cyclopentyl-3-ethyl-6-(1-pyridin-2-yl-1H-pyrazol-5-yl)-1H-indazole,
4) 1-cyclopentyl-6-[1-(3,4-difluorophenyl)-1H-pyrazol-5-yl]-3-ethyl-1H-indazole,
5) 6-(1-benzyl-1H-pyrazol-5-yl)-1-cyclopentyl-3-ethyl-1H-indazole,
6) 1-cyclopentyl-3-ethyl-6-(1-pyridin-4-yl-1H-pyrazol-5-yl)-1H-indazole,
7) 1-cyclopentyl-3-ethyl-6-(1-piperidin-4-yl-1H-pyrazol-5-yl)-1H-indazole,
8) 1-cyclopentyl-3-ethyl-6-[1-(4-pyrimidin-5-ylphenyl)-1H-pyrazol-5-yl]-1H-indazole,
9) 1-cyclopentyl-3-ethyl-6-{1-[4-(1H-pyrazol-4-yl)phenyl]-1H-pyrazol-5-yl}-1H-indazole,
10) 1-cyclopentyl-3-ethyl-6-{1-[4-(1H-pyrrol-2-yl)phenyl]-1H-pyrazol-5-yl}-1H-indazole,
11) 1-cyclopentyl-3-ethyl-6-[1-(4-pyridin-3-ylphenyl)-1H-pyrazol-5-yl]-1H-indazole,
12) 4-[5-(1-cyclopentyl-3-ethyl-1H-indazol-6-yl)-1H-pyrazol-1-yl]benzamide,
13) 1-cyclopentyl-3-ethyl-6-{1-[4-(trifluoromethoxy)phenyl]-1H-pyrazol-5-yl}-1H-indazole,
14) 1-cyclopentyl-3-ethyl-6-[1-(4-fluorophenyl)-1H-pyrazol-5-yl]-1H-indazole,
15) 4-[5-(1-cyclopentyl-3-ethyl-1H-indazol-6-yl)-1H-pyrazol-1-yl]benzonitrile,
16) 6-[1-(4-chlorophenyl)-1H-pyrazol-5-yl]-1-cyclopentyl-3-ethyl-1H-indazole,
17) 1-cyclopentyl-3-ethyl-6-[1-(4-methylphenyl)-1H-pyrazol-5-yl]-1H-indazole,
18) 4-[5-(1-cyclopentyl-3-ethyl-1H-indazol-6-yl)-1H-pyrazol-1-yl]benzenesulfonamide,
19) 4-[5-(1-cyclopentyl-3-ethyl-1H-indazol-6-yl)-1H-pyrazol-1-yl]-N-(methylsulfonyl)benzamide,
20) 4-[5-(1-cyclopentyl-3-ethyl-1H-imidazol-6-yl)-1H-pyrazol-1-yl]-N-(ethylsulfonyl)benzamide,
22) 1-cyclopentyl-3-ethyl-6-{1-[4-(methylsulfonyl)phenyl]-1H-pyrazol-5-yl}-1H-indazole,
24) 1-{4-[5-(1-cyclopentyl-3-ethyl-1H-indazol-6-yl)-1H-pyrazol-1-yl]phenyl}ethanone,
25) 4-[5-(1-cyclopentyl-3-ethyl-1H-indazol-6-yl)-1H-pyrazol-1-yl]-N,N-diethylbenzamide,
26) 1-cyclopentyl-6-{1-[4-(difluoromethoxy)phenyl]-1H-pyrazol-5-yl}-3-ethyl-1H-indazole,
27) 4-[4-(5-{4-methoxy-3-[(3R)-tetrahydrofuran-3-yloxy]phenyl}-1H-pyrazol-1-yl)phenyl]morpholine,
28) 4-{[5-(3-fluoro-4-methoxyphenyl)-1H-pyrazol-1-yl]methyl}benzoic acid,
30) 5-{4-methoxy-3-[(3R)-tetrahydrofuran-3-yloxy]phenyl}-1-[4-(methylsulfonyl)phenyl]-1H-pyrazole,
31) 2-(5-{4-methoxy-3-[(3R)-tetrahydrofuran-3-yloxy]phenyl}-1H-pyrazol-1-yl)-1,3-thiazole,
32) 1-benzyl-5-(3,4-dimethoxyphenyl)-1H-pyrazole,
33) 2-(5-{4-methoxy-3-[(3R)-tetrahydrofuran-3-yloxy]phenyl}-1H-pyrazol-1-yl)benzoic acid,
34) 3-(5-{4-methoxy-3-[(3R)-tetrahydrofuran-3-yloxy]phenyl}-1H-pyrazol-1-yl)benzoic acid,
35) 1-[4-(3-furyl)phenyl]-5-{4-methoxy-3-[(3R)-tetrahydrofuran-3-yloxy]phenyl}-1H-pyrazole,
36) 4-[(5-{4-methoxy-3-[(3R)-tetrahydrofuran-3-yloxy]phenyl}-1H-pyrazol-1-yl)methyl]-N-(phenylsulfonyl)benzamide, 37) N-[(4-methoxyphenyl)sulfonyl]-4-[(5-{4-methoxy-3-[(3R)-tetrahydrofuran-3-yloxy]phenyl}-1H-pyrazol-1-yl)methyl]benzamide,
38) N-[(4-fluorophenyl)sulfonyl]-4-[(5-{4-methoxy-3-[(3R)-tetrahydrofuran-3-yloxy]phenyl}-1H-pyrazol-1-yl)methyl]benzamide,
39) tert-butyl 4-[4-(5-{4-methoxy-3-[(3R)-tetrahydrofuran-3-yloxy]phenyl}-1H-pyrazol-1-yl)phenyl]piperazine-1-carboxylate,
40) 4-[5-(3,4-dimethoxyphenyl)-1H-pyrazol-1-yl]pyridine,
41) 4-(5-{4-methoxy-3-[(3R)-tetrahydrofuran-3-yloxy]phenyl}-1H-pyrazol-1-yl)pyridine,
42) 4-(5-{4-methoxy-3-[(3R)-tetrahydrofuran-3-yloxy]phenyl}-1H-pyrazol-1-yl)piperidine,
43) 1-(4-(5-[4-methoxy-3-[(3R)-tetrahydrofuran-3-yloxy]phenyl)-1H-pyrazol-1-yl)phenyl]piperazine,
44) 1-(4-fluorobenzyl)-5-{4-methoxy-3-[(3R)-tetrahydrofuran-3-yloxy]phenyl}-4-methyl-1H-pyrazole,
45) 5-(3-Bromo-4-methoxyphenyl)-1-(4-methoxyphenyl)-1H-pyrazole,
46) 5-{4-methoxy-3-[(3R)-tetrahydrofuran-3-yloxy]phenyl}-1-[4-(1H-pyrrol-2-yl)phenyl]-1H-pyrazole,
47) 3-[4-(5-{4-methoxy-3-[(3R)-tetrahydrofuran-3-yloxy]phenyl}-1H-pyrazol-1-yl)phenyl]pyridine,
48) 2-(5-{4-Methoxy-3-[(3R)-tetrahydrofuran-3-yloxy]phenyl}-1H-pyrazol-1-yl)ethyl (4-fluorophenyl)carbamate,
49) 2-(5-{4-Methoxy-3-[(3R)-tetrahydrofuran-3-yloxy]phenyl}-1H-pyrazol-1-yl)ethyl benzylcarbamate,
50) 2-(5-{4-Methoxy-3-[(3R)-tetrahydrofuran-3-yloxy]phenyl}-1H-pyrazol-1-yl)ethyl 1-methylpropylcarbamate,
51) 1-Isobutyl-5-(4-methoxy-3-[(3R)-tetrahydrofuran-3-yloxy]phenyl)-1H-pyrazole,
52) 5-[3,4-bis(difluoromethoxy)phenyl]-1-(4-methoxyphenyl)-1H-pyrazole,
53) 2-(5-{4-Methoxy-3-[(3R)-tetrahydrofuran-3-yloxy]phenyl}-1H-pyrazol-1-yl)ethyl phenylcarbamate,
54) 2-(5-{4-Methoxy-3-[(3R)-tetrahydrofuran-3-yloxy]phenyl}-1H-pyrazol-1-yl)ethyl propylcarbamate,
55) 2-(5-{4-Methoxy-3-[(3R)-tetrahydrofuran-3-yloxy]phenyl}-1H-pyrazol-1-yl)ethyl (2-fluorophenyl)carbamate,
56) 5-[4-(difluoromethoxy)-3-methoxyphenyl]-1-(4-methoxyphenyl)-1H-pyrazole,
57) 2-(5-{4-Methoxy-3-[(3R)-tetrahydrofuran-3-yloxy]phenyl}-1H-pyrazol-1-yl)ethyl (4-methoxyphenyl)carbamate,
58) 2-(5-{4-Methoxy-3-[(3R)-tetrahydrofuran-3-yloxy]phenyl}-1H-pyrazol-1-yl)ethyl
59) 2-(5-{4-Methoxy-3-[(3R)-tetrahydrofuran-3-yloxy]phenyl}-1H-pyrazol-1-yl)ethyl
60) 1-benzyl-4-[4-(5-{4methoxy-3-[(3R)-tetrahydrofuran-3-yloxy]phenyl}-1H-pyrazol-1-yl)phenyl]1H-pyrazole,
62) 5-[4-(5-{4-methoxy-3-[(3R)-tetrahydrofuran-3-yloxy]phenyl)}-1H-pyrazol-1-yl)phenyl]pyrimidine,
63) N-[4'-(5-{4-methoxy-3-[(3R)-tetrahydrofuran-3-yloxy]phenyl}-1H-pyrazol-1-yl)biphenyl-2-yl]acetamide,
64) 4'-(5-{4-methoxy-3-[(3R)-tetrahydrofuran-3-yloxy]phenyl}-1H-pyrazol-1-yl)biphenyl-2-carboxamide,
65) N-[4'-(5-{4-methoxy-3-[(3R)-tetrahydrofuran-3-yloxy]phenyl}-1H-pyrazol-1-yl)biphenyl-2-yl]acetamide,
66) 3-fluoro-4-[4-(5-{4-methoxy-3-[(3R)-tetrahydrofuran-3-yloxy]phenyl}-1H-pyrazol-1-yl)phenyl]pyridine,
67) 2-methoxy-5-[4-(5-{4-ethoxy-3-[(3R)-tetrahydrofuran-3-yloxy]phenyl}-1H-pyrazol-1-yl)phenyl]pyridine,
68) 4-[4-(5-{4-methoxy-3-[(3R)-tetrahydrofuran-3-yloxy]phenyl}-1H-pyrazol-1-yl)phenyl]-3,5-dimethylisoxazole,
69) 2-(5-{4-methoxy-3-[(3R)-tetrahydrofuran-3-yloxy]phenyl}-1H-pyrazol-1-yl)ethyl (2-furylmethyl)carbamate,
70) 2-(5-{4-Methoxy-3-[(3R)-tetrahydrofuran-3-yloxy]phenyl}-1H-pyrazol-1-yl)ethyl (4-methylphenyl)carbamate,
71) 4-(5-{4-methoxy-3-[(3R)-tetrahydrofuran-3-yloxy]phenyl}-1H-pyrazol-1-yl)benzenesulfonamide,
72) 4-(5-{4-methoxy-3-[(3R)-tetrahydrofuran-3-yloxy]phenyl}-1H-pyrazol-1-yl)benzonitrile,
73) 2-(5-{4-Methoxy-3-[(3R)-tetrahydrofuran-3-yloxy]phenyl}-1H-pyrazol-1-yl)ethyl (cyclopentyl)carbamate,
74) 4-(5-{4-methoxy-3-[(3R)-tetrahydrofuran-3-yloxy]phenyl}-1H-pyrazol-1-yl)aniline,
75) 2-(5-{4-Methoxy-3-[(3R)-tetrahydrofuran-3-yloxy]phenyl}-1H-pyrazol-1-yl)ethyl 2-thienylcarbamate,
76) 5-[4-(5-{4-methoxy-3-[(3R)-tetrahydrofuran-3-yloxy]phenyl}-1H-pyrazol-1-yl)phenyl]-1H-tetrazole,
77) 2-(5-{4-Methoxy-3-[(3R)-tetrahydrofuran-3-yloxy]phenyl}-1H-pyrazol-1-yl)ethyl (4-cyanophenyl)carbamate,
78) 2-(5-{4-Methoxy-3-[(3R)-tetrahydrofuran-3-yloxy]phenyl}-1H-pyrazol-1-yl)ethyl [2-(2-thienyl)ethyl]carbamate,
79) 2-(5-{4-Methoxy-3-[(3R)-tetrahydrofuran-3-yloxy]phenyl}-1H-pyrazol-1-yl)ethyl (3,5-dimethylisoxazol-4-yl)carbamate,
80) 2-(5-{4-Methoxy-3-[(3R)-tetrahydrofuran-3-yloxy]phenyl}-1H-pyrazol-1-yl)ethyl 3-thienylcarbamate,
81) 5-[1-(4-fluorophenyl)-1H-pyrazol-5-yl]-2-methoxyphenol,
83) 2-(5-{4-Methoxy-3-[(3R)-tetrahydrofuran-3-yloxy]phenyl}-1H-pyrazol-1-yl)ethyl (3,4-dichlorophenyl)carbamate,
84) 2-(5-{4-Methoxy-3-[(3R)-tetrahydrofuran-3-yloxy]phenyl}-1H-pyrazol-1-yl)ethyl (3,4-difluorophenyl)carbamate,
85) 5-(3,4-dimethoxyphenyl)-1-(4-fluorophenyl)-1H-pyrazole,
86) 5-(3-ethoxy-4-methoxyphenyl)-1-(4-fluorophenyl)-1H-pyrazole,
87) 5-[3-(cyclopropylmethoxy)-4-methoxyphenyl]-1-(4-fluorophenyl)-1H-pyrazole,
88) 5-[3-(cyclopentyloxy)-4-methoxyphenyl]-1-(4-fluorophenyl)-1H-pyrazole,
89) 5-[3,4-bis(difluoromethoxy)phenyl]-1-[4-(difluoromethoxy)phenyl]-1H-pyrazole,
and physiologically acceptable salts thereof,
wherein a compound listed above (in either a free base form or in the form of a pharmaceutically acceptable salt thereof) can also be in the form of a solvate (such as a hydrate),
wherein a compound listed above (in a free base form or solvate thereof, or in the form of a pharmaceutically acceptable salt or solvate thereof) can also be in the form of a polymorph, and
wherein if the compound exhibits chirality it can be in the form of a mixture of enantiomers such as a racemate or a mixture of diastereomers, or can be in the form of a single enantiomer or a single diastereomer.

According to a further preferred compound and/or method aspect of the invention, the compounds of Formulas I, I, III, IV, V, VI, VII, VIII, and IX are selected from:

90) 4-[5-(3-ethyl-2-methyl-2H-indazol-6-yl)-1H-pyrazol-1-yl]benzoic acid,
91) 1,3-diethyl-6-{1-[4-(methylsulfonyl)phenyl]-1H-pyrazol-5-yl}-1H-indazole,
92) 1-(cyclopropylmethyl)-3-ethyl-6-{1-[4-(methylsulfonyl)phenyl]-1H-pyrazol-5-yl}-1H-indazole,
93) 3-ethyl-1-isopropyl-6-{1-[4-(methylsulfonyl)phenyl]-1H-pyrazol-5-yl}-1H-indazole, 94) 3-ethyl-1-(2-methoxyethyl)-6-{1-[4-(methylsulfonyl)phenyl]-1H-pyrazol-5-yl}-1H-indazole,
95) 6-[1-(1-acetylpiperidin-4-yl)-1H-pyrazol-5-yl]-1-cyclopentyl-3-ethyl-1H-indazole,
96) 4-[5-(1-cyclopentyl-3-ethyl-1H-indazol-6-yl)-1H-pyrazol-1-yl]-N,N-dimethylbenzenesulfonamide,
97) 1-(ethoxymethyl)-3-ethyl-6-{1-[4-(methylsulfonyl)phenyl]-1H-pyrazol-5-yl}-1H-indazole,
98) 3-ethyl-1-(1-ethylpropyl)-6-{1-[4-(methylsulfonyl)phenyl]-1H-pyrazol-5-yl}-1H-indazole,
99) 3-ethyl-2-(1-ethylpropyl)-6-{1-[4-(methylsulfonyl)phenyl]-1H-pyrazol-5-yl}-2H-indazole,
100) 3-ethyl-6-{1-[4-(methylsulfonyl)phenyl]-1H-pyrazol-5-yl}-1-(tetrahydro-2H-pyran-2-ylmethyl)-1H-indazole,
101) 3-ethyl-6-{1-[4-(methylsulfonyl)phenyl]-1H-pyrazol-5-yl}-2-(tetrahydro-2H-pyran-2-ylmethyl)-2H-indazole,
102) 3-ethyl-6-{1-[4-(methylsulfonyl)phenyl]-1H-pyrazol-5-yl}-2-(2-pyrrolidin-1-ylethyl)-2H-indazole,
103) Isopropyl 3-ethyl-6-{1-[4-(methylsulfonyl)phenyl]-1H-pyrazol-5-yl}-1H-indazole-1-carboxylate,
104) 3-ethyl-6-{1-[4-(methylsulfonyl)phenyl]-1H-pyrazol-5-yl}-1-(2-pyrrolidin-1-ylethyl)-1H-indazole,
105) N-(sec-butyl)-3-ethyl-6-{1-[4-(methylsulfonyl)phenyl]-1H-pyrazol-5-yl}-1H-indazole-1-carboxamide,
106) 3-ethyl-6-{1-[4-(methylsulfonyl)phenyl]-1H-pyrazol-5-yl}-1-pyridin-3-yl-1H-indazole,
107) N-cyclopentyl-3-ethyl-6-{1-[4-(methylsulfonyl)phenyl]-1H-pyrazol-5-yl}-1H-indazole-1-carboxamide,
108) N,3-diethyl-6-{1-[4-(methylsulfonyl)phenyl]-1H-pyrazol-5-yl}-1H-indazole-1-carboxamide,
109) 3-ethyl-N-(2-furylmethyl)-6-{1-[4-(methylsulfonyl)phenyl]-1H-pyrazol-5-yl}-1H-indazole-1-carboxamide,
110) 3-ethyl-6-{1-[4-(methylsulfonyl)phenyl]-1H-pyrazol-5-yl}-1-pyrimidin-2-yl-1H-indazole,
111) 3-ethyl-6-{1-[4-(methylsulfonyl)phenyl]-1H-pyrazol-5-yl}-1-pyrimidin-5-yl-1H-indazole,
112) 1-cyclopropyl-3-ethyl-6-{1-[4-(methylsulfonyl)phenyl]-1H-pyrazol-5-yl}-1H-indazole,
113) 2-[5-(1-cyclopentyl-3-ethyl-1H-indazol-6-yl)-1H-pyrazol-1-yl]quinoxaline,
114) 1-{4-[5-(1-cyclopentyl-3-ethyl-1H-indazol-6-yl)-1H-pyrazol-1-yl]phenyl}-N-methylmethanesulfonamide,
115) 1-(3-ethyl-6-{1-[(methylsulfonyl)phenyl]-1H-pyrazol-5-yl}-1H-indazol-1-yl)-2-methylpropan-2-ol,
116) 3-ethyl-6-{1-[4-(methylsulfonyl)phenyl]-1H-pyrazol-5-yl}-1-(tetrahydro-2H-pyran-4-yl)-1H-indazole,
117) 1-(difluoromethyl)-3-ethyl-6-{1-[4-(methylsulfonyl)phenyl]-1H-pyrazol-5-yl}-1H-indazole,
118) 3-ethyl-6-{1-[4-(methylsulfonyl)phenyl]-1H-pyrazol-5-yl}-1-pyridin-2-yl-1H-indazole,
119) 1-(5-cyclopropyl-1,3,4-thiadiazol-2-yl)-3-ethyl-6-{1-[4-(methylsulfonyl)phenyl]-1H-pyrazol-5-yl}-1H-indazole,
120) 3-ethyl-6-{1-[4-(methylsulfonyl)phenyl]-1H-pyrazol-5-yl}-1-(tetrahydrofuran-3-yl)-1H-indazole,
121) Tert-butyl 3-(3-ethyl-6-{1-[4-(methylsulfonyl)phenyl]-1H-pyrazol-5-yl}-1H-indazol-1-yl)pyrrolidine-1-carboxylate,
122) 1-cyclopropyl-3-ethyl-6-(1-isopropyl-1H-pyrazol-5-yl)-1H-indazole,
123) 1-cyclopropyl-3-ethyl-6-(1-methyl-1H-pyrazol-5-yl)-1H-indazole,
124) 1-cyclopropyl-3-ethyl-6-(1H-pyrazol-5-yl)-1H-indazole,
125) 1-cyclopropyl-3-ethyl-6-(1-ethyl-1H-pyrazol-5-yl)-1H-indazole,
126) 1-cyclopropyl-3-ethyl-6-(1-pyridin-4-yl-1H-pyrazol-5-yl)-1H-indazole,
127) 2-[5-(1-cyclopropyl-3-ethyl-1H-indazol-6-yl)-1H-pyrazol-1-yl]quinoxaline,
128) {4-[5-(1-cyclopropyl-3-ethyl-1H-indazol-6-yl)-1H-pyrazol-1-yl]phenyl}methanol,
129) 2-{4-[5-(1-cyclopropyl-3-ethyl-1H-indazol-6-yl)-1H-pyrazol-1-yl]phenyl}propan-2-ol,
130) 1-{4-[5-(1-cyclopropyl-3-ethyl-1H-indazol-6-yl)-1H-pyrazol-1-yl]phenyl}-N-methylmethanesulfonamide,
131) 1-cyclopropyl-3-ethyl-6-[1-(tetrahydro-2H-pyran-4-yl)-1H-pyrazol-5-yl]-1H-indazole,
132) 1-cyclopropyl-3-ethyl-6-[1-(tetrahydro-2H-pyran-4-yl)-1H-pyrazol-3-yl]-1H-indazole,
133) 1-cyclopropyl-6-[1-(1,1-dioxidotetrahydro-3-thienyl)-1H-pyrazol-5-yl]-3-ethyl-1H-indazole,
134) 6-(1-cyclopentyl-1H-pyrazol-5-yl)-1-cyclopropyl-3-ethyl-1H-indazole,
135) 1-cyclopentyl-3-ethyl-6-(1-{4-[(2-methoxyethoxy)methyl]phenyl}-1H-pyrazol-5-yl)-1H-indazole,
136) 1-cyclopropyl-3-ethyl-6-[1-(2,2,6,6-tetramethylpiperidin-4-yl)-1H-pyrazol-5-yl]-1H-indazole,
137) 6-{1-[3-(benzyloxy)phenyl]-1H-pyrazol-5-yl}-1-cyclopropyl-3-ethyl-1H-indazole,
138) 3-[5-(1-cyclopropyl-3-ethyl-1H-indazol-6-yl)-1H-pyrazol-1-yl]phenol,
139) 3-ethyl-1-isopropyl-6-{1-[4-(methylsulfonyl)phenyl]-1H-pyrazol-5-yl}-1H-pyrazolo[3,4-b]pyridine,
140) 2-{3-[5-(1-cyclopropyl-3-ethyl-1H-indazol-6-yl)-1H-pyrazol-1-yl]phenoxy}ethanol,
141) 6-{1-[4-(benzyloxy)phenyl]-1H-pyrazol-5-yl}-1-cyclopropyl-3-ethyl-1H-indazole,
142) 3-ethyl-6-{1-[4-(methylsulfonyl)phenyl]-1H-pyrazol-5-yl}-1-(tetrahydro-2H-pyran-4-yl)-1H-pyrazolo[3,4-b]pyridine,
143) 4-[5-(1-cyclopropyl-3-ethyl-1H-indazol-6-yl)-1H-pyrazol-1-yl]phenol,
144) (4-{5-[3-ethyl-1-(tetrahydro-2H-pyran-4-yl)-1H-pyrazolo[3,4-b]pyridin-6-yl]-1H-pyrazol-1-yl}phenyl)methanol,
145) 2-(4-{5-[3-ethyl-1-(tetrahydro-2H-pyran-4-yl)-1H-pyrazolo[3,4-b]pyridin-6-yl]-1H-pyrazol-1-yl}phenyl)propan-2-ol,
146) 1-cyclopropyl-3-ethyl-6-{1-[3-(2-methoxyethoxy)phenyl]-1H-pyrazol-5-yl}-1H-indazole,
147) 1-cyclopropyl-3-ethyl-6-[1-(3-methoxyphenyl)-1H-pyrazol-5-yl]-1H-indazole,
148) 1-cyclopropyl-3-ethyl-6-{1-[4-(2-methoxyethoxy)phenyl]-1H pyrazol-5-yl}-1H-indazole,
149) 1-cyclopropyl-3-ethyl-6-[1-(4-methoxyphenyl)-1H-pyrazol-5-yl]-1H-indazole,
150) 1-cyclopropyl-3-ethyl-6-(1-pyrimidin-2-yl-1H-pyrazol-5-yl)-1H-indazole,
151) 3-ethyl-1-(2-methoxypyridin-4-yl)-6-(1-pyrimidin-2-yl-1H-pyrazol-5-yl)-1H-indazole,
152) 1-[4-(difluoromethoxy)phenyl]-5-{4-methoxy-3-[(3R)-tetrahydrofuran-3-yloxy]phenyl}-1H-pyrazole
153) 1-cyclopentyl-3-ethyl-6-[1-(pyridin-4-ylmethyl)-1H-pyrazol-5-yl]-1H-indazole
154) 4-[(5-{4-methoxy-3-[3R)-tetrahydrofuran-3-yloxy]phenyl}-1H-pyrazol-1H-1-yl)methyl]pyridine
155) 4-[5-(3-ethyl-1-methyl-1H-indazol-6-yl)-1H-pyrazol-1-yl]benzoic acid
156) 4-[5-(3-ethyl-1-methyl-1H-indazol-6-yl)-1H-pyrazol-1-yl]benzenesulfonamide
157) 3-ethyl-1-methyl-6-{1-[4-(methylsulfonyl)phenyl]-1H-pyrazol-5-yl}-1H-indazole 158) 4-[5-(3-ethyl-1-methyl-1H-indazol-6-yl)-1H-pyrazol-1-yl]benzonitrile
159) 4-[5-(3-ethyl-2-methyl-2H-indazol-6-yl)-1H-pyrazol-1-yl]benzenesulfonamide
160) 3-ethyl-2-methyl-6-{1-[4-(methylsulfonyl)phenyl]-1H-pyrazol-5-yl}-2H-indazole
161) 4-[5-(3-ethyl-2-methyl-2H-indazol-6-yl)-1H-pyrazol-1-yl]benzonitrile
162) 6-{1-[4-(difluoromethoxy)phenyl]-1H-pyrazol-5-yl}-3-ethyl-1H-(tetrahydro-2H-pyran-4-yl)-1H-pyrazolo[3,4-b]pyridine
163) 3-ethyl-6-[1-(4-fluorophenyl)-1H-pyrazol-5-yl]-1-(tetrahydro-2H-pyran-4-yl)-1H-pyrazolo[3,4-b]pyridine
164) 3-ethyl-6-(1-pyridin-4-yl-1H-pyrazol-5-yl)-1-(tetrahydro-2H-pyran-4-yl)-1H-pyrazolo[3,4-b]pyridine
165) 3-ethyl-6-(1-phenyl-1H-pyrazol-5-yl)-1-(tetrahydro-2H-pyran-4-yl)-1H-pyrazolo[3,4-b]pyridine
166) 3-ethyl-6-(1-pyridin-2-yl-1H-pyrazol-5-yl)-1-(tetrahydro-2H-pyran-4-yl)-1H-pyrazolo[3,4-b]pyridine
167) 3-ethyl-6-[1-(3-fluorophenyl)-1H-pyrazol-5-yl]-1-(tetrahydro-2H-pyran-4-yl)-1H-pyrazolo[3,4-b]pyridine
168) 3-ethyl-6-[1-(4-methoxyphenyl)-1H-pyrazol-5-yl]-1-(tetrahydro-2H-pyran-4-yl)-1H-pyrazolo[3,4-b]pyridine
169) 3-ethyl-6-[1-(3-methoxyphenyl)-1H-pyrazol-5-yl]-1-(tetrahydro-2H-pyran-4-yl)-1H-pyrazolo[3,4-b]pyridine
170) 6-{1-[4-(benzyloxy)phenyl]-1H-pyrazol-5-yl}-3-ethyl-1-(tetrahydro-2H-pyran-4-yl)-1H-pyrazolo[3,4-b]pyridine
171) 6-{1-[3-(benzyloxy)phenyl]-1H-pyrazol-5-yl}-3-ethyl-1-(tetrahydro-2H-pyran-4-yl)-1H-pyrazolo[3,4-b]pyridine
172) 4-{5-[3-ethyl-1-(tetrahydro-2H-pyran-4-yl)-1H-pyrazolo[3,4-b]pyridin-6-yl]-1H-pyrazol-1-yl}phenol
173) 3-{5-[3-ethyl-1-(tetrahydro-2H-pyran-4-yl)-1H-pyrazolo[3,4-b]pyridin-6-yl]-1H-pyrazol-1-yl}phenol
174) 6-{1-[3-(2-methoxyethoxy)phenyl]-1H-pyrazol-5-yl}-3-ethyl-1-(tetrahydro-2H-pyran-4-yl)-1H-pyrazolo[3,4-b]pyridine
175) 6-{1-[4-(2-methoxyethoxy)phenyl]-1H-pyrazol-5-yl}-3-ethyl-1-(tetrahydro-2H-pyran-4-yl)-1H-pyrazolo[3,4-b]pyridine
176) 2-(3-{5-[3-ethyl-1-(tetrahydro-2H-pyran-4-yl)-1H-pyrazolo[3,4-b]pyridin-6-yl]-1H-pyrazol-1-yl}phenoxy)ethanol
177) 2-(4-{5-[3-ethyl-1-(tetrahydro-2H-pyran-4-yl)-1H-pyrazolo[3,4-b]pyridin-6-yl]-1H-pyrazol-1H-pyrazol-1-yl}phenoxy)ethanol 3-ethyl-6-{1-[3-(2-methoxyethoxy)phenyl]-1H-pyrazol-5-yl}-1-(tetrahydro-2H-pyran-4-yl)-1H-indazole 3-ethyl-6-{1-[4-(2-methoxyethoxy)phenyl]-1H-pyrazol-5-yl}-1-(tetrahydro-2-H-pyran-4-yl)-1H-indazole 2-(3-{5-[3-ethyl-1-(tetrahydro-2H-pyran-4-yl)-1H-indazol-6-yl]-1H-pyrazol-1-yl}phenoxy)ethanol 2-(4-{5-[3-ethyl-1-(tetrahydro-2H-pyran-4-yl)-1H-indazol-6-yl]-1H-pyrazol-1-yl}phenoxy)ethanol and physiologically acceptable salts thereof,
wherein a compound listed above (in either a free base form or in the form of a pharmaceutically acceptable salt thereof) can also be in the form of a solvate (such as a hydrate),
wherein a compound listed above (in a free base form or solvate thereof, or in the form of a pharmaceutically acceptable salt or solvate thereof) can also be in the form of a polymorph, and
wherein if the compound exhibits chirality it can be in the form of a mixture of enantiomers such as a racemate or a mixture of diastereomers, or can be in the form of a single enantiomer or a single diastereomer.

The following table presents the structures for selected compounds of Formulas I-IX in accordance with the present invention:

1) 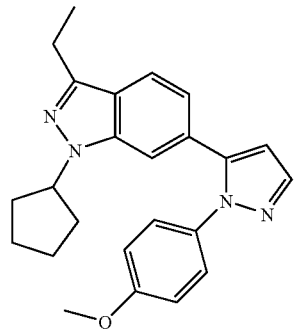

2) 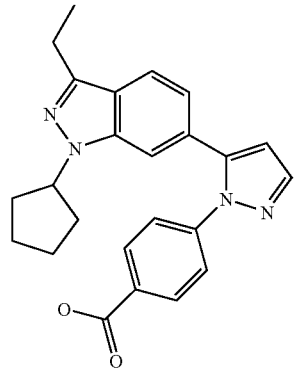

3) 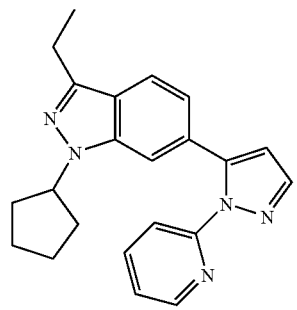

4) 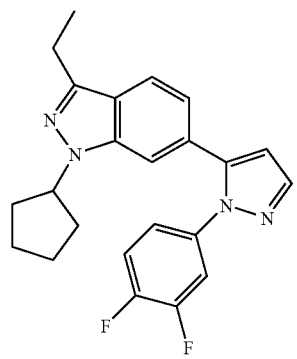

5) 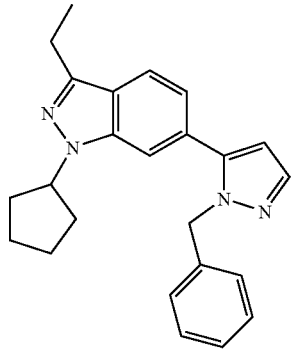
6) 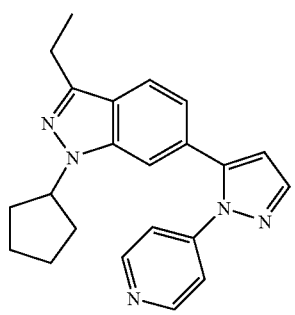
7) 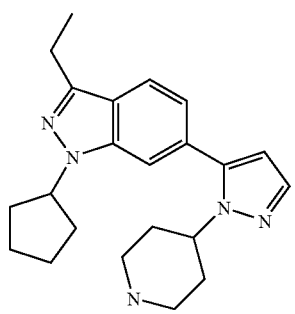
8) 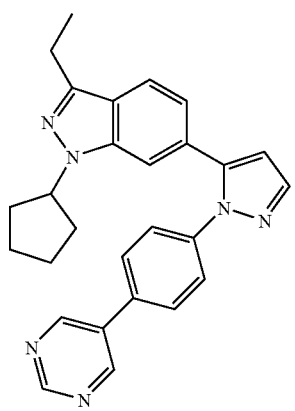
9) 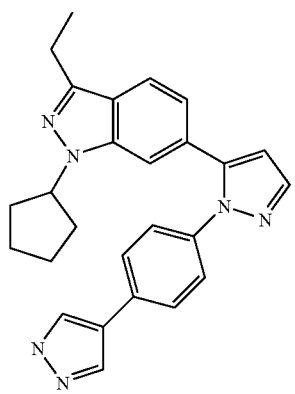
10) 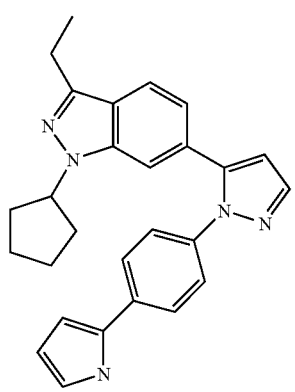
11) 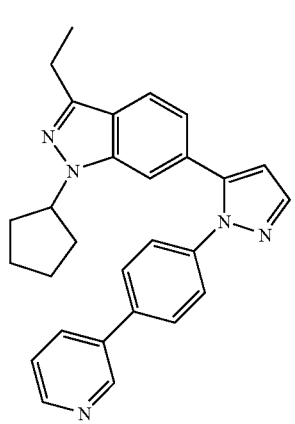
12) 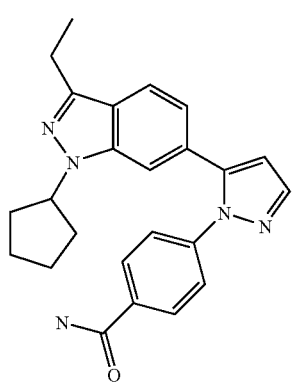

-continued
13) 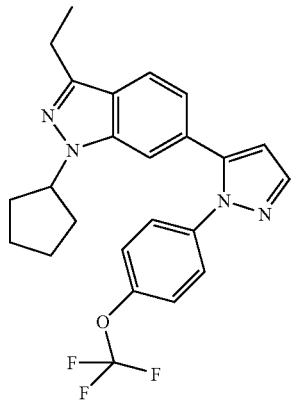
14) 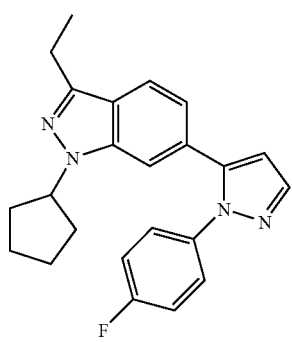
15) 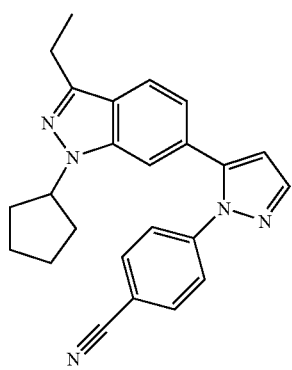
16) 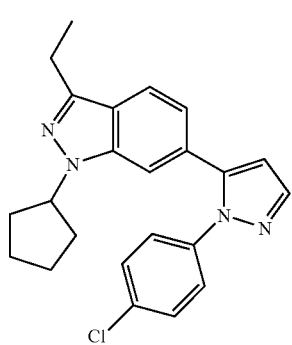
-continued
17) 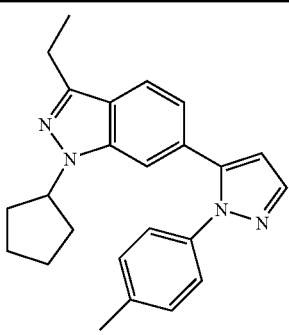
18) 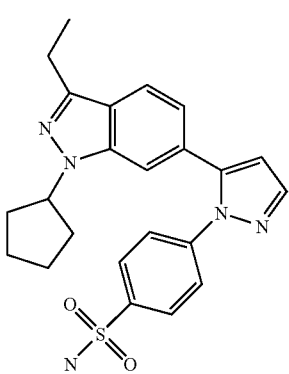
19) 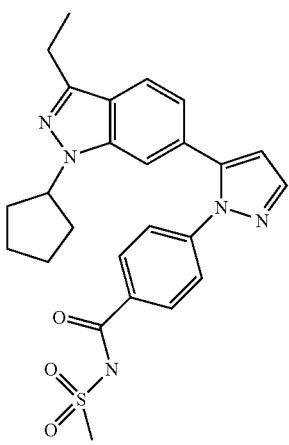
20) 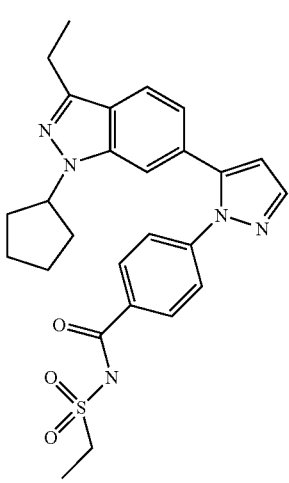

-continued
21) 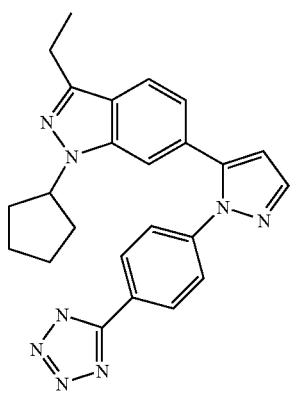
22) 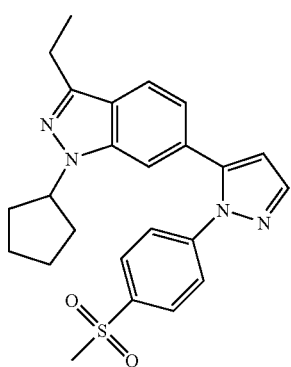
23) 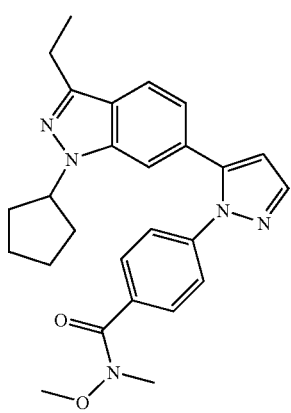
24) 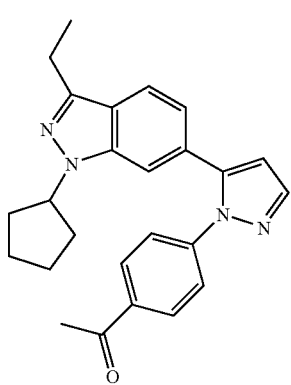
-continued
25) 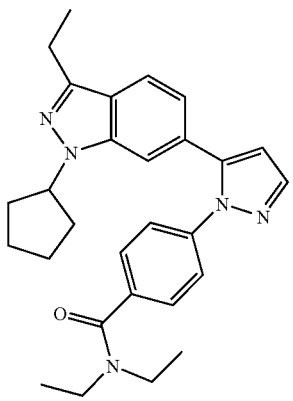
26) 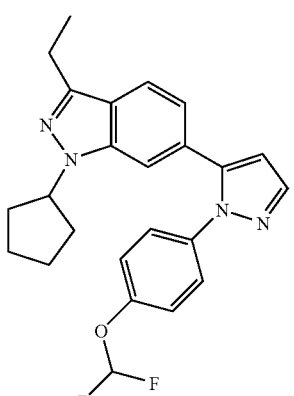
27) 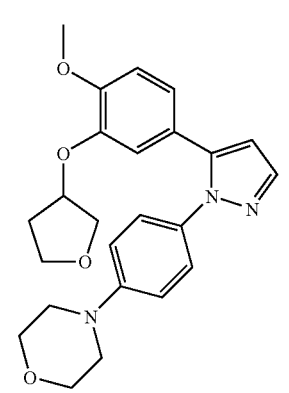
28) 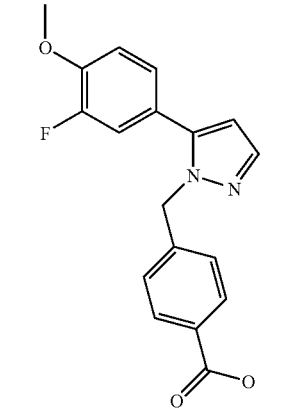

-continued
29) 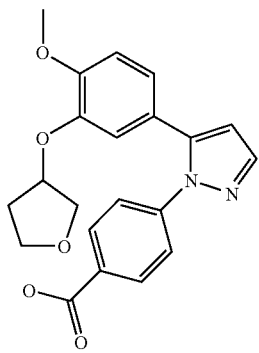
30) 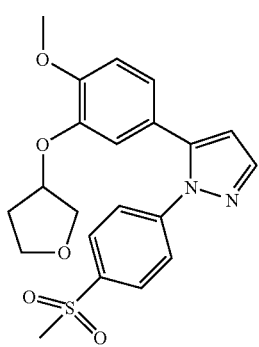
31) 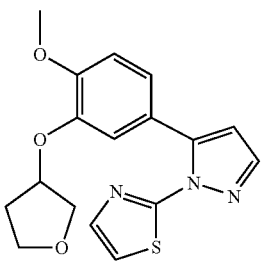
32) 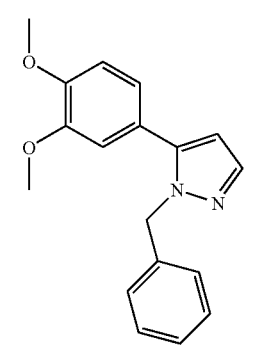
33) 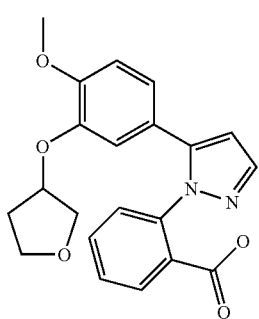
-continued
34) 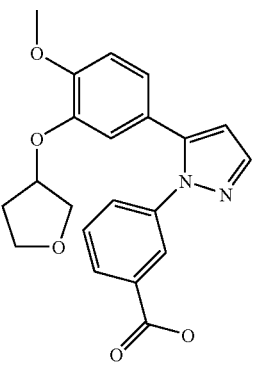
35) 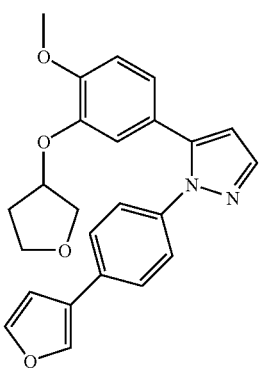
36) 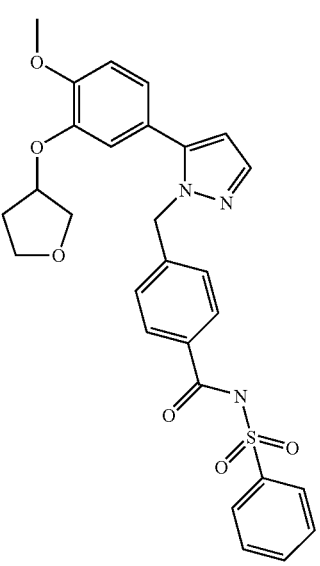

37) 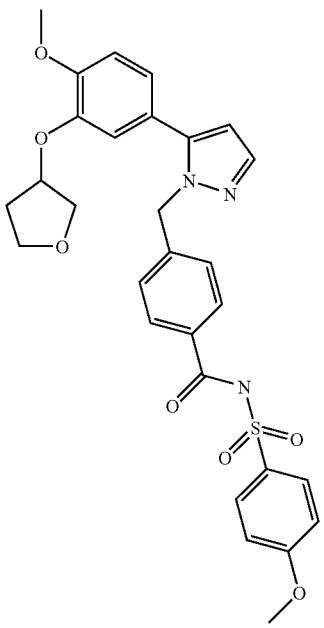
39) 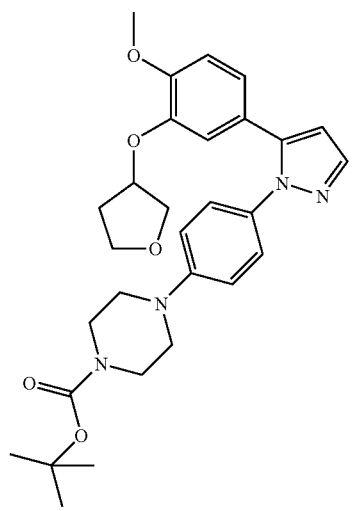
40) 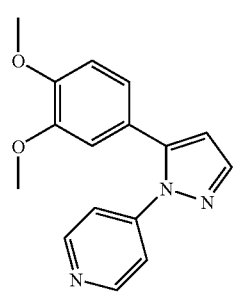
38) 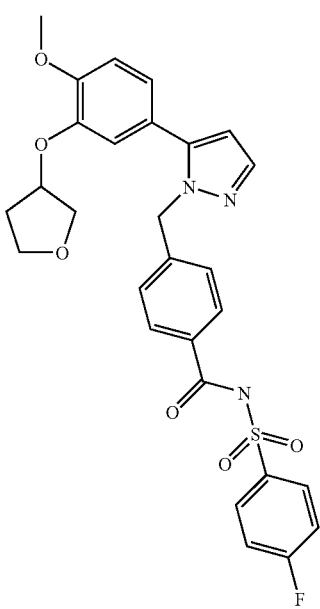
41) 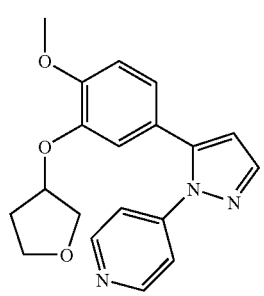
42) 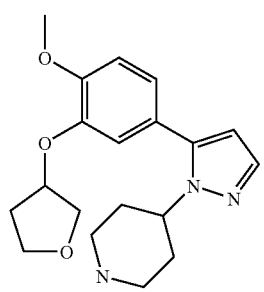

43) 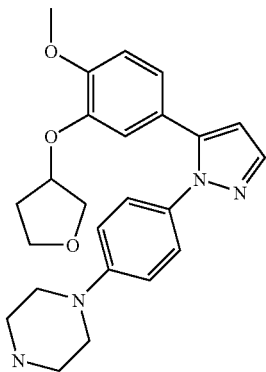
44) 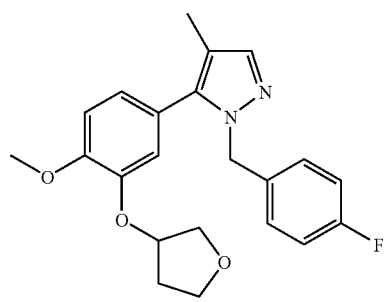
45) 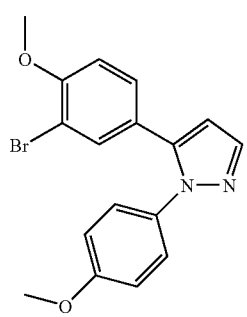
46) 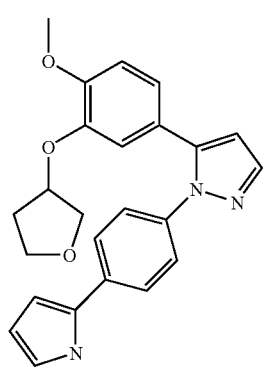
47) 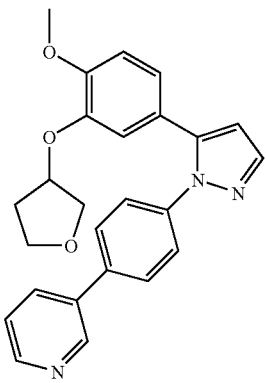
48) 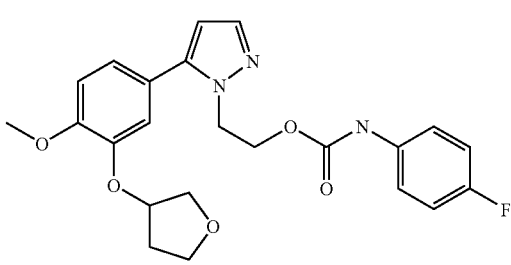
49) 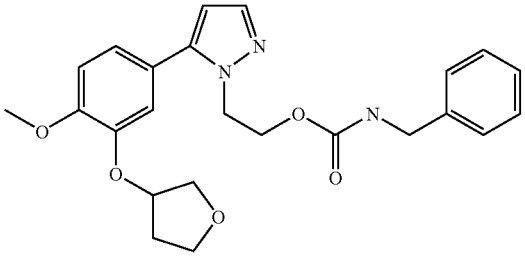
50) 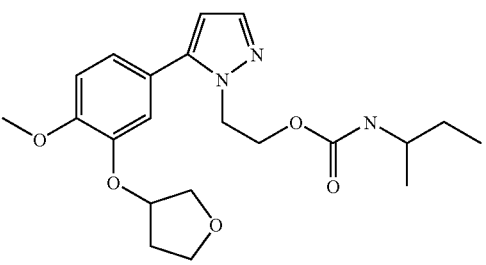
51) 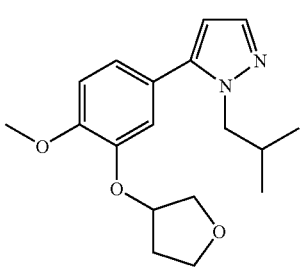

-continued
52) 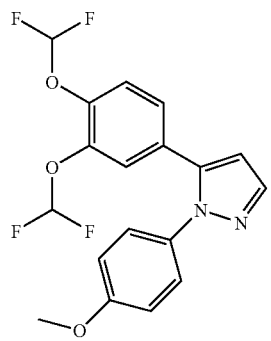
53) 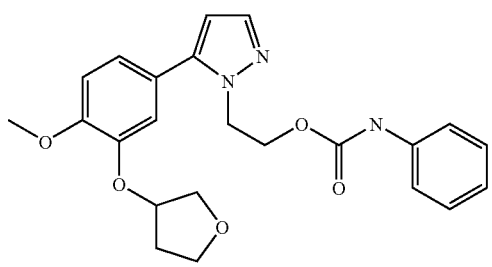
54) 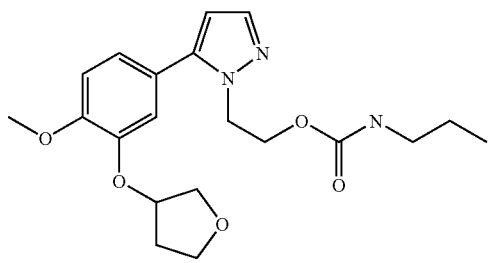
55) 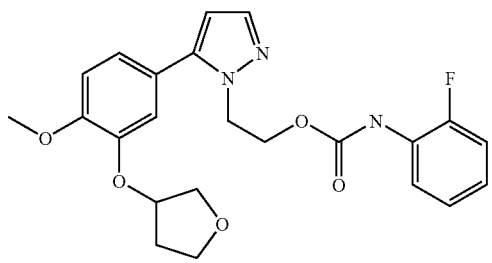
56) 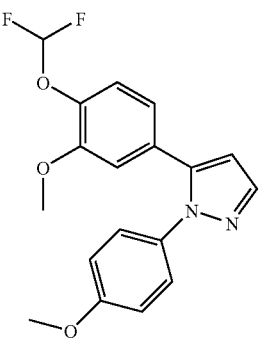
-continued
57) 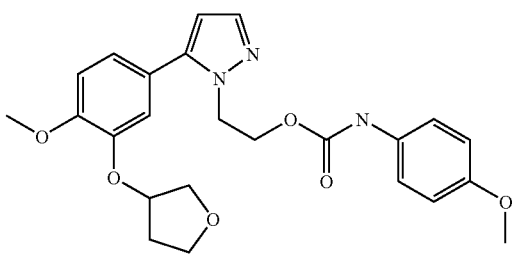
58) 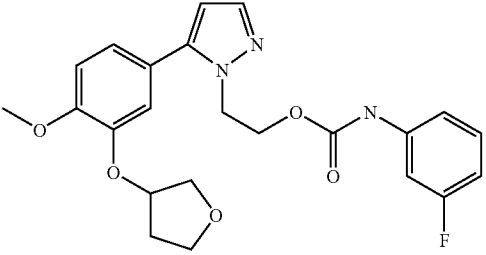
59) 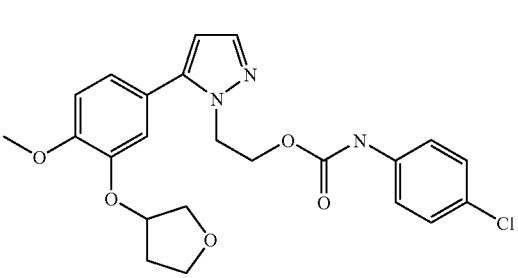
60) 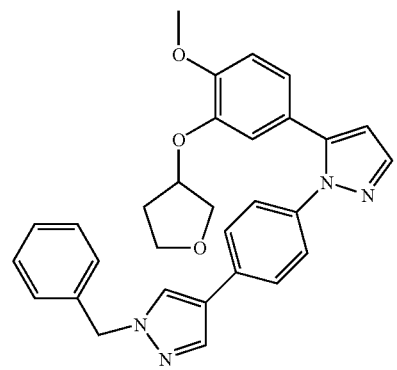
61) 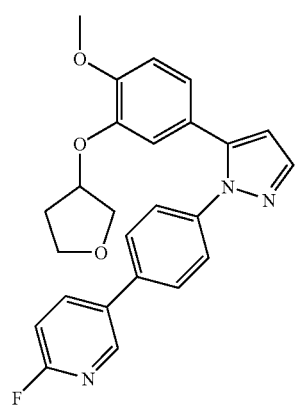

| 62) 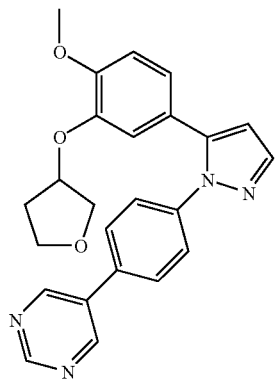 | 65) 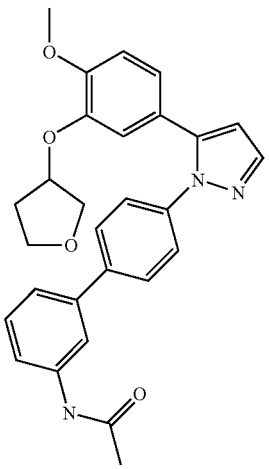 |
| --- | --- |
| 63) 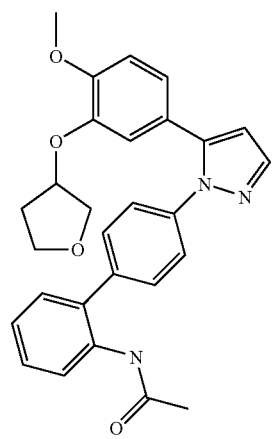 | 66) 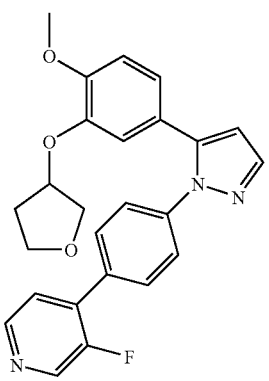 |
| 64) 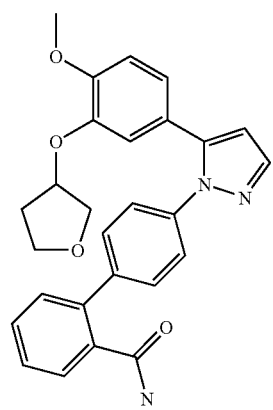 | 67) 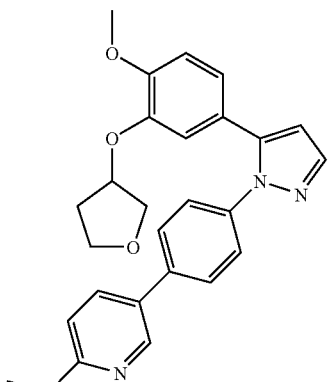 |
| | 68) 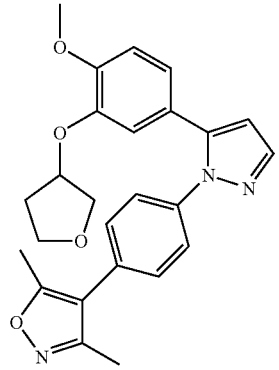 |

-continued
69) 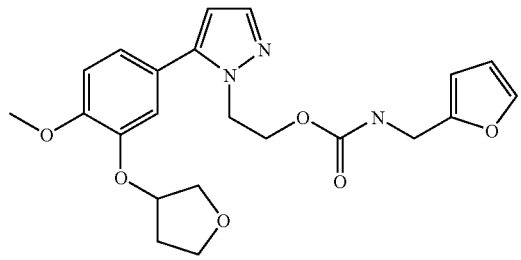
70) 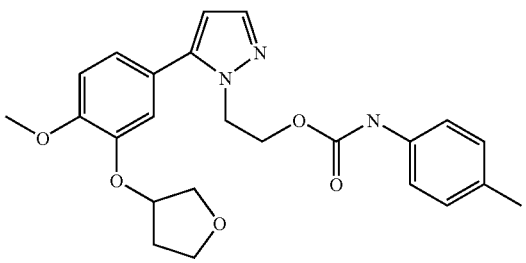
71) 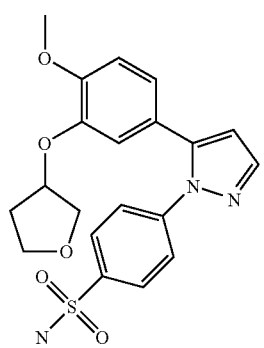
72) 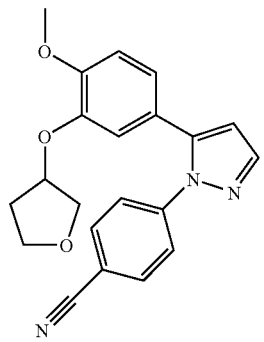
73) 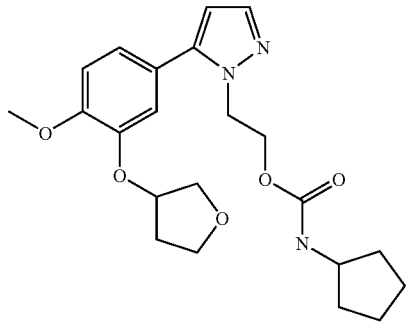
-continued
74) 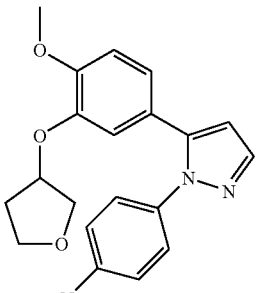
75) 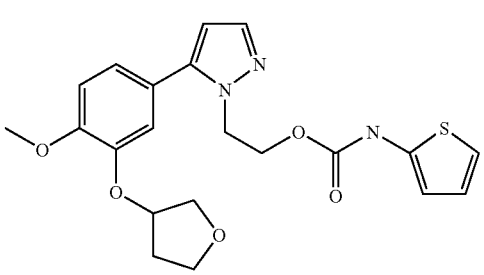
76) 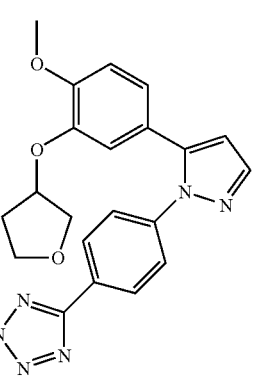
77) 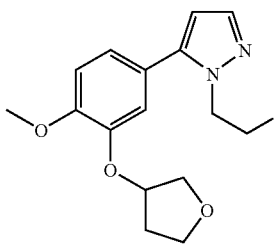
78) 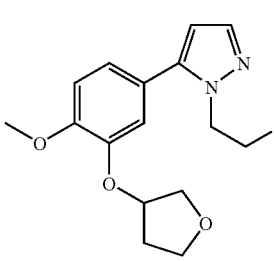

79) 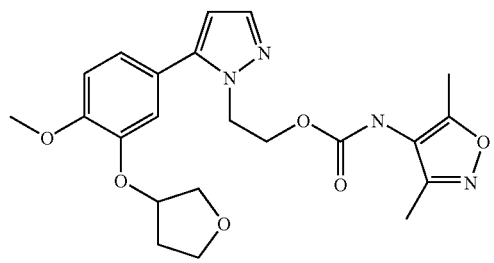
80) 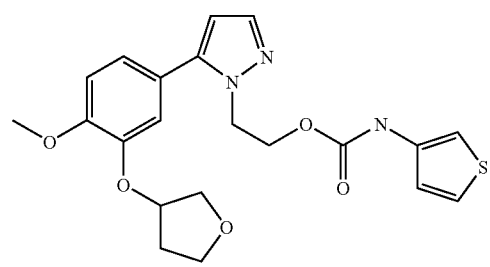
81) 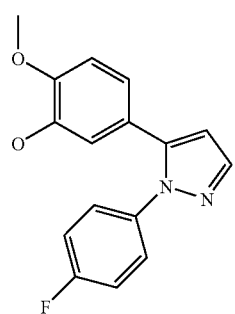
82) 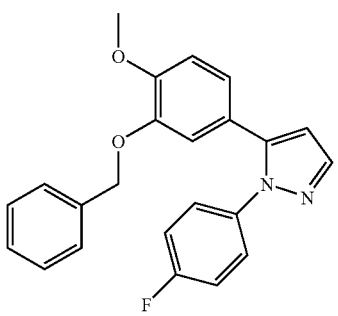
83) 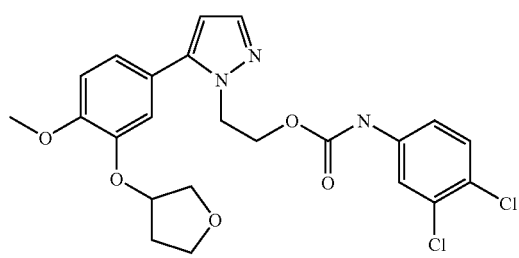
84) 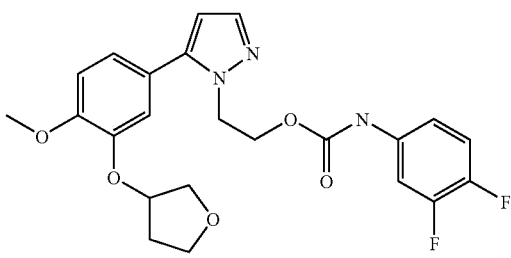
85) 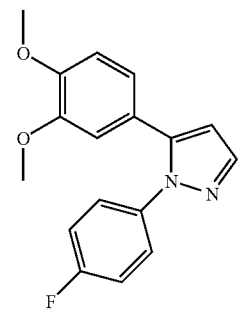
86) 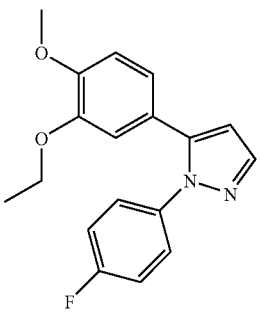
87) 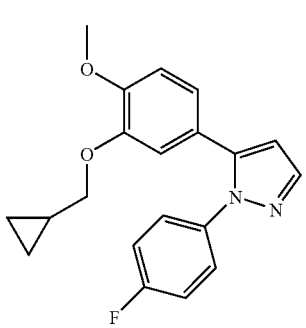
88) 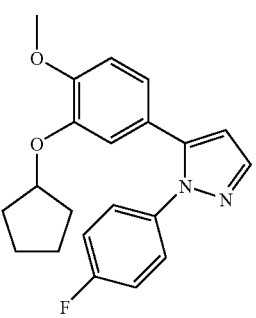

-continued
89) 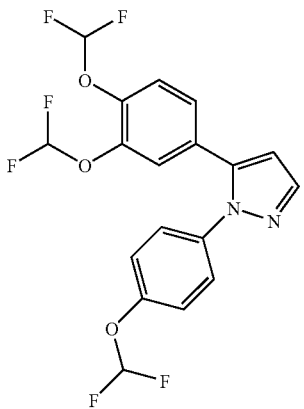
90) 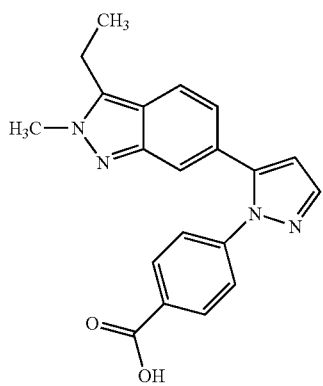
91) 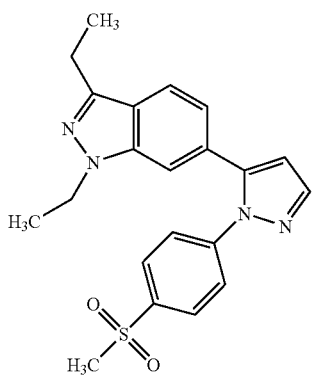
92) 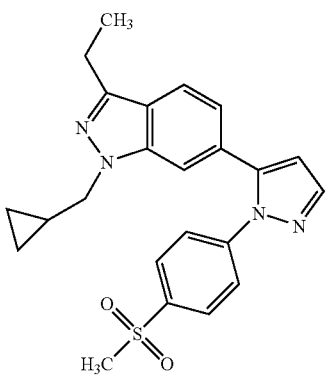
-continued
93) 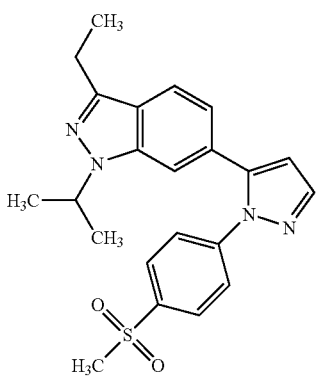
94) 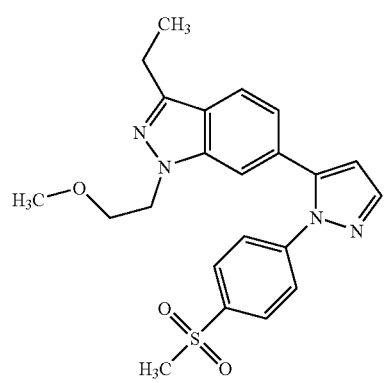
95) 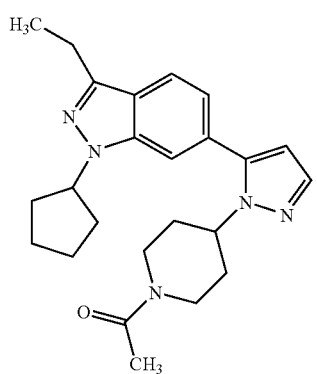
96) 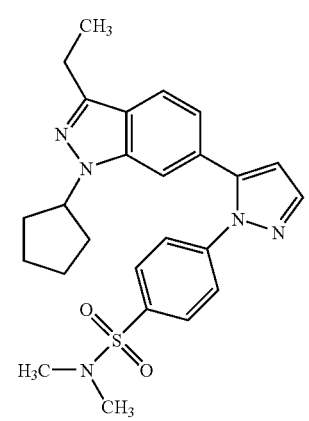

97) 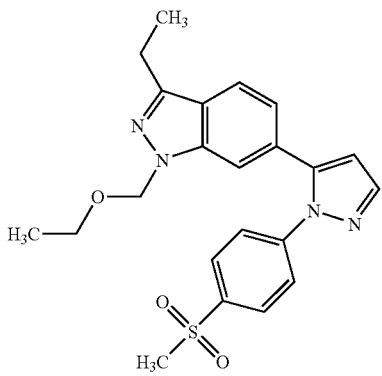
98) 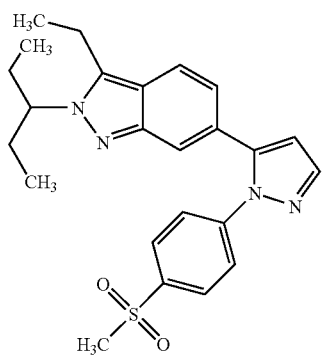
99) 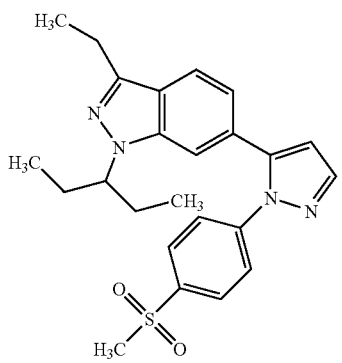
100) 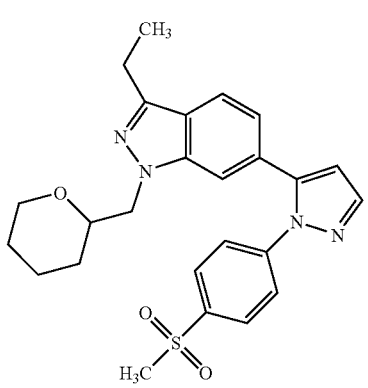
101) 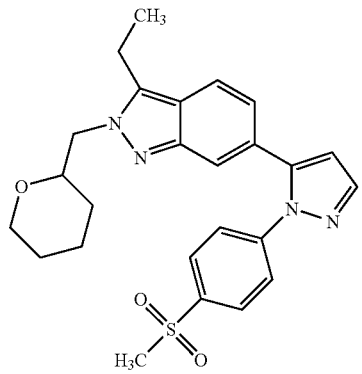
102) 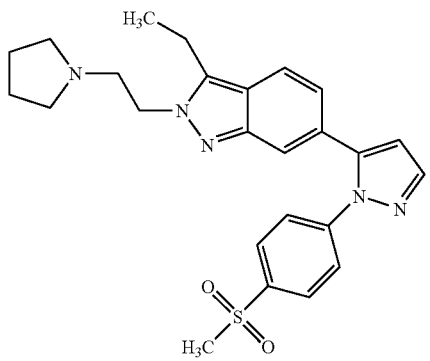
103) 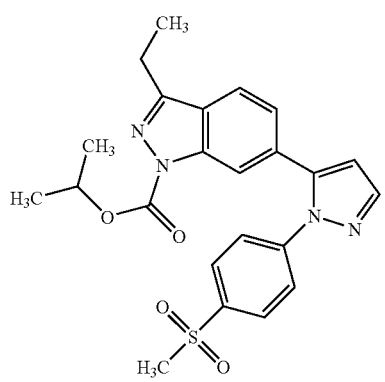
104) 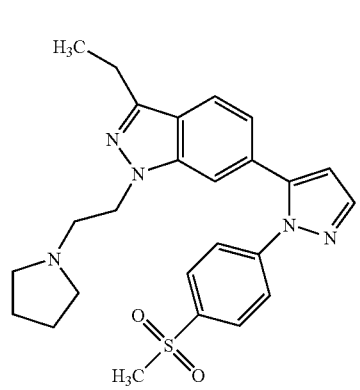

-continued
105) 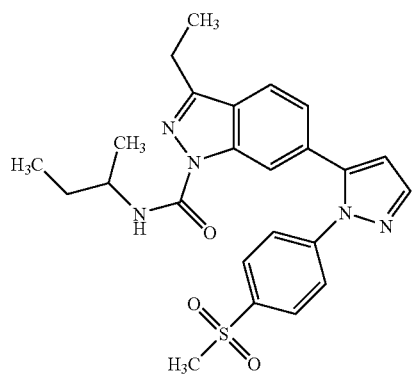
106) 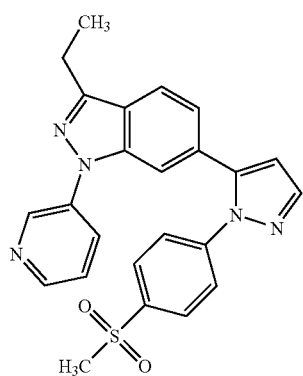
107) 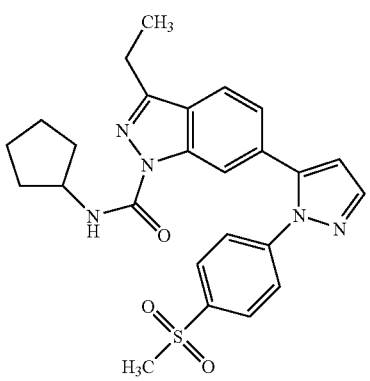
108) 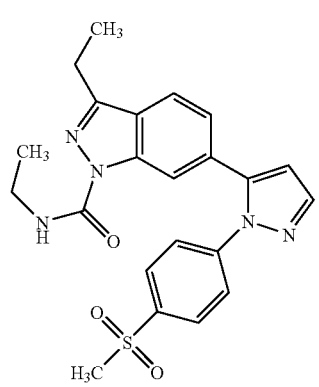
-continued
109) 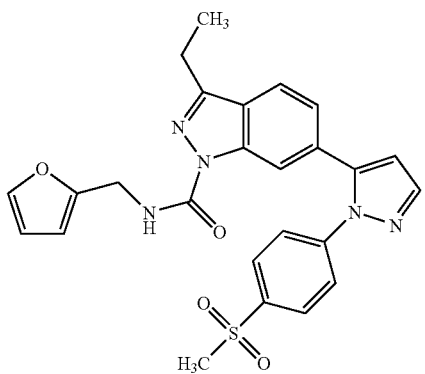
110) 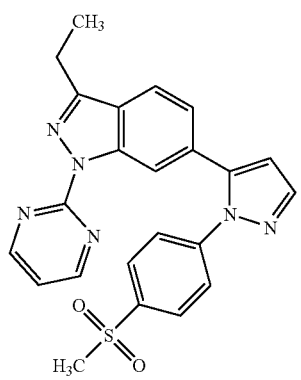
111) 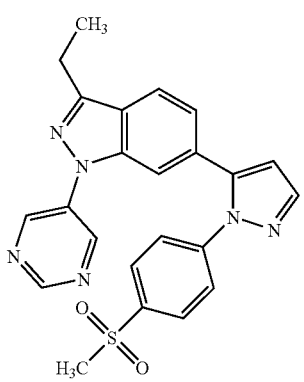
112) 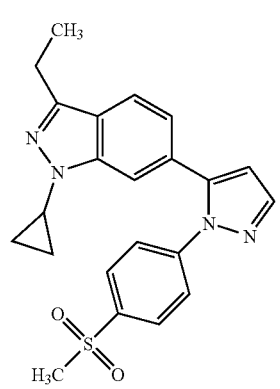

-continued
113) 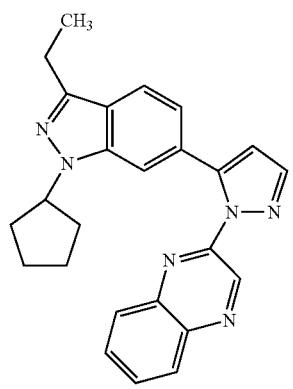
114) 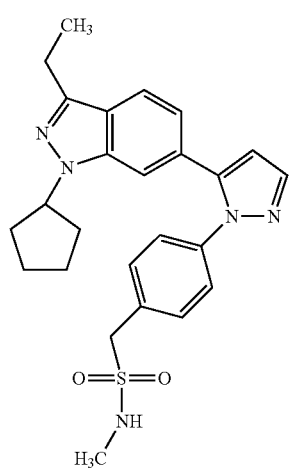
115) 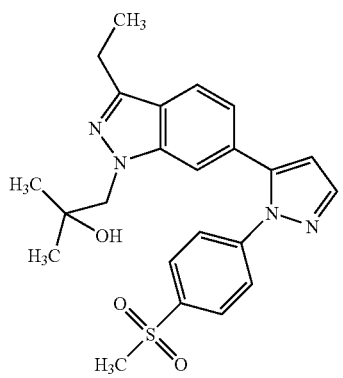
116) 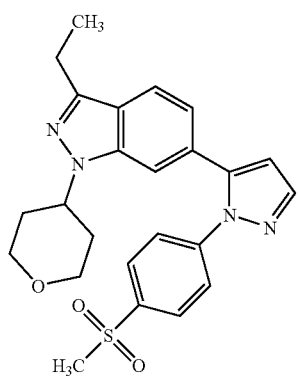
-continued
117) 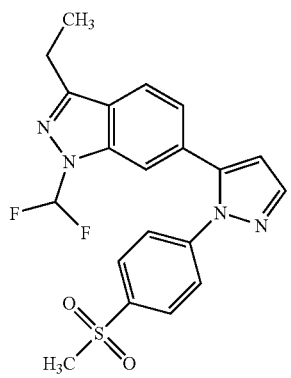
118) 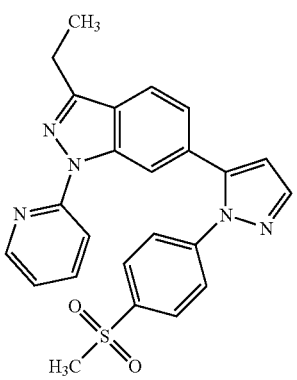
119) 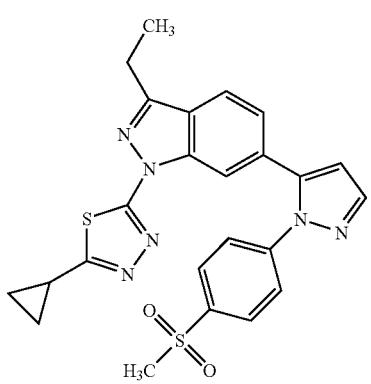
120) 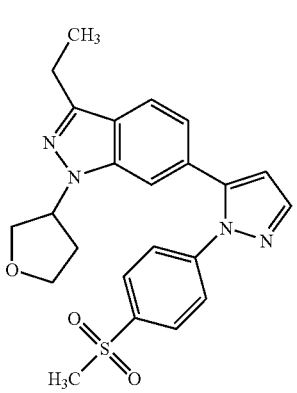

121) 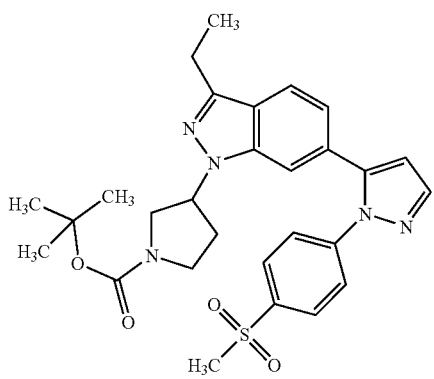
122) 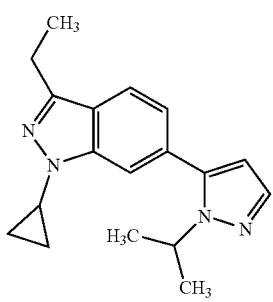
123) 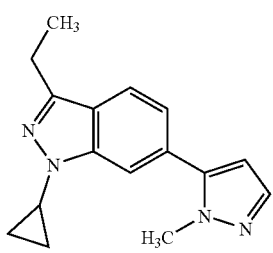
124) 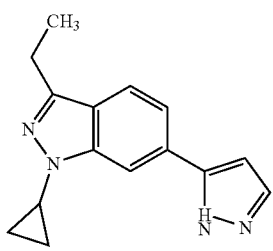
125) 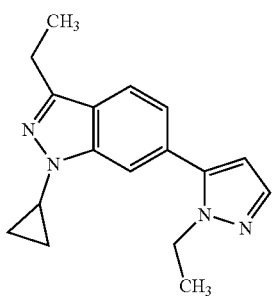
126) 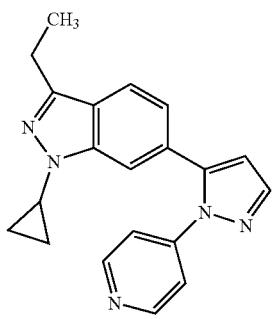
127) 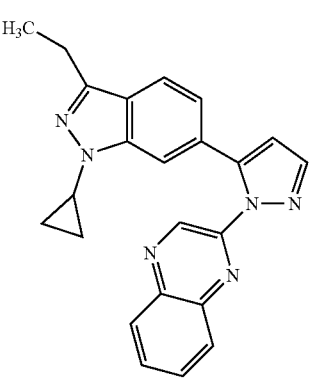
128) 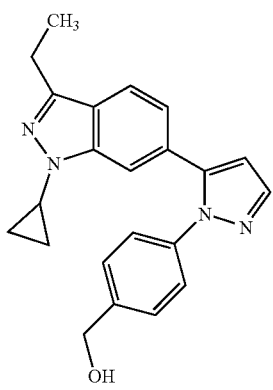
129) 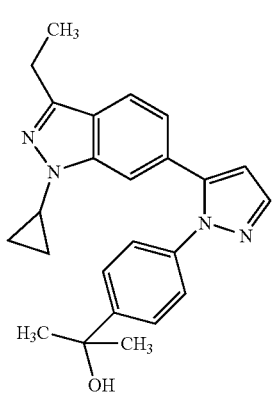

-continued
130) 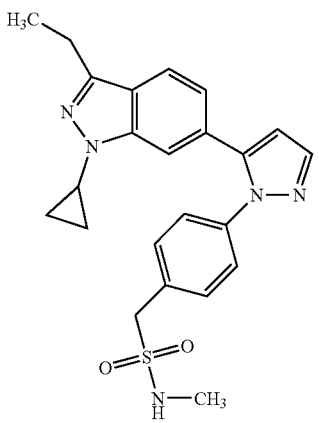
131) 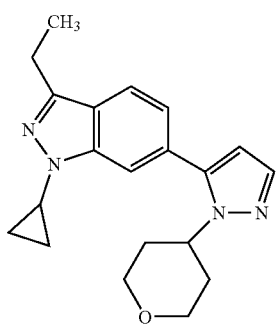
132) 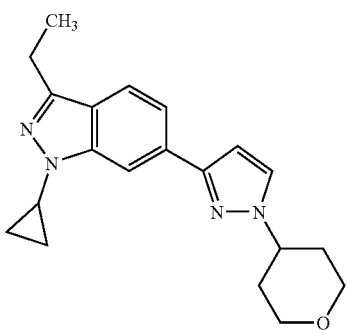
133) 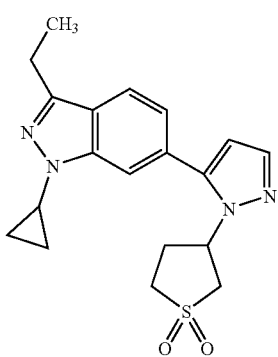
-continued
134) 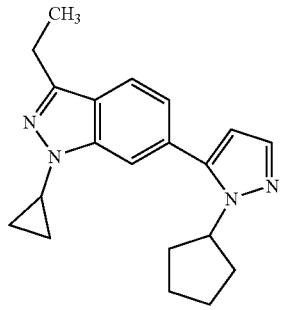
135) 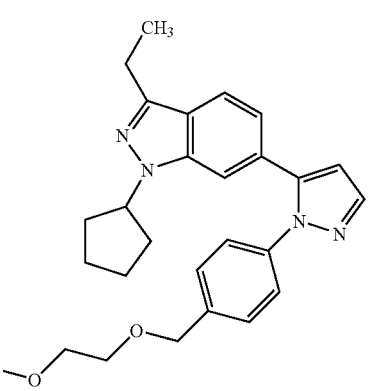
136) 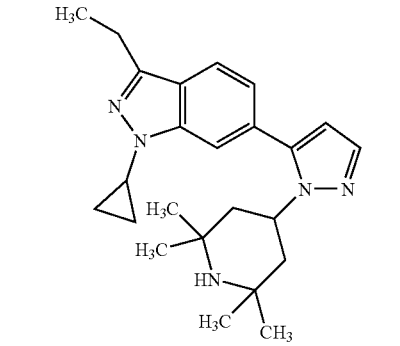
137) 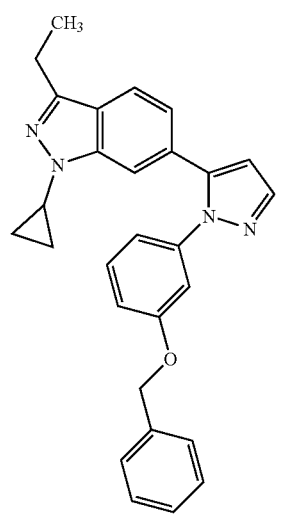

-continued
138) 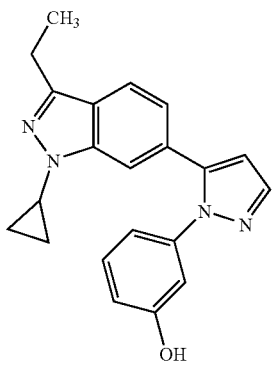
139) 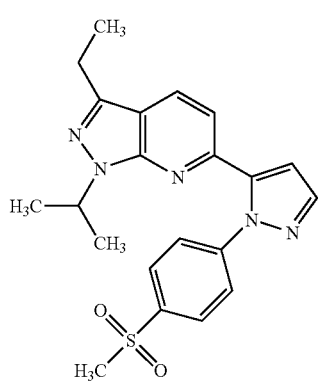
140) 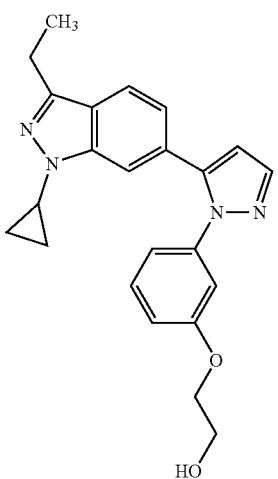
141) 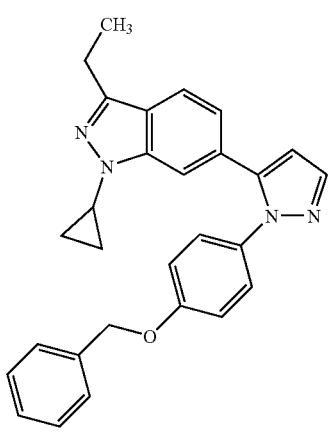
-continued
142) 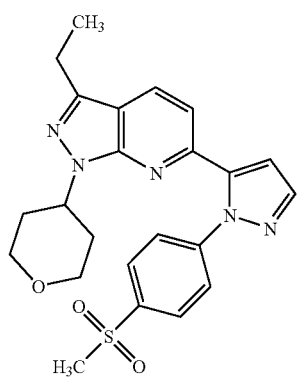
143) 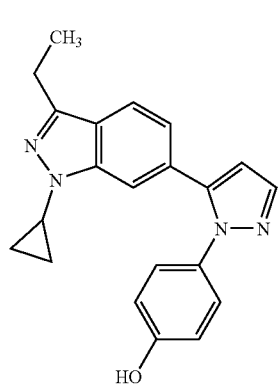
144) 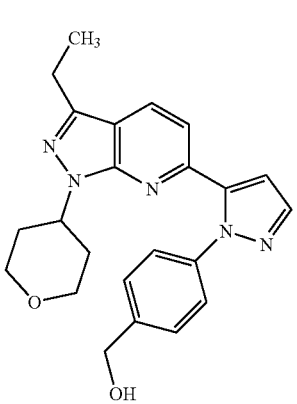
145) 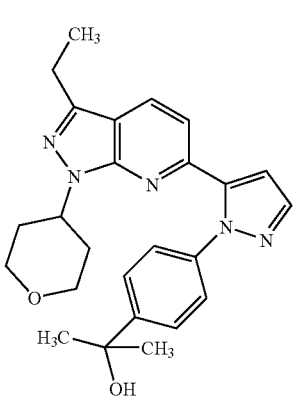

146) 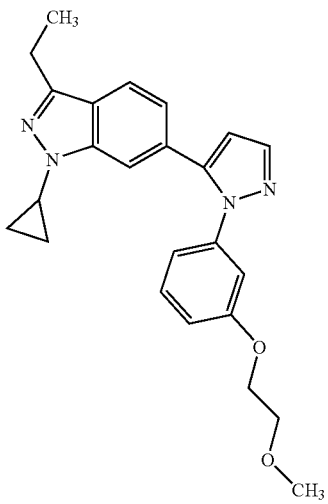
147) 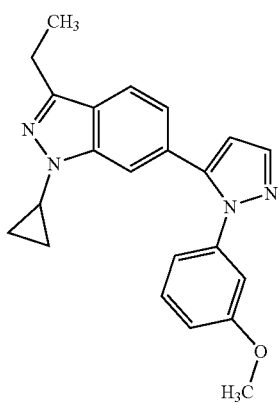
148) 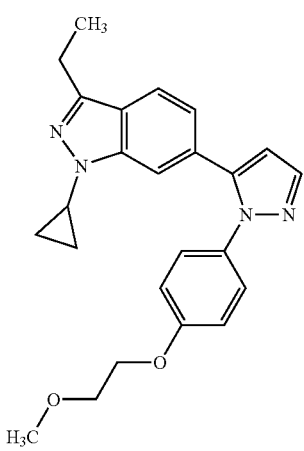
149) 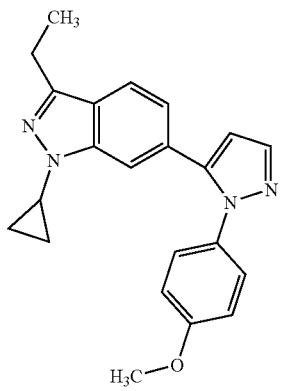
150) 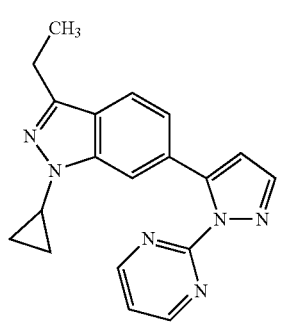
151) 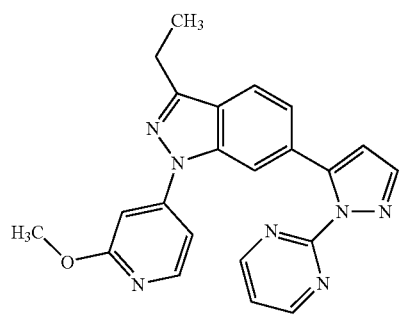
152) 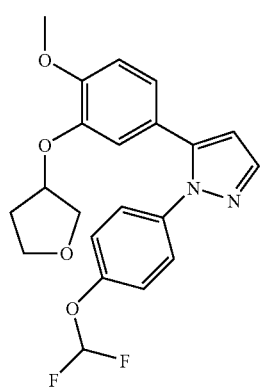

-continued
153) 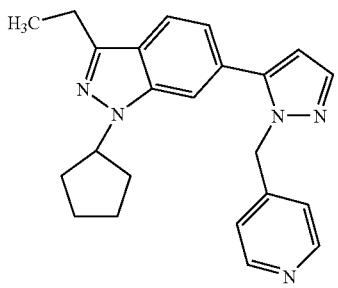
154) 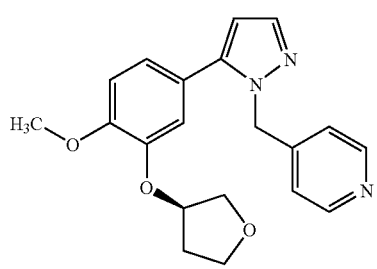
155) 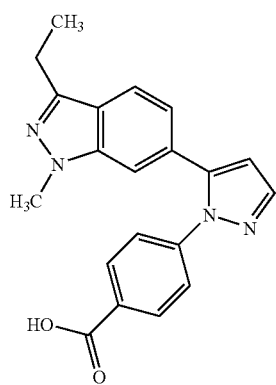
156) 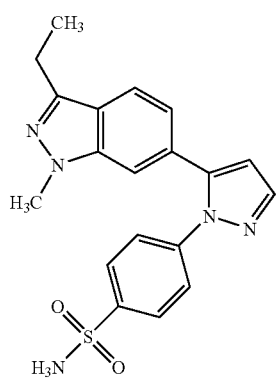
-continued
157) 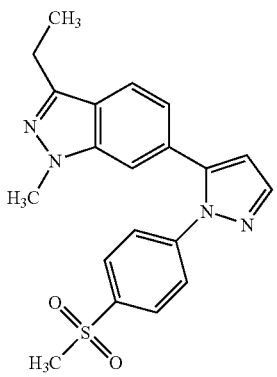
158) 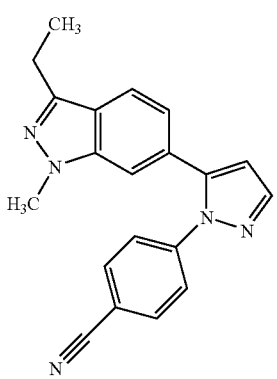
159) 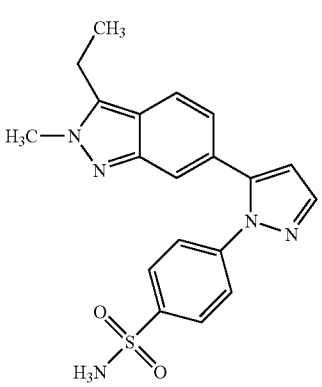
160) 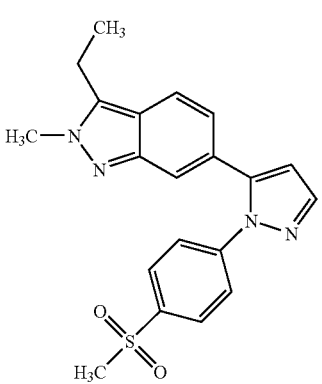

-continued
161) 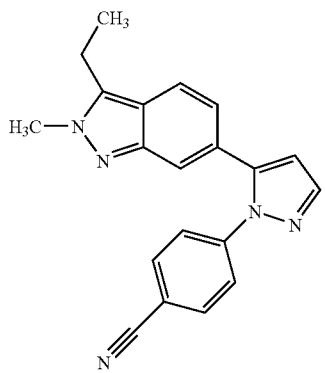
162) 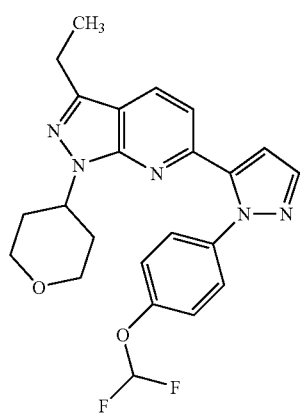
163) 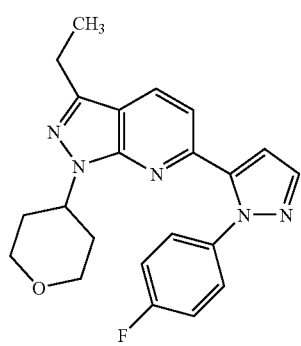
164) 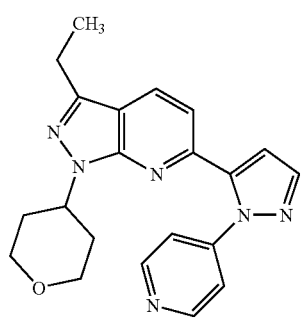
-continued
165) 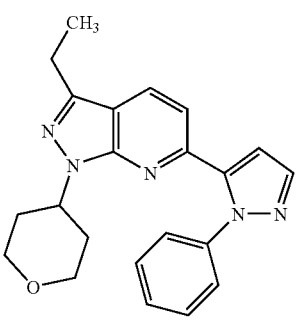
166) 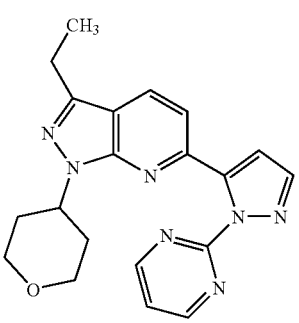
167) 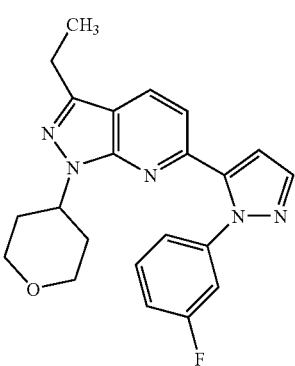
168) 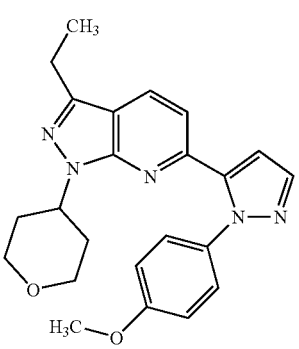

| 169) | 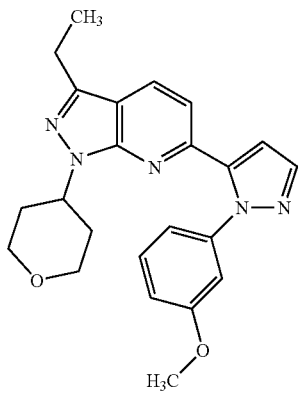 | 172) | 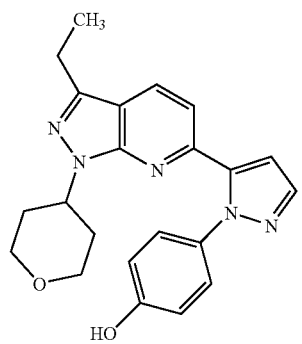 |
| 170) | 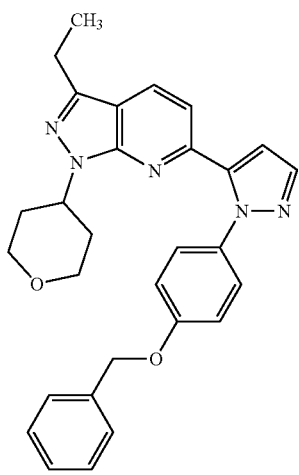 | 173) | 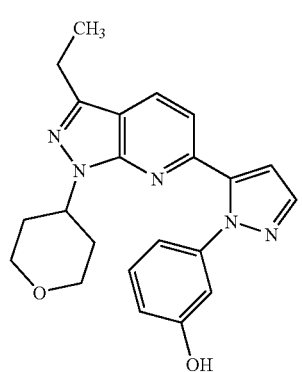 |
|  |  | 174) | 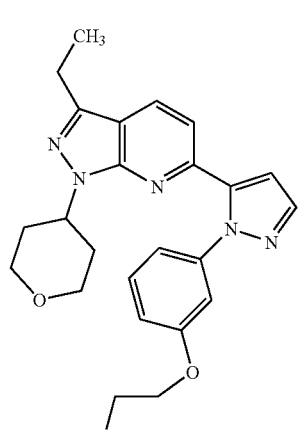 |
| 171) | 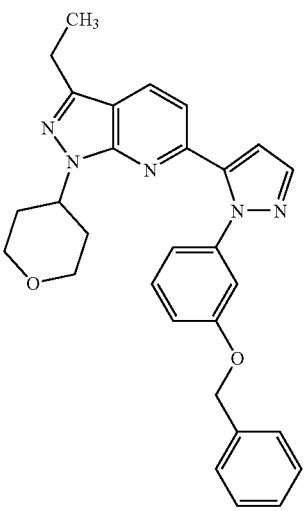 | 175) | 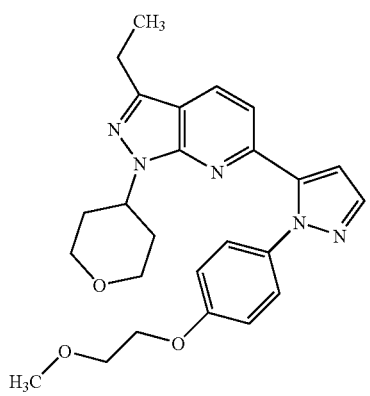 |

176)

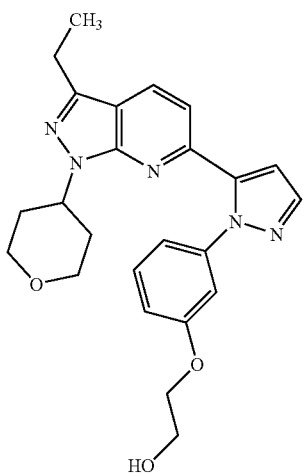

177)

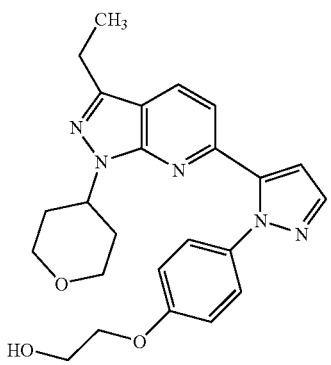

Preferred aspects include pharmaceutical compositions comprising a compound of this invention and a pharmaceutically acceptable carrier and, optionally, another active agent as discussed below. A further preferred aspect includes a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating a psychiatric or neurological syndrome, e.g., depression and loss of memory, especially major depression and long-term memory, cognitive impairment or decline, memory impairment, etc.; a method of treating a disease state modulated by PDE4 activity, in a mammal, e.g., a human, e.g., those disease states mentioned herein.

Methods of the invention include, but are not limited to, methods of enhancing cognition in a patient in whom such enhancement is desired, methods of treating a patient suffering from cognition impairment or decline, methods of treating a patient having a disease involving decreased cAMP levels, methods of inhibiting PDE4 enzyme activity in a patient, methods of treating a patient suffering from memory impairment due to neurodegenerative disease, methods of treating a patient suffering from depression, methods of treating a patient suffering from an allergic or inflammatory disease. All methods comprise administering to the patient an effective amount of a compound of the invention. Preferably, the patient is human.

The compounds of the present invention may be prepared conventionally. Some of the known processes that can be used are described below. All starting materials are known or can be conventionally prepared from known starting materials.

Preparation of starting materials:

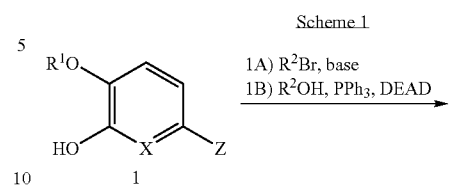

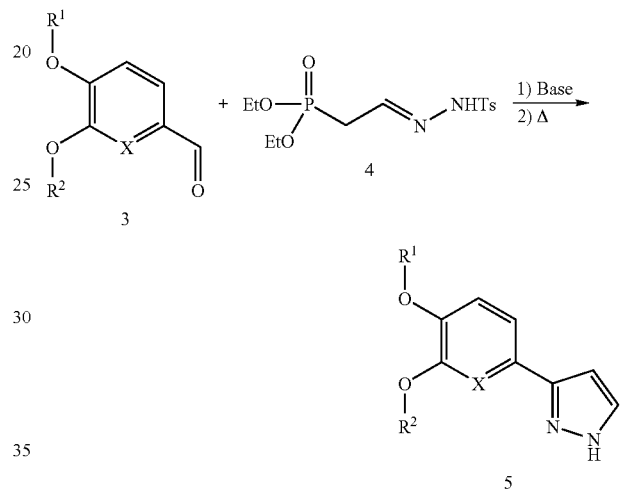

The starting materials for Formulas I and IV are prepared as shown in Scheme 1. Thus, appropriately substituted benzaldehydes 3 (X=CH, N) are subjected to Horner-Wadsworth-Emmons conditions with phosphonate 2. The resulting olefin is not isolated, but heated to induce cyclization [Almirante, N.; Cerri, A.; Fedrizzi, G.; Marazzi, G.; Santagostino, M. *Tetrahedron Lett.*, 1998, 39, 3287-3290] to provide the corresponding pyrazoles 5.

Alternatively, 3-substituted pyrazoles can be made from beta-ketoaldehydes and hydrazine [Murray, W.; Wachter, M.; Barton, D.; Forenro-Kelly, Y. *Synthesis*, 1991, 18] or from various palladium couplings using a pyrazole aptly substituted in the 3 position, for example with a bromine or a boron. [Cacchi, S.;. Fabrizi, G.; Carnaio, A. *Syn. Lett.* 1997, 959-961].

Substitution on the pyrazole nitrogen is accomplished by treatment of the pyrazole 5 with an appropriate base such as NaH, LDA or $K_2CO_3$ in a polar aprotic solvent. This is followed by the addition of electrophile $R^3$-L-X', where X' is a suitable leaving group such as a halogen or sulfonate (Cl, Br, methanesulfonyl, etc.). A mixture of substituted pyrazoles 6a and 6b are obtained with the major isomer being the 1,3-disubstituted pyrazoles (6a). These isomers can be separated by HPLC.

Scheme 2

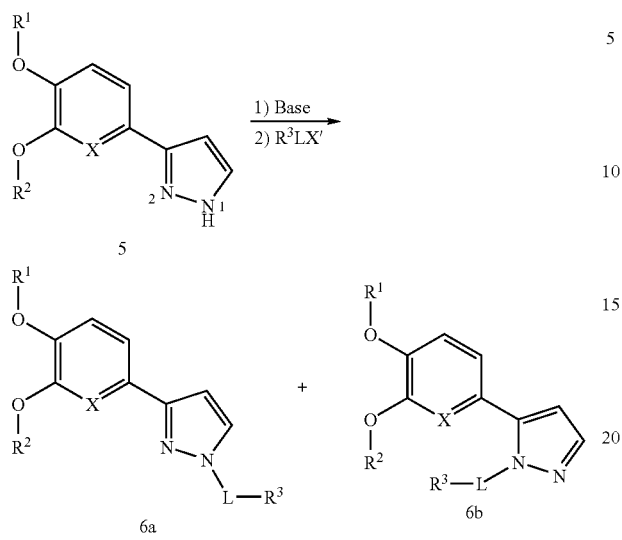

Reaction of pyrazole 5 with alkyl bromoacetate (preferably t-butyl bromoacetate) gives pyrazole substituted acetate esters. These esters are saponified to acetic acid derivatives 6a and 6b (L=CH$_2$CO, R$^3$=H) by treatment with either an acid, such as trifluoroacetic acid, or use of a base, such as sodium hydroxide. Treatment of the resultant acetic acid products with thionyl chloride or oxalyl chloride generates the corresponding acid chloride. Subsequent reaction with a nucleophile such as an amine (e.g., aniline) gives the acetamide derivatives 6a and 6b (e.g., L=CH$_2$CONH, R$^3$=phenyl). Similarly, the acetic acid derivative (L=CH$_2$CO$_2$, R$_3$=H) can be treated with HBTU or a suitable coupling reagent (i.e., DCC, HOBT, etc) and an amine compound to give the desired acetamide analogues 6a and 6b.

Alternatively, (Scheme 3) compounds of the type 6a where R$^2$=arylalkyl, alkyl, cycloalkyl, heteroalkyl, cycloalkylalkyl, heterocyclic or heterocyclic-alkyl groups can be prepared by either Mitsunobu reaction between phenol 7b and an appropriate alcohol (R$^2$OH) or alkylation with a suitable electrophile, R$^2$—X' (X' is a suitable leaving group such as a halogen or sulfonate (Cl, Br, methanesulfonyl etc.)), and an appropriate base (i.e., K$_2$CO$_3$, NaH, NaOH). (R$^2$=arylalkyl, alkyl, cycloalkyl, heteroalkyl, cycloalkylalkyl, heterocyclic and heterocyclic-alkyl groups.)

3-Aryloxy 3-heteroaryloxy pyrazole derivatives of the type 6a (i.e., where R$^2$ is aryl or heteroaryl) are prepared by cross coupling reaction of phenol 7b with aryl boronic acids using a copper catalyst in the presence of an amine base. Suitable copper catalysts include copper diacetate, copper (II) chloride, etc. Generally, halogenated solvents are utilized, such as chloroform, dichloromethane, 1,2-dichloroethane, and the like. Commonly used bases include triethylamine, diisopropylethylamine, and pyrrolidine. Alternatively, 3-aryloxy and 3-heteroaryloxy pyrazole compounds can be synthesized in an analogous method as described previously for 3-phenyloxyrolipram, which utilizes an Ullman type coupling reaction starting with iodobenzene and 3-hydroxyrolipram [Schmiechen, R. et al., U.S. Pat. No. 4,193,926]. The other regioisomer 6b may be formed in an analogous manner.

Scheme 3

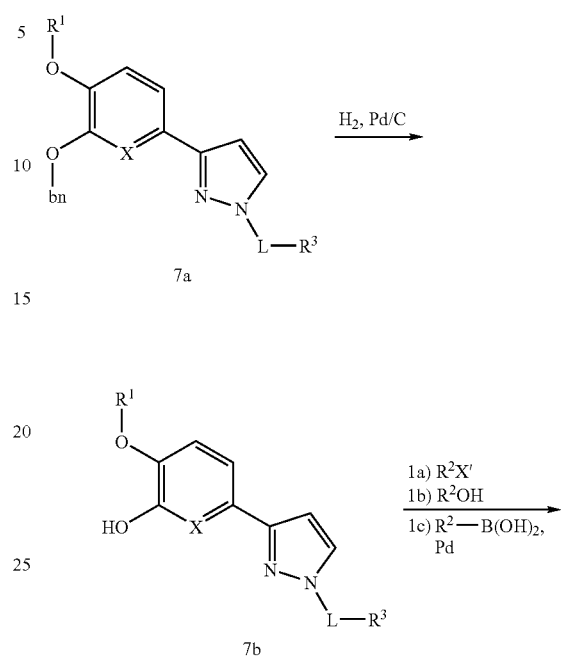

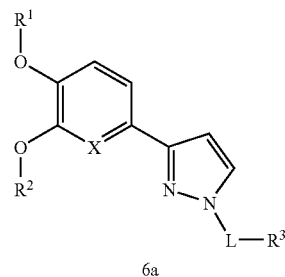

Compounds of Formulas II and V are synthesized in a similar manner starting from aldehyde 8. For these reactions, the ketone should be protected before pyrazole formation and can be deprotected afterwards. Suitable protecting groups include, but are not limited to, ketals and cyclic ketals.

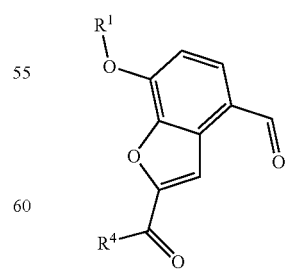

Compounds of Formulas III and VI are synthesized in a similar manner starting from aldehyde 9. [Marfat, A., et al., U.S. Pat. No. 6,262,040.]

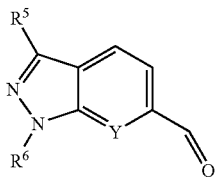

9

Synthesis of 1,5-pyrazoles

A. Cross-Coupling Reactions

Alternatively, the 1,5-disubstituted compounds of Formula IV through VII can be prepared from 1-hydroxypyrazole 10 (Scheme 4) (Eskildsen, J., Vedso, P., Begtrup, M., *Synthesis*, 2001, 1053-1056. Eskildsen, J., Kristensen, J., Vedso, P., Begtrup, M., *J. Org. Chem.*, 2001, 66, 8654-8656. Paulson, A. S., Eskildsen J., Vedso, P., Begtrup, M., *J. Org. Chem.*, 2002, 67, 3904-3907). Thus, warning a solution of 1-hydroxypyrazole 10 with an electrophile such as a benzyl bromide or α-bromoacetate in CHCl$_3$ to 60 to 100° C. provides 2-substituted-pyrazol-1-oxides 11. Subsequent treatment with POCl$_3$ or POBr$_3$ in a halogenated solvent such as CHCl$_3$ yields 5-halo-1-substituted pyrazoles 12. Such 5-halo-1-substituted pyrazoles can undergo cross-coupling type reaction with aryl boronic acids 2 (Z=B(OH)$_2$) or can be metalated (e.g., halogen-magnesium exchange, transmetalation with ZnCl$_2$) for a Negishi-type reaction with an aryl halide 2 (Z=halogen).

Scheme 4

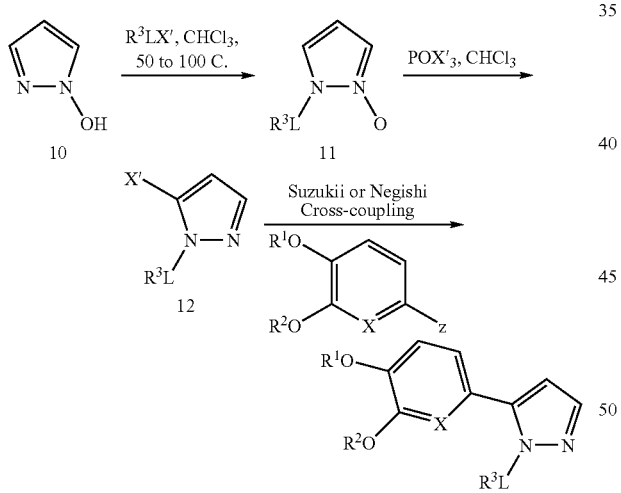

Alternatively, 1,5-disubstituted pyrazoles 6b can be prepared from 2-aryldithianes 13 in a three step synthesis. Thus, dithiane intermediate 13 can be prepared by reaction of aldehyde 3 with propane dithiol and a Lewis acid catalyst such as BF$_3$-Et$_2$O in an aprotic solvent (Hatch, R.P., Shringarpure, J., Weinreb, S. M., *J. Org. Chem.*, 1978, 43, 4172-4177). Subsequent reaction of the alkyl lithium produced dithiane anion with appropriately substituted epoxides provides-2,2-disubstituted dithianes 14. Oxidation of alcohol 14 to the protected β-keto dithiane followed by treatment with an appropriately substituted hydrazine salt provides 1,5-disubstituted pyrazoles 6b.

Scheme 5

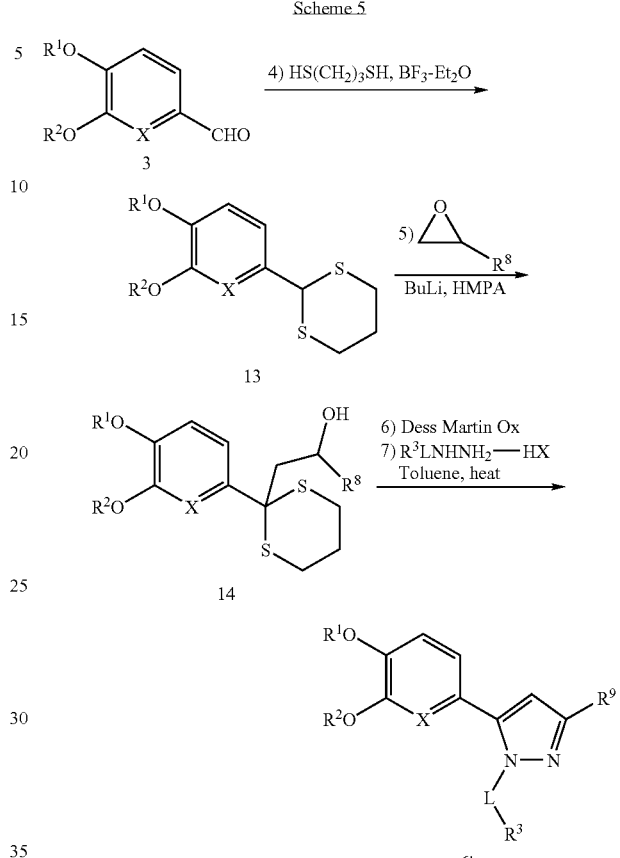

Another method to prepare 1,5-disubstituted pyrazoles of type 6b is through condensation reaction between 1,3-diketo derivative 16 and a substituted hydrazine (Nakamura, Toshio, et al., *J. Med Chem*, 2003, 46, 5416; Penning, T. D., et al, *J. Med. Chem.*, 1997, 40, 1347-1365.) The selectivity of this reaction for 1,5 versus 1,3-disubstituted pyrazoles varies pending the substitution at $R^8$. Formation of the 1,5-disubstituted pyrazoles are favored when $R^8$ is an electron withdrawing group such as carboxylate or trifluoromethyl, or a small group such as hydrogen. Starting 1,3-diketo derivatives 16 are prepared from acetophenone derivatives 15 by reaction with sodium hydride and an appropriately substituted ethyl acetate.

Scheme 6

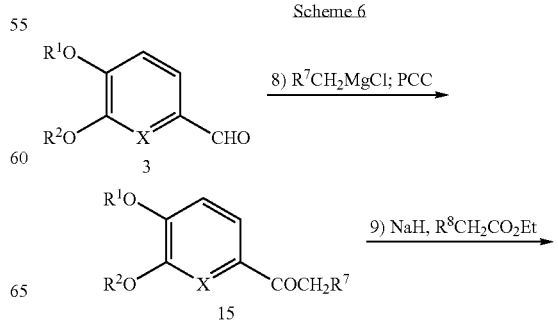

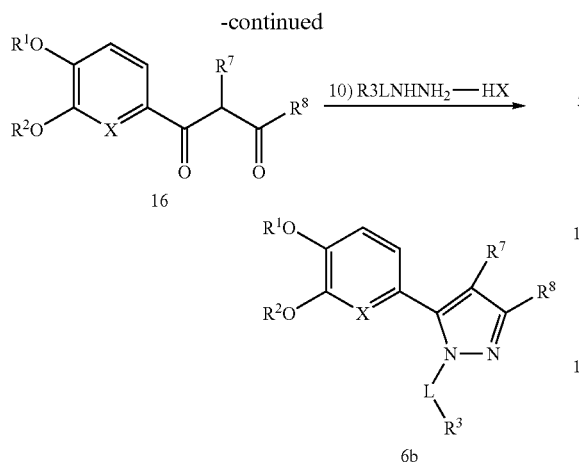

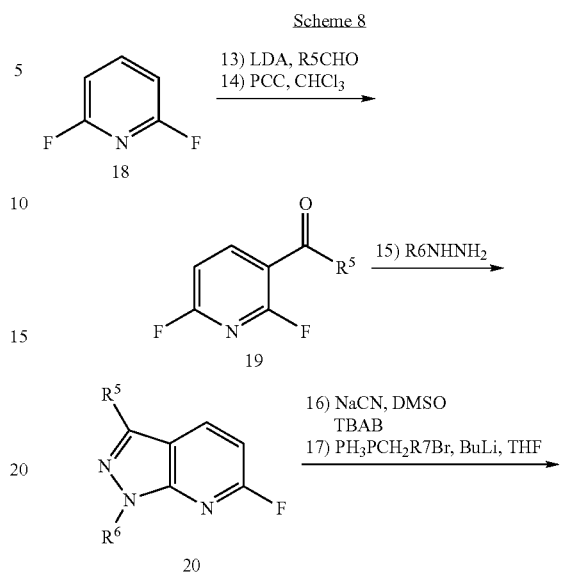

In a similar fashion, enamines of the type 17 undergo reaction with appropriately substituted hydrazines to provide target pyrazoles 6b (Yang, Ji, et al., *J. Med. Chem.* 2004, 47(6), 1547).

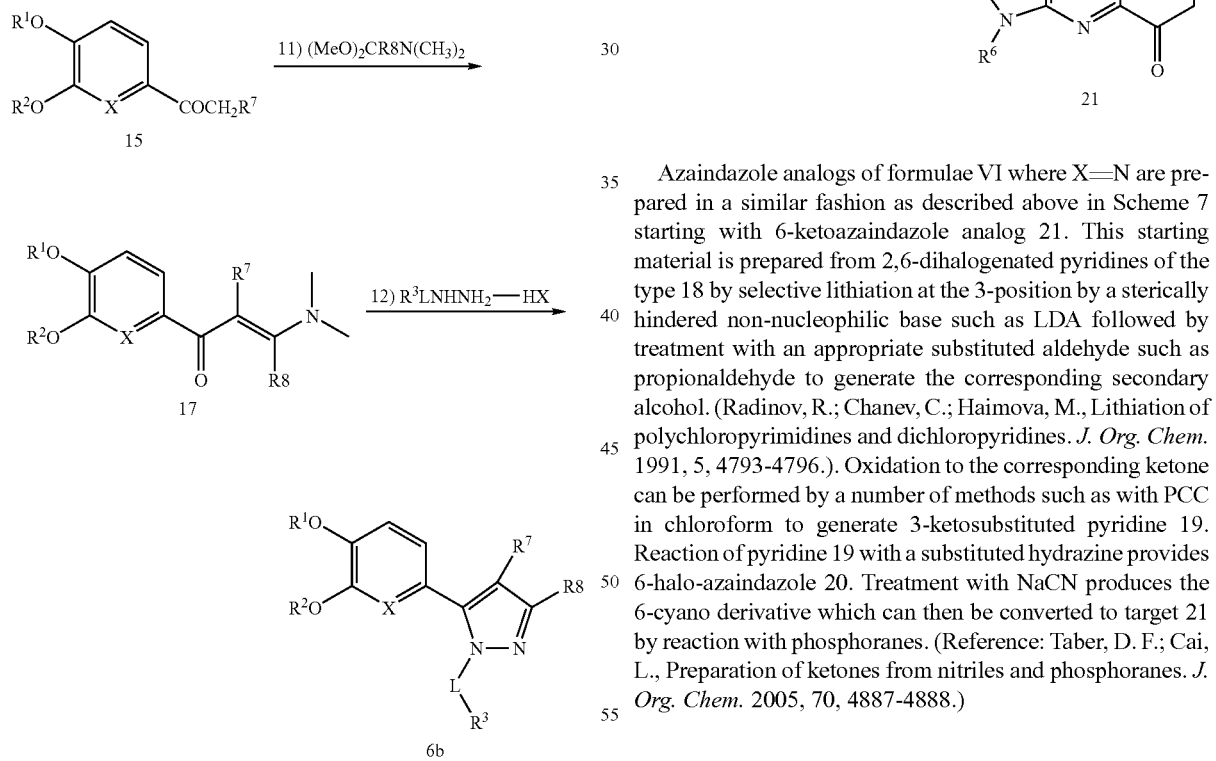

Compounds of Formula VIII can also be prepared using the general procedure described above.

Subsequent reaction with the appropriately substituted isocyanates in halogenated solvents provides the desired carbamates. Compounds of formulas I-VIII where L is $CH_2CH_2OCONHR^3$ can be prepared by the reaction of hydroxyethyl hydrazine with an enamine of the type 17 to form the ethanol derivative 6b (L=$CH_2CH_2OH$).

Azaindazole analogs of formulae VI where X=N are prepared in a similar fashion as described above in Scheme 7 starting with 6-ketoazaindazole analog 21. This starting material is prepared from 2,6-dihalogenated pyridines of the type 18 by selective lithiation at the 3-position by a sterically hindered non-nucleophilic base such as LDA followed by treatment with an appropriate substituted aldehyde such as propionaldehyde to generate the corresponding secondary alcohol. (Radinov, R.; Chanev, C.; Haimova, M., Lithiation of polychloropyrimidines and dichloropyridines. *J. Org. Chem.* 1991, 5, 4793-4796.). Oxidation to the corresponding ketone can be performed by a number of methods such as with PCC in chloroform to generate 3-ketosubstituted pyridine 19. Reaction of pyridine 19 with a substituted hydrazine provides 6-halo-azaindazole 20. Treatment with NaCN produces the 6-cyano derivative which can then be converted to target 21 by reaction with phosphoranes. (Reference: Taber, D. F.; Cai, L., Preparation of ketones from nitriles and phosphoranes. *J. Org. Chem.* 2005, 70, 4887-4888.)

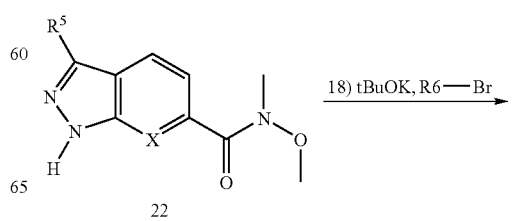

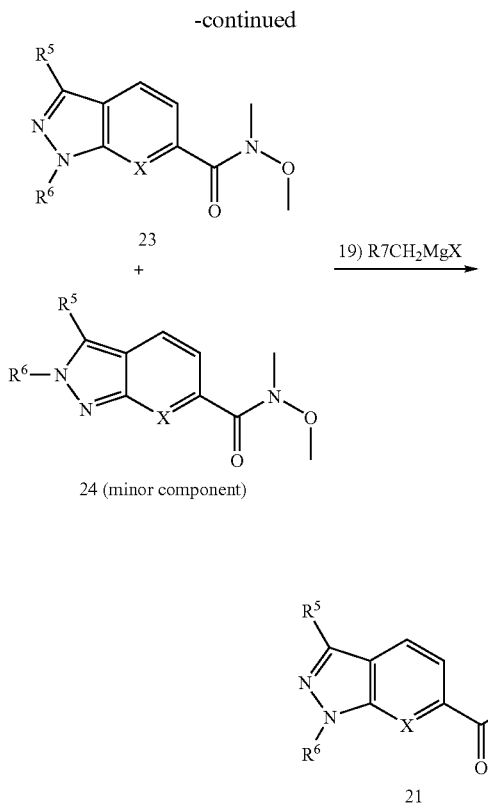

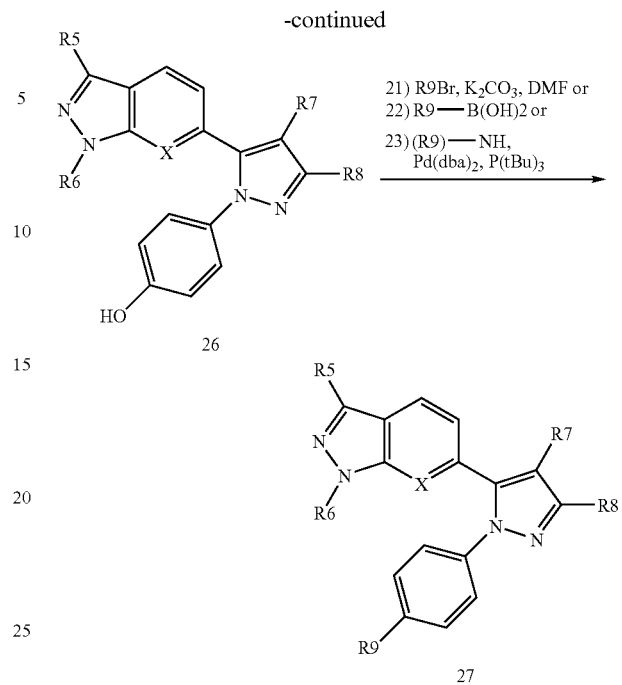

Alternatively, target compounds of formula VI or IX can be prepared from 6-keto-indazole intermediates of the type 21 or 24 as described in Scheme 7. Thus, Weinreb amide analog 22 is prepared by conventional methods from the previously described carboxylic acid. Treatment of 22 with a strong base such as potassium tert-butoxide followed by addition of a suitable $R^6$-bromide provides primarily 1-substituted indazoles 23 with minor amounts of the 2-substituted analogs 24. Treatment of the Weinreb amide analog 23 with a Grignard reagent provides key intermediate 21.

Scheme 10

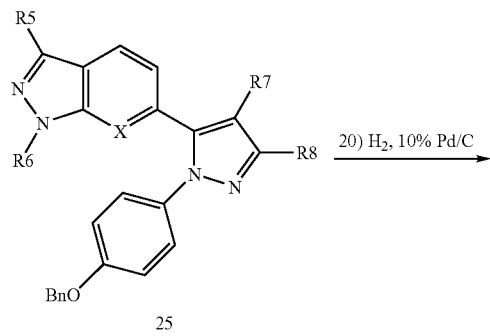

In addition, a variety of ethers can be synthesized by alkylation of phenolic analogs 26 by reaction with various alkyl bromides to provide targets 27. In addition these phenols can be functionalized by Mitsunobu reaction with an appropriate alcohol to provide compounds where $R^9$=OAlkyl. Still further, reaction with trifluoromethylsulfonyl chloride provides the triflate ($R^9$=$CF_3SO_3$—) which can readily undergo Suzuki type reactions with boronic acids or Buchwald reactions with amines to generate biaryls (R9=aryl or heteroaryl) and amino substituted compounds ($R^9$=$N(R)_2$) respectively.

One of ordinary skill in the art will recognize that some of the compounds of Formulas I, II, III, IV, V, VI, VII, VIII, IX and X can exist in different geometrical isomeric forms. In addition, some of the compounds of the present invention possess one or more asymmetric atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereomeric salts using an optically active acid or base or formation of covalent diastereomers.

Examples of appropriate acids are tartaric, diacetyltartaric, dibenzoyltartaric, ditoluoyltartaric and camphorsulfonic acid. Mixtures of diastereomers can be separated into their individual diastereomers on the basis of their physical and/or chemical differences by methods known to those skilled in the art, for example, by chromatography or fractional crystallization. The optically active bases or acids are then liberated from the separated diastereomeric salts.

A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., as Chiracel OD and Chiracel OJ among many others, all routinely selectable. Enzymatic separations, with or without derivitization, are also useful. The optically active compounds of Formulas I-X can likewise be obtained by utilizing optically active starting materials in chiral syntheses processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The Synthesis of Radiolabeled Compounds via Organometallic Intermediates. Tetrahedron (1989), 45(21), 6601-21, CODEN: TETRAB ISSN: 0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

The present invention also relates to useful forms of the compounds as disclosed herein, such as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, a hydroformate, hydrobromide, or a maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of Formulas I-X can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formulas I-X can exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates.

The compounds of the invention can be administered alone or as an active ingredient of a formulation. Thus, the present invention also includes pharmaceutical compositions of one or more compounds of Formulas I, II, III, IV, V, VI, VII, VIII, IX and X containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of selective PDE4 inhibition, the compounds of the present invention can be administered to anyone requiring PDE4 inhibition. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable, propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, ampakines, NMDA-R modulators, mGluR modulators, and cholinesterase inhibitors (e.g., donepezil, rivastigimine, and galanthamine). In such combinations, each active ingredient can be administered either in accordance with their usual dosage range or a dose below their usual dosage range.

The present invention further includes methods of treatment that involve inhibition of PDE4 enzymes. Thus, the present invention includes methods of selective inhibition of PDE4 enzymes in patients, such as animals, e.g., mammals, especially humans, wherein such inhibition has a therapeutic effect, such as where such inhibition may relieve conditions involving neurological syndromes, such as the loss of memory, especially long-term memory. Such methods comprise administering to a patient in need thereof, such as an animal, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (Alzheimer's, Parkinson's disease, Pick's disease), vascular (Infarcts, Hemorrhage, Cardiac Disorders), mixed vascular and Alzheimer's, bacterial meningitis, Creutzfeld-Jacob Disease, multiple sclerosis, traumatic (subdural hematoma or traumatic brain injury), infectious (HIV), toxic (heavy metals, alcohol, medications), metabolic (Vitamin $B_{12}$ or folate deficiency), CNS hypoxia, Cushing's disease, psychiatric (depression and schizophrenia) and hydrocephalus.

The present invention also includes methods for treating memory loss separate from dementias, including mild cognitive impairment (MCI) and age-related cognitive decline. The present invention includes methods of treatment for memory impairment as a result of disease including Huntington's disease and Down's syndrome. According to another aspect, the invention includes methods for treating memory loss from anesthetics, chemotherapy, radiation treatment, post-surgical trauma, post-traumatic stress disorder (PTSD), obesity, and diabetes.

The compounds of the invention can also be used to treat schizophrenia, bipolar or manic depression, major depression, and drug addiction. PDE4 inhibitors can be used to raise cAMP levels and prevent neurons from undergoing apoptosis. PDE4 inhibitors are also known to be anti-inflammatory. The combination of preventing neuronal apoptosis and inhibiting inflammatory responses make these compounds useful to treat neurodegeneration resulting from any disease or injury, including stroke, Alzheimer's disease, multiple sclerosis, amyolaterosclerosis (ALS), and multiple systems atrophy (MSA), as well as spinal injury.

PDE4 inhibitors have been shown to produce antidepressant effects in humans and antidepressant-like effects in animal models of depression. Clinical studies in humans suffering from major depression have demonstrated efficacy of the PDE4 inhibitor, rolipram, with comparable results in some of these studies to those of desipramine [Bobon D, Breulet M, Gerard-Vandenhove M A, Guito-Goffioul F, Plomteux G, Satre-Heinandez M, Schratzer M, Troisfontaines B, von Frenckell R, Wachtel H (1988) Is Phosphodiesterase Inhibition a New Mechanism of Antidepressant Action? *Eur Arch Psychiatr Neurol Sci.,* 238:2-6; Meya U, Wachtel H, Sastre-Hernandez M (1991) inhibition of Phosphodiesterase as an Antidepressive Mechanism: Clinical Properties of Rolipram. In Ansseau M, von Frenckell, Franck G (eds) *Biological Markers of Depression: State of the art*, Elsevier Science Publishers B. V., Pp: 209-213; Zhu J, Mix E, Winblad B (2001) The Antidepressant and Anti-inflammatory Effects of Rolipram in the Central Nervous System. *CNS Drug Reviews,* 7:387-398]. Rolipram was active in a number of biochemical and behavioral preclinical models of antidepressant activity [Wachtel H (1983) Potential Antidepressant Activity of Rolipram and other Selective Cyclic Adenosine 3',5'-Monophosphate Phosphodiesterase Inhibitors. *Neuropharmacology,* 22: 267-272; and Wachtel H., Schneider H H (1986) Rolipram, a novel antidepressant drug, reverses the hypothermia and hypokinesia of monoamine-depleted mice by an action beyond postsynaptic monoamine receptors. *Neuropharmacology,* 25:1119-1126]. More recently, studies with rolipram have demonstrated efficacy of this compound in the tail suspension and forced swimming models of antidepressant activity; these effects were eliminated in animals transgenically modified to lack the PDE4D subtype suggesting that the antidepressant effects of rolipram are mediated by its inhibition of the PDE4 enzyme, specifically the PDE4D subtype [Zhang H-T, Huang Y, Jin S-L, Frith S A, Suvarna N, Conti M, O'Donnell J M (2002) Antidepressant-like Profile and Reduced Sensitivity to Rolipram in Mice Deficient in the PDE4D Phosphodiesterase Enzyme, *Neuropsychopharmacology*, 27:587-595].

Thus, in accordance with a preferred embodiment, the present invention includes methods of treating patients suffering from memory impairment due to, for example, mild cognitive impairment due to aging, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions, as well as HIV and cardiovascular diseases, comprising administering an effective amount of a compound according to Formulas I, II, III, IV, V, VI, VII, VIII, IX and X or a pharmaceutically acceptable salt or solvate (e.g., hydrate) thereof, or a solvate of a pharmaceutically acceptable salt thereof.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to Formulas I, I, III, IV, V, VI, VII, VIII, IX and X or a pharmaceutically acceptable salt or solvate (e.g., hydrate) thereof, or a solvate of a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, emphysema, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases, osteoporosis, and the like. The compounds can also be used in a method of treating patients suffering from disease states characterized by decreased NMDA function, such as schizophrenia. The compounds may also be used for neuronal regeneration. The compounds can also be used to treat psychosis characterized by elevated levels of PDE4, for example, various forms of depression, such as manic depression, major depression, and depression associated with psychiatric and neurological disorders. The compounds may additionally be used for neurogenesis.

The use of trisubstituted phenyl derivatives for treating asthma, chronic bronchitis, psoriasis, allergic rhinitis, and other inflammatory diseases, and for inhibiting tumor necrosis factor is known within the art. See, e.g., WO 98/58901, JP 11-189577, JP 10-072415, WO 93/25517, WO 94/14742, U.S. Pat. No. 5,814,651, and U.S. Pat. No. 5,935,978. These references describe 1,3,4-trisubstituted phenyl compounds said to exhibit PDE4 inhibition activity. They also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The invention is also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also known as Kennedy disease (androgen receptor).

Thus, in accordance with a further aspect of the invention, there is provided a method of treating a polyglutamine-repeat disease or CAG repeat expansion disease comprising administering to a patient, especially a human, a therapeutically effective amount of a compound according to Formulas I-X or a pharmaceutically acceptable salt or solvate (e.g., hydrate) thereof, or a solvate of a pharmaceutically acceptable salt thereof. In accordance with a further embodiment, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, especially a human, a therapeutically effective amount of a compound according to Formulas I-X or a pharmaceutically acceptable salt or solvate (e.g., hydrate) thereof, or a solvate of a pharmaceutically acceptable salt thereof.

The compounds of the present invention can be administered as the sole active agent or in combination with other pharmaceutical agents such as other agents used in the treatment of cognitive impairment and/or in the treatment of psychosis, e.g., other PDE4 inhibitors, PDE10 inhibitors, calcium channel blockers, chloinergic drugs, adenosine receptor modulators, ampakines, NMDA-R modulators, mGluR modulators, and cholinesterase inhibitors (e.g., donepezil, rivastigimine, and galanthamine). In such combinations, each active ingredient can be administered either in accordance with their usual dosage range or a dose below their usual dosage range.

The compounds of Formulas I-X can be administered as the sole active agent or in combination with other pharmaceutical agents such as other agents used in the treatment of allergic and/or inflammatory conditions, e.g. respiratory conditions. Suitable examples of other pharmaceutical agents which may be used in combination with the compounds of the present invention include, but are not limited to, other PDE-4 inhibitors, 5-lipoxygenase (5-LO) inhibitors or 5-lipoxygenase activating protein (FLAP) antagonists (e.g., zileuton, fenleuton), leukotriene antagonists (LTRAs) including, antagonists of a $LTB_4$, $LTC_4$, $LTD_4$, and $LTE_4$ (e.g., ontazolast, ablukast, pranlukast, verlukast, zarifllukast, montelukast, zileuton), histaminic receptor antagonists, including H1 and H3 antagonists (e.g., cetirizine, loratidine, desloratidine, fexofenadine, astemizole, azelastine, chlorpheniramine, cimetidine, ranitidine, famotidine, nizatidine), $\alpha_1$ and $\alpha_2$ adrenoceptor agonist vasoconstrictor sympathomimetic agents for decongestant use (e.g.; propylhexedrine, phenylephrine, phenylpropanolamine, pseudoephedrine, naphazoline hydrochloride), muscarinic receptor (M1, M2, and M3) antagonists (e.g., ipratropium salts, namely bromide, tiotropium salts, namely bromide, oxitropium salts, namely bromide, perenzepine, and telenzepine), anticholinergic agents, $\beta_1$ to $\beta_4$ (e.g. $\beta_2$) adrenoceptor agonists (e.g., isoprenaline, albuterol, salbutamol, formoterol, salmeterol), COX-1 inhibitors NSAIDs), COX-2 selective inhibitors, nitric oxide NSAIDs, oral or inhaled glucocorticosteroids (e.g., prednisone, prednisolone, flunisolide, triamcinolone acetonide, beclomethasone diproprionate), acetylcholinesterase inhibitors (e.g., aricept), and adenosine A2a receptor agonists. Further examples of suitable other pharmaceutical agents which may be used in combination with the compounds of the present invention are disclosed in U.S. Pat. Nos. 6,559,168 and 6,756,392, which are hereby incorporated by reference in their entireties. In such combinations, each active ingredient can be administered either in accordance with their usual dosage range or a dose below its usual dosage range.

The compounds of the invention are also suitable for use in the treatment of asbestos-related diseases or disorders. See, for example, U.S. Published Application No. 2005/0142104, which is hereby incorporated by reference in its entirety.

Thus, in accordance with a further aspect of the invention, there is provided a method of treating asbestos-related diseases or disorders comprising administering to a patient, such as a mammal, e.g., a human, a therapeutically effective amount of a compound of the invention (e.g., in the form of a pharmaceutically acceptable salt or solvate (e.g., hydrate) thereof). In accordance with a further embodiment, there is provided a method of treating, for example, mesothelioma, asbestosis, pleural effusion, pleural plaque, pleural calcification, diffuse pleural thickening, round atelectasis, and bronchogenic carcinoma, comprising administering to a patient, such as a mammal, e.g., a human, a therapeutically effective amount of a compound of the invention (e.g., in the form of a pharmaceutically acceptable salt or solvate (e.g., hydrate) thereof).

The compounds of the present invention may also be administered in combination with other known therapeutics for the treatment of asbestos-related diseases or disorders including, but not limited to, other PDE-4 inhibitors, anticancer agents, antibiotics, anti-inflammatory agents, cytokines, steroids, immunomodulatory agents, immunosuppressive agents, and combinations thereof. In addition, the compounds of the present invention can be used in combination with conventional therapies used to treat, prevent, or manage asbestos-related diseases or disorders, including, but not limited to, chemotherapy, surgery, radiation therapy, photodynamic therapy, and combinations thereof.

When used in combination with one or more additional pharmaceutical agent or agents for the treatment of asbestos-related diseases or disorders, the compounds of the present invention may be administered prior to, concurrently with, or following administration of the additional pharmaceutical agent or agents. When used in combination with one or more conventional therapies for the treatment of asbestos-related diseases or disorders, the compounds of the present invention may be administered prior to, concurrently with, or following the conventional therapy.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of generally 0.001-100 mg/kg/day, for example, 0.01-100 mg/kg/day, preferably 0.1-70 mg/kg/day, especially 0.5-10 mg/kg/day. Unit dosage forms can contain generally 0.01-1000 mg of active compound, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications; patents and publications, cited above and below, are hereby incorporated by reference in their entirety.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm). Sulfonic acid ion exchange resins (SCX) were purchased from Varian Technologies. Analytical HPLC was performed on 4.6 mm×100 mm Waters Sunfire RP C18 5 μm column using (i) a gradient of 20/80 to 80/20 acetonitrile (0.1% formic acid)/water (0.1% formic acid) over 6 min (Method A), (ii) a gradient of 20/80 to 80/20 acetonitrile (0.1% formic acid)/water (0.1% formic acid) over 8 min (Method B), (iii) a gradient of 40/60 to 80/20 acetonitrile (0.1% formic acid)/water (0.1% formic acid) over 6 min (Method C), (iv) a gradient of 40/60 to 80/20 acetonitrile (0.1% formic acid)/water (0.1% formic acid) over 8 min (Method D), (v) an isocratic eluent of 80/20 acetonitrile/water (0.1% formic acid) over 8 minutes (Method E), (vi) or a gradient of 10/90 to 90/10 acetonitrile (0.1% formic acid)/water (0.1% formic acid) over 6 min (Method F). Preparative HPLC was performed on 30 mm×100 mm Xtera Prep RP_5μ columns using an 8 min gradient of 95/5 to 20/80 water (0.1% formic acid)/acetonitrile (0.1% formic acid).

Example 1

Example 1A

Synthesis of 4-Methoxy-3-(3R)-tetrahydrofuryloxybenzaldehyde

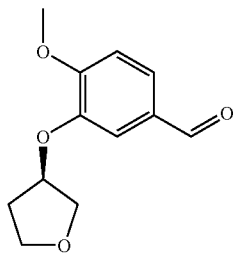

3-Hydroxy-4-methoxybenzaldehyde (7.6 g; 50 mmol) was dissolved in THF (200 mL) followed by addition of (S)-3-hydroxytetrahydrofuran (6.0 mL; 75 mmol) and triphenylphosphine (19.7 g; 75 mmol). The resulting solution was cooled to 5° C. and diisopropyl azodicarboxylate (14.8 mL; 75 mmol) was added dropwise over 10 minutes. The clear orange solution was stirred at ambient temperature for 16 hours. Thin layer chromatography analysis using a 1:1 mixture of hexane/ethyl acetate determined the reaction to be complete. The solvent was removed under reduced pressure and the residue was taken up in ethyl acetate (60 mL) and extracted twice with 20% aqueous sodium bisulfite (150 mL/extraction). The extracts were pooled and washed with ethyl acetate (75 mL). The aqueous layer was basified with solid sodium hydroxide (26 g) and then extracted with 3×150 mL of ethyl acetate (150 mL/extraction). The organic extracts were pooled, washed with 40 mL of brine, dried (Na$_2$SO$_4$), and concentrated to afford 7.4 g (66%) of a pale yellow oil. $^1$H NMR (CDCl$_3$; 300 MHz) δ 2.2-2.4 (m, 2H); 3.8-4.1 (m, 7H); 5.0 (m, 1H); 7.0 (d, 1H); 7.4 (s, 1H); 7.5 (d, 1H); 9.9 (s, 1H). ES-MS [M+H]+=223.2

The following compounds were prepared in a similar fashion with different starting materials:

1-Bromo-4-methoxy-3-(3R)-tetrahydrofuranyloxybenzene.
4-Methoxy-3-(3S)-tetrahydrofuryloxybenzaldehyde.

Example 1B

Synthesis of 3-[4-Methoxy-3-(3R)-tetrahydrofuranyloxyphenyl]-1H-pyrazole

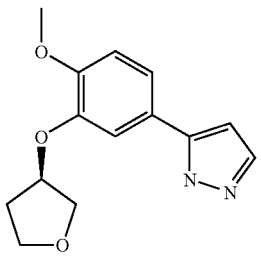

Sodium hydride (60% in mineral oil, 1.51 g, 37.7 mmol) was suspended in THF (20 mL) and cooled to 5° C. followed by addition of diethoxyphosphorylacetaldehyde tosylhydrazone (6.51 g, 18.7 mmol) in THF (20 mL) over 10 minutes. After stirring for 30 minutes at 5° C., the yellow suspension was treated with a solution of 4-methoxy-3-(3R)-tetrahydrofuryloxybenzaldehyde (2.84 g, 12.8 mmol) in TBTf (20 mL) and stirred for 1 hour at room temperature and 16 hours at 80° C. in an oil bath. After cooling to room temperature, the reaction was poured into 5% aqueous NaH$_2$PO$_4$ and extracted with ethyl acetate. The extract was washed with water and brine, dried over Na$_2$SO$_4$ and concentrated to afford a yellow solid. Recrystallization from ethyl acetate furnished 1.9 g (57%) of 3-[4-Methoxy-3-(3R)-tetrahydrofuranyloxyphenyl]-1H-pyrazole in two crops as light yellow solids. (mp 149-151° C.); $^1$H NMR (CDCl$_3$, 300 MHz) δ 2.23 (m, 2H), 3.85-4.10 (nm 4H), 3.89 (s, 3H), 5.02 (m, 1H), 6.54 (m, 1H), 6.92 (m, 1H), 7.25 (m, 2H), 7.60 (m, 1H); MS [M+H]=261.

The following compounds were prepared in a similar fashion with different starting materials:

3-(3,4-Dimethoxyphenyl)-1H-pyrazole 3-(3-Cyclopentyloxy-4-methoxyphenyl)-1H-pyrazole 3-[3,4-Bis(difluoromethoxy)phenyl]-1H-pyrazole 3-[1-Difluoromethoxy-3-(3R)-tetrahydrofuranyloxyphenyl]-1H-pyrazole 3-(3-Benzyloxy-4-methoxyphenyl)pyrazole 3-[3-(2,3-Difluorobenzyloxy)-4-methoxyphenyl]pyrazole

Example 2

Synthesis of 1-(2,3-difluorobenzyl)-3-[4-methoxy-3-(3R)-tetrahydrofuranyloxyphenyl]-1H-pyrazole

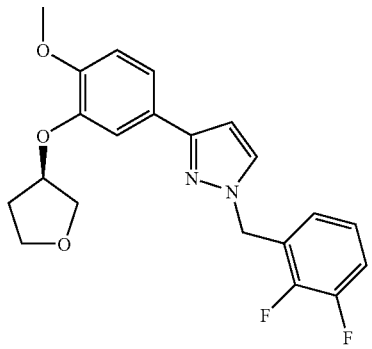

3-[4-Methoxy-3-(3R)tetrahydrofuranyloxyphenyl]-1H-pyrazole (243 mg, 0.96 mmol) was dissolved in DMF (8 mL) at room temperature and treated with sodium hydride (75 mg, 1.86 mmol) with stirring for 3 hours. The reaction mixture was treated with a solution of 2,3-difluorobenzyl bromide (0.35 mL, 2.79 mmol) in DMF (1 mL) and stirred at room temperature for 16 hours. The reaction was diluted with ethyl acetate and washed with water three times and brie once. The organic layer was dried over sodium sulfate and concentrated to an oil which was purified on a column of silica gel using a hexane/ethyl acetate gradient. Tubes containing the compound were pooled and evaporated under vacuum to afford 327 mg (90%) of 1-(2,3-difluorobenzyl)-3-[4-methoxy-3-(3R)-tetrahydrofuranyloxyphenyl]-1H-pyrazole as a colorless oil. MS [M+H]=387; $^1$H NMR (CDCl$_3$, 300 MHz) δ 2.23 (m, 2H), 3.8-4.1 (m, 4H), 3.92 (s, 3H), 5.1 (m, 1H), 5.4 (s, 2H), 6.5 (s, 1H), 6.9 (m, 2H), 6.95-7.11 (m, 2H), 7.3 (m, 2H), 7.45 (s, 1H). A minor product consisting of 1-(2,3-difluorobenzyl)-5-[4-methoxy-3-(3R)-tetrahydrofuranyloxy-phenyl]-1H-pyrazole was also formed, which can be separated and isolated by preparative HPLC (see, e.g., Example 3).

The following compounds were prepared in a similar fashion with different starting materials (in some cases, the 5-regioisomer was also formed and could be separated by methods known in the art such as preparative HPLC):

3-(3-Cyclopentyloxy-4-methoxyphenyl)-1-(2-methylbenzyl)-1H-pyrazole, 3-(3-Cyclopentyloxy-4-methoxyphenyl)-1-(2,3-difluorobenzyl)-1H-pyrazole, 3-(3-Cyclopentyloxy-4-methoxyphenyl)-1-(4-nitrobenzyl)-1H-pyrazole, 3-[4-Methoxy-3-(3R)-tetrahydrofuranyloxyphenyl]-1-(2-methylbenzyl)-1H-pyrazole, 1-(4-Aminobenzyl)-3-(3-cyclopentyloxy-4-methoxyphenyl)-1H-pyrazole, 3-[4-Methoxy-3-(3R)-tetrahydrofuranyloxyphenyl]-1-(4-nitrobenzyl)-1H-pyrazole, 1-(4-Aminobenzyl)-3-[4-methoxy-3-(R)-tetrahydrofuranyloxyphenyl]-1H-pyrazole, 3-[4-Difluoromethoxy-3-(3R)-tetrahydrofuranyloxyphenyl]-1-(4-nitrobenzyl)-1H-pyrazole, 3-[4-Difluoromethoxy-3-(3R)-tetrahydrofuranyloxyphenyl]-1-(2-methylbenzyl)-1H-pyrazole, 1-(2,3-Difluorobenzyl)-3-[4-difluoromethoxy-3-(3R)-tetrahydrofuranyloxyphenyl]-1H-pyrazole, 1-(4-Aminobenzyl)-3-[4-difluoromethoxy-3-(3R)-tetrahydrofuranyloxyphenyl]-1H-pyrazole, 1-(2,3-Difluorobenzyl)-3-[4-methoxy-3-(3S)-tetrahydrofuranyloxyphenyl]-1H-pyrazole, 1-Cyclohexylmethyl-3-[4-methoxy-3-(3R)-tetrahydrofuranyloxyphenyl]-1H-pyrazole, 3-[4-Methoxy-3-(3R)-tetrahydrofuranyloxyphenyl]-1-(3-phenpropyl)-1H-pyrazole, 3-[4-Methoxy-3-(3R)-tetrahydrofuranyloxyphenyl]-1-(4-pyridylmethyl)-1H-pyrazole, 1-Ethylsulfonyl-3-[4-methoxy-3-(3R)-tetrahydrofuranyloxyphenyl]-1H-pyrazole, 3-[4-Methoxy-3-(3R)-tetrahydrofuranyloxyphenyl]-1-(1-propyl)-1H-pyrazole, 1-Benzylsulfonyl-3-[4-Methoxy-3-(3R)-tetrahydrofuranyloxyphenyl]-1H-pyrazole, 3-[4-Methoxy-3-(3R)-tetrahydrofuranyloxyphenyl]-1-(2-pyridylmethyl)-1H-pyrazole, 3-(3-Benzyloxy-4-methoxyphenyl)-1-(2,3-difluorobenzyl)-1H-pyrazole, 3-[4-Methoxy-3-(3R)-tetrahydrofuranyloxyphenyl]-[N-(1,2,3,4-tetrahydroisoquinolyl)carbonylmethyl]-1H-pyrazole, 1-[N-(7-Azaindolyl)carbonylmethyl]-3-[4-Methoxy-3-(3R)-tetrahydrofuranyloxyphenyl]-1H-pyrazole, 1-(2,3-Difluorobenzyl)-3-[3-(2,3-difluorobenzyloxy)-4-methoxyphenyl]-1H-pyrazole, 3-(2,3-Difluorobenzyl)-3-(3-hydroxy-4-methoxyphenyl)-1H-pyrazole, 3-[4-Methoxy-3-(3R)-tetrahydrofuranyloxyphenyl]-1-(2-phenethyl)-1H-pyrazole, 2-{3-[4-methoxy-3-(3R)-tetrahydrofuranyloxyphenyl]-pyrazol-1-yl}-1-phenyl-1-ethanone, 1-Benzyl-3-[4-Methoxy-3-(3R)-tetrahydrofuranyloxyphenyl]-1H-pyrazole, 1-Cyclopentyl-3-([4-Methoxy-3-(3R)-tetrahydrofuranyloxyphenyl]-1H-pyrazole, 3-[4-Methoxy-3-(3R)-tetrahydrofuranyloxyphenyl]-1-[2-(6-methylpyridyl)]-1H-pyrazole, 1-Cyclohexylmethyl-3-(4-methoxy-3-(3S)-tetrahydrofuranyloxyphenyl)-1H-pyrazole, 3-[4-Methoxy-3-(3R)-tetrahydrofuranyloxyphenyl]-1-(methylsulfonylbenzyl)-1H-pyrazole, 3-(2-Acetyl-7-methoxybenzofuran-4-yl)-1-(2,3-difluorobenzyl)-1H-pyrazole, 3-(2-Acetyl-7-methoxybenzofuran-4-yl)-1-(4-methylsulfonylbenzyl)-1H-pyrazole, 3-(2-Acetyl-7-methoxybenzofuran-4-yl)-1-(2-methylbenzyl)-1H-pyrazole, 1-(2-Methoxyethyl)-5-[4-methoxy-3-(3R)-tetrahydrofuranyloxyphenyl]-1H-pyrazole, 1-(2-Cyclopropylmethoxyethyl)-5-[4-methoxy-3-(3R)-tetrahydrofuranyloxyphenyl]-1H-pyrazole.

Example 3

1-Cyclohexylmethyl-3-[4-methoxy-3-(3R)-tetrahydrofuranyloxyphenyl]-1H-pyrazole

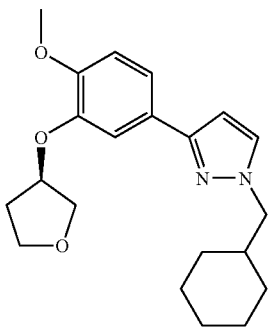

and 1-Cyclohexylmethyl-5-[4-methoxy-3-(3R)-tetrahydrofuranyloxyphenyl]-1H-pyrazole

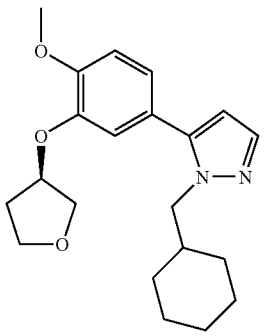

A solution of 3-[4-methoxy-3-(3R)-tetrahydrofuranyloxyphenyl]-1H-pyrazole (78 mg, 0.3 mmol) in DMF (2 mL) was treated with sodium hydride (60% in oil, 24 mg, 0.6 mmol) and stirred at room temperature for three hours. The reaction mixture was then treated with a solution of (bromomethyl)cyclohexane (0.13 mL, 0.9 mmol) in DMF (0.8 mL) and stirred at ambient temperature for 16 hours. The mixture was diluted with ethyl acetate (60 mL) and washed with water (2×20 mL) and brine (1×15 mL), dried (Na$_2$SO$_4$) and concentrated to 250 mg of an oil, which was chromatographed over silica gel using a 10-30% ethyl acetate/hexane gradient. Concentration of fractions afforded 92 mg of an oil consisting of a mixture of regioisomers in a ratio of 3.5:1 as determined by LCMS. The mixture of regioisomers was taken in 1 mL of acetonitrile/water (3:2 with 0.1% formic acid) and resolved by preparative hplc using a Waters C18, 5 um, 30×100 mm column with a flow rate of 45 mL/min. A gradient of 35-80% acetonitrile/water containing 0.1% formic acid over 6 minutes was employed and a Waters 2996 PDA detector was utilized to trigger collection at 248 nm. Baseline resolution was achieved with peak A eluting at 7.61 min and peak B eluting at 8.15 min. Tubes containing each regioisomer were concentrated on a Genevac HT4 Series II Evaporator supplying 14 mg of (peak A; retention time=7.61 minutes) 1-cyclohexylmethyl-5-[4-methoxy-3-(3R)-tetrahydrofuranyloxyphenyl]-1H-pyrazole and 54 mg of (peak B; retention time=8.15 minutes) 1-cyclohexylmethyl-3-[4-methoxy-3-(3R)-tetrahydrofuranyloxyphenyl]-1H-pyrazole, each as colorless oils. Both peaks exhibit [M+H]=357. $^1$H NMR for peak A (CDCl$_3$, 300 MHz) δ 0.80 (m, 2H), 1.1-1.3 (m, 3H), 1.4-1.7 (m, 5H), 1.9 (m, 1H), 2.2 (m, 2H), 3.8-4.2 (m, 9H), 4.97 (s, 1H), 6.22 (s, 1H), 6.82 (s, 1H), 6.96 (s, 2H), 7.55 (s, 1H). $^1$H NMR of peak B (CDCl$_3$, 300 MHz) δ 0.80 (m, 2H), 1.1-1.3 (m, 3H), 1.4-1.7 (m, 5H), 1.9 (m, 1H), 2.2 (m, 2H), 3.8-4.2 (m, 9H), 5.08 (s, 1H), 6.44 (s, 1H), 6.9 (d, 1H), 7.35 (m, 3H).

The following compounds were prepared in a similar fashion with different starting materials:

1-Cyclohexylmethyl-5-[4-methoxy-3-(3S)-tetrahydrofuranyloxyphenyl]-1H-pyrazole,

Isopropyl 2-{5-[4-methoxy-3-(3R)-tetrahydrofuranylphenyl]-pyrazol-1-yl}acetate, 1-(2,3-Difluorobenzyl)-5-[4-methoxy-3-(3R)-tetrahydrofuranylphenyl]-1H-pyrazole, 1-(4-fluorobenzyl)-2-{4-methoxy-3-[(3R)-tetrahydrofuran-3-yloxy]phenyl}-1H-pyrrole

Example 4

Intermediate B: Synthesis of 2-Acetyl-4-bromo-7-methoxybenzofuran

2-Acetyl-7-methoxybenzofuran (1.0 g, 5.3 mmol) was dissolved in glacial acetic acid (29 mL) followed by addition of sodium acetate (1.3 g, 15.8 mmol). The reaction was treated dropwise with a solution of bromine (0.26 mL, 5.26 mmol) in glacial acetic acid (10 mL) at room temperature followed by stirring for one hour. The solvent was removed under vacuum. The residue was dissolved in water and extracted three times with dichloromethane. The combined organic extracts were washed with 2% aqueous sodium bicarbonate, dried over sodium sulfate and concentrated under vacuum. The residue was purified on silica gel using a 50-100% dichloromethane/hexane gradient affording 1.00 g (75%) of the product as a white solid. $^1$H NMR (CDCl$_3$, 300 MHz) δ 7.44 (s, 1H), 7.32 (d, 1H), 6.80 (d, 1H), 4.0 (s, 3H), 2.62 (s, 3H).

Intermediate C: Synthesis of 4-bromo-7-methoxy-2-[2-methyl-(1,3-dioxolan)-2-yl]benzofuran A solution of 2-acetyl-4-bromo-7-methoxybenzofuran (0.50 g, 1.86 mmol), 5 mL of ethylene glycol, and PPTS (46 mg, 0.186 mmol) was refluxed overnight in benzene (37 mL) using a Dean Stark apparatus. The reaction was cooled to room temperature, washed with aqueous sodium bicarbonate, dried over sodium sulfate and evaporated under vacuum to afford 293 mg (50%) of 4-bromo-7-methoxy-2-[2-methyl-(1,3-dioxolan)-2-yl]benzofuran as an oil. $^1$H NMR (CDCl$_3$, 300 MHz) δ 7.28 (d, 1H), 6.74 (s, 1H), 6.69 (d, 1H), 4.04 (m, 4H), 1.84 (s, 3H).

Intermediate D: Synthesis of 7-methoxy-2-[2-methyl-(1,3-dioxolan)-2-yl]-benzofuran-4-carboxaldehyde 4-Bromo-7-methoxy-2-[2-methyl-(1,3-dioxolan)-2-yl] benzofuran (666 mg, 2.1 mmol) was dissolved in THF (21 mL), cooled to −60° C. under an argon atmosphere, and t-butyl lithium (2.6 mL, 1.7 M) was added with stirring at −60° C. The mixture was stirred at −60° C. for one hour, DMF (0.82 mL, 10.6 mmol) in THF (20 mL) was added, and the reaction was stirred at ambient temperature overnight. The reaction was poured into aqueous sodium bicarbonate and extracted three times with ethyl acetate. The combined extracts were washed once with water, once with brine, and dried over sodium sulfate. Evaporation of the solvent under reduced pressure followed by purification on silica gel using a 10-50% ethyl acetate/hexane gradient afforded 7-methoxy-2-[2-methyl-(1,3-dioxolan)-2-yl]-benzofuran-4-carboxaldehyde (399 mg; 72%) as an oil. $^1$H NMR (CDCl$_3$, 300 MHz) δ 10.01 (s, 1H), 7.66 (d, 1H), 7.45 (s, 1H), 6.88 (d, 1H), 4.08 (m, 7H), 1.84 (s, 3H).

Example 5

Synthesis of
3-(2-Acetyl-7-methoxybenzofuran-4-yl)pyrazole

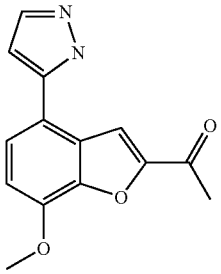

A suspension of sodium hydride (60% in oil, 174 mg, 4.36 mmol) in THF (5 mL) was cooled to 0° C. under argon, and then treated with a solution of diethoxyphosphorylacetaldehyde tosylhydrazone (759 mg, 2.2 mmol) in THF (7 mL). After stirring at 0° C. for 30 minutes a solution of 7-methoxy-2-(2-methyl-[1,3]dioxolan-2-yl)benzofuran-4-carboxaldehyde (381 mg, 1.45 mmol) in THF (5 mL) was added and the reaction stirred at room temperature overnight followed by stirring at 65° C. for 5 hours. After cooling to room temperature, the reaction was poured into 5% aqueous NaH$_2$PO$_4$ and extracted with ethyl acetate. The extract was washed with water, washed with brine, dried over Na$_2$SO$_4$, and concentrated. The residue was chromatographed on silica gel using a 25-50% ethyl acetate/hexane gradient to afford the dioxolane protected pyrazole (306 mg, 70%). The masked ketone (306 mg) was taken in 3M HCl in THF (10 mL) and stirred at room temperature for 2 hours. The solution was neutralized with sodium bicarbonate and extracted with ethyl acetate three times. The combined extracts were washed with water, washed with brine, dried over sodium sulfate and concentrated under vacuum. The residue was purified on silica gel using hexane/ethyl acetate (1:1; v/v) to isolate 3-(2-Acetyl-7-methoxybenzofuran-4-yl)pyrazole (192 mg, 74%) as a yellow solid. $^1$H NMR (CDCl3, 300 MHz) δ 8.09 (s, 1H), 7.70 (d, 1H), 7.53 (d, 1H), 6.98 (d, 1H), 6.70 (d, 1H), 4.07 (s, 3H), 2.65 (s, 3H).

Example 6

Intermediate E: Synthesis of
4-difluoromethoxy-3-hydroxybenzaldehyde 3,4-Dihydroxybenzaldehyde (20 g, 145 mmol), chlorodifluoroacetic acid sodium salt (55.19 g, 362 mmol) and sodium hydroxide (5.50 g, 138 mmol) were stirred in DMF (1200 mL) at 55° C. under nitrogen for 16 hours. The pH was adjusted to 1.0 by the addition of 10% aqueous HCl followed by extraction with ethyl acetate (3×500 mL). The combined extracts were evaporated under vacuum. The residue was purified on silica gel using a 10-20% ethyl acetate/hexane gradient. 4-difluoromethoxy-3-hydroxybenzaldehyde was isolated in 24% yield (6.62 g). $^1$H NMR (CDCl$_3$, 400 MHz) δ 6.1 (br s, 1H), 6.48-6.85 (t, 1H OCHF$_2$), 7.26 (d, 1H), 7.44 (d, 1H), 7.55 (s, 1H), 9.91 (s, 1H).

Intermediate F: Synthesis of tert-Butyl 2-{3-[4-difluoromethoxy-3-(3R)-tetrahydrofuranyloxyphenyl]pyrazol-1-yl}acetate 3-[4-Difluoromethoxy-3-(3R)-tetrahydrofuranyloxyphenyl]-1H-pyrazole (199 mg, 0.67 mmol) was dissolved in DMF (9 mL). Sodium hydride (60% in oil, 54 mg, 1.34 mmol) was added at room temperature and stirred for 1 hour followed by addition of tert-butyl bromoacetate (0.30 mL, 2.01 mmol) in DMF (1 mL). The reaction was stirred for 16 hours at room temperature, diluted with ethyl acetate, and washed with water twice and brine once. The solvent was dried over sodium sulfate and concentrated to 500 mg of a pale yellow oil, which was purified on silica gel using a 20-50% ethyl acetate/hexane gradient to afford tert-butyl 2-{3-[4-difluoromethoxy-3-(3R)-tetrahydrofuranyloxyphenyl]pyrazol-1-yl}acetate as a colorless oil (145 mg, 53%). MS [M+H]=411. $^1$H NMR (DMSO 300 MHz) δ 1.42 (s, 9H), 2.05 (m, 1H), 2.23 (m, 1H), 3.8-4.0 (m, 4H), 4.98 (s, 2H), 5.18 (br 5, 1H), 6.78-7.28 (t, 1H OCHF$_2$), 6.80 (s, 1H), 7.21 (d, 1H), 7.38 (d, 1H), 7.45 (s, 1H), 7.77 (s, 1H).

Synthesis of 2-{3-[4-difluoromethoxy-3-(3R)-tetrahydrofuranyloxyphenyl]pyrazole-1-yl}acetic acid

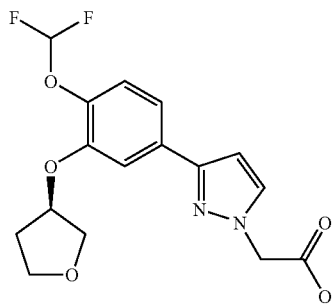

tert-Butyl 2-{3-[4-difluoromethoxy-3-(3R)-tetrahydrofuranyloxyphenyl]pyrazol-1-yl}acetate (762 mg, 1.85 mmol) was stirred in dichloromethane (11 mL) and treated with trifluoroacetic acid (11 mL) with stirring for 90 minutes. The solvent was removed under reduced pressure and partitioned between ethyl acetate/water. The organic layer was washed with water three times and brine once. After drying over sodium sulfate, the solvent was stripped to furnish 2-{3-[4-difluoromethoxy-3-(tetrahydrofuryloxy)phenyl]pyrazole-1-yl}acetic acid as a semisolid (657 mg, 100%) MS [M+H]= 355. $^1$H NMR (CDCl$_3$ 300 MHz) δ 2.25 (m, 2H), 4.02 (m, 4H), 5.07 (m, 2H), 5.2 (br s, 1H), 6.31-6.81 (t, 1H OCHF$_2$), 6.61 (s, 1H), 7.19-7.28 (m, 3H), 7.29 (s, 1H), 7.52 (s, 1H).

2-{3-(4-Methoxy-3-(3R)-tetrahydrofuranyloxyphenyl)pyrazole-1-yl}acetic acid was synthesized in a similar manner with different starting materials.

Example 7

Synthesis of 2-{3-[4-Difluoromethoxy-3-(3R)-tetrahydrofuranyloxyphenyl]-pyrazol-1-yl}-N-(2,3-difluorophenyl)acetamide

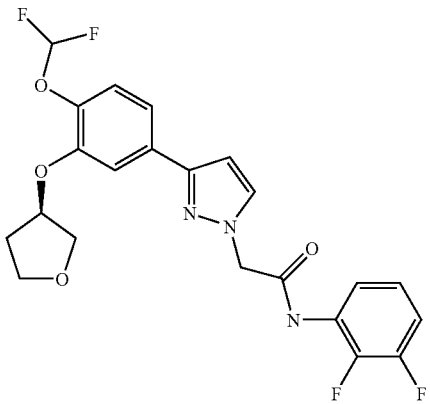

2-{3-[4-difluoromethoxy-3-(3R)-tetrahydrofuranyloxyphenyl]pyrazol-1-yl}acetic acid (84 mg, 0.23 mmol) was dissolved in dichloromethane (2 mL), cooled to 5° C. and treated the oxalyl chloride (2M in dichloromethane, 0.13 mL, 0.26 mmol) and stirred for 90 minutes. In a separate flask, 2,3-difluoroaniline (0.35 mL, 0.35 mmol) in THF (2 mL) was treated with sodium hydride (60% in oil, 22 mg, 0.56 mmol) and stirred for 90 minutes. The solvent from the initial flask was removed under reduced pressure. The residue was taken in THF (2 mL), cooled to 5° C. and treated with the difluoroaniline/hydride suspension followed by stirring at ambient temperature for 16 hours. The solvent was removed under vacuum and the residue was partitioned between ethyl acetate/water. The organic layer was washed with water and brine, dried over sodium sulfate and evaporated to afford 57 mg of a brown oil. This was adsorbed onto a preparative thin layer chromatography silica gel plate (20×20 cm, 2000 micron) using ethyl acetate/hexane (1:1 v/v) to elute. The product was isolated from the plate by scraping and suspending the silica gel in ethyl acetate following by filtering through a bed of Celite. Evaporation of the solvent afforded 2-{3-[4-difluoromethoxy-3-(3R)-tetrahydrofuranyloxyphenyl]-pyrazol-1-yl}-N-(2,3-difluorophenyl)acetamide as a white foam (15 mg, 14%) MS [M+H]=446; $^1$H NMR (CDCl$_3$, 300 MHz) δ 2.28 (m, 2H), 4.05 (m, 4H), 4.98 (s, 2H). 5.1 (s, 1H), 6.3-6.7 (t, 1H OCHF$_2$) 6.65 (s, 1H), 6.8 (1H, 1H) 6.9 (m, 1H), 7.25 (m, 2H), 7.56 (s, 2H) 8.3 (t, 1H), 9.8 (s, 1H).

The following compounds were prepared in a similar fashion with different starting materials:

2-{3-[3,4-Bis(difluoromethoxy)-phenyl]-pyrazol-1-yl}-N-(2-methylphenyl)acetamide, 2-{3-[3,4-Bis(difluoromethoxy)-phenyl]-pyrazol-1-yl}-N-(2,3-difluorophenyl)acetamide, 1-N-(2-cyanophenyl)-2-{3-[4-difluoromethoxy-3-(3R)-tetrahydrofuranyloxyphenyl]pyrazol-1-yl}acetamide, 2-{3-[4-Difluoromethoxy-3-(3R)-tetrahydrofuranyloxyphenyl]-pyrazol-1-yl}-N-[2-(6-methylpyridyl)]acetamide.

Example 8

Intermediate G: Methyl 3-ethyl-1H-indazol-6-yl-carboxylate

To a solution of 1.35 g (7.1 mmol) of 3-ethyl-1H-indazol-6-yl-carboxylic acid, [Marfat, A., et al., U.S. Pat. No. 6,262,040], 2.9 mL (71 mmol) of methanol, and 0.95 g (7.8 mmol) of DMAP in 60 mL of CH$_2$Cl$_2$ was added 1.5 g (7.8 mmol) of EDCI-HCl. This mixture was stirred at room temperature overnight, concentrated and the residue dissolved in 50 mL of ethyl acetate. The organic layer was successively washed with 40 mL of 1N HCl, 40 mL of water and 40 mL of brine, dried (Na$_2$SO$_4$), and concentrated. The residue was purified by chromatography over silica gel using a gradient of 35% to 50% ethyl acetate in hexanes over 20 minutes as eluant to yield 860 mg (4.2 mmol) of methyl 3-ethyl-1H-indazol-6-yl-carboxylate. $^1$H NMR (CDCl$_3$) δ 11.7 (s, 1H), 8.18 (s, 1H), 7.73 (apparent q, 9.0 Hz, 2H), 3.94 (s, 3H), 3.03 (q, 7.5 Hz, 2H), 1.42 (t, 7.5 Hz, 3H).

Intermediate H: Methyl 1-Cyclopentyl-3-ethyl-1H-indazol-6-yl-carboxylate

To a flask containing 337 mg (8.4 mmol) of NaH (60% in mineral oil), 1.7 mL (8.4 mmol) of 15-crown-5 and 42 mL of DMF was added 860 mg (4.2 mmol) of methyl 3-ethyl-1H-indazol-6-yl-carboxylate. This mixture was stirred at room temperature for 3 hours and then 1.35 mL (12.6 mmol) of cyclopentyl bromide was added and the reaction was stirred at room temperature overnight. The solvent was removed and the residue was dissolved in 40 mL ethyl acetate, washed with 30 mL of water and 30 mL of brine, dried (Na$_2$SO$_4$), and concentrated. The residue was purified by column chromatography over SiO$_2$ using a step gradient of 10% ethyl acetate in hexanes until the first compound eluted and then 50% ethyl acetate in hexanes to provide 662 mg (2.4 mmol) of methyl 1-cyclopentyl-3-ethyl-1H-indazol-6-yl-carboxylate as a clear oil along with 144 mg (0.53 mmol) methyl 2-(cyclopentyl-3-ethyl)-2H-indazol-6-yl-carboxylate as a yellow oil. $^1$H-NMR (CDCl$_3$) δ 8.17 (s, 1H), 7.71 (dd, J1=8.4 Hz, J2=6.7 Hz, 2H), 5.0 (p, J=7.5 Hz, 1H), 3.97 (s, 3H), 3.00 (q, J=7.5 Hz, 2H), 2.16 (m, 4H), 1.92 (m, 2H), 1.74 (m, 2H), 1.39 (t, J=7.6 Hz, 3H).

Intermediate I: 1-Cyclopentyl-3-ethyl-6-hydroxymethyl-1H-indazole

DIBAL (10 mL, 1M in toluene) was slowly added with stirring at −50° C. to a solution of 886 mg (3.25 mmol) of methyl 1-cyclopentyl-3-ethyl-1H-indazol-6-yl-carboxylate in 32 mL of CH$_2$Cl$_2$. The reaction stirred at −50° C. for 1 hour and was quenched by the slow addition of 4 mL of MeOH and then, with stirring, poured into a saturated Rochelle's salt and ethyl acetate mixture (60 each). Stirring continued at room temperature until both layers were clear. The organic layer was separated and the aqueous layer was extracted with 3×40 mL of ethyl acetate. The organic fractions were combined, dried (Na$_2$SO$_4$), and concentrated. The compound was purified via column chromatography over SiO$_2$ using a 1:4 solution of EtOAc in hexanes as eluant to yield 427 mg (1.75 mmol) of 1-cyclopentyl-3-ethyl-6-hydroxymethanol-1H-indazole as a clear oil. $^1$H-NMR (CDCl$_3$) δ 7.66 (d, J=8.2 Hz, 1H), 7.42 (s, 1H), 7.07 (d, J=8.2 Hz), 4.92 (p, J=7.7 Hz, 1H), 4.84 (d, J=5.5 Hz, 2H), 2.99 (q, J=7.6 Hz, 2H), 2.15 (m, 4H), 2.04 (m, 2H), 11.73 (m, 2H), 1.38 (t, J=1.6 Hz, 3H).

Intermediate J: 1-Cyclopentyl-3-ethyl-1H-indazol-6-yl-carboxaldehyde

To a solution of 427 mg (1.75 mmol) 1-cyclopentyl-3-ethyl-6-hydroxymethanol-1-1H-indazole in 58 mL of CHCl₃ was added 2.1 g (24.1 mmol) of MnO₂. The reaction was stirred at room temperature for 6 hours, the solids were removed by filtration and the filtrate was concentrated. The residue was purified via column chromatography over SiO₂ using 3% ethyl acetate in hexanes as eluant to give 332 mg (1.37 mmol) of 1-cyclopentyl-3-ethyl-1H-indazol-6-yl-carboxaldehyde as a clear oil. ¹H-NMR (CDCl₃) δ 10.13 (s, 1H), 7.94 (s, 1H), 7.78 (d, J=8.2 Hz, 1H), 7.61 (d, J=8.2 Hz, 1H), 5.02 (p, J=7.4 Hz, 1H), 3.02 (q, J=7.5 Hz, 2H), 2.19 (m, 4H), 2.02 (m, 2H), 1.76 (m, 2H), 1.40 (t, J=7.5 Hz, 3H).

3-[(1-Cyclopentyl-3-ethylindazol)-6-yl]-1H-pyrazole

A flask containing 165 mg (4.12 mmol) of NaH (60% in mineral oil) and 4 mL of THF was placed under Ar and cooled to 0° C. A solution of 716 mg (2.06 mmol) of diethoxyphosphorylacetaldehyde tosylhydrazone in 7 mL of THF was added over 5 minutes. The reaction stirred at 0° C. for 30 minutes followed by the addition of a solution of 332 mg (1.37 mmol) of 1-cyclopentyl-3-ethyl-1H-indazol-6-yl-carboxaldehyde in 4.5 mL THF. The ice bath was removed and the solution was stirred at room temperature for 4 hours, and then heated to 65° C. overnight. The reaction mixture was cooled to room temperature, poured into 50 mL of 5% NaH₂PO₄ and extracted with 3×25 mL of ethyl acetate. The organic layers were combined, dried over Na₂SO₄, concentrated, and purified by column chromatography over SiO₂ using a gradient from 10% to 50% ethyl acetate in hexanes over 20 minutes to yield 185 mg (0.66 mmol) of 1-cyclopentyl-3-ethyl-6-(1H-pyrazol-3-yl)-1H-indazole as a white foam. ¹H-NMR (CDCl₃) δ 7.80 (s, 1H), 7.69 (d, J=8.3 Hz, 1H), 7.65 (s, 1H), 7.5 (d, J=8.3 Hz, 1H), 6.7 (s, 1H) 4.90 (p, J=–7.5 Hz, 1H), 3.00 (q, J=7.5 Hz, 2H), 2.13 (m, 4H), 2.00 (m, 2H), 1.71 (m, 2H), 1.40 (t, J=7.5, 3H).

Example 9

3-[(1-Cyclopentyl-3-ethylindazol)-6-yl]-1-(2,3-difluorobenzyl)-1H-pyrazole

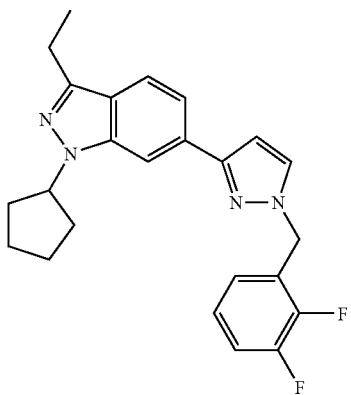

A solution of 31.8 mg (0.11 mmol) of 3-[(1-cyclopentyl-3-ethylindazol)-6-yl]-1H-pyrazole in 1 mL of DMF was added to a flask containing 12.9 mg (0.32 mmol) of NaH (60% in mineral oil) and 1 mL of DMF. This was stirred at room temperature for 3 hours. Then, a solution of 43 µL (0.33 mmol) of 2,3-difluorobenzyl bromide in 1 mL of DMF was added and the reaction was stirred at room temperature overnight. The mixture was poured into a mixture of 10 mL of water and 10 mL of ethyl acetate. The organic layer was washed with 2×10 mL of water and 1×10 mL of brine. The organic layer was then dried over Na₂SO₄, filtered and the solvent was removed under reduced pressure. Purification via column chromatography over 4 g of silica using 5% ethyl acetate in hexanes to 10% ethyl acetate in hexanes gradient over 10 minutes to give 24 mg (0.06 mmol, 52% yield) of 3-[(1-cyclopentyl-3-ethylindazol)-6-yl]-1-(2,3-difluorobenzyl)-1H-pyrazole as a clear oil. ¹H-NMR (CDCl₃) δ 7.84 (s, 1H), 7.69 (d, J=8.3 Hz, 1H), 7.54 (d, J=8.3 Hz, 1H), 7.50 (s, 1H), 7.15-7.04 (m, 3H), 6.68 (s, 1H), 5.48 (s, 2H), 4.99 (p, J=7.6 Hz, 1H), 3.01 (q, J=7.4 Hz, 2H), 2.12 (s, 4H), 1.98 (s, 2H), 1.75-1.72 (m, 2H), 1.40 (t, 7.4 Hz, 3H).

The following compounds were synthesized in a similar manner with different starting materials:

3-[(1-Cyclopentyl-3-ethylindazol)-6-yl]-1-(2,3-difluorophenyl)-1H-pyrazole

3-[(5-Cyclopentyl-3-ethylindazol)-6-yl])-1-(2-methylbenzyl)-1H-pyrazole

3-[(1-Cyclopentyl-3-ethylindazol)-6-yl])-1-(4-methylsulfonylbenzyl)-1H-pyrazole

3-[(1-Cyclopentyl-3-ethylindazol)-6-yl])-1-(2-pyridylmethyl)-1H-pyrazole.

Example 10

Synthesis of 2-[4-Methoxy-3-(3R)tetrahydrofuranyloxyphenyl]-1,3-dithiane

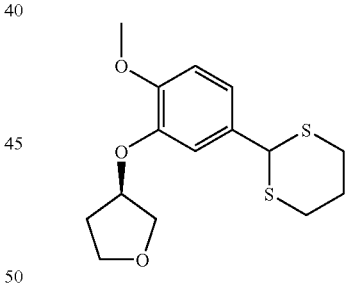

4-Methoxy-3-(3R)-tetrahydrofuranyloxybenzaldehyde (8.37 g; 37.6 mmol) was dissolved in dichloromethane (120 mL) followed by addition of 1,3-propanedithiol (11.3 mL; 113 mmol) and boron trifluoride etherate (0.6 mL). The reaction mixture became mildly exothermic and turbid. Reaction monitoring by LC-MS showed complete conversion taking place in 90 minutes. The reaction was washed with 30 mL of water and 30 mL of brine, dried over anhydrous sodium sulfate and concentrated. Trituration of the residue with ether produced a white solid that was collected by filtration and dried yielding 9.09 g (77%) of 2-[4-methoxy-3-(3R)-tetrahydrofuranyloxyphenyl]-1,3-dithiane. ¹H-NMR (CDCl₃; 300 MHz) δ 1.85-2.25 (m, 4H); 2.85-2.95 (m, 2H); 3.0-3.1 (m, 2H); 3.85 (s, 3H); 3.9-4.1 (m, 4H); 4.95-5.00 (m, 1H); 5.1 (s, 1H); 6.85 (d, 1H); 7.00 (d, 1H); 7.05 (d, 1H). ES-MS [M+H]+=313.2

Example 11

Synthesis of 2-{2-[4-Methoxy-3-(3R)-tetrahydrofuranyloxyphenyl]-1,3-dithian-2-yl}propanol

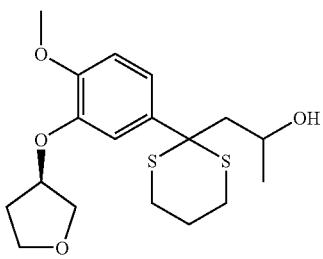

Solid 2-[4-methoxy-3-(3R)-tetrahydrofuranyloxyphenyl]-1,3-dithiane (2.5 g; 8 mmol) was added to an oven-dried flask equipped with a stir bar, septum and an inert gas line. Dry tetrahydrofuran (40 mL) was added and stirred at −40° C. using an acetonitrile/dry ice bath. To the resulting solution was added n-butyl lithium (2.5M in hexanes; 4.2 mL; 10.4 mmol) via syringe over 15 minutes. After stifling at 40° C. for thirty minutes, HMPA (1.4 mL; 8 mmol) was injected over two minutes and stirred for 10 minutes followed by rapid addition of propylene oxide (0.62 mL; 8.8 mmol). After stirring at −40° C. for 1 hour, the reaction was quenched with aqueous ammonium chloride (5 mL), diluted with water (30 mL) and extracted with ethyl acetate (70 mL). The organic layer was washed with 25 mL of water and 25 mL of brine, dried over anhydrous sodium sulfate and evaporated to yield 3.5 g of a viscous yellow oil. The crude alcohol was purified by flash chromatography on silica gel using a 20-60% ethyl acetate/hexane gradient affording the product as a colorless, viscous oil (2.7 g; 91%). $^1$H NMR (CDCl$_3$; 300 MHz) δ 1.1 (d, 3H); 2.0-2.5 (m, 7H); 2.75 (m, 4H); 3.8 (s, 3H); 3.9-4.1 (m, 5H); 5.0 (m, 1H) 6.9 (d, 1H); 7.5 (m, 2H). ES-MS [M+H]+=371.2

The following compound was synthesized in a similar manner with different starting materials:
1-{2-[4-Methoxy-3-(3R)-tetrahydrofuranyloxyphenyl]-1,3-dithian-2-yl}butan-2-ol.

Example 12

Synthesis of 1-{2-[4-Methoxy-3-(3R)-tetrahydrofuranyloxyphenyl]-1,3-dithian-2-yl}propan-2-one

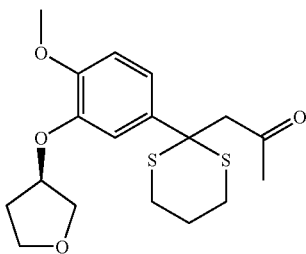

1-{2-[4-Methoxy-3-(3R)-tetrahydrofuranyloxyphenyl]-1,3-dithian-2-yl}propan-2-ol (158 mg; 0.42 mmol) was stirred in dichloromethane (5 mL) and treated with Dess Martin periodinane (15% solution in dichloromethane; 356 mg; 0.84 mmol) and stirred at room temperature for 15 minutes. The solvent was concentrated under reduced pressure and the residue was loaded onto a column of silica gel and eluted with a 20-60% ethyl acetate/hexane gradient. The product was isolated as an oil (23 mg; 15%). $^1$H NMR (CDCl$_3$; 300 MHz) δ 2.0 (s, 3H); 2.1-2.5 (m, 4H); 2.8 (m, 4H); 3.2 (s, 2H); 3.8-4.2 (m, 7H); 5.0 (m, 1H); 6.9 (m, 1H); 7.5 (m, 2H). ES-MS [M+H]+=369.1.

The following compound was synthesized in a similar manner with different starting materials:
1-{2-[4-Methoxy-3-(3R)-tetrahydrofuranyloxyphenyl]-1,3-dithian-2-yl}butan-2-one.

Alternative Method for Example 12

1-{2-[4-Methoxy-3-(3R)-tetrahydrofuranyloxyphenyl]-1,3-dithian-2-yl}propan-2-ol (119 mg; 0.32 mmol) was stirred in dichloromethane (5 mL) and treated with Dess-Martin periodinane (15% solution in dichloromethane; 173 mg; 0.41 mmol) and stirred at room temperature for 10 minutes. Upon formation of a precipitate, thin layer chromatography analysis using hexane/ethyl acetate (1:1 v/v) determined the reaction to be complete. The reaction was diluted with dichloromethane (40 mL) and washed with 20 mL portions of aqueous sodium bicarbonate and brine. The organic layer was dried over anhydrous sodium sulfate and evaporated to a crude solid, which was used as such in Example 7.

Example 13

Synthesis of 1-(2-Methoxybenzyl)-5-[4-methoxy-3-3R)-tetrahydrofuranyloxy-phenyl]-3-methyl-1H-pyrazole

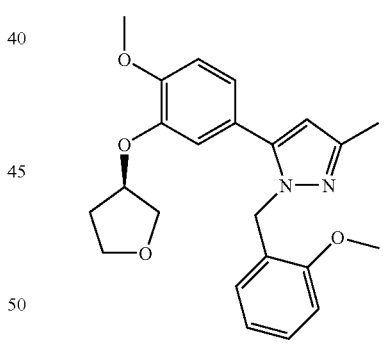

1-{2-[4-Methoxy-3-(3R)-tetrahydrofuranyloxyphenyl]-1,3-dithian-2-yl}propan-2-one (115 mg, 0.32 mmol) was reconstituted in toluene (5 mL) and treated with 2-methoxybenzyl hydrazine dihydrochloride (144 mg; 0.64 mmol) and molecular sieves (4A; 500 mg). The reaction was heated at 100° C. for two hours and cooled to room temperature. Molecular sieves were removed via filtration and the filtrate was diluted with ethyl acetate (50 mL), washed with 20 mL portions of water and brine. The organic layer was dried over anhydrous sodium sulfate and concentrated to an oil. The product was isolated by flash chromatography on silica gel using a 20-50% ethyl acetate/hexane gradient to afford 57 mg (45%) of 1-(2-methoxybenzyl)-5-[4-methoxy-3-(3R)-tetrahydrofuranyloxyphenyl]-3-methyl-1H-pyrazole as a yellow foam. $^1$H NMR (CDCl$_3$; 300 MHz) δ 1.7-2.0 (m, 2H); 2.3 (s, 3H); 3.6-4.0 (m, 10H); 4.5 (m, 1H); 5.3 (s, 2H); 6.2 (s, 1H); 6.6 (m, 1H); 6.7 (d, 1H): 6.8-7.0 (m, 4H); 7.2 (d, 1H). ES-MS [M+H]+=395.3

The following compounds were synthesized in a similar manner with different starting materials:

1-Benzyl-5-[4-methoxy-3-(3R)-tetrahydrofuranyloxyphenyl]-3-methyl-1H-pyrazole;

5-[4-Methoxy-3-(3R)-tetrahydrofuranyloxyphenyl]-3-methyl-1-phenyl-1H-pyrazole;

1-Cyclohexyl-5-[4-methoxy-3-3R)-tetrahydrofuranyloxyphenyl]-3-methyl-1H-pyrazole;

1-(1-Butyl)-5-[4-methoxy-3-(3R)-tetrahydrofuranyloxyphenyl]-3-methyl-1H-pyrazole;

1-(2-Fluorophenyl)-5-[4-methoxy-3-(3R)-tetrahydrofuranyloxyphenyl]-3-methyl-1H-pyrazole;

1-(4-Chlorophenyl)-5-[4-methoxy-3-(3R)-tetrahydrofuranyloxyphenyl]-3-methyl-1H-pyrazole;

3-Ethyl-1-(2-methoxybenzyl)-5-[4-methoxy-3-(3R)-tetrahydrofuranyloxyphenyl]-1H-pyrazole;

1-Cyclohexyl-3-ethyl-5-[4-methoxy-3-(3R)-tetrahydrofuranyloxyphenyl]-1H-pyrazole;

1-Benzyl-3-ethyl-5-[4-methoxy-3-(3R)-tetrahydrofuranyloxyphenyl]-1H-pyrazole;

Ethyl 3-ethyl-[5-(4-methoxy-3-(3R)-tetrahydrofuranyloxyphenyl)-1H-pyrazol-1-yl]acetate;

1-(2,3-Dimethylphenyl)-3-ethyl-5-[4-methoxy-3-(3R)-tetrahydrofuranyloxyphenyl]-1H-pyrazole;

1-(3,4)-Dimethylphenyl)-3-ethyl-5-[4-methoxy-3-(3R)-tetrahydrofuranyloxyphenyl]-1H-pyrazole;

3-Ethyl-5-[4-methoxy-3-(3R)-tetrahydrofuranyloxyphenyl]-1-(2-methylphenyl)-1H-pyrazole;

1-(2-Benzothiazolyl)-5-[4-methoxy-3-(3R)-tetrahydrofuranyloxyphenyl]-3-methyl-1H-pyrazole;

1-(3,4-Dimethylphenyl)-5-[4-methoxy-3-(3R)-tetrahydrofuranyloxyphenyl]-3-methyl-1H-pyrazole;

1-(2,3-Dimethylphenyl)-5-[4-methoxy-3-(3R)-tetrahydrofuranyloxyphenyl]-3-methyl-1H-pyrazole;

5-[4-Methoxy-3-(3R)-tetrahydrofuranyloxyphenyl]-3-methyl-1-(3-nitrophenyl)-1H-pyrazole;

5-[4-Methoxy-3-(3R)-tetrahydrofuranyloxyphenyl]-3-methyl-1-(2-methylphenyl)-1H-pyrazole;

5-[4-Methoxy-3-(3R)-tetrahydrofuranyloxyphenyl]-3-methyl-1-(2-phenylethyl)-1H-pyrazole;

5-[4-Methoxy-3-(3R)-tetrahydrofuranyloxyphenyl]-3-methyl-1-(4-trifluoromethoxyphenyl)-1H-pyrazole;

5-[4-Methoxy-3-(3R)-tetrahydrofuranyloxyphenyl]-1-(2-methoxycarbonyl-3-thienyl)-3-methyl-1H-pyrazole;

1-[2-(6-Fluoropyridyl)]-5-[4-methoxy-3-(3R)-tetrahydrofuranyloxyphenyl]-3-methyl-1H-pyrazole;

5-[4-Methoxy-3-(3R)-tetrahydrofuranyloxyphenyl]-3-methyl-1-(2-pyridyl)-1H-pyrazole;

1-[2-(6-Chloropyridyl)]-5-[4-methoxy-3-(3R)-tetrahydrofuranyloxyphenyl]-3-methyl-1H-pyrazole.

Example 14

Synthesis of 1-(3,4-Difluorobenzyl)-5-[4-methoxy-3-(3R)-tetrahydrofuranyloxy-phenyl]-1H-pyrazole

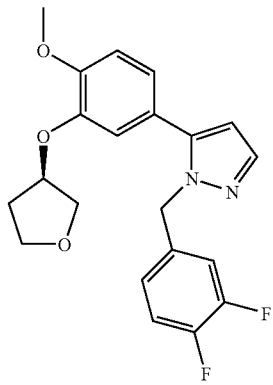

2-{4-Methoxy-3-(3R)-tetrahydrofuranyloxyphenyl}-5,5-dimethyl-[1,3,2]dioxaborinane (87 mg, 0.28 mmol), 5-bromo-1-(3,4-difluorobenzyl)-1H-pyrazole (65 mg, 0.23 mmol), Pd(PPh$_3$)$_2$Cl$_2$ (37 mg. 0.004 mmol), 2 M Na$_2$CO$_3$ aqueous solution (0.2 mL) and 3 mL of a solvent mixture which consisted of 7:3:2::DME:H$_2$O:EtOH was placed into a 2.0-5.0 mL Smith Process vial. This was sealed and placed into a Personal Chemistry Emrys Optimizer, stirred for 30 seconds, and then heated to 140° C. for 120 seconds. The solution was then diluted with 10 mL water and 10 mL ethyl acetate. The organic layer was separated, dried over Na$_2$SO$_4$, filtered and the solvent was removed. Purification by silica gel column chromatography using a gradient elution from 10% to 50% ethyl acetate in hexanes provided 72 mg (79%) of 1-(3,4-difluorobenzyl)-5-[4-methoxy-3-(3R)-tetrahydrofuranyloxyphenyl]-1H-pyrazole as a clear oil. $^1$H-NMR (CDCl$_3$, 300 MHz) δ 7.6 (d, 1H), 7.1-6.8 (m, 5H), 6.7 (d, 1H), 6.3 (d, 1H), 5.3 (s, 2H), 4.8 (m, 1H), 4.0-3.8 (m, 7H), 2.1-2.0 (m, 2H). (M+1)=387.2

The following compounds were synthesized in a similar manner with different starting materials:

1-(2,3-Difluorobenzyl)-5-(3,4-dimethoxyphenyl)-1H-pyrazole;

5-[4-Methoxy-3-(3R)-tetrahydrofuranyloxyphenyl]-1-(4-methylbenzyl)-1H-pyrazole;

1-(4-tert-Butylbenzyl)-5-[4-methoxy-3-(3R)-tetrahydrofuranyloxyphenyl]-1H-pyrazole;

5-[4-Methoxy-3-(3R)-tetrahydrofuranyloxyphenyl]-1-(4-trifluoromethylbenzyl)-1H-pyrazole;

1-(3,4-Difluorobenzyl)-5-[4-methoxy-3-(3R)-tetrahydrofuranyloxyphenyl]-1H-pyrazole;

1-(2-Fluorobenzyl)-5-[4-methoxy-3-(3R)-tetrahydrofuranyloxyphenyl]-1H-pyrazole;

5-[4-Methoxy-3-(3R)-tetrahydrofuranyloxyphenyl]-1-(3-nitrobenzyl)-1H-pyrazole;

5-[4-Methoxy-3-(3R)-tetrahydrofuranyloxyphenyl]-1-(4-methoxycarbonylbenzyl)-1H-pyrazole;

1-(3-Fluorobenzyl)-5-[4-methoxy-3-(3R)-tetrahydrofuranyloxyphenyl]-1H-pyrazole;

1-(3,5-Dimethoxybenzyl)-5-[4-methoxy-3-(3R)-tetrahydrofuranyloxyphenyl]-1H-pyrazole;

1-Benzyl-5-[4-methoxy-3-(3R)-tetrahydrofuranyloxyphenyl]-1H-pyrazole;

1-(3-Methoxybenzyl)-5-[4-methoxy-3-(3R)-tetrahydrofuranyloxyphenyl]-1H-pyrazole;

1-(4-Fluorobenzyl)-5-[4-methoxy-3-(3R)-tetrahydrofuranyloxyphenyl]-1H-pyrazole;

1-(3,4-Difluorobenzyl)-5-(3-fluoro-4-methoxyphenyl)-1H-pyrazole;

5-(3-Fluoro-4-methoxyphenyl)1-(4-methoxycarbonylbenzyl)-1H-pyrazole; pyrazole;

1-(2,6-Difluorobenzyl)-5-[4-methoxy-3-(3R)-tetrahydrofuranyloxyphenyl]1H-pyrazole;

1-(4-Fluorobenzyl)-5-(3-fluoro-4-methoxyphenyl)-1H-pyrazole; and 44) 1-(4-fluorobenzyl)-5-{4-methoxy-3-[(3R)-tetrahydrofuran-3-yloxy]phenyl}-4-methyl-1H-pyrazole LC/MS (EI) $t_R$ 4.2 (Method C), m/z 383.1 (M$^+$+1).

Example 15

Synthesis of 2-[4-Methoxy-3-(3R)-tetrahydrofuranyloxyphenyl]-5,5-dimethyl-[1,3,2]dioxaborinane

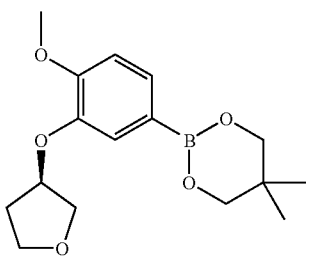

1-Bromo-4-methoxy-3-(3R)-tetrahydrofuranyloxybenzene (500 mg, 1.83 mmol) was added to a flask containing 10 mL of THF. This was cooled to −78° C. under argon and butyllithium (1.5 mL, 2.5 M) was slowly added. After stirring at −78° C. for 1.5 hours, trimethyl borate (0.41 mL, 3.7 mmol) in 10 mL of THF was added and the mixture was allowed to warm to room temperature overnight. The reaction was quenched by the addition of 20 mL of an aqueous saturated solution of NH$_4$Cl and 20 mL of diethyl ether. The organic layer was washed with 10 mL of water, 10 mL of brine, dried over Na$_2$SO$_4$, and concentrated. The residue was dissolved in 18 mL of toluene and 270 mg of (2.6 mmol) 2,2-dimethylpropane-1,3-diol was added. This was heated to reflux for 4 hours, concentrated, and diluted with hexanes. The insoluble material was washed three times with hexanes. The combined organic layer was removed and the product was purified using column chromatography using a gradient elution from 10% to 100% ethyl acetate in hexanes to give 198 mg (35%) of 2-[4-methoxy-3-(3R)-tetrahydrofuranyloxyphenyl]-5,5-dimethyl-[1,3,2]dioxaboriane as a clear oil. $^1$H-NMR (CDCl$_3$, 300 MHz) δ 7.4 (d, 1H), 7.3 (d, 1H), 6.9 (d, 1H), 5.0 (m, 1H), 4.0 (m, 3H), 3.9-3.8 (n 4H), 3.7, (s, 4H), 2.1 (m, 2H) 1.0 (s, 6H).

Example 16

Synthesis of 1-[4-Methoxy-3-(3R)-tetrahydrofuranyloxyphenyl]ethanol

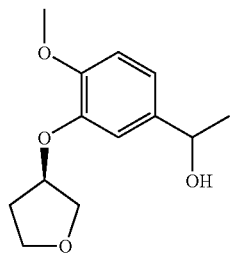

A flask containing 1.7 g (7.5 mmol) of 4-methoxy-3-(3R)-tetrahydrofuranyloxybenzaldehyde and 75 mL of THF was cooled to −78° C. under argon and 5.0 mL (3 M) of MeMgCl was slowly added. The reaction was stirred at room temperature for 12 hours and was quenched by the addition of 100 mL of saturated aqueous NH$_4$Cl. The aqueous layer was extracted with 3×50 mL of ethyl acetate and the combined organic extracts were dried over Na$_2$SO$_4$, filtered and concentrated. Purification by silica gel column chromatography using a gradient elution from 50% to 100% ethyl acetate in hexanes yielded 1.46 g (80%) of 1-[4-methoxy-3-(3R)-tetrahydrofuranyloxyphenyl]-ethanol as a white solid. $^1$H-NMR (CDCl$_3$, 300 MHz) δ 6.9 (m, 3H), 5.0 (m, 1H), 4.8 (m, 1H), 4.0-3.8 (m, 4H), 3.8 (s, 3H), 2.1 (m, 2H), 1.4 (d, 3H). (M−H$_2$O+1)=221.2

Example 17

Synthesis of 1-[4-Methoxy-3-(3R)-tetrahydrofuranyloxyphenyl]ethanone

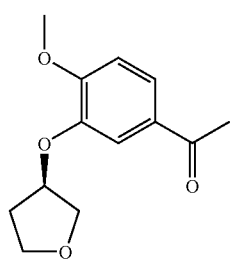

Pyridium chlorochromate (2.8 g; 12.3 mmol) was added to a flask containing 1.46 g (6.1 mmol) of 1-[4-methoxy-3-(3R)-tetrahydrofuranyloxyphenyl]ethanol and 65 mL of CH$_2$Cl$_2$. The mixture was stirred at room temperature for one hour and the solids were filtered through silica gel, rinsing with 200 mL ethyl acetate. The solvent was removed and the residue was purified by column chromatography using a gradient elution from 20% to 50% ethyl acetate in hexanes to give 1.2 g (83%) of 1-[4-methoxy-3-(3R)-tetrahydrofuranyloxyphenyl]ethanone as a white solid. $^1$H-NMR (CDCl$_3$, 300 MHz) δ 7.5 (d, 1H), 7.4 (d, 1H), 6.8 (d, 1H); 4.9 (m, 1H), 4.0-3.9 (m, 3H), 3.8 (m, 4H), 2.5 (s, 3H), 2.1 (m, 2H). (M+1)=237.2.

Example 18

Synthesis of 3-[4-Methoxy-3-(3R)-tetrahydrofuranyloxyphenyl]-3-oxopropionaldehyde

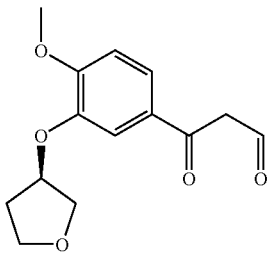

A suspension of sodium hydride (60% suspension in mineral oil, 210 mg, 5.25 mmol) in 4 mL of THF under argon was treated sequentially with 0.4 mL (4.77 mmol) of ethyl formate and a solution of 939 mg (3.98 mmol) of 1-[4-methoxy-3-(3R)-tetrahydrofuranyloxyphenyl]ethanone in 2 mL of THF. The resulting mixture was stirred at room temperature for 4 hours, and then acidified with 0.5 N HCl to pH 2 and extracted with 3×10 mL of ethyl acetate. The organic layer was dried over Na$_2$SO$_4$, filtered and the solvent removed. Purification by column chromatography on silica gel using a gradient elution from 20% to 50% ethyl acetate in hexanes famished 218 mg (21%) of 3-[4-methoxy-3-(3R)-tetrahydrofuranyloxyphenyl]-3-oxopropionaldehyde as a yellow solid. $^1$H-NMR (CDCl$_3$, 300 MHz) δ 8.0 (s, 1H), 7.6-7.5 (m, 2H), 7.4 (d, 1H), 6.1 (d, 1H), 5.0 (m, 1H), 4.0 (m, 4H), 3.9 (s, 3H), 2.2 (m, 2H). (M+1)=265.2

The following compounds were synthesized in a similar manner with different starting materials:

4,4,4-trifluoro-1-{4-methoxy-3-[(3R)-tetrahydrofuran-3-yloxy]phenyl}butane-1,3-dione;

Ethyl 1-[4-methoxy-3-(3R)-tetrahydrofuranyloxyphenyl]-1,3-dionebutanoate.

Example 19

Synthesis of 3-Dimethylamino-1-[4-methoxy-3-(3R)-tetrahydrofuranyloxyphenyl]propenone

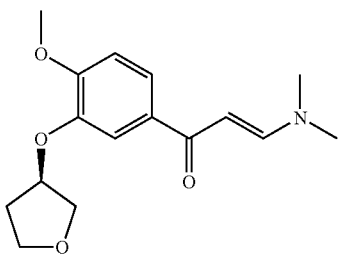

To a solution of 440 mg (1.86 mmol) of 1-[4-methoxy-3-(3R)-tetrahydrofuranyloxyphenyl]-ethanone in 15 mL of DMF was added 0.30 mL (2.24 mmol) of N,N-dimethylformamide dimethyl acetal. The resulting mixture was heated to 140° C. for 16 hours, then cooled to room temperature and quenched by the addition of 25 mL of water. The mixture was extracted with 4×25 mL of ethyl acetate and the combined organic fractions were dried over Na$_2$SO$_4$, filtered and concentrated. Purification by column chromatography over silica gel using a gradient elution from 100% CH$_2$Cl$_2$ to 90:10:5:: CH$_2$Cl$_2$:MeOH:NH$_4$OH provided 257 mg (56%) of 3-dimethylamino-1-[4-methoxy-3-(3R)-tetrahydrofuranyloxyphenyl]propenone as a yellow oil and 115 mg of the starting ketone. $^1$H-NMR (CDCl$_3$, 300 MHz) δ 8.0 (s, 1H), 7.7 (d, 1H), 7.5 (m, 2H), 6.9 (d, 1H), 5.7 (d, 1H), 5.1 (m, 1H), 4.0 (m, 3H), 3.9 (s, 4H), 2.9 (s, 3H), 2.8 (s, 3H), 2.2 (m, 2H). (M+1)=292.1

The following compounds were synthesized in a similar manner with different starting materials:

(2E)-3-(dimethylamino)-1-(3-fluoro-4-methoxyphenyl)prop-2-en-1-one;

(2E)-1-(3,4-dimethoxyphenyl)-3-(dimethylamino)prop-2-en-1-one;

(E)-1-(3-Bromo-4-methoxy-phenyl)-3-dimethylamino-propenone;

(2E)-1-[3,4-bis(difluoromethoxy)phenyl]-3-(dimethylamino)prop-2-en-1-one;

(2E)-1-[4-(difluoromethoxy)-3-methoxyphenyl]-3-(dimethylamino)prop-2-en-1-one.

Example 20

Synthesis of 1-(4-Methoxyphenyl)-5-[4-methoxy-3-(3R)-tetrahydrofuranyloxy-phenyl]-1H-pyrazole

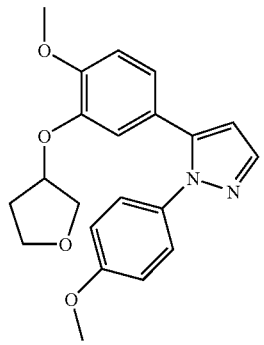

3-[4-Methoxy-3-(3R)-tetrahydrofuranyloxyphenyl]-3-oxopropionaldehyde (45 mg, 0.17 mmol), 4-methoxyphenyl hydrazine hydrochloride (36 mg, 0.20 mmol) and 1.7 mL of ethanol were combined in a 0.5-2.0 mL Smith Process Vial. The vial was sealed and heated to 140° C. for 300 seconds using a Personal Chemistry Emrys Optimizer. The solvent was removed and purification by silica gel column chromatography using a gradient elution from 20% to 100% ethyl acetate in hexanes provided 40 mg (65%) of 1-(4-methoxyphenyl)-5-[4-methoxy-3-(3R)-tetrahydrofuranyloxyphenyl]-1H-pyrazole as a brown solid. $^1$H-NMR (CDCl$_3$, 300 MHz) δ 7.6 (d, 1H), 7.2 (m, 2H), 6.9 (m, 4H), 6.5 (d, 1H, 6.4 (d, 1H, 4.6 (m, 1H, 3.9-3.7 (m, 10H), 1.9 (m, 2H). (M+1)=367.2

The following compounds were synthesized in a similar manner with different starting materials:

Ethyl 1-Benzyl-5-[4-methoxy-3-(3R)-tetrahydrofuranyloxyphenyl]-1H-pyrazole-3-carboxylate;

1-Benzyl-5-[4-methoxy-3-(3R)-tetrahydrofuranyloxyphenyl]-3-trifluoromethyl-1H-pyrazole;

5-[4-Methoxy-3-(3R)-tetrahydrofuranyloxyphenyl]-1-phenyl-3-trifluoromethyl-1H-pyrazole;

Ethyl [5-(4-methoxy-3-(3R)-tetrahydrofuranyloxyphenyl)-3-trifluoromethyl-1H-pyrazol-1-yl]acetate;

[5-(4-Methoxy-3-(3R)-tetrahydrofuranyloxyphenyl)-3-trifluoromethyl-1H-pyrazol-1-yl]acetic acid;

Isopropyl [5-(4-methoxy-3-(3R)-tetrahydrofuranyloxyphenyl)-3-trifluoromethyl-1H-pyrazol-1-yl]acetate;

1-(3-Fluorobenzyl)-5-[4-methoxy-3-(3R)-tetrahydrofuranyloxyphenyl]-3-trifluoromethyl-1H-pyrazole;

5-[4-Methoxy-3-(3R)-tetrahydrofuranyloxyphenyl]-1-phenyl-1H-pyrazole;

1-Cyclohexyl-5-[4-methoxy-3-(3R)-tetrahydrofuranyloxyphenyl]-1H-pyrazole;

Ethyl 1-Benzyl-5-[4-methoxy-3-(3R)-tetrahydrofuranyloxyphenyl]-1H-pyrazole-3-carboxylate;

1-(4-Methoxyphenyl)-5-[4-methoxy-3-(3R)-tetrahydrofuranyloxyphenyl]-1H-pyrazole;

5-[4-Methoxy-3-(3R)-tetrahydrofuranyloxyphenyl]-1-(2-phenylethyl)-1H-pyrazole;

1-(4-Fluorophenyl)-5-[4-methoxy-3-(3R)-tetrahydrofuranyloxyphenyl]-1H-pyrazole;

1-(4-Bromophenyl)-5-[4-methoxy-3-(3R)-tetrahydrofuranyloxyphenyl]-1H-pyrazole;

5-[4-Methoxy-3-(3R)-tetrahydrofuranyloxyphenyl]-1-(4-trifluoromethoxyphenyl)-1H-pyrazole;

5-[4-Methoxy-3-(3R)-tetrahydrofuranyloxyphenyl]-1-(2-pyridyl)-1H-pyrazole;

1-(2-Benzothiazolyl)-5-[4-methoxy-3-(31R)-tetrahydrofuranyloxyphenyl]-1H-pyrazole;

5-(3-Fluoro-4-methoxyphenyl)-1-(4-methoxyphenyl)-1H-pyrazole;

1-(2-Methoxyphenyl)-5-[(4-methoxy-3-(3R)-tetrahydrofuranyloxyphenyl]-1H-pyrazole;

1-[2-(6-Fluoropyridyl)]-5-[4-methoxy-3-(3R)-tetrahydrofuranyloxyphenyl]-1H-pyrazole.

Example 21

Synthesis of 1-(4-Methoxyphenyl)-5-[4-methoxy-3-(3R)-tetrahydrofuranyloxyphenyl]-1H-pyrazole

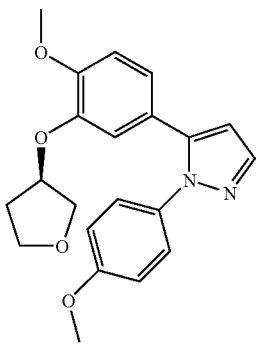

3-Dimethylamino-1-[4-methoxy-3-(3R)-tetrahydrofuranyloxyphenyl]propenone, (461 mg, 1.6 mmol), 4-methoxyphenyl hydrazine hydrochloride (304 mg, 1.74 mmol), and 5 mL of ethanol were combined in a 2.0-5.0 mL Smith Process Vial. The vial was sealed and heated to 140° C. for 300 seconds, quenched with 10 mL of water, and the aqueous layer was extracted with 3×10 mL of ethyl acetate. The combined organic fractions were dried over $Na_2SO_4$, filtered and concentrated. Purification by silica gel column chromatography using a gradient elution from 20% to 100% ethyl acetate in hexanes provided 436 mg (75%) of 1-(4-methoxyphenyl)-5-[4-methoxy-3-(3R)-tetrahydrofuranyloxyphenyl]-1H-pyrazole as a brown solid. $^1$H-NMR ($CDCl_3$, 300 MHz) δ 7.6 (d, 1H), 7.2 (m, 2H), 6.9 (m, 4H), 6.5 (d, 1H), 6.4 (d, 1H), 4.6 (m, 1H), 3.9-3.7 (m, 10H), 1.9 (m, 2H). (M+1)=367.2

The following compounds were synthesized in a similar manner with different starting materials:

1-Benzyl-5-(3-fluoro-4-methoxyphenyl)-1H-pyrazole;

Ethyl 2-{5-[4-methoxy-3-(3R)-tetrahydrofuranyloxyphenyl]pyrazol-1-yl}acetate;

5-(3,4-Dimethoxyphenyl)-1-(4-fluorobenzyl)-1H-pyrazole;

5-(3,4-Dimethoxyphenyl)-1-(4-methoxyphenyl)-1H-pyrazole;

3-[(1-Cyclopentyl-3-ethylindazol)-6-yl]-1-(4-carboxyphenyl)-1H-pyrazole;

3-[(1-Cyclopentyl-3-ethylindazol)-6-yl]-1-(4-methoxyphenyl)-1H-pyrazole;

5-[4-Methoxy-3-(3R)-tetrahydrofuranyloxyphenyl]-1-[4-(4-morpholinyl)phenyl]-1H-pyrazole;

1-(4-Carboxyphenyl)-5-(4-methoxy-3-(3R)-tetrahydrofuranyloxyphenyl)-1H-pyrazole;

1) 1-cyclopentyl-3-ethyl-6-[1-(4-methoxyphenyl)-1H-pyrazol-5-yl]-1H-indazole; LC/MS (EI) $t_R$ 5.55 (Method C), m/z 387.3 ($M^+$+1)

2) 4-[5-(1-cyclopentyl-3-ethyl-1H-indazol-6-yl)-1H-pyrazol-1-yl]benzoic acid; LC/MS (EI) $t_R$ 4.82 (Method C), m/z 401.2 ($M^+$+1)

3) 1-cyclopentyl-3-ethyl-6-(1-pyridin-2-yl-1H-pyrazol-5-yl)-1H-indazole; LC/MS (EI) $t_R$ 4.79 (Method C), m/z 358.3 ($M^+$+1)

4) 1-cyclopentyl-6-[1-(3,4-difluorophenyl)-1H-pyrazol-5-yl]-3-ethyl-1H-indazole; LC/MS (EI) $t_R$ 5.95 (Method C), m/z 393.3 ($M^+$+1)

5) 6-(1-benzyl-1H-pyrazol-5-yl)-1-cyclopentyl-3-ethyl-1H-indazole; LC/MS (EI) $t_R$ 5.92 (Method C), m/z 371.3 ($M^+$+1)

6) 1-cyclopentyl-3-ethyl-6-(1-pyridin-4-yl-1H-pyrazol-5-yl)-1H-indazole; LC/MS (EI) $t_R$ 3.81 (Method C), m/z 358.2 ($M^+$+1)

7) 1-cyclopentyl-3-ethyl-6-(1-piperidin-4-yl-1H-pyrazol-5-yl)-1H-indazole; LC/MS (EI) $t_R$ 2.24 (Method C), m/z 364.2 ($M^+$+1)

13) 1-cyclopentyl-3-ethyl-6-{1-[4-(trifluoromethoxy)phenyl]-1H-pyrazol-5-yl}-1H-indazole; LC/MS (EI) $t_R$ 7.99 (Method E), m/z 441.2 ($M^+$+1)

14) 1-cyclopentyl-3-ethyl-6-[1-(4-fluorophenyl)-1H-pyrazol-5-yl]-1H-indazole; LC/MS (EI) $t_R$ 6.65 (Method E), m/z 375.2 ($M^+$+1)

15) 4-[5-(1-cyclopentyl-3-ethyl-1H-indazol-6-yl)-1H-pyrazol-1-yl]benzonitrile; LC/MS (EI) $t_R$ 6.32 (Method E), m/z 382.2 ($M^+$+1)

16) 6-[1-(4-chlorophenyl)-1H-pyrazol-5-yl]-1-cyclopentyl-3-ethyl-1H-indazole; LC/MS (EI) $t_R$ 391.2/393.1 (Method E), m/z 7.76 ($M^+$+1)

17) 1-cyclopentyl-3-ethyl-6-[1-(4-methylphenyl)-1H-pyrazol-5-yl]-1H-indazole, LC/MS (EI) $t_R$ 7.14 (Method E), m/z 371.2 ($M^+$+1)

18) 4-[5-(1-cyclopentyl-3-ethyl-1H-indazol-6-yl)-1H-pyrazol-1-yl]benzenesulfonamide, LC/MS (EI) $t_R$ 4.31 (Method C), m/z 436.1 ($M^+$+1)

22) 1-cyclopentyl-3-ethyl-6-{1-[4-(methylsulfonyl)phenyl]-1H-pyrazol-5-yl}-1H-indazole; LC/MS (EI) $t_R$ 4.83 (Method C), m/z 435.2 ($M^+$+1) and 26) 1-cyclopentyl-6-{1-[4-(difluoromethoxy)phenyl]-1H-pyrazol-5-yl}-3-ethyl-1H-indazole LC/MS (EI) $t_R$ 4.94 (Method C), m/z 423.1 (M$^+$+1)

29) 4-(5-{4-methoxy-3-[(3R)-tetrahydrofuran-3-yloxy]phenyl}-1H-pyrazol-1-yl)benzoic acid 30) 5-{4-methoxy-3-[(3R)-tetrahydrofuran-3-yloxy]phenyl}-1-[4-(methylsulfonyl)phenyl]-1H-pyrazole; LC/MS (EI) $t_R$ 3.2 (Method C), m/z 415.2 (M$^+$+1)

31) 2-(5-{4-methoxy-3-[(3R)-tetrahydrofuran-3-yloxy]phenyl}-1H-pyrazol-1-yl)-1,3-thiazole; LC/MS (EI) $t_R$ 3.39 (Method C), m/z 344.2 (M$^+$+1)

32) 1-benzyl-5-(3,4-dimethoxyphenyl)-1H-pyrazole; LC/MS (EI) $t_R$ 3.81 (Method C), m/z 295.3 (M$^+$+1)

33) 2-(5-{4-methoxy-3-[(3R)-tetrahydrofuran-3-yloxy]phenyl}-1H-pyrazol-1-yl)benzoic acid; LC/MS (EI) $t_R$ 2.85 (Method C), m/z 381.1 (M$^+$+1)

34) 3-(5-{4-methoxy-3-[(3R)-tetrahydrofuran-3-yloxy]phenyl}-1H-pyrazol-1-yl)benzoic acid; LC/MS (EI) $t_R$ 3.18 (Method C), m/z 381.2 (M$^+$+1)

40) 4-[5-(3,4-dimethoxyphenyl)-1H-pyrazol-1-yl]pyridine; LC/MS (EI) $t_R$ 2.11 (Method C), m/z 282.2 (M$^+$+1)

41) 4-(5-{4-methoxy-3-[(3R)-tetrahydrofuran-3-yloxy]phenyl}-1H-pyrazol-1-yl)pyridine; LC/MS (EI) $t_R$ 2.2 (Method C), m/z 338.1 (M$^+$+1)

42) 4-(5-{4-methoxy-3-[(3R)-tetrahydrofuran-3-yloxy]phenyl}-1H-pyrazol-1-yl)piperidine; LC/MS (EI) $t_R$ 2.07 (Method C), m/z 344.2 (M$^+$+1)

45) 5-(3-Bromo-4-methoxyphenyl)-1-(4-methoxyphenyl)-1H-pyrazole; LC/MS (EI) $t_R$ 4.51 (Method C), m/z 359.0/361.0 (M$^+$+1)

51) 1-Isobutyl-5-(4-methoxy-3-[(3R)-tetrahydrofuran-3-yloxy]phenyl)-1H-pyrazole; LC/MS (EI) $t_R$ 3.8, m/z 317.2 (M$^+$+1)

52) 5-[3,4-bis(difluoromethoxy)phenyl]-1-(4-methoxyphenyl)-1H-pyrazole; LC/MS (EI) $t_R$ 4.28 (Method C), m/z 383 (M$^+$+1)

56) 5-[4-(difluoromethoxy)-3-methoxyphenyl]-1-(4-methoxyphenyl)-1H-pyrazole, LC/MS (EI) $t_R$ 4.31, m/z 347.1 (M$^+$+1)

71) 4-(5-{4-methoxy-3-[(3R)-tetrahydrofuran-3-yloxy]phenyl}-1H-pyrazol-1-yl)benzenesulfonamide, LC/MS (EI) $t_R$ 3.29, m/z 416.1 (M$^+$+1)

72) 4-(5-{4-methoxy-3-[(3R)-tetrahydrofuran-3-yloxy]phenyl}-1H-pyrazol-1-yl)benzonitrile, LC/MS (EI) $t_R$ 3.98, m/z 362.1 (M$^+$+1)

82) 5-[3-(benzyloxy)-4-methoxyphenyl]-1-(4-fluorophenyl)-1H-pyrazole (prepared in 94% yield), 89) 5-[3,4-bis(difluoromethoxy)phenyl]-1-[4-(difluoromethoxy)phenyl]-1H-pyrazole; LC/MS (EI) $t_R$ 4.79 (Method C), m/z 419.1 (M$^+$+1)

90) 4-[5-(3-ethyl-2-methyl-2H-indazol-6-yl)-1H-pyrazol-1-yl]benzoic acid, LC/MS (EI) $t_R$ 3.24 (Method C), m/z 347.2 (M$^+$+1)

91) 1,3-diethyl-6-{1-[4-(methylsulfonyl)phenyl]-1H-pyrazol-5-yl}-1H-indazole, LC/MS (EI) $t_R$ 3.99 (Method C), m/z 395.2 (M$^+$+1)

92) 1-(cyclopropylmethyl)-3-ethyl-6-{1-[4-(methylsulfonyl)phenyl]-1H-pyrazol-5-yl}-1H-indazole, LC/MS (EI) $t_R$ 4.24 (Method C), m/z 421.2 (M$^+$+1)

93) 3-ethyl-1-isopropyl-6-{1-[4-(methylsulfonyl)phenyl]-1H-pyrazol-5-yl}-1H-indazole, LC/MS (EI) $t_R$ 4.31 (Method C), m/z 409.2 (M$^+$+1)

94) 3-ethyl-1-(2-methoxyethyl)-6-{1-[4-(methylsulfonyl)phenyl]-1H-pyrazol-5-yl}-1H-indazole, LC/MS (EI) $t_R$ 3.81 (Method C), m/z 425.2 (M$^+$+1)

96) 4-[5-(1-cyclopentyl-3-ethyl-1H-indazol-6-yl)-1H-pyrazol-1-yl]-N,N-dimethylbenzenesulfonamide, LC/MS (EI) $t_R$ 5.63 (Method C), m/z 464.2 (M$^+$+1)

97) 1-(ethoxymethyl)-3-ethyl-6-{1-[4-(methylsulfonyl)phenyl]-1H-pyrazol-5-yl}-1H-indazole, LC/MS (EI) $t_R$ 4.29 (Method C), m/z 425.1 (M$^+$+1)

113) 2-[5-(1-cyclopentyl-3-ethyl-1H-indazol-6-yl)-1H-pyrazol-1-yl]quinoxaline, LC/MS (EI) $t_R$ 4.78 (Method E), m/z 409.2 (M$^+$+1)

114) 1-{4-[5-(1-cyclopentyl-3-ethyl-1H-imidazol-6-yl)-1H-pyrazol-1-yl]phenyl}-N-methylmethanesulfonamide, LC/MS (EI) $t_R$ 3.12 (Method E), m/z 464.2 (M$^+$+1)

115) 1-(3-ethyl-6-{1-[4-(methylsulfonyl)phenyl]-1H-pyrazol-5-yl}-1H-indazol-1-yl)-2-methylpropan-2-ol, LC/MS (EI) $t_R$ 3.67 (Method A), m/z 439.2 (M$^+$+1)

122) 1-cyclopropyl-3-ethyl-6-(1-isopropyl-1H-pyrazol-5-yl)-1H-indazole, LC/MS (EI) $t_R$ 4.64 (Method A), m/z 295.2 (M$^+$+1)

123) 1-cyclopropyl-3-ethyl-6-(1-methyl-1H-pyrazol-5-yl)-1H-indazole, LC/MS (EI) $t_R$ 4.04 (Method A), m/z 267.1 (M$^+$+1)

124) 1-cyclopropyl-3-ethyl-6-(1H-pyrazol-5-yl)-1H-indazole, LC/MS (EI) $t_R$ 3.78 (Method A), m/z 253.2 (M$^+$+1)

125) 1-cyclopropyl-3-ethyl-6-(1-ethyl-1H-pyrazol-5-yl)-1H-indazole, LC/MS (EI) $t_R$ 4.36 (Method A), m/z 281.2 (M$^+$+1)

126) 1 cyclopropyl-3-ethyl-6-(1-pyridin-4-yl-1H-pyrazol-5-yl)-1H-indazole, LC/MS (EI) $t_R$ 3.27 (Method A), m/z 330.2 (M$^+$+1)

127) 2-[5-(1-cyclopropyl-3-ethyl-1H-indazol-6-yl)-1H-pyrazol-1-yl]quinoxaline, LC/MS (EI) $t_R$ 5.18 (Method A), m/z 381.1 (M$^+$+1)

130) 1-{4-[5-(1-cyclopropyl-3-ethyl-1H-indazol-6-yl)-1H-pyrazol-1-yl]phenyl}-N-methylmethanesulfonamide, LC/MS (EI) $t_R$ 3.98 (Method A), m/z 436.1 (M$^+$+1)

131) 1-cyclopropyl-3-ethyl-6-[1-(tetrahydro-2H-pyran-4-yl)-1H-pyrazol-5-yl]-1H-indazole, LC/MS (EI) $t_R$ 4.15 (Method A), m/z 337.2 (M$^+$+1)

132) 1-cyclopropyl-3-ethyl-6-[1-(tetrahydro-2H-pyran-4-yl)-1H-pyrazol-3-yl]-1H-indazole, LC/MS (EI) $t_R$ 4.34 (Method A), m/z 337.2 (M$^+$+1)

133) 1-cyclopropyl-6-[1-(1,1-dioxidotetrahydro-3-thienyl)-1H-pyrazol-5-yl]-3-ethyl-1H-indazole, LC/MS (EI) $t_R$ 4.45 (Method A), m/z 371.2 (M$^+$+1)

134) 6-(1-cyclopentyl-1H-pyrazol-5-yl)-1-cyclopropyl-3-ethyl-1H-indazole, LC/MS (EI) $t_R$ 5.30 (Method A), m/z 371.2 (M$^+$+1)

136) 1-cyclopropyl-3-ethyl-6-[1-(2,2,6,6-tetramethylpiperidin-4-yl)-1H-pyrazol-5-yl]-1H-indazole, LC/MS (EI) $t_R$ 4.86 (Method A), m/z 392.3 (M$^+$+1)

137) 6-{1-[3-(benzyloxy)phenyl]-1H-pyrazol-5-yl}-1-cyclopropyl-3-ethyl-1H-indazole, LC/MS (EI) $t_R$ 7.0 (Method E), m/z 435.2 (M$^+$+1)

139) 3-ethyl-1-isopropyl-6-{1-[4-(methylsulfonyl)phenyl]-1H-pyrazol-5-yl}-1H-pyrazolo[3,4-b]pyridine, LC/MS (EI) $t_R$ 5.09 (Method A), m/z 410.2 (M$^+$+1)

140) 2-{3-[5-(1-cyclopropyl-3-ethyl-1H-indazol-6-yl)-1H-pyrazol-1-yl]phenoxy}ethanol, LC/MS (EI) $t_R$ 2.99 (Method E), m/z 389.3 (M$^+$+1)

141) 6-{1-[4-(benzyloxy)phenyl]-1H-pyrazol-5-yl}-1-cyclopropyl-3-ethyl-1H-indazole, LC/MS (EI) $t_R$ 6.74 (Method E), m/z 435.3 (M$^+$+1)

142) 3-ethyl-6-{1-[4-(methylsulfonyl)phenyl]-1H-pyrazol-5-yl}-1-(tetrahydro-2H-pyran-4-yl)-1H-pyrazolo[3,4-b]pyridine, LC/MS (EI) $t_R$ 4.42 (Method A), m/z 452.2 (M$^+$+1)

144) (4-{5-[3-ethyl-1-(tetrahydro-2H-pyran-4-yl)-1H-pyrazolo[3,4-b]pyridin-6-yl]-1H-pyrazol-1-yl}phenyl)methanol, LC/MS (EI) $t_R$ 4.09 (Method A), m/z 404.2

147) 1-cyclopropyl-3-ethyl-6-[1-(3-methoxyphenyl)-1H-pyrazol-5-yl]-1H-indazole, LC/MS (EI) $t_R$ 4.38 (Method E), m/z 359.2 (M$^+$+1)

149) 1-cyclopropyl-3-ethyl-6-[1-(4-methoxyphenyl)-1H-pyrazol-5-yl]-1H-indazole, LC/MS (EI) $t_R$ 4.5 (Method E), m/z 359.2 (M$^+$+1)

150) 1-cyclopropyl-3-ethyl-6-(1-pyrimidin-2-yl-1H-pyrazol-5-yl)-1H-indazole, LC/MS (EI) $t_R$ 3.97 (Method A), m/z 331.2 (M$^+$+1)

151) 3-ethyl-1-(2-methoxypyridin-4-yl)-6-(1-pyrimidin-2-yl-1H-pyrazol-5-yl)-1H-indazole LC/MS (EI) $t_R$ 4.67 (Method A), m/z 398.2 (M$^+$+1)

152) 1-[4-(difluoromethoxy)phenyl]-5-{4-methoxy-3-[(3R)-tetrahydrofuran-3-yloxy]phenyl}-1H-pyrazole, LC/MS (EI) $t_R$ 3.94 (Method C), m/z 419.1 (M$^+$+1)

153) 1-cyclopentyl-3-ethyl-6-[1-(pyridin-4-ylmethyl)-1H-pyrazol-5-yl]-1H-indazole, LC/MS (EI) $t_R$ 3.17 (Method C), m/z 372.3 (M$^+$+1)

154) 4-[(5-{4-methoxy-3-[(3R)-tetrahydrofuran-3-yloxy]phenyl}-1H-pyrazol-1-yl)methyl]pyridine, LC/MS (EI) $t_R$ 1.84 (Method C), m/z 352.2 (M$^+$+1)

155) 4-[5-(3-ethyl-1-methyl-1H-indazol-6-yl)-1H-pyrazol-1-yl]benzoic acid, LC/MS (EI) $t_R$ 3.56 (Method C), m/z 3417.2 (M$^+$+1)

156) 4-[5-(3-ethyl-1-methyl-1H-indazol-6-yl)-1H-pyrazol-1-yl]benzenesulfonamide, LC/MS (EI) $t_R$ 3.27 (Method C), m/z 382.2 (M$^+$+1)

157) 3-ethyl-1-methyl-6-{1-[4-(methylsulfonyl)phenyl]-1H-pyrazol-5-yl}-1H-indazole, LC/MS (EI) $t_R$ 3.56 (Method C), m/z 381.3 (M$^+$+1)

158) 4-[5-(3-ethyl-1-methyl-1H-indazol-6-yl)-1H-pyrazol-1-yl]benzonitrile, LC/MS (EI) $t_R$ 4.15 (Method C), m/z 328.2 (M$^+$+1)

159) 4-[5-(3-ethyl-2-methyl-2H-indazol-6-yl)-1H-pyrazol-1-yl]benzenesulfonamide, LC/MS (EI) $t_R$ 2.97 (Method C), m/z 382.2 (M$^+$+1)

160) 3-ethyl-2-methyl-6-{1-[4-(methylsulfonyl)phenyl]-1H-pyrazol-5-yl}-2H-indazole, LC/MS (EI) $t_R$ 3.22 (Method C), m/z 381.3 (M$^+$+1)

161) 4-[5-(3-ethyl-2-methyl-2H-indazol-6-yl)-1H-pyrazol-1-yl]benzonitrile, LC/MS (EI) $t_R$ 3.65 (Method C), m/z 328.2 (M$^+$+1)

162) 6-{1-[4-(difluoromethoxy)phenyl]-1H-pyrazol-5-yl}-3-ethyl-1-(tetrahydro-2H-pyran-4-yl)-1H-pyrazolo[3,4-b]pyridine, LC/MS (EI) $t_R$ 440.2 (Method E), m/z 4.56 (M$^+$+1)

163) 3-ethyl-6-[1-(4-fluorophenyl)-1H-pyrazol-5-yl]-1-(tetrahydro-2H-pyran-4-yl)-1H-pyrazolo[3,4-b]pyridine, LC/MS (EI) $t_R$ 4.26 (Method E), m/z 392.2 (M$^+$+1)

164) 3-ethyl-6-(1-pyridin-4-yl-1H-pyrazol-5-yl)-1-(tetrahydro-2H-pyran-4-yl)-1H-pyrazolo[3,4-b]pyridine, LC/MS (EI) $t_R$ ×2.57 (Method E), m/z 375.2 (M$^+$+1)

165) 3-ethyl-6-(1-phenyl-1H-pyrazol-5-yl)-1-(tetrahydro-2H-pyran-4-yl)-1H-pyrazolo[3,4-b]pyridine, LC/MS (EI) $t_R$ 4.2 (Method E), m/z 374.3 (M$^+$+1)

166) 3-ethyl-6-(1-pyrimidin-2-yl-1H-pyrazol-5-yl)-1-(tetrahydro-2H-pyran-4-yl)-1H-pyrazolo[3,4-b]pyridine, LC/MS (EI) $t_R$ 2.55 (Method E), m/z 376.2 (M$^+$+1)

167) 3-ethyl-6-[1-(3-fluorophenyl)-1H-pyrazol-5-yl]-1-(tetrahydro-2H-pyran-4-yl)-1H-pyrazolo[3,4-b]pyridine, LC/MS (EI) $t_R$ 4.65 (Method E), m/z 392.2 (M$^+$+1)

168) 3-ethyl-6-[1-(4-methoxyphenyl)-1H-pyrazol-5-yl]-1-(tetrahydro-2H-pyran-4-yl)-1H-pyrazolo[3,4-b]pyridine, LC/MS (EI) $t_R$ 4.07 (Method E), m/z 404.2 (M$^+$+1)

169) 3-ethyl-6-[1-(3-methoxyphenyl)-1H-pyrazol-5-yl]-1-(tetrahydro-2H-pyran-4-yl) 1H-pyrazolo[3,4-b]pyridine, LC/MS (EI) $t_R$ 4.17 (Method E), m/z 404.2 (M$^+$+1)

170) 6-{1-[4-(benzyloxy)phenyl]-1H-pyrazol-5-yl}-3-ethyl-1-(tetrahydro-2H-pyran-4-yl)-1H-pyrazolo[3,4-b]pyridine, LC/MS (EI) $t_R$ 6.59 (Method E), m/z 480.3 (M$^+$+1)

171) 6-{1-[3-(benzyloxy)phenyl]-1H-pyrazol-5-yl}-3-ethyl-1-(tetrahydro-2H-pyran-4-yl)-1H-pyrazolo[3,4-b]pyridine, LC/MS (EI) $t_R$ 6.5 (Method E), m/z 480.3 (M$^+$+1).

Example 22

Synthesis of 5-(3-Cyclopentyloxy-4-methoxyphenyl)-3-methyl-1-phenyl-1H-pyrazole

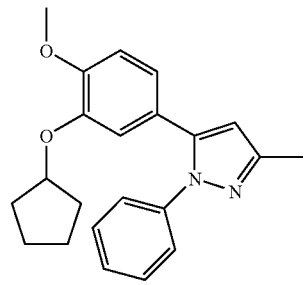

A solution of 5-chloro-3-methyl-1-phenyl-1H-pyrazole (61.8 mg, 0.32 mmol) in 5 mL of THF was cooled to −78° C. and t-butyllithium (0.47 mL, 1.7 M in heptane) was slowly added. The mixture was stirred at −78° C. for 1.5 hours and then zinc chloride (1.56 mL, 0.5 M) was added and after stirring at −78° C. for 15 minutes was warmed to room temperature. A solution containing 4-bromo-2-cyclopentyloxy-1-methoxybenzene (148 mg, 0.54 mmol) and Pd(PPh$_3$)$_4$ (35 mg, 0.03 mmol) in 1 mL of THF was added and the reaction was heated to 60° C. for 12 hours. The mixture was diluted with 20 mL of ethyl acetate and the organic layer was washed with 10 mL of a saturated ammonium chloride solution, 20 mL of water and 20 mL of brine. The organic layer was dried over sodium sulfate, filtered and concentrated. Purification by silica gel column chromatography using a gradient elution from 20% to 50% ethyl acetate in hexanes yielded 31 mg of 5-(3-cyclopentyloxy-4-methoxyphenyl)-3-methyl-1-phenyl-1H-pyrazole. $^1$H-NMR (CDCl$_3$, 300 MHz) δ 7.3 (m, 5H), 6.8 (m, 2H), 6.6 (d, 1H), 6.3 (s, 1H), 4.4 (m, 1H), 3.8 (s, 3H). 2.4 (s, 3H), 1.7-1.5 (m, 8H). (M+1)=349.1

The following compounds were synthesized in a similar manner with different starting materials:

5-[4-Methoxy-3-(3R)-tetrahydrofuranyloxyphenyl]-1-(4-trifluoromethoxybenzyl)-1H-pyrazole.

Example 23

Synthesis of {5-[4-Methoxy-3-(3R)-tetrahydrofuranyloxyphenyl]-3-trifluoromethyl-1H-pyrazol-1-yl}acetic acid

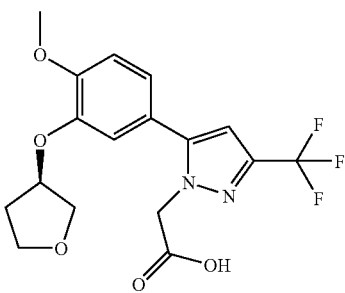

{5-[4-Methoxy-3-(3R)-tetrahydrofuranyloxyphenyl]-3-trifluoromethyl-pyrazol-1-yl}-acetic acid ethyl ester (239 mg, 0.58 mmol) was dissolved in 5 mL of a solution made of 35 g KOH in 25 mL water. The reaction mixture was diluted with 100 mL of methanol, heated to 100° C. for 1 hour, and cooled to room temperature. Acidification with 1N HCl resulted in the formation of a white solid, which was isolated by filtration to give 100 mg of {5-[4-methoxy-3-(3R)-tetrahydrofuranyloxyphenyl]-3-trifluoromethyl-1H-pyrazol-1-yl}acetic acid. $^1$H-NMR (CDCl$_3$, 300 MHz) δ 6.9 (s, 2H), 6.8 (s, 1H), 6.5 (s, 1H), 4.9 (m, 4H), 4.0 (s, 4H), 3.9 (s, 3H); 2.2 (s, 2H). (M+1)

The following compounds were synthesized in a similar manner with different starting materials:
1-Benzyl-5-[4-methoxy-3-(3R)-tetrahydrofuranyloxyphenyl]-1H-pyrazole-3-carboxylic acid;
1-(4-Carboxybenzyl)-5-[4-methoxy-3-(3R)-tetrahydrofuranyloxyphenyl]-1H-pyrazole;
1-(4-Carboxybenzyl)-5-(3-fluoro-4-methoxyphenyl)-1H-pyrazole.

Example 24

Synthesis of N-(3-Fluorophenyl)-2-{5-[4-methoxy-3-(3R)-tetrahydrofuranyloxyphenyl]-3-trifluoromethylpyrazol-1-yl}acetamide

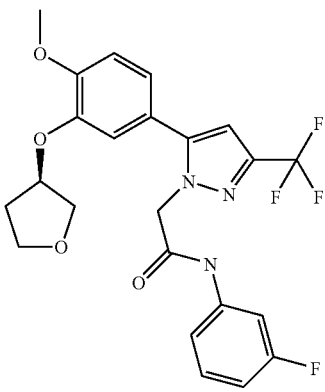

A solution of {5-[4-methoxy-3-(3R)-tetrahydrofuranyloxyphenyl]-3-trifluoromethyl-1H-pyrazol-1-yl}acetic acid (50 mg, 0.13 mmol) in 2 mL of DMF was treated with HOBt (33 mg, 0.22 mmol), diisopropylethylamine (38 uL, 0.22 mmol), 3-fluoroaniline (21 uL, 0.22 mmol), and EDCI (38 uL, 0.22 mmol) and was then stirred at room temperature for 16 h. The reaction was diluted with 10 mL of ethyl acetate; the organic layer was separated and sequentially washed with 10 mL of water, 10 mL of 1N HCl, 10 mL of saturated NaHCO$_3$, and 10 mL of brine, dried (Na$_2$SO$_4$) and concentrated. Purification by silica gel column chromatography using 10% ethyl acetate in hexanes provided 21 mg of N-(3-fluorophenyl)-2-{5-[4-methoxy-3-(3R)-tetrahydrofuranyloxyphenyl]-3-trifluoromethyl-pyrazol-1-yl}acetamide as a white solid. $^1$H-NMR (CDCl$_3$, 300 MHz) δ 8.6 (s, 1H), 7.5 (d, 1H), 7.3 (m, 1H), 7.1-7.0 (m, 3H), 7.0-6.8 (m, 2H), 6.6 (s, 1H), 5.0 (m, 1H), 4.9 (s, 2H), 4.0-3.9 (m, 7H), 2.2 (m, 2H).

The following compounds were synthesized in a similar manner with different starting materials:
N-Cyclopropyl-2-{5-[4-methoxy-3-(3R)-tetrahydrofuranyloxyphenyl]-pyrazol-1-yl}acetamide;
N-Isopropyl-2-{5-[4-methoxy-3-(3R)-tetrahydrofuranyloxyphenyl]-pyrazol-1-yl}acetamide;
N-Phenyl-2-{5-[4-methoxy-3-(3R)-tetrahydrofuranyloxyphenyl]-pyrazol-1-yl}acetamide;
N,N-Diethyl-2-{5-[4-methoxy-3-(3R)-tetrahydrofuranyloxyphenyl]-pyrazol-1-yl}acetamide;

Example 25

Synthesis of 2-{1-Benzyl-5-[4-methoxy-3-(3R)tetrahydrofuranyloxyphenyl]-1H-pyrazol-3-yl}propan-2-ol (A) and 1-{1-Benzyl-5-[4-methoxy-3-(3R)tetrahydro-furanyloxyphenyl]-1H-pyrazol-3-yl}ethanone (B)

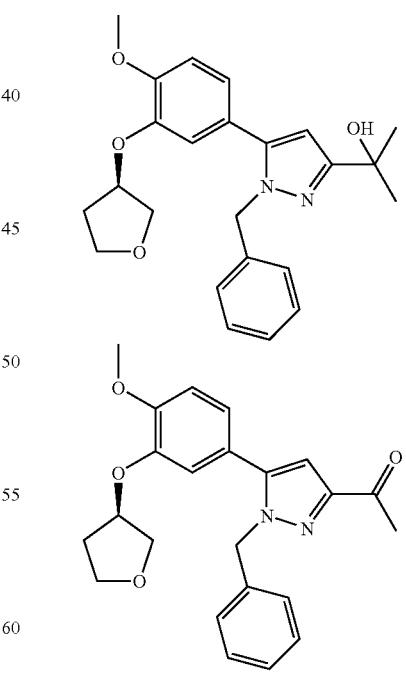

A solution of 1-benzyl-5-[4-methoxy-3-(3R)-tetrahydrofuranyloxyphenyl]-1H-pyrazole-3-carboxylic acid ethyl ester (144 mg, 0.34 mmol) in 3 mL of THF was cooled to −78° C. under argon and MeMgCl (0.34 mL, 3.0 M) was added slowly. The solution was warmed to room temperature over 2 hours and then 10 mL of saturated aqueous NH₄Cl was added. The mixture was extracted with 3×10 mL of ethyl acetate and the combined organic fractions were dried over Na₂SO₄, filtered and concentrated. Purification by silica gel column chromatography using a gradient elution from 20% to 50% ethyl acetate in hexanes yielded 55 mg of 2-{1-benzyl-5-[4-methoxy-3-(3R)-tetrahydrofuranyloxyphenyl]-1H-pyrazol-3-yl}propan-2-ol A as a clear oil and 20 mg of 1-{1-benzyl-5-[4-methoxy-3-(3R)-tetrahydrofuranyloxyphenyl]-1H-pyrazol-3-yl}ethanone B as a clear oil. ¹H-NMR (CDCl₃, 300 MHz) A δ 7.3 (m, 3H), 7.0 (d, 2H), 6.9 (m, 2H), 6.6 (d, 1H), 6.2 (s, 1H), 5.3 (s, 2H), 4.6 (m, 1H), 4.0-3.7 (m, 7H), 2.0 (m, 2H), 1.6 (s, 6H). ¹H-NMR (CDCl₃, 300 MHz) B δ 7.3 (m, 3H), 7.0 (d, 2H), 6.9 (s, 2H), 6.8 (s, 1H), 6.6 (s, 1H), 5.3 (s, 2H), 4.6 (m, 1H), 4.0-3.7 (m, 7H), 2.6 (s, 3H), 1.9 (m, 2H), (M+1) A409.2 B 393.2.

The following compound was synthesized in a similar manner with different starting materials:

145) 2-(4-{5-[3-ethyl-1-(tetrahydro-2H-pyran-4-yl)-1H-pyrazolo[3,4-b]pyridin-6-yl]-1H-pyrazol-1-yl}phenyl)propan-2-ol, LC/MS (EI) t_R 4.73 (Method A), m/z 432.2 (M⁺+1)

Example 26

Synthesis of {1-Benzyl-5-[4-methoxy-3-(3R)-tetrahydrofuranyloxyphenyl]-1H-pyrazol-3-yl}methanol

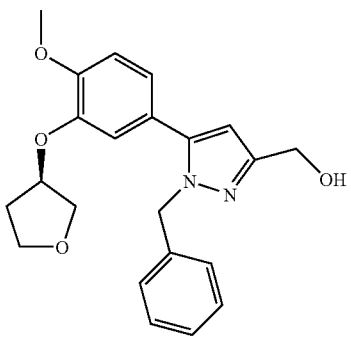

A solution of 1-benzyl-5-[4-methoxy-3-(3R)-tetrahydrofuranyloxyphenyl]-1H-pyrazole-3-carboxylic acid ethyl ester (62 mg, 0.15 mmol) in 3 mL THF was cooled to 0° C. under argon. LAH (0.25 mL, 1M) was added and after stirring for 1 hour the reaction was quenched by the slow addition of 5 mL of methanol and 5 mL of 0.1 N HCl. The aqueous layer was extracted with 2×10 mL of ethyl acetate and the combined organic factions were concentrated. Purification by silica gel column chromatography using a gradient elution from 50% to 100% ethyl acetate in hexanes yielded 20 mg of {1-Benzyl-5-[4-methoxy-3-(3R)-tetrahydrofuranyloxyphenyl]-1H-pyrazol-3-yl}methanol as a clear oil. ¹H-NMR (CDCl₃, 300 MHz) δ 7.3 (m, 3H), 7.0 (d, 2H), 6.9 (m, 2H), 6.6 (d, 1H), 6.3 (s, 1H), 5.3 (s, 2H), 4.7 (s, 2H), 4.6 (m, 1H), 3.9-3.7 (m, 7H), 2.5 (s, 1H), 2.0-1.4 (m, 2H). (M+1)=381.2

The following compounds were synthesized in a similar manner with different starting materials:

1-(2-Hydroxyethyl)-5-[4-methoxy-3-(3R)-tetrahydrofuranyloxyphenyl]-1H-pyrazole.

Example 27

Synthesis of 5-Bromo-1-(2,6-difluorobenzyl)-1H-pyrazole

Step 1: 2-(2,6-Difluorobenzyl)-1-hydroxy-1H-pyrazole

1-Hydroxypyrazole (49.3 mg, 0.59 mmol, 1.0 eq) was mixed with 165.8 mg (0.80 mmol, 1.36 eq) of 2,6-difluorobenzyl bromide in ~1-2 mL of anhydrous CHCl₃ under argon. The mixture was heated at 80° C. for 18 b tinder inert atmosphere in a sealed flask without condenser. The residue was partitioned between 37 weight percent aqueous HCl and toluene. The aqueous layer was collected and the toluene fraction extracted again with 37 weight percent aqueous HCl. The combined aqueous HCL fractions were neutralized with 5N aqueous NaOH to pH~11-12 and then back-extracted with 3×30 mL of CHCl₃. The organic layers were combined, washed with brine, dried over Na₂SO₄ and concentrated under reduced pressure to yield 86.3 mg (70.1% yield) of 2-(2,6-difluorobenzyl)-1-hydroxy-1H-pyrazole as a tan brown solid. ¹H NMR (CDC₃ 300 MHz) δ 7.37 (m, 1H), 7.18 (d, 1H), 6.95 (t, 2H), 6.85 (d, 1H), 6.11 (t, 1H), 5.43 (s, 2.00H) LC/MS (ES) M+1=211.2

Step 2: 5Bromo-1-(2,6-difluorobenzyl)-1H-pyrazole 2-(2,6-Difluorobenzyl)-1-hydroxy-1H-pyrazole (81.2 mg, 0.386 mmol, 1.0 eq) and 5 of anhydrous CHCl₃ were combined in a flame-dried 25 mL round-bottom flask under argon and cooled in an ice/water bath. A solution of POBr₃ (398.1 mg, 1.39 mmol, 3.60 eq) in 3 mL of CHCl₃ was added using a syringe in aliquots over an hour period with stirring. The reaction solution was warmed to room temperature and stirred for 16 hours. The CHCl₃ was removed in vacuo and the resulting orange mixture was neutralized with saturated aqueous NaHCO₃ and extracted with 3×30 mL of diethyl ether. The combined ether fractions were washed with brine, dried over Na₂SO₄ and concentrated in vacuo to yield 101.5 mg (96.7% yield) of 5-bromo-1-(2,6-difluorobenzyl)-1H-pyrazole as a hygroscopic orange-tan colored solid. ¹H NMR (CDCl₃ 300 MHz) δ 7.51 (d, 1H), 7.34 (m, 1H), 6.94 (t, 2H), 6.29 (d, 1H), 5.50 (s, 2H). LC/MS (ES) M+1=273.1, 275.1

The following compounds were synthesized in a similar manner with different starting materials:

5-Bromo-1-(4-trifluoromethoxybenzyl)-1H-pyrazole;
5-Bromo-1-(2,3-difluorobenzyl)-1H-pyrazole;
5-Bromo-1-(4-methylbenzyl)-1H-pyrazole;
5-Bromo-1-(4-tert-butylbenzyl)-1H-pyrazole;
5-Bromo-1-(4-trifluoromethylbenzyl)-1H-pyrazole;
5-Bromo-1-(3,4-difluorobenzyl)-1H-pyrazole;
5-Bromo-1-(2-fluorobenzyl)-1H-pyrazole;
5-Bromo-1-(3-nitrobenzyl)-1H-pyrazole;
5-Bromo-1-(4-methoxycarbonylbenzyl)-1H-pyrazole;
5-Bromo-1-(3-fluorobenzyl)-1H-pyrazole;
5-Bromo-1-(3,5-dimethoxybenzyl)-1H-pyrazole;
1-Benzyl-5-bromo-1H-pyrazole;
5-Bromo-1-(3-methoxybenzyl)-1H-pyrazole;
5-Bromo-1-(4-fluorobenzyl)-1H-pyrazole;
5-Bromo-1-(2,6-difluorobenzyl)-1H-pyrazole.

Example 28

76) 5-[4-(5-{4-Methoxy-3-[(3R)tetrahydrofuran-3-yloxy]phenyl}-1H-pyrazol-1-yl)phenyl]-1H-tetrazole

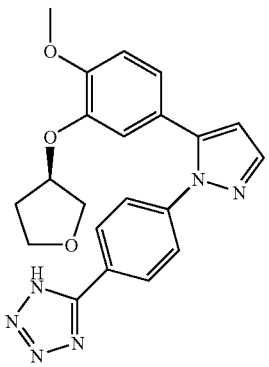

4-(5-{4-Methoxy-3-[(3R)-tetrahydrofuran-3-yloxy]phenyl}-1H-pyrazol-1-yl)benzonitrile (40.0 mg, 0.111 mmol), sodium azide (35.82 mg, 0.5510 mmol), ammonium chloride (29.5 mg, 0.552 mmol), and 1 mL of N,N-dimethylformamide were mixed in a 500 mL flask and heated under an atmosphere of $N_2$ at 110° C. for 6 hours. The mixture was cooled to room temperature and poured into 5 mL of ice cold 3.0 M aqueous HCl. The precipitate was collected by vacuum filtration and washed with several portions of water. The solid was dried in vacuo overnight to give 20 mg (0.044 mmol, 40%) of 5-[4-(5-{4-methoxy-3-[(3R)-tetrahydrofuran-3-yloxy]phenyl}-1H-pyrazol-1-yl)phenyl]-1H-tetrazole as a yellow solid. LC/MS (EI) $t_R$ 3.52, m/z 405.1 ($M^++1$) $^1$H NMR (CDCl$_3$ 300 MHz) δ 2.0 (m, 2H); 3.7-3.9 (m, 4H); 3.9 (s, 3H); 4.8 (m, 1H); 6.6 (s, 2H); 7.0 (d, 1H); 7.1 (d, 1H); 7.4 (d, 2H); 7.8 (d, 2H); 7.8 (s, 1H).

The following compound was synthesized in a similar manner with different starting materials:

21) 1-cyclopentyl-3-ethyl-6-{1-[4-(1H-tetrazol-5-yl)phenyl]-1H-pyrazol-5-yl}-1H-indazole (prepared in 49% yield).

Example 29

43) 1-[4-(5-{4-methoxy-3-[(3R)-tetrahydrofuran-3-yloxy]phenyl}-1H-pyrazol-1-yl)phenyl]piperazine

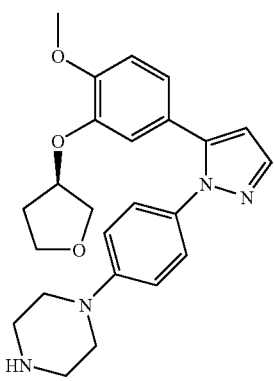

Into a vial was added tert-butyl 4-[4-(5-{4-methoxy-3-[(3R)-tetrahydrofuran-3-yloxy]phenyl}-1H-pyrazol-1-yl)phenyl]piperazine-1-carboxylate (20.0 mg, 0.0384 mmol) and 1 mL of a 20% (v/v) solution of TFA in $CH_2Cl_2$. The reaction was stirred at room temperature for 1 hour and then the solvent was removed under reduced pressure. The residue was dissolved in 10 mL of ethyl acetate and washed once with 10 mL of saturated aqueous NaHCO$_3$. The organic layer was then dried over sodium sulfate and concentrated under reduced pressure to give 13 mg (0.0309 mmol, 80%) of 1-[4-(5-{4-methoxy-3-[(3R)-tetrahydrofuran-3-yloxy]phenyl}-1H-pyrazol-1-yl)phenyl]piperazine as a yellow oil. LC/MS (EI) $t_R$ 2.02 (Method C), m/z 421.2 ($M^++1$). $^1$H NMR (CDCl$_3$ 300 MHz) δ 1.9 (m, 4H); 3.0 (d, 4H); 3.1 (d, 4H); 3.7-3.9 (m, 3H); 3.8 (s, 3H); 4.6 (m, 1H); 6.4 (s, 1H); 6.5 (s, 1H); 6.8 (m, 3H); 7.0 (d, 1H); 7.2 (d, 2H); 7.7 (s, 1H).

Example 30

25) 4-[5-(1-Cyclopentyl-3-ethyl-1H-indazol-6-yl)-1H-pyrazol-1-yl]-N,N-diethylbenzamide

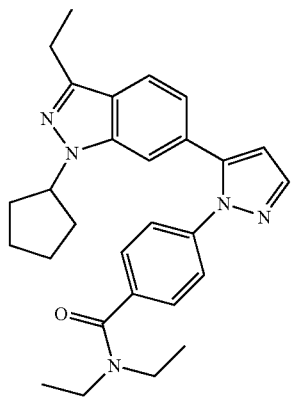

Into a 1-neck round-bottom flask was added 4-[5-(1-cyclopentyl-3-ethyl-1H-indazol-6-yl)-1H-pyrazol-1-yl]benzoic acid (50.0 mg, 0.125 mmol), 2 mL of N,N-dimethylformamide, diethylamine (0.00913 g, 0.125 mmol), HATU (47.4 mg, 0.125 mmol) and N,N-diisopropylethylamine (43.5 uL, 0.250 mmol). The reaction was stirred for 3 days at room temperature, concentrated under reduced pressure, and purified by preparative HPLC (UV detection) to give 33 mg (0.0725 mmol, 58%) of 4-[5-(1-cyclopentyl-3-ethyl-1H-indazol-6-yl)-1H-pyrazol-1-yl]-N,N-diethylbenzamide as a clear oil. LC/MS (EI) $t_R$ 5.26 (Method C), m/z 456.1 ($M^++1$). $^1$H NMR (CDCl$_3$ 300 MHz) δ 1.0-1.2 (m, 5H); 1.3 (t, 3H); 1.7-1.9 (m, 5H); 2.0 (m, 4H); 3.0 (q, 2H); 3.1 (br s, 2H); 3.4 (br s, 2H); 4.8 (m, 1H); 6.6 (s, 1H); 6.9 (d, 1H); 7.2 (m, 5H); 7.5 (d, 1H); 7.7 (s, 1H).

Example 31

Synthesis of (2E)-1-(1-Cyclopentyl-3-ethyl-1H-indazol-6-yl)-3-(dimethylamino)prop-2-en-1-one

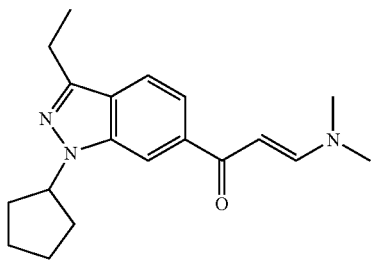

Under argon 1-(1-cyclopentyl-3-ethyl-1H-indazol-6-yl)ethanone (815 mg, 3.18 mmol), N,N-dimethylformamide dimethyl acetal (0.634 mL, 4.77 mmol) and 30 mL of N,N-dimethylformamide were combined and warmed to 140° C. overnight. The reaction mixture was poured into 50 mL of water and extracted with 3×75 mL of ethyl acetate. The combined organic fractions were dried over sodium sulfate and concentrated under reduced pressure. The residue was purified by column chromatography over silica gel eluting with $CH_2Cl_2$ for 10 minutes and then with a linear gradient over 30 minutes to 100% of [10% MeOH in $CH_2Cl_2$ with 0.1% $NH_4OH$] to give 954 mg (3.18 mmol, 96%) of (2E)-1-(1-cyclopentyl-3-ethyl-1H-indazol-6-yl)-3-(dimethylamino)prop-2-en-1-one as a yellow oil. LCMS m/z 312.2 ($M^+$+1).

Example 32

37) N-[(4-Methoxyphenyl)sulfonyl]-4-[(5-{4-methoxy-3-[(3R)tetrahydrofuran-3-yloxy]phenyl}-1H-pyrazol-1-yl)methyl]benzamide

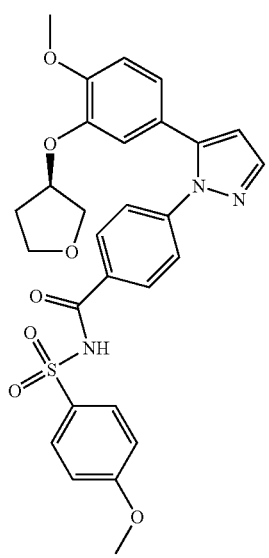

Into a vial was added 4-[(5-{4-methoxy-3-[(3R)-tetrahydrofuran-3-yloxy]phenyl}-1H-pyrazol-1-yl)methyl]benzoic acid (50.0 mg, 0.127 mmol), N-(3-dimethylaminopropyl)-N'-ethylcarbodiimide hydrochloride (30.2 mg, 0.158 mmol), 4-dimethylaminopyridine (19.3 mg, 0.158 mmol), 4-methoxybenzenesulphonamide (29.5 mg, 0.158 mmol) and 2 mL of methylene chloride. The reaction was stirred overnight at room temperature, poured into 10 mL of water and 10 mL of ethyl acetate and the pH of the aqueous layer was adjusted to pH~6 by adding saturated aqueous $NaHCO_3$. The organic layer was dried over sodium sulfate, filtered and approximately 1 g of silica gel was added and the mixture was evaporated to dryness under reduced pressure. The residue was purified by column chromatography on silica gel using a gradient elution going from 0% to 10% methanol in dichloromethane over 20 minutes to give N-[(4-methoxyphenyl)sulfonyl]-4-[(5-{4-methoxy-3-[(3R)-tetrahydrofuran-3-yloxy]phenyl}-1H-pyrazol-1-yl)methyl]benzamide (53 mg, 74%) as a yellow foam. LC/MS (EI) $t_R$ 5.22 (Method C), m/z 564.2 ($M^+$+1). $^1$H NMR ($CDCl_3$ 300 MHz) δ 1.8-2.0 (m, 2H); 2.6 (br s, 2H); 3.6 (m, 2H); 3.8 (m, 2H); 3.9 (s, 3H); 4.4 (br s, 1H); 5.2 (s, 2H); 6.3 (s, 1H); 6.4 (s, 1H); 6.9 (m, 3H); 7.2-7.6 (m, 3H); 7.7 (t, 2H); 7.8 (d, 2H); 7.9 (d, 2H).

The following compounds were synthesized in a similar manner with different starting materials:

36) 4-[(5-{4-methoxy-3-[(3R)-tetrahydrofuran-3-yloxy]phenyl}-1H-pyrazol-1-yl)methyl]-N-(phenylsulfonyl)benzamide; LC/MS (EI) $t_R$ 534.5 (Method C), m/z 2.7 ($M^+$+1)

38) N-[(4-fluorophenyl)sulfonyl]-4-[(5-{4-methoxy-3-[(3R)-tetrahydrofuran-3-yloxy]phenyl}-1H-pyrazol-1-yl)methyl]benzamide; LC/MS (EI) $t_R$ 5.45 (Method C), m/z 552.1 ($M^+$+1)

19) 4-[5-(1-cyclopentyl-3-ethyl-1H-indazol-6-yl)-1H-pyrazol-1-yl]-N-(methylsulfonyl)benzamide; LC/MS (EI) $t_R$ 5.04, m/z 478.2 ($M^+$+1)

20) 4-[5-(1-cyclopentyl-3-ethyl-1H-indazol-6-yl)-1H-pyrazol-1-yl]-N-(ethylsulfonyl)benzamide LC/MS (EI) $t_R$ 5.19, m/z 492.2 ($M^+$+1).

Example 33

53) 2-(5-{4-Methoxy-3-[(3R)-tetrahydrofuran-3-yloxy]phenyl}-1H-pyrazol-1-yl)ethyl phenylcarbamate

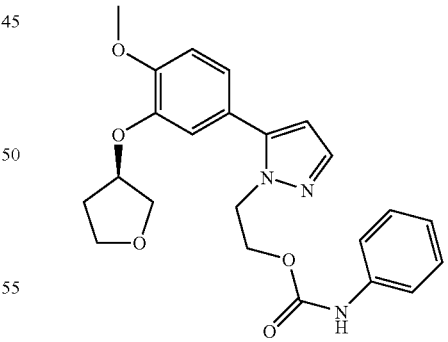

2-(5-{4-Methoxy-3-[(3R)-tetrahydrofuran-3-yloxy]phenyl}-1H-pyrazol-1-yl)ethanol (20 mg, 0.066 mmol), 0.50 mL of methylene chloride, phenyl isocyanate (30 uL, 0.28 mmol) were combined in a test tube and stirred for 3 days at room temperature. Trisamine scavenger resin (Argonaut P/N 800228, ~3-5 equiv) was added and the mixture was stirred for 2-3 hours, filtered through an Acro Disc (0.45 um) filter and concentrated to yield 29.3 mg of a light yellow solid. The crude product was recrystallized from 0.5 mL of methanol to give 2-(5-{4-methoxy-3-[(3R)-tetrahydrofuran-3-yloxy]phenyl}-1H-pyrazol-1-yl)ethyl phenylcarbamate (14.5 mg, 52%) as white needle-like crystals. LC/MS (EI) $t_R$ 4.6 (Method C), m/z 424.2 (M+1). $^1$H NMR (CDCl$_3$ 300 MHz) δ 2.1-2.2 (m, 2H); 3.8 (s, 3H); 3.8-4.0 (m, 2H); 4.0-4.2 (m, 2H); 4.5 (m, 2H); 4.6 (m, 2H); 4.9 (m, 1H); 6.3 (s, 1H); 6.7 (m, 1H); 6.9 (s, 2H); 7.0-7.1 (m, 2H); 7.3 (m, 3H); 7.6 (s, 1H).

The following compounds were synthesized in a similar manner with different starting materials:

48) 2-(5-{4-Methoxy-3-[(3R)-tetrahydrofuran-3-yloxy]phenyl}-1H-pyrazol-1-yl)ethyl (4-fluorophenyl)carbamate; LC/MS (EI) $t_R$ 4.0, m/z 442.1 (M$^+$+1)

49) 2-(5-{4-Methoxy-3-[(3R)-tetrahydrofuran-3-yloxy]phenyl}-1H-pyrazol-1-yl)ethyl benzylcarbamate; LC/MS (EI) $t_R$ 3.9, m/z 438.1 (M$^+$+1)

50) 2-(5-{4-Methoxy-3-[(3R)-tetrahydrofuran-3-yloxy]phenyl}-1H-pyrazol-1-yl)ethyl 1-methylpropylcarbamate; LC/MS (EI) $t_R$ 3.5, m/z 404.2 (M$^+$+1)

54) 2-(5-{4-Methoxy-3-[(3R)-tetrahydrofuran-3-yloxy]phenyl}-1H-pyrazol-1-yl)ethyl propylcarbamate; LC/MS (EI) $t_R$ 3.4 (Method C), m/z 390.2 (M$^+$+1)

55) 2-(5-{4-Methoxy-3-[(3R)-tetrahydrofuran-3-yloxy]phenyl}-1H-pyrazol-1-yl)ethyl (2-fluorophenyl)carbamate; LC/MS (EI) $t_R$ 3.6, m/z 440.2 (M$^+$+1)

57) 2-(5-{4-Methoxy-3-[(3R)-tetrahydrofuran-3-yloxy]phenyl}-1H-pyrazol-1-yl)ethyl (4-methoxyphenyl)carbamate; LC/MS (EI) $t_R$ 3.6, m/z 454.2 (M$^+$+1).

58) 2-(5-{4-Methoxy-3-[(3R)-tetrahydrofuran-3-yloxy]phenyl}-1H-pyrazol-1-yl)ethyl (3-fluorophenyl)carbamate; LC/MS (EI) $t_R$ 3.8, m/z 442.1 (M$^+$+1)

59) 2-(5-{4-Methoxy-3-[(3R)-tetrahydrofuran-3-yloxy]phenyl}-1H-pyrazol-1-yl)ethyl (4-chlorophenyl)carbamate; LC/MS (EI) $t_R$ 4.1, m/z 458.1 (M$^+$+1)

69) 2-(5-{4-methoxy-3-[(3R)-tetrahydrofuran-3-yloxy]phenyl}-1H-pyrazol-1-yl)ethyl (2-furylmethyl)carbamate; LC/MS (EI) $t_R$ 3.4, m/z 428.2 (M$^+$+1)

70) 2-(5-{4-Methoxy-3-[(3R)-tetrahydrofuran-3-yloxy]phenyl}-1H-pyrazol-1-yl)ethyl (4-methylphenyl)carbamate; LC/MS (EI) $t_R$ 3.9, m/z 438.2 (M$^+$+1)

73) 2-(5-{4-Methoxy-3-[(3R)-tetrahydrofuran-3-yloxy]phenyl}-1H-pyrazol-1-yl)ethyl (cyclopentyl)carbamate; LC/MS (EI) $t_R$ 3.7, m/z 416.2 (M$^+$+1).

77) 2-(5-{4-Methoxy-3-[(3R)-tetrahydrofuran-3-yloxy]phenyl}-1H-pyrazol-1-yl)ethyl (4-cyanophenyl)carbamate; LC/MS (EI) $t_R$ 3.6, m/z 449.1 (M$^+$+1)

78) 2-(5-{4-Methoxy-3-[(3R)-tetrahydrofuran-3-yloxy]phenyl}-1H-pyrazol-1-yl)ethyl [2-(2-thienyl)ethyl]carbamate; LC/MS (EI) $t_R$ 3.6, m/z 458.1 (M$^+$+1)

79) 2-(5-{4-Methoxy-3-[(3R)-tetrahydrofuran-3-yloxy]phenyl}-1H-pyrazol-1-yl)ethyl (3,5-dimethylisoxazol-4-yl)carbamate; LC/MS (EI) $t_R$ 3.1, m/z 443.1 (M$^+$+1)

80) 2-(5-{4-Methoxy-3-[(3R)-tetrahydrofuran-3-yloxy]phenyl}-1H-pyrazol-1-yl)ethyl 3-thienylcarbamate; LC/MS (EI) $t_R$ 3.7, m/z 430.1 (M$^+$+1)

75) 2-(5-{4-Methoxy-3-[(3R)-tetrahydrofuran-3-yloxy]phenyl}-1H-pyrazol-1-yl)ethyl 2-thienylcarbamate LC/MS (EI) $t_R$ 3.11 (Method C), m/z 430.1 (M$^+$+1)

83) 2-(5-{4-Methoxy-3-[(3R)-tetrahydrofuran-3-yloxy]phenyl}-1H-pyrazol-1-yl)ethyl (3,4-dichlorophenyl)carbamate; LC/MS (EI) $t_R$ 4.5, m/z 492.1 (M$^+$+1) and 84) 2-(5-{4-Methoxy-3-[(3R)-tetrahydrofuran-3-yloxy]phenyl}-1H-pyrazol-1-yl)ethyl (3,4-difluorophenyl)carbamate LC/MS (EI) $t_R$ 4.0, m/z 460.2 (M$^+$+1).

Example 34

67) 2-Methoxy-5-[4-(5-{4-methoxy-3-[(3R)tetrahydrofuran-3-yloxy]phenyl}-1H-pyrazol-1-yl)phenyl]pyridine

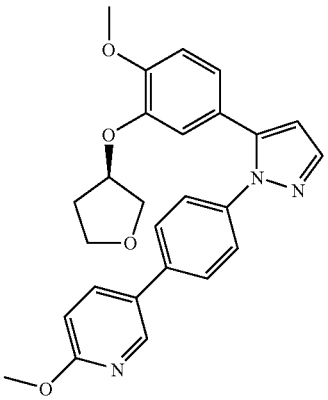

1-(4-Bromophenyl)-5-{4-methoxy-3-[(3R)-tetrahydrofuran-3-yloxy]phenyl}-1H-pyrazole (52.0 mg, 0.125 mmol), bis(triphenylphosphine)palladium(II) chloride (20 mg, 0.02 mmol), 0.1 mL of 2.00 M aqueous sodium carbonate, 2 mL of a mixture of DME, water and ethanol in a 7:3:2 ratio, and 2-methoxy-5-pyridineboronic acid (21.1 mg, 0.138 mmol) were combined in a 2.0-5.0 mL Smith Process vial. This was sealed and placed into a Personal Chemistry Emrys Optimizer, stirred for 30 seconds, and then heated to 140° C. for 300 seconds. Upon cooling, 10 mL of water and 10 mL of ethyl acetate were added and the organic layer was separated, dried over sodium sulfate, filtered and approximately 1 g of silica gel was added and the mixture was evaporated to dryness under reduced pressure. The residue was purified by column chromatography on silica gel eluting with 10% ethyl acetate in hexanes for 3 minutes, then with a linear gradient to 100% ethyl acetate over 18 minutes and then with 100% ethyl acetate for an additional 10 minutes to give 2-methoxy-5-[4-(5-{4-methoxy-3-[(3R)-tetrahydrofuran-3-yloxy]phenyl}-1H-pyrazol-1-yl)phenyl]pyridine-(45 mg, 82%) as a yellow oil. LC/MS (EI) $t_R$ 4.3 (Method C), m/z 444.1 (M$^+$+1). $^1$H NMR (CDCl$_3$ 300 MHz) δ 1.9 (m, 2H); 3.7-3.9 (m, 4H); 3.9 (s, 3H); 4.0 (s, 3H); 4.8 (m, 1H) 6.5 (s, 1H); 6.6 (s, 1H); 6.9 (m, 2H); 7.0 (d, 2H); 7.4 (d, 2H); 7.5 (d, 2H); 7.8 (t, 2H); 8.3 (2, 1H).

The following compounds were synthesized in a similar manner with different starting materials:

8) 1-cyclopentyl-3-ethyl-6-[1-(4-pyrimidin-5-ylphenyl)-1H-pyrazol-5-yl]-1H-indazole; LC/MS (EI) $t_R$ 4.98 (Method C), m/z 435.2 (M$^+$+1)

9) 1-cyclopentyl-3-ethyl-6-{1-[4-(1H-pyrazol-4-yl)phenyl]-1H-pyrazol-5-yl}-1H-indazole; LC/MS (I) $t_R$ 4.71 (Method C), m/z 423.1 (M$^+$+1)

10) 1-cyclopentyl-3-ethyl-6-{1-[4-(1H-pyrrol-2-yl)phenyl]-1H-pyrazol-5-yl}-1H-indazole; LC/MS (EI) $t_R$ 6.0 (Method C), m/z 422.2 (M$^+$1)

11) 1-cyclopentyl-3-ethyl-6-[1-(4-pyridin-3-ylphenyl)-1H-pyrazol-5-yl]-1H-indazole; LC/MS (EI) $t_R$ 4.56 (Method C), m/z 434.2 (M$^+$+1)

35) 1-[4-(3-furyl)phenyl]-5-{4-methoxy-3-[(3R)-tetrahydrofuran-3-yloxy]phenyl}-1H-pyrazole; LC/MS (EI) $t_R$ 4.07 (Method C), m/z 403.2 (M$^+$+1).

46) 5-{4-methoxy-3-[(3R)-tetrahydrofuran-3-yloxy]phenyl}-1-[4-(1H-pyrrol-2-yl)phenyl]-1H-pyrazole; LC/MS (EI) $t_R$ 4.03 (Method C), m/z 402.1 (M$^+$+1)

47) 3-[4-(5-{4-methoxy-3-[(3R)-tetrahydrofuran-3-yloxy]phenyl}-1H-pyrazol-1-yl)phenyl]pyridine; LC/MS (EI) $t_R$ 2.57 (Method C), m/z 414.1 (M$^+$+1)

60) 1-benzyl-4-[4-(5-{4-methoxy-3-[(3R)-tetrahydrofuran-3-yloxy]phenyl}-1H-pyrazol-1-yl)phenyl]-1H-pyrazole; LC/MS (EI) $t_R$ 4.39 (Method C), m/z 493.2(M$^+$+1)

61) 2-fluoro-5-[4-(5-{4-methoxy-3-[(3R)-tetrahydrofuran-3-yloxy]phenyl}-1H-pyrazol-1-yl)phenyl]pyridine, 62) 5-[4-(5-{4-methoxy-3-[(3R)-tetrahydrofuran-3-yloxy]phenyl}-1H-pyrazol-1-yl)phenyl]pyrimidine; LC/MS (EI) $t_R$ 3.29 (Method C), m/z 415.1 (M$^+$+1)

63) N-[4'-(5-{4-methoxy-3-[(3R)-tetrahydrofuran-3-yloxy]phenyl}-1H-pyrazol-1-yl)biphenyl-2-yl]acetamide; LC/MS (EI) $t_R$ 3.61 (Method C), m/z 470.1 (M$^+$+1)

64) 4'-(5-{4-methoxy-3-[(3R)-tetrahydrofuran-3-yloxy]phenyl}-1H-pyrazol-1-yl)biphenyl-2-carboxamide; LC/MS (EI) $t_R$ 3.36 (Method C), m/z 456.1 (M$^+$+1)

65) N-[4'-(5-{4-methoxy-3-[(3R)-tetrahydrofuran-3-yloxy]phenyl}-1H-pyrazol 1-yl)biphenyl-3-yl]acetamide; LC/MS (EI) $t_R$ 3.89 (Method C), m/z 470.1 (M$^+$+1)

66) 3-fluoro-4-[4-(5-{4-methoxy-3-[(3R)-tetrahydrofuran-3-yloxy]phenyl}-1H-pyrazol-1-yl)phenyl]pyridine; LC/MS (EI) $t_R$ 3.7 (Method C), m/z 432.1 (M$^+$+1) and 68)-4-[4-(5-{4-methoxy-3-[(3R)-tetrahydrofuran-3-yloxy]phenyl}-1H-pyrazol-1-yl)phenyl]-3,5-dimethylisoxazole LC/MS (EI) $t_R$ 4.3 (Method C), m/z 432.2 (M$^+$+1).

Example 35

23) 4-[5-(1-Cyclopentyl-3-ethyl-1H-indazol-6-yl)-1H-pyrazol-1-yl]-N-methoxy-N-methylbenzamide

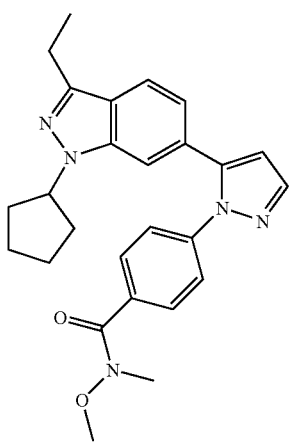

To a solution of 4-[5-(1-cyclopentyl-3-ethyl-1H-indazol-6-yl)-1H-pyrazol-1-yl]benzoic acid (100.0 mg, 0.250 mmol) in 1.2 mL of methylene chloride under at atmosphere of argon at 0° C. was added N,N-carbonyldiimidazole (48.2 mg, 0.297 mmol) with stirring. After 30 minutes N,O-dimethylhydroxylamine hydrochloride (59.9 mg, 0.614 mmol) was added and the resultant suspension was warmed to room temperature, stirred for 24 hours and then 10 mL of water and 10 mL of ethyl acetate were added. The organic layer was separated, washed with 10 mL of 1N NaOH, 10 mL of water, 10 mL of brine, dried over sodium sulfate, and filtered. Approximately 2 g of silica gel were added and the mixture was evaporated to dryness under reduced pressure. The residue was purified by column chromatography over silica gel eluting with a linear gradient from 10% ethyl acetate in hexanes to 50% ethyl acetate in hexanes over 20 minutes to yield 4-[5-(1-cyclopent)$_{4-3}$-ethyl-1H-indazol-6-yl)-1H-pyrazol-1-yl]-N-methoxy-N-methylbenzamide (55 mg, 50%) as a white solid.

Example 36

74) 4-(5-{4-Methoxy-3-[(3R)-tetrahydrofuran-3-yloxy]phenyl}-1H-pyrazol-1-yl)aniline

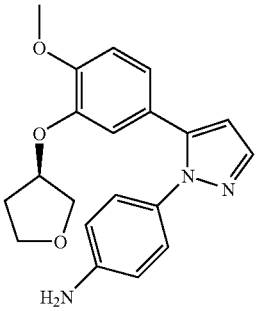

Into a 1-neck round-bottom flask was added N-(diphenylmethylene)-4-(5-{4-methoxy-3-[(3R)-tetrahydrofuran-3-yloxy]phenyl}-1H-pyrazol-1-yl) aniline (52.0 mg, 0.101 mmol), 1.0 mL of tetrahydrofuran, and 0.1 mL of 2.0 M aqueous HCl. The reaction was stirred at room temperature for 2 hours and 10 mL of 0.5 N HCl in water and 10 mL of a 2:1 mixture of hexanes and ethyl acetate were added. The clear aqueous layer was basified with 1 N NaOH and extracted with 3×10 mL of ethyl acetate. The combined organic fractions were dried over sodium sulfate and concentrated under reduced pressure to yield 4-(5-{4-methoxy-3-[(3R)-tetrahydrofuran-3-yloxy]phenyl}-1H-pyrazol-1-yl) aniline (28 mg, 79%) as a tan solid. LC/MS (EI) $t_R$ 3.11 (Method C), m/z 352.1 (M$^+$+1)

Example 37

12) 4-[5-(1-Cyclopentyl-3-ethyl-1H-indazol-6-yl)-1H-pyrazol-1-yl]benzamide

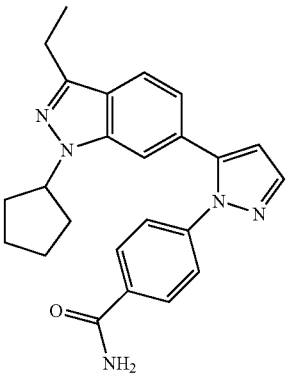

4-[5-(1-Cyclopentyl-3-ethyl-1H-indazol-6-yl)-1H-pyrazol-1-yl]benzoic acid (7 mg, 0.02 mmol), PYBOP (14 mg, 0.026 mmol), 1.0 mL of N,N-dimethylformamide, 1-hydroxybenzotriazole (3.5 mg, 0.026 mmol), N,N-diisopropylethylamine (12 uL, 0.070 mmol) and ammonium chloride (1.9 mg, 0.035 mmol) were combined in a 1-neck round-bottom flask and stirred at room temperature for two hours. The mixture was treated with 10 mL of saturated aqueous NaHCO$_3$ and 10 mL of ethyl acetate. The organic layer was separated, dried over sodium sulfate, filtered and approximately 500 mg of silica gel was added. The mixture was evaporated to dryness under reduced pressure and the residue was purified by column chromatography over silica gel eluting with a gradient of 10% ethyl acetate in hexanes for 5 minutes and then increasing linearly to 100% ethyl acetate at 25 minutes to yield 4-[5-(1-cyclopentyl-3-ethyl-1H-indazol-6-yl)-1H-pyrazol-1-yl]benzamide (5 mg, 62%) as a white solid. LC/MS (EI) t$_R$ 4.09 (Method C), m/z 400.2 (M$^+$+1). $^1$H NMR (CDCl$_3$ 300 MHz) δ 1.4 (t, 3H); 1.6 (m, 2H); 1.8 (m, 2H); 2.1 (m, 4H); 3.0 (q, 2H); 4.8 (m, 1H); 5.7 (br s, 1H); 6.0 (br s, 1H); 6.6 (s, 1H); 6.9 (d, 1H); 7.3-7.5 (m, 3H); 7.6 (d, 1H); 7.8 (m, 3H).

Example 38

Synthesis of 1-(1-Cyclopentyl-3-ethyl-1H-indazol-6-yl)ethanol

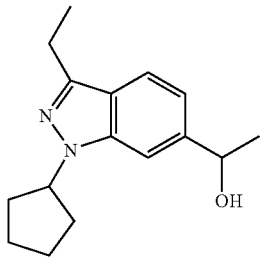

A solution of 1-cyclopentyl-3-ethyl-1H-indazole-6-carboxaldehyde (1.00 g, 4.13 mmol) in 40 mL of tetrahydrofuran under argon was cooled to −78° C. and with stirring treated with 3 mL of 3 M methylmagnesium chloride in tetrahydrofuran. The reaction was stirred at −78° C. for 1 hour, slowly warmed to room temperature overnight and then quenched by addition of 100 mL of saturated aqueous NH$_4$Cl. The mixture was extracted with 3×50 mL of ethyl acetate and the combined organic fractions were dried over sodium sulfate and concentrated to give 1-(1-cyclopentyl-3-ethyl-1H-indazol-6-yl)ethanol as a yellow solid. The crude residue was not purified but used as such in the next step.

Example 39

Synthesis of 1-(1-Cyclopentyl-3-ethyl-1H-indazol-6-yl)ethanone

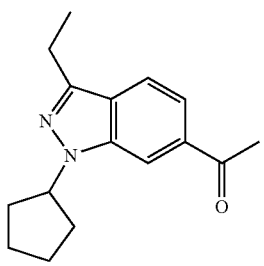

Into a 1-neck round-bottom flask was added 1-(1-cyclopentyl-3-ethyl-1H-indazol-6-yl)ethanol (1.06 g, 4.10 mmol), pyridinium chlorochromate (1.77 g, 8.20 mmol) and 40 mL of methylene chloride. The reaction was stirred at room temperature for 1 hour, filtered through Celite, and rinsed with 200 mL of ethyl acetate. Approximately 20 g of silica gel were added and the mixture was evaporated to dryness under reduced pressure. The residue was purified by column chromatography over silica gel eluting with 20% ethyl acetate in hexanes to yield 1-(1-cyclopentyl-3-ethyl-1H-indazol-6-yl)ethanone (809 mg, 77%).

Example 40

24) 1-4-[5-(1-Cyclopentyl-3-ethyl-1H-indazol-6-yl)-1H-pyrazol-1-yl]phenylethanone

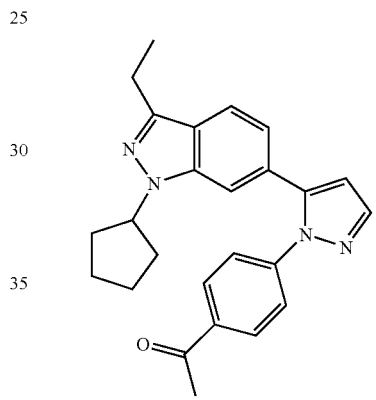

4-[5-(1-Cyclopentyl-3-ethyl-1H-indazol-6-yl)-1H-pyrazol-1-yl]-N-methoxy-N-methylbenzamide (66 mg, 0.15 mmol) and 2 mL of tetrahydrofuran were combined in a one-necked round-bottom, placed under an atmosphere of argon, cooled to −78° C., and 0.10 mL of 3 M methylmagnesium chloride in tetrahydrofuran was slowly added. The reaction was stirred at −78° C. for 30 minutes, warmed to 0° C. for 60 minutes and another 0.2 mL of 3 M methylmagnesium chloride in THF was added. The reaction was allowed to stir at 0° C. for 30 minutes and 10 mL of saturated aqueous NH$_4$Cl was added and the mixture was allowed to warm to room temperature. The aqueous layer was extracted with 20 mL of ethyl acetate and the separated organic layer was dried over sodium sulfate, filtered and concentrated under reduced pressure to yield 1-4-[5-(1-cyclopentyl-3-ethyl-1H-indazol-6-yl)-1H-pyrazol-1-yl]phenylethanone (35 mg, 59%) as a white solid. LC/MS (EI) t$_R$ 5.68 (Method C), m/z 399.1 (M$^+$+1). $^1$H NMR (CDCl$_3$ 300 MHz) δ 1.3 (t, 3H); 1.6 (m, 2H); 1.9 (m, 2H); 2.0 (m, 4H); 2.5 (s, 3H); 3.0 (t, 2H); 4.8 (m, 1H); 6.5 (s, 1H); 6.8 (d, 1H); 7.2 (s, 1H); 7.3 (d, 2H); 7.4 (d, 1H); 7.7 (s, 1H); 7.6 (d, 2H).

Example 41

81) 5-[1-(4-Fluorophenyl)-1H-pyrazol-5-yl]-2-methoxyphenol

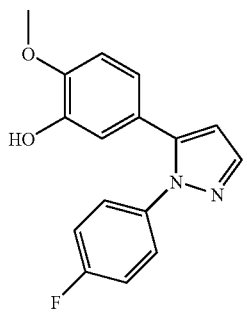

Into a 1-neck round-bottom flask was added 5-[3-(benzyloxy)-4-methoxyphenyl]-1-(4-fluorophenyl)-1H-pyrazole (3.5 g, 9.3 mmol) and 100 mL of ethanol. The flask was flushed with nitrogen for 10 minutes and 350 mg of 10% Pd/C was added. The reaction was then stirred under one atmosphere of hydrogen at room temperature overnight. The reaction was degassed under reduced pressure, flushed with argon for 5 minutes, filtered through Celite and concentrated to yield 2.6 g (98%) of 5-[1-(4-fluorophenyl)-1H-pyrazol-5-yl]-2-methoxyphenol as a grey oil. m/z 285.0 (M$^+$+1). $^1$H NMR (CDCl$_3$ 300 MHz) δ 3.9 (s, 3H); 5.6 (s, 1H); 6.4 (s, 1H); 6.8 (d, 1H); 7.0 (d, 2H); 7.4 (d, 2H); 7.6 (m, 2H); 7.7 (s, 1H).

Example 42

39) Tert-butyl 4-[4-(5-{4-methoxy-3-[(3R)-tetrahydrofuran-3-yloxy]phenyl}-1H-pyrazol-1-yl)phenyl]piperazine-1-carboxylate

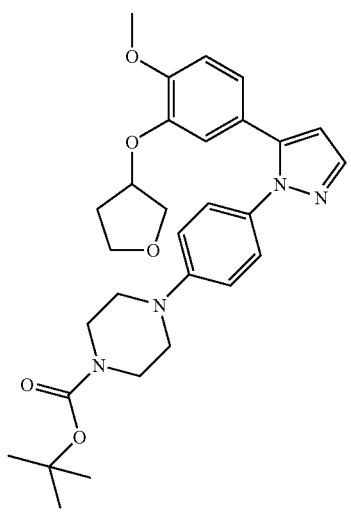

Into a 1-neck round-bottom flask was added 2-dicyclohexylphosphino-2'-(N,N-dimethylamino)biphenyl (4.74 mg, 0.0120 mmol), 1-(4-bromophenyl)-5-{4-methoxy-3-[(3R)-tetrahydrofuran-3-yloxy]phenyl}-1H-pyrazole (50.0 mg, 0.120 mmol), tert-butyl 1-piperazinecarboxylate (26.9 mg, 0.144 mmol) and tris(dibenzylideneacetone) dipalladium(0) (11.0 mg, 0.0120 mmol). The reaction was placed under an atmosphere of argon, 0.4 mL of 1.00 M lithium bis(trimethylsilyl)amide in tetrahydrofuran was added and the mixture was heated to 65° C. for 16 hours. After cooling to room temperature, 30 mL of saturated aqueous NH$_4$Cl solution was added and the aqueous layer was extracted with 30 mL ethyl acetate. The separated organic layer was dried over sodium sulfate, filtered, and approximately 1 g silica gel was added and the mixture was evaporated to dryness under reduced pressure. The residue was purified by column chromatography on silica gel eluting with 20% ethyl acetate in hexanes to yield tert-butyl 4-[4-(5-{4-methoxy-3-[(3R)-tetrahydrofuran-3-yloxy]phenyl}-1H-pyrazol-1-yl)phenyl]piperazine-1-carboxylate (21 mg, 34%) as a yellow oil. LC/MS (EI) t$_R$ 4.62 (Method C), m/z 521.3 (M$^+$+1). $^1$H NMR (CDCl$_3$ 300 MHz) δ 1.5 (s, 9H); 1.9 (m, 2H); 3.1 (m, 4H); 3.6 (m, 4H); 3.7-3.9 (m, 4H); 3.9 (s, 3H); 4.6 (m, 1H); 6.4 (s, 1 h); 6.6 (s, 1H); 6.9-7.1 (m, 4H); 7.2 (d, 2H); 7.6 (S, 1H).

The following compound was synthesized in a similar manner with different starting materials:

27) 4-[4-(5-{4-methoxy-3-[(3R)-tetrahydrofuran-3-yloxy]phenyl}-1H-pyrazol-1-yl)phenyl]morpholine LC/MS (EI) t$_R$ 3.45 (Method C), m/z 422.2 (M$^+$+1).

Example 43

Synthesis of 4-[(5-{4-methoxy-3-[(3R)-tetrahydrofuran-3-yloxy]phenyl}-1H-pyrazol-1-yl)methyl]benzoic acid

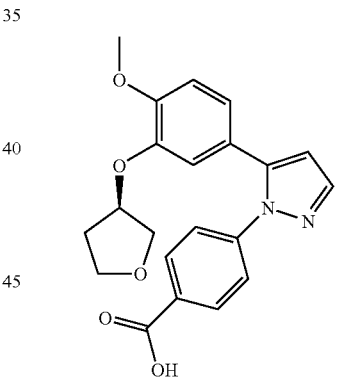

Into a 1-neck round-bottom flask was added methyl 4-[(5-{4-methoxy-3-[(3R)-tetrahydrofuran-3-yloxy]phenyl}-1H-pyrazol-1-yl)methyl]benzoate (330 mg, 0.808 mmol), 5 mL of 1,4-dioxane, 20 mL of water and 8 mL of 2 M aqueous sodium hydroxide. The reaction was heated at 90° C. for 1.5 hours, acidified with 1N HCl until pH~3 and extracted with 3×20 mL CH$_2$Cl$_2$. The combined organic fractions were dried over sodium sulfate, filtered and concentrated under reduced pressure to yield 4-[(5-{4-methoxy-3-[(3R)-tetrahydrofuran-3-yloxy]phenyl}-1H-pyrazol-1-yl)methyl]benzoic acid (260 mg, 81%) as a brown solid. LCMS M+1=395.2

The following compound was synthesized in a similar manner with different starting materials:

28) 4-{[5-(3-fluoro-4-methoxyphenyl)-1H-pyrazol-1-yl]methyl}benzoic acid LC/MS (EI) t$_R$ 3.49 (Method C), m/z 327.2 (M$^+$+1).

Example 44

85) 5-(3,4-Dimethoxyphenyl)-1-(4-fluorophenyl)-1H-pyrazole

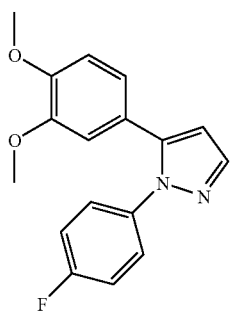

5-[1-(4-Fluorophenyl)-1H-pyrazol-5-yl]-2-methoxyphenol (50.0 mg, 0.176 mmol), 5 mL of N,N-dimethylformamide and methyl iodide (16.4 uL, 0.264 mmol) were combined in a vial and stirred at room temperature overnight. An additional 0.5 mL of methyl iodide was added and stirring continued for 2 days at room temperature and then 10 mL of ethyl acetate and 10 mL of water were added. The organic layer was separated, dried over sodium sulfate, filtered and concentrated under reduced pressure. The residue was purified by column chromatography on silica gel eluting with a gradient of 10% ethyl acetate in hexanes to 50% ethyl acetate in hexanes over 20 minutes to give 5-(3,4-dimethoxyphenyl)-1-(4-fluorophenyl)-1H-pyrazole (25 mg, 48%) as a white solid. LC/MS (EI) $t_R$ 4.14, m/z 299.1 ($M^+$+1). $^1$H NMR (CDCl$_3$ 300 MHz) δ 3.7 (s, 3H); 3.9 (s, 3H); 6.5 (s, 1H); 6.7 (s, 1H); 7.0 (s, 2H); 7.1 (m, 2H); 7.3 (m, 2H); 7.7 (s, 1H).

The following compounds were synthesized in a similar manner with different starting materials:
86) 5-(3-ethoxy-4-methoxyphenyl)-1-(4-fluorophenyl)-1H-pyrazole; LC/MS (EI) $t_R$ 4.41, m/z 313.2 ($M^+$+1)
87) 5-[3-(cyclopropylmethoxy)-4-methoxyphenyl]-1-(4-fluorophenyl)-1H-pyrazole; LC/MS (EI) $t_R$ 4.69, m/z 339.1 ($M^+$+1)
88) 5-[3-(cyclopentyloxy)-4-methoxyphenyl]-1-(4-fluorophenyl)-1H-pyrazole LC/MS (EI) $t_R$ 5.11 (Method C), m/z 353.2 ($M^+$+1)

Example 45

Synthesis of 1-[4-(Difluoromethoxy)-3-hydroxyphenyl]ethanone and 1-[3,4-bis(difluoromethoxy)phenyl]ethanone

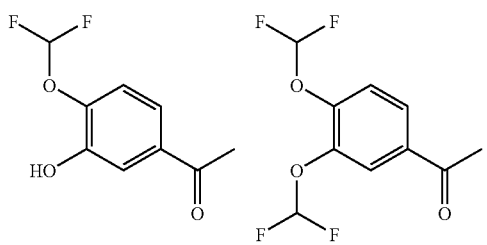

A solution of 1-(3,4-dihydroxyphenyl)ethan-1-one (2.00 g, 13.1 mmol) in 200 mL of N,N-dimethylformamide was treated with potassium hydroxide (6.64 g, 118 mmol) and the reaction was stirred at room temperature for one hour. The reaction mixture was cooled with a dry ice/acetone bath to maintain an internal temperature <25° C. and chlorodifluoroacetic acid (5.57 mL, 65.7 mmol) was slowly added and the reaction was then allowed to warm to room temperature for one hour. The reaction was heated to 65° C. overnight and after cooling to room temperature, the reaction was diluted with 400 mL of water and extracted with 3×150 mL methyl t-butyl ether making sure the water layer was pH~3. The organic layer was extracted with 3×100 mL of 1 N NaOH. To obtain 1-[3,4-bis(difluoromethoxy)phenyl]ethanone, the separated organic layer was dried over sodium sulfate, filtered, and concentrated under reduced pressure. The residue was purified by column chromatography on silica gel eluting with a gradient of 10% ethyl acetate in hexanes to 100% ethyl acetate over 30 minutes to yield 1-[3,4-bis(difluoromethoxy)phenyl]ethanone (531 mg, 16%).

To obtain 1-[4-(difluoromethoxy)-3-hydroxyphenyl]ethanone, the NaOH solution was acidified with 1N HCl and extracted with 3×100 mL diethyl ether. The combined organic fractions were dried over sodium sulfate, filtered and concentrated under reduced pressure. The residue was purified by column chromatography on silica gel eluting with a gradient of 10% ethyl acetate in hexanes to 100% ethyl acetate over 30 minutes to yield 1-[4-(difluoromethoxy)-3-hydroxyphenyl]ethanone (314 mg, 12%).

Example 46

Synthesis of (2E)-1-[4-(Difluoromethoxy)-3-methoxyphenyl]-3-(dimethylamino)prop-2-en-1-one

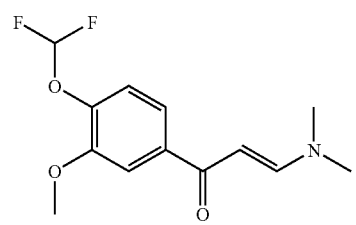

Into a 1-necked flask were added 1-[4-(difluoromethoxy)-3-hydroxyphenyl]ethanone (0.317 g, 1.57 mmol), 16 mL of N,N-dimethylformamide, and N,N-dimethylformamide dimethy acetal (0.25 mL, 1.9 mmol). The mixture was heated to 140° C. overnight and after cooling to room temperature, poured into 50 mL water and extracted 3×50 mL ethyl acetate. The combined organic fractions were dried over sodium sulfate, filtered and concentrated under reduced pressure. The residue was purified by column chromatography on silica gel eluting with a gradient of 50% ethyl acetate in hexanes to 100% ethyl acetate over 30 minutes to give (2E)-1-[4-(difluoromethoxy)-3-methoxyphenyl]-3-dimethylamino)prop-2-en-1-one (51 mg, 0.188 mmol) as a yellow oil.

Example 47

Synthesis of 3-Ethyl-N-methoxy-N-methyl-1H-indazole-6-carboxamide

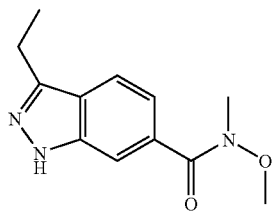

3-ethyl-1H-indazole-6-carboxylic acid (3.9 g, 0.020 mol), N-(3-dimethylaminopropyl)-N'-ethylcarbodiimide hydrochloride (4.3 g, 0.022 mol) and 4-dimethylaminopyridine (3.11 g, 0.0254 mol), N,O-dimethylhydroxylamin hydrochloride (2.8 g, 0.028 mol) were dissolved in methylene chloride (200 mL) and N,N-dimethylformamide (20 mid) and the solution stirred at room temperature for one hour. The resulting mixture was poured in iced water. The aqueous layer was removed, and extracted with ethyl acetate (2×50 mL). The combined organics were washed with 1 N HCl, 2N NaOH, water, and brine, then dried. The solvent was removed in vacuo, and the residue was purified by column chromatography on silica gel eluting with a gradient of 50% ethyl acetate in hexanes to 100% ethyl acetate over 30 minutes to give 1.6 g (33%) of 3-ethyl-N-methoxy-N-methyl-1H-indazole-6-carboxamide.

Example 48

Synthesis of 3-Ethyl-N-methoxy-N-methyl-2-{[2-(trimethylsilyl)ethoxy]methyl}-2H-indazole-6-carboxamide

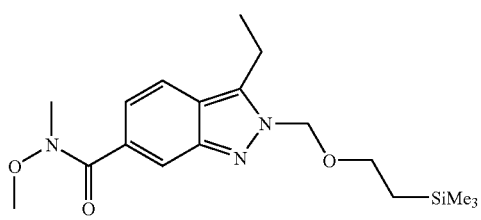

NaH (1.3 g, 60% dispersion in mineral oil, 0.033 mol) and tetrahydrofuran (223 mL) were mixed in a 1-necked flask and cooled to 0° C. To this was added dropwise a mixture of 3-ethyl-N-methoxy-N-methyl-1H-indazole-6-carboxamide (2.6 g, 0.011 mol) in tetrahydrofuran (60 mL), and the mixture was stirred at 0° C. for 1 hour. [β-(Trimethylsilyl)ethoxy]methyl chloride (2.4 mL, 0.013 mol) was then added and the reaction mixture was allowed to warm to room temperature. The resulting mixture was partitioned between water (50 mL) and ethyl acetate (50 mL). The layers were separated and the organics were washed with brine (25 mL), dried (sodium sulfate) and concentrated in vacuo to afford 4.0 g (quantitative yield) of 3-ethyl-N-methoxy-N-methyl-2-{[2-(trimethylsilyl)ethoxy]methyl}-2H-indazole-6-carboxamide, which was used without further purification.

Example 49

Synthesis of 1-(3-Ethyl-1-{[2-(trimethylsilyl)ethoxy]methyl}-1H-indazol-6-yl)ethanone

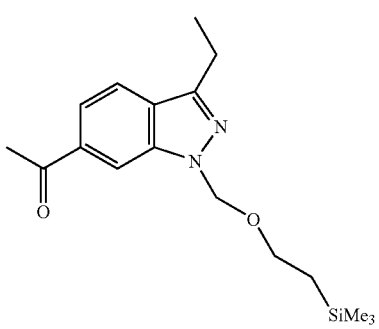

Methylmagnesium chloride (7.7 mL, 3M in tetrahydrofuran) was added dropwise at −78° C. under an atmosphere of argon to a solution of 3-Ethyl-N-methoxy-N-methyl-1-{[2-(trimethylsilyl)ethoxy]methyl}-1H-indazole-6-carboxamide (4.0 g, 0.011 mol) in tetrahydrofuran (114 mL). The resulting mixture was allowed to warm slowly to room temperature. The reaction was then quenched by the addition of a saturated solution of ammonium chloride. Ethyl acetate (150 mL) and water (100 mL) were then added, and the organic layer was separated, washed with water and with brine, and then dried (sodium sulfate). After filtration, the solvent was concentrated, and the residue was purified by column chromatography on silica gel, eluting with a gradient of 50% ethyl acetate in hexanes to 100% ethyl acetate over 30 minutes, to give 3.5 g (quantitative yield) of 1-(3-Ethyl-1-{[2-(trimethylsilyl)ethoxy]methyl}-1H-indazol-6-yl)ethanone. $^1$H NMR (CDCl$_3$) δ 0.0 (m, 1H), 1.0 (t, 3H), 1.1-1.4 (m, 2H), 2.7 (s, 3H), 2.9-3.1 (m, 2H), 3.5 (1, 2H), 5.7 (s, 2H), 7.5 (m, 2H), 8.0 (s, 1H).

Example 50

Synthesis of (2E)-3-(Dimethylamino)-1-(3-Ethyl-1-{[2-(trimethylsilyl)ethoxy]methyl}-1H-indazol-6-yl)prop-2-en-1-one

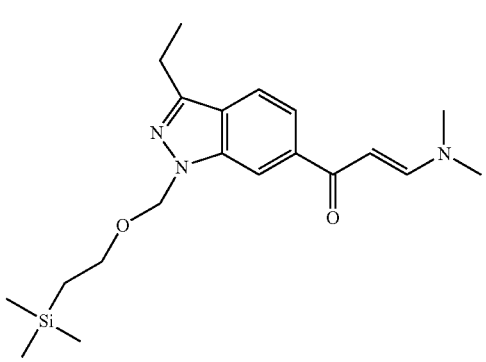

Under an atmosphere of argon, 1,1-Dimethoxy-N,N-dimethylmethanamine (4.4 mL, 0.033 mol) and 1-(3-Ethyl-1-{

[2-(trimethylsilyl)ethoxy]methyl}-1H-indazol-6-yl)etha-none (3.5 g, 0.011 mol) were mixed in N,N-dimethylformamide (110 mL) and the resulting mixture was heated at 140° C. for 16 hours. After cooling to room temperature, water (250 mL) and ethyl acetate (250 mL) were added, the layers were separated, and the product was extracted with ethyl acetate (3×100 mL). The combined organic layers, were washed with water and brine, dried (sodium sulfate), and the volatiles were removed in vacuo to afford 4.1 g (quantitative yield) of (2E)-3-(dimethylamino)-1-(3-Ethyl-1-{[2-(trimethylsilyl)ethoxy]methyl}-1H-indazol-6-yl)prop-2-en-1-one, which was used without further purification.

Example 51

Synthesis of 6-{1-[3-(Benzyloxy)phenyl]-1H-pyrazol-5-yl}-3-ethyl-1H-indazole

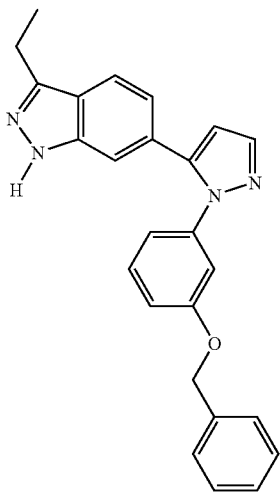

(2E)-3-(dimethylamino)-1-(3-Ethyl-1-{[2-(trimethylsilyl)ethoxy]methyl}-1H-indazol-6-yl)prop-2-en-1-one (256 mg, 0.685 mmol) and 3-benzyloxyphenylhydrazine hydrochloride (270 mg, 1.1 mmol) were dissolved in ethanol (4 mL) in a 10 mL sealed tube. The mixture was subjected to microwave radiation (300 watts, 160° C.) for 5 minutes. The solvent was removed and the residue was extracted with ethyl acetate, then washed with water and brine. Removal of volatiles provided a tan solid, which was purified by column chromatography on silica gel, eluting with a 10-50% hexane/ethyl acetate gradient over 10 minutes (flow rate 20 mL/min), to give 160 mg (59%) of 6-{1-[3-(benzyloxy)phenyl]-1H-pyrazol-5-yl}-3-ethyl-1H-indazole. $^1$H NMR (CDCl$_3$) δ 1.4 (t, 3H), 3.0 (q, 2H), 5.0 (s, 2H), 6.6 (d, 1H), 6.8 (d, 1H), 6.9 (d, 1H), 7.1 (m, 2H), 7.2 (t, 1H), 7.3, (m, 5H), 7.6 (d, 1H), 7.8 (m, 1H), 9.7 (br s, 1H).

Example 52

99) 3-Ethyl-2-(1-ethylpropyl)-6-{1-[(methylsulfonyl)phenyl]-1H-pyrazol-5-yl}-2H-indazole

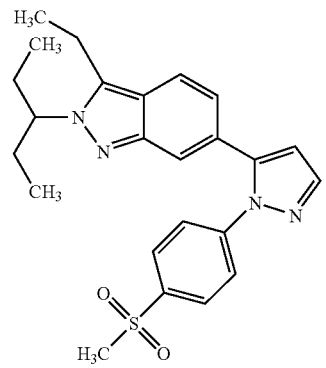

3-ethyl-6-{1-[4-(methylsulfonyl)phenyl]-1H-pyrazol-5-yl}-1H-indazole (100 mg, 0.27 mmol), 3-bromopentane (70 mg, 0.46 mmol), potassium carbonate (45 mg, 0.33 mmol) and N,N-dimethylformamide (2 mL) were added to a 1-necked flask. The mixture was heated to 60° C. for 6 hours, then slowly cooled to room temperature and stirred for a further 48 hours. A further equivalent of 3-bromopentane (41 mg, 0.27 mmol) was then added, and the reaction was heated to 120° C. After cooling to room temperature, water and ethyl acetate were added. The product was extracted once with ethyl acetate, and washed with water and brine. The combined organics were dried, and filtered and concentrated. The reside was purified by column chromatography on silica gel (eluting using 50% ethyl acetate in hexanes for 10 minutes and then a linear gradient to 100% ethyl acetate in hexanes at 20 minutes) to give 4.4 mg (3.7%) of 3-ethyl-2-(1-ethylpropyl)-6-{1-[4-(methylsulfonyl)phenyl]-1H-pyrazol-5-yl}-2H-indazole. LC/MS (EI) t$_R$ 4.36 (Method C), m/z 437.1 (M$^+$+1), $^1$H NMR (CDCl$_3$) δ 0.6 (t, 3H), 1.4 (t, 2H), 1.8 (m, 2H), 1.9 (m, 2H), 3.0 (m, 6H), 4.0 (m, 1H), 6.5 (s, 1H), 7.0 (d, 1H), 7.1 (s, 1H), 7.5 (d, 2H), 7.7 (m, 1H), 7.8 (s, 1H), 7.8 (d, 2H). 13 mg (11%) of the corresponding isomer (3-ethyl-1-(1-ethylpropyl)-6-{1-[4-(methylsulfonyl)phenyl]-1H-pyrazol-5-yl}-1H-indazole) was also isolated.

The following compounds were synthesized in a similar manner with different starting materials:

98) 3-ethyl-1-(1-ethylpropyl)-6-{1-[4-(methylsulfonyl)phenyl]-1H-pyrazol-5-yl}-1H-indazole, LC/MS (EI) t$_R$ 4.76 (Method C), m/z 437.1 (M$^+$+1)

100) 3-ethyl-6-{1-[4-(methylsulfonyl)phenyl]-1H-pyrazol-5-yl}-1-(tetrahydro-2H-pyran-2-ylmethyl)-1H-indazole, LC/MS (EI) t$_R$ 4.36 (Method C), m/z 465.2 (M$^+$+1)

101) 3-ethyl-6-{1-[4-(methylsulfonyl)phenyl]-1H-pyrazol-5-yl}-2-(tetrahydro-2H-pyran-2-ylmethyl)-2H-indazole, LC/MS (EI) t$_R$ 4.3 (Method C), m/z 465.2 (M$^+$+1)

102) 3-ethyl-6-{1-[4-(methylsulfonyl)phenyl]-1H-pyrazol-5-yl}-2-(2-pyrrolidin-1-ylethyl)-2H-indazole, LC/MS (EI) t$_R$ 4.11 (Method C), m/z 464.1 (M$^+$+1)

104) 3-ethyl-6-{1-[4-(methylsulfonyl)phenyl]-1H-pyrazol-5-yl}-1-(2-pyrrolidin-1-ylethyl)-1H-indazole, LC/MS (EI) $t_R$ 4.24 (Method C), m/z 464.1 (M$^+$+1)

Example 53

108) N,3-Diethyl-6-{1-[4-(methylsulfonyl)phenyl]-1H-pyrazol-5-yl}-1H-indazole-1-carboxamide

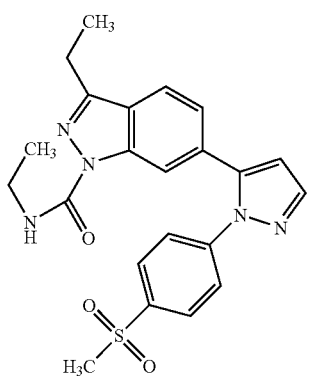

Isocyanatoethane (0.014 mL, 0.18 mmol) was added to a solution of 3-ethyl-6-{1-[4-(methylsulfonyl)phenyl]-1H-pyrazol-5-yl}-1H-indazole (50 mg, 0.14 mmol) in pyridine (2 mL) and the mixture was heated at 100° C. for 16 hours. Upon cooling, water and ethyl acetate were added and the product was washed once with 0.1 N HCl, once with water and once with brine. The combined organics were dried, the solvent was removed, and the reside was purified by column chromatography on silica gel, eluting with 20% ethyl acetate in hexanes for 5 minutes, a linear gradient to 50% ethyl acetate in hexanes over 15 minutes, and then 50% ethyl acetate for an additional 10 minutes, to afford 32 mg (54%) of N,3-diethyl-6-{1-[4-(methylsulfonyl)phenyl]-1H-pyrazol-5-yl}-1H-indazole-1-carboxamide. LC/MS (EI) $t_R$ 4.33 (Method C), m/z 438.2 (M$^+$+1), $^1$H NMR (CDCl$_3$) δ 1.0 (t, 3H), 1.4 (t, 3H), 2.9 (t, 2H), 3.0 (s, 3H), 3.4 (m, 2H), 6.5 (s, 1H), 7.0 (d, 1H), 7.1 (s, 1H), 7.4 (d, 2H), 7.5 (m, 1H), 7.8 (s, 1H), 7.9 (d, 2H), 8.4 (s, 1H).

The following compounds were synthesized in a similar manner with different starting materials:

105) N-(sec-butyl)-3-ethyl-6-{1-[4-(methylsulfonyl)phenyl]-1H-pyrazol-5-yl}-1H-indazole-1-carboxamide, LC/MS (EI) $t_R$ 5.04 (Method A), m/z 466.1 (M$^+$+1)

107) N-cyclopentyl-3-ethyl-6-{(1-[4-(methylsulfonyl)phenyl]-1H-pyrazol-5-yl}-1H-indazole-1-carboxamide, LC/MS (EI) $t_R$ 5.34 (Method A), m/z 478.2 (M$^+$+1)

109) 3-ethyl-N-(2-furylmethyl)-6-{1-[4-(methylsulfonyl)phenyl]-1H-pyrazol-5-yl}-1H-indazole-1-carboxamide, LC/MS (EI) $t_R$ 4.6 (Method A), m/z 490.2 (M$^+$+1).

Example 54

103) Isopropyl 3-ethyl-6-{1-[4-(methylsulfonyl)phenyl]-1H-pyrazol-5-yl}-1H-indazole-1-carboxylate

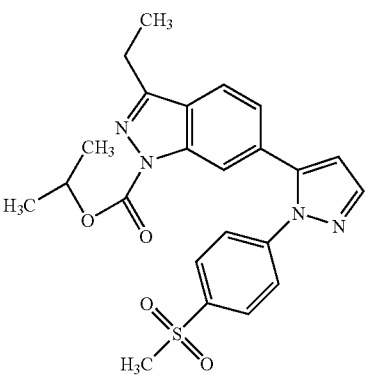

A mixture of 3-ethyl-6-{1-[4-(methylsulfonyl)phenyl]-1H-pyrazol-5-yl}-1H-indazole (5.0 mg, 0.14 mmol), tetrahydrofuran (2 mL), triphenylphospine (71.6 mg, 0.27 mmol), and (3S)-tetrahydrofuran-3-ol (21.8 μL, 0.27 mmol) was stirred at room temperature, and diisopropyl azodicarboxylate (53.7 μL, 0.27 mmol) was added. The resulting mixture was stirred at room temperature for 16 hours. The crude product was then absorbed onto silica gel and isolated by flash chromatography using a hexane:ethyl acetate (1:1) methanol gradient (0-10%) over 10 minutes (20 mL/min flow rate) to provide 40 mg (63%) of Isopropyl 3-ethyl-6-{1-[4-(methylsulfonyl)phenyl]-1H-pyrazol-5-yl}-1H-indazole-1-carboxylate. LC/MS (EI) $t_R$ 2.27 (Method C), m/z 453.1 (M$^+$+1), $^1$H NMR (CDCl$_3$) δ 1.4 (m, 9H); 2.9 (m, 2H); 3.0 (s, 3H); 5.2 (m, 1H); 6.7 (s, 1H); 7.1 (d, 1H); 7.5 (d, 2H); 7.6 (d, 1H); 7.7 (d, 2H); 7.8 (s, 1H); 8.1 (m, 1H).

Example 55

110) 3-Ethyl-6-{1-[4-(methylsulfonyl)phenyl]-1H-pyrazol-5-yl}-1-pyrimidin-2-yl-1H-indazole

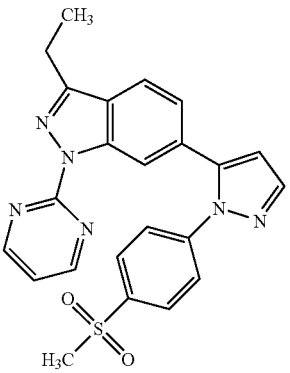

A mixture of 3-ethyl-6-{1-[4-(methylsulfonyl)phenyl]-1H-pyrazol-5-yl}-1H-indazole (50 mg, 0.14 mmol), tris(dibenzylideneacetone)dipalladium(0) (10 mg, 0.01 mmol), 7-bromopyrimidine (26 mg, 0.16 mmol), 9,9-dimethyl-4,5-bis(diphenylphosphino)xanthene (16 mg, 0.03 mmol), sodium tert-butoxide (19.7 mg, 0.21 mmol) and toluene (2.3 mL) was subjected to microwave irradiation (300 watts, 140° C.) for 300 seconds in a 10 mL sealed tube. The solvent was removed and the crude product absorbed onto silica gel. The residue was purified by column chromatography using as eluent 10% ethyl acetate in hexanes for 10 minutes, then a gradient to 50% ethyl acetate in hexanes at 20 minutes, then 50% for 5 minutes, then 100% at 35 minutes to provide 42 mg (70%) of 3-ethyl-6-{1-[4-(methylsulfonyl)phenyl]-1H-pyrazol-5-yl}-1-pyrimidin-2-yl-1H-indazole. LC/MS (EI) $t_R$ 3.82 (Method C), m/z 445.1 (M$^+$+1), $^1$H NMR (CDCl$_3$) δ 1.5 (t, 3H); 3.0 (s, 3H); 3.1 (q, 2H); 6.6 (s, 1H); 7.1 (d, 2H); 7.6 (d, 2H); 7.7 (d, 1H); 7.8 (d, 1H); 7.9 (m, 2H); 8.7 (m, 3H).

The following compound was synthesized in a similar manner with different starting materials:

118) 3-ethyl-6-{1-[4-(methylsulfonyl)phenyl]-1H-pyrazol-5-yl}-1-pyridin-2-yl-1H-indazole, LC/MS (EI) $t_R$ 5.37 (Method A), m/z 444.2 (M$^+$+1)

Example 56 a) Synthesis of 1-(2,6-difluoropyridin-3-yl)propan-2-ol

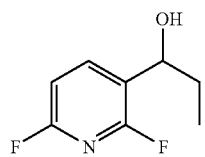

2,6-difluoropyridine (5.0 mL, 0.0551 mol) in tetrahydrofuran (55 mL) was slowly added to a 1-necked flask containing lithium diisopropylamide (31 mL, 1.8 M in tetrahydrofuran) at −78° C. The reaction was stirred at this temperature for 30 minutes and then propionaldehyde (3.96 mL, 0.0551 mol) was added. After stirring at this temperature for an additional 30 minutes, the reaction was quenched by the addition of a saturated solution of ammonium chloride (20 mL). The product was extracted with diethylether, and purified by column chromatography using as eluent 10% ethyl acetate in hexanes to provide 6.7 g (70%) of 1-(2,6-difluoropyridin-3-yl)propan-2-ol.

b) Synthesis of 1-(2,6-difluoropyridin-3-yl)propan-1-one

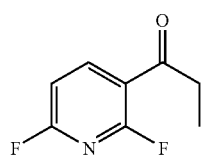

A mixture of 1-(2,6-difluoropyridin-3-yl)propan-2-ol (6.3 g, 0.036 mol) pyridinium chlorochromate (27.1 g, 0.126 mol) and chloroform (320 mL) was stirred at room temperature for 16 hours. The mixture was filtered through silica gel, which was then washed with dichloromethane, to afford 4.8 g (77%) of 1-(2,6-difluoropyridin-3-yl)propan-1-one.

Example 57

Synthesis of 3-Ethyl-6-fluoro-1-(tetrahydro-2H-pyran-4-yl)-1H-pyrazolo[3,4-b]pyridine

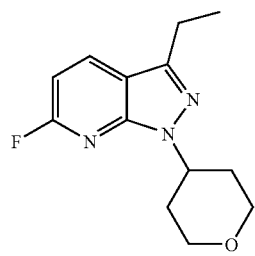

A mixture of tert-butyl 2-(tetrahydro-2H-pyran-4-yl)hydrazinecarboxylate (3.8 g, 0.018 mol) and trifluoroacetic acid (20 mL, 0.3 mol) were stirred in dichloromethane (20 mL) for 90 minutes. The mixture was concentrated, and the residue was taken up in acetonitrile (30 mL). 1-(2,6-difluoropyridin-3-yl)propan-1-one (2.34 g, 0.0137 mol) was then added, and the resulting mixture was stirred at 75° C. for 72 hours. After cooling to room temperature, the mixture was concentrated, and the residue was purified by flash chromatography on silica gel using a 10-50% hexane:ethyl acetate gradient (flow rate 20 mL/min). The organics were combined and the crude product was then extracted with ethyl acetate. The combined extracts were washed with saturated sodium bicarbonate and then concentrated to afford 2.86 g (83.9%) of 3-ethyl-6-fluoro-1-(tetrahydro-2H-pyran-4-yl)-1H-pyrazolo[3,4-b]pyridine as a white solid. LC/MS (EI) $t_R$ 3.5 (Method E), m/z 250 (M$^+$+1).

The following compound was prepared in a similar fashion with different starting materials:
3-Ethyl-6-fluoro-1-isopropyl-1H-pyrazolo[3,4-b]pyridine.

Example 58

Synthesis of 3-Ethyl-1-(tetrahydro-2H-pyran-4-yl)-1H-pyrazolo[3,4-b]pyridine-6-carbonitrile

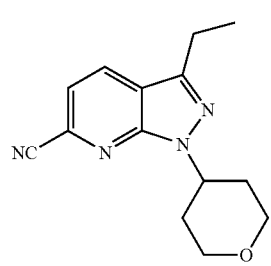

A mixture of 3-ethyl-6-fluoro-1-(tetrahydro-2H-pyran-4-yl)-1H-pyrazolo[3,4-b]pyridine (2.92 g, 0.0117 mol), sodium cyanide (3.9 g, 0.079 mol), tetra-N-butylammonium bromide (7.6 g, 0.023 mol) and dimethyl sulfoxide (60 mL) was heated at 150° C. for 2 hours. After cooling, the product was extracted using ethyl acetate (300 mL). The extract was washed with water (5×50 mL) and brine (50 mL), and then concentrated to provide the crude product as a brown solid, which was purified by flash chromatography on silica gel using a 10-50% hexane:ethyl acetate gradient over 15 minutes (flow rate 20 mL/min) to afford 2.22 g (73.9%) of 3-ethyl-1-(tetrahydro-2H-pyran-4-yl)-1H-pyrazolo[3,4-b]pyridine-6-carbonitrile as an off-white solid, which was used without further purification. LC/MS (EI) $t_R$ 3.57 (Method E), m/z 257.2 (M$^+$+1).

The following compound was prepared in a similar fashion with different starting materials:

3-Ethyl-1-isopropyl-1H-pyrazolo[3,4-b]pyridine-6-carbonitrile.

Example 59

Synthesis of 1-[3-Ethyl-1-(tetrahydro-2H-pyran-4-yl)-1H-pyrazolo[3,4b]pyridin-6-yl]ethanone

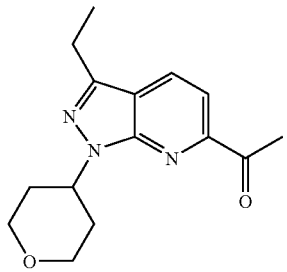

Methyltriphenylphosphonium bromide (4.64 g, 0.0130 mol) and lithium iodide (0.48 g, 0.0036 mot) were mixed in tetrahydrofuran (70 mL) in a 3-necked flask under an atmosphere of nitrogen. The flask was wrapped in aluminum foil to exclude light, and chilled to 0° C. n-Butyllithium (5.8 mL, 2.5 M in hexanes, 0.014 mol) was then added and the resulting mixture stirred for 30 minutes. A solution of 3-ethyl-1-(tetrahydro-2H-pyran-4-yl)-1H-pyrazolo[3,4-b]pyridine-6-carbonitrile (1.85 g, 7.22 mmol) in tetrahydrofuran (19.8 mL) was then added and the reaction stirred at 50° C. for 90 minutes. After cooling to room temperature, the product was extracted using dichloromethane (250 mL). The extract was washed brine and concentrated to afford the crude product as a semi-solid, which was purified by flash chromatography on silica gel using a 10-50% hexane:ethyl acetate gradient over 10 minutes (flow rate 20 mL/min). Concentration of the organics afforded 1.39 g (70.4%) of 1-[3-Ethyl-1-(tetrahydro-2H-pyran-4-yl)-1H-pyrazolo[3,4-b]pyridine-6-yl]ethanone as a colorless oil. LC/MS (EI) $t_R$ 3.72 (Method E), m/z 274.1 (M$^+$+1). All reagents were stored in a desiccator prior to use.

The following compound was prepared in a similar fashion with different starting materials:

1-(3-Ethyl-1-isopropyl-1H-pyrazolo[3,4-b]pyridine-6-yl)ethanone.

Example 60

116) 3-ethyl-6-{1-[4-methylsulfonyl)phenyl]-1H-pyrazol-5-yl}-1(tetrahydro-2H-pyran)-1H-indazole

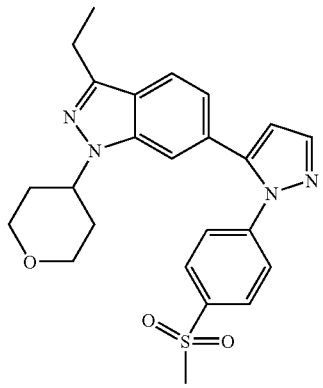

3-ethyl-6-{1-[4-(methylsulfonyl)phenyl]-1H-pyrazol-5-yl}-1H-indazole (0.18 g, 0.49 mmol) in N,N-dimethylformamide (6 mL) was added to a mixture of sodium hydride (29 mg, 60% in mineral oil, 0.74 mmol) and N,N-dimethylformamide (6 mL) under an atmosphere of argon, and the resulting mixture was stirred for 30 minutes. 4-iodotetrahydro-2H-pyran (0.16 g, 0.74 mmol) in N,N-dimethylformamide (6 mL) was then added and the reaction was heated at 60° C. for 50 hours. After cooling, the reaction mixture was concentrated and the residue diluted with water/acetonitrile (40 mL) and filtered (0.45 µm). The product was purified by preparative HPLC using a gradient of 20-80% acetonitrile:water (with 0.1% formic acid and a flow rate of 45 mL/min to afford 10 mg (4.6%) of 3-ethyl-6-{1-[4-methylsulfonyl)phenyl]-1H-pyrazol-5-yl}-1 (tetrahydro-2H-pyran)-1H-indazole as a yellow solid. LC/MS (EI) $t_R$ 4.54 (Method A), m/z 451.2 (M$^+$+1). $^1$H NMR (CDCl$_3$) δ 1.4 (t, 3H); 1.9 (d, 2H); 2.4 (m, 2H); 3.0 (m, 1H); 3.1 (s, 3H); 3.6 (m, 3H); 4.1 (d, 2H); 4.5 (m, 1H); 6.6 (s, 1H); 6.9 (d, 1H); 7.2-7.3 (m, 3H); 7.5-7.7 (m, 2H); 7.8-7.9 (m, 2H).

The following compounds were made using a similar procedure using different starting materials:

117) 1-(difluoromethyl)-3-ethyl-6-{1-[4-(methylsulfonyl)phenyl]-1H-pyrazol-5-yl}-1H-indazole, LC/MS (EI) $t_R$ 4.21 (Method A), m/z 417.1 (M$^+$+1)

119) 1-(5-cyclopropyl-1,3,4-thiadiazol-2-yl)-3-ethyl-6-{1-[4-(methylsulfonyl)phenyl]-1H-pyrazol-5-yl}-1H-indazole, LC/MS (EI) $t_R$ 5.19 (Method A), m/z 491.1 (M$^+$+1)

120) 3-ethyl-6-{1-[4-(methylsulfonyl)phenyl]-1H-pyrazol-5-yl}-1-(tetrahydrofuran-3-yl)-1H-indazole, LC/MS (EI) $t_R$ 4.02 (Method A), m/z 437.2 (M$^+$+1)

121) Tert-butyl 3-(3-ethyl-6-{1-[4-(methylsulfonyl)phenyl]-1H-pyrazol-5-yl}-1H-indazol-1-yl)pyrrolidine-1-carboxylate, LC/MS (EI) $t_R$ 4.97 (Method B), m/z 436.2 (M$^+$+1).

Example 61

112) 1-Cyclopropyl-3-ethyl-6-{1-[4-(methylsulfonyl)phenyl]-1H-pyrazol-5-yl}-1H-indazole

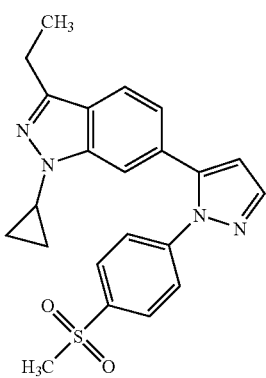

3-ethyl-6-{1-[4-(methylsulfonyl)phenyl]-1H-pyrazol-5-yl}-1H-indazole (20 mg, 0.054 mmol), cyclopropylboronic acid (14 mg, 0.16 mmol), cupric acetate (20 mg, 0.11 mmol), triethylamine (0.038 mL, 0.27 mmol), pyridine (0.035 mL, 0.44 mmol), and tetrahydrofuran (2.0 mL) were added to a 10 mL sealed tube. The mixture was subjected to microwave radiation (300 watts, 140° C.) for 10 minutes. The solvent was removed and the residue was extracted with ethyl acetate (10 mL). The extract was washed with saturated sodium bicarbonate solution (2×50 mL). Concentration afforded 22 mg (40%) of 1-cyclopropyl-3-ethyl-6-{1-[4-(methylsulfonyl)phenyl]-1H-pyrazol-5-yl}-1H-indazole. LC/MS (EI) $t_R$ 4.15 (Method A), m/z 407.1 (M$^+$+1). $^1$H NMR (CDCl$_3$) δ 1.1 (m, 4H); 1.4 (t, 3H); 2.9 (m, 2H); 3.1 (s, 3H); 3.5 (m, 1H): 6.5 (s, 1H); 6.9 (d, 1H); 7.4 (s, 1H); 7.5 (d, 1H); 7.6 (d, 2H); 7.8 (s, 1H); 7.9 (d, 2H).

The following compounds were made using a similar procedure using different starting materials:

106) 3-ethyl-6-{1-[4-(methylsulfonyl)phenyl]-1H-pyrazol-5-yl}-1-pyridin-3-yl-1H-indazole, LC/MS (EI) $t_R$ 3.92 (Method C), m/z 444.2 (M$^+$+1)

111) 3-ethyl-6-{1-[4-(methylsulfonyl)phenyl]-1H-pyrazol-5-yl}-1-pyrimidin-5-yl 1H-indazole, LC/MS (EI) $t_R$ 3.41 (Method C), m/z 445.1 (M$^+$+1)

118) 3-ethyl-6-{1-[4-(methylsulfonyl)phenyl]-1H-pyrazol-5-yl}-1-pyridin-2-yl-1H-indazole, LC/MS (EI) $t_R$ 5.37 (Method A), m/z 444.2 (M$^+$+1).

Example 62

Synthesis of 1,3-Diethyl-1H-indazole-6-carboxylic acid methoxy-methyl-amide

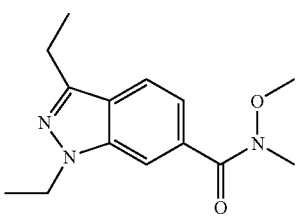

A mixture of potassium tert-butoxide (0.144 g, 1.28 mmol) and iodoethane (0.20 g, 1.28 mmol) in THF (1 mL) was added to a solution of 3-ethyl-1H-indazole-6-carboxylic acid methoxy-methyl-amide (0.20 g, 0.86 mmol) in THF (3 mL) and the resulting mixture stirred at room temperature for 16 hours. Ethyl acetate (30 mL) was then added and the product was extracted with 0.5 N HCl (10 mL). The aqueous layer was then re-extracted with ethyl acetate (30 mL). The organics were combined, dried, filtered and concentrated to afford 250 mg of 1,3-diethyl-1H-indazole-6-carboxylic acid methoxy-methyl-amide that was used without further purification.

The following compounds were made using a similar procedure using different starting materials:

3-ethyl-1-(2-methoxyethyl)-1H-indazole-6-carboxylic acid methoxy-methyl-amide, 3-ethyl-1-isopropyl-1H-indazole-6-carboxylic acid methoxy-methyl-amide, 1-cyclopropylmethyl-3-ethyl-1H-indazole-6-carboxylic acid methoxy-methyl-amide, 1-cyclopentyl-1H-indazole-6-carboxylic acid methoxy-methyl-amide.

Example 63

Synthesis of 1-(1,3-Diethyl-1H-indazol-6-yl)-ethanone

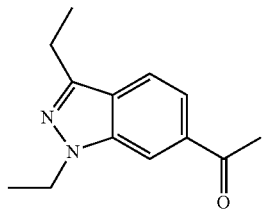

1,3-Diethyl-1H-indazole-6-carboxylic acid methoxy-methyl-amide (0.22 g, 0.86 mmol) was dissolved in tetrahydrofuran (8 mL) and cooled to −70° C. Methylmagnesium chloride (2 mL, 3M in tetrahydrofuran, 0.06 mol) was added dropwise and the resulting mixture was stirred for 30 minutes at −70° C. After warming to room temperature, the mixture was stirred for a further 3 minutes, then quenched by the addition of a chilled saturated solution of ammonium chloride. Ethyl acetate (150 mL) and water (40 mL) were then added and the product was extracted. The aqueous layer was re-extracted with ethyl acetate (75 mL). The organic layers were combined, dried, filtered, and concentrated to afford 200 mg of 1-(1,3-Diethyl-1H-indazol-6-yl)-ethanone.

The following compounds were made using a similar procedure using different starting materials:

1-(1-cyclopentyl-3-ethyl-1H-indazol-6-yl)-ethanone, 1-(3-ethyl-1H-indazol-6-yl)-ethanone, 1-[1-(cyclopropylmethyl)-3-ethyl-1H-indazol-6-yl]-ethanone, 1-(3-ethyl-1-(2-methoxyethyl)-1H-indazol-6-yl)-ethanone, 1-(3-ethyl-1-isopropyl-1H-indazol-6-yl)-ethanone.

Example 64

Synthesis of (2E)-1-(1,3-diethyl-1H-indazol-6-yl)-3-(dimethylamino)prop-2-en-1-one

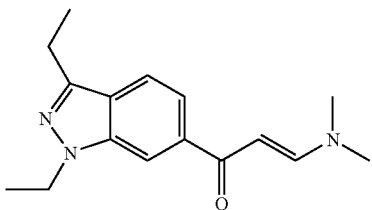

1,1-dimethoxy-N,N-dimethylmethanamine (0.891 g, 0.0075 mol) was added to a solution of 1-(1,3-Diethyl-1H-indazol-6-yl)-ethanone (0.187 mg, 8.64 mmol) in N,N-dimethylformamide (8 mL), and the resulting mixture was shaken at 120° C. for 16 hours. 1,1-dimethoxy-N,N-dimethylmethanamine (0.618 g, 0.0052 mol) was added, and the reaction was refluxed at 140° C. for a further 16 hours. The solvent was removed in vacuo, and the residue extracted with ethyl acetate (30 mL) and water (10 mL). The aqueous layer was re-extracted with ethyl acetate (30 mL). The organic layers were combined, dried, filtered and concentrated. The resulting crude product was purified by silica-gel chromatography, using an eluent gradient of 0.25-0.5% methanol in dichloromethane (mobile phase contained 0.5% ammonium hydroxide solution) to afford 35 mg of (2E)-1-(1,3-diethyl-1H-indazol-6-yl)-3-(dimethylamino)prop-2-en-1-one.

The following compounds were made using a similar procedure using different starting materials:
(2E)-1-[1-(cyclopropylmethyl)-3-ethyl-1H-indazol-6-yl)-3-(dimethylamino)prop-2-en-1-one,
(2E)-3-(dimethylamino)-1-(3-ethyl-1-isopropyl-1H-indazol-6-yl)-3-(dimethylamino)prop-2-en-1-one,
(2E)-3-(dimethylamino)-1-(3-ethyl-1-(2-methoxyethyl)-1H-indazol-6-yl)-3-(dimethylamino)prop-2-en-1-one,
(2E)-1-[1-(cyclopentyl)-3-ethyl-1H-indazol-6-yl)-3-(dimethylamino)prop-2-en-1-one,
(2E)-3-(dimethylamino)-1-(3-ethyl-1-isopropyl-1H-pyrazaol[3,4-b]-pyridin-6-yl)-prop-2-en-1-one,
(2E)-3-(dimethylamino)-1-[3-ethyl-1-(tetrahydro-2H-pyran-4-yl)-1H-pyrazaol[3,4-b]-pyridin-6-yl]-prop-2-en-1-one.

Example 65

129) 2-{4-[5-(1-cyclopropyl-3-ethyl-1H-indazol-6-yl)-1H-pyrazol-1-yl]phenyl}propan-2-ol

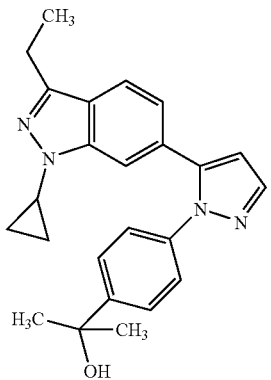

Methylmagnesium chloride (0.09 mL, 3 M in tetrahydrofuran, 0.3 mmol) in tetrahydrofuran (0.09 mL) was added dropwise to a solution of methyl 4-[5-(1-cyclopropyl-3-ethyl-1H-indazol-6-yl)-1H-pyrazol-1-yl]benzoate (36 mg, 0.093 mmol) in tetrahydrofuran (4 mL) under an atmosphere of argon at −78° C. The reaction was allowed to warm to room temperature with stirring over 1 hour. A further charge of methylmagnesium chloride (1.2 mL, 3 M in tetrahydrofuran, 4 mmol) was added and the reaction was stirred for a further 30 minutes. The reaction was cooled to 0° C. and a saturated solution of ammonium chloride was slowly added. The mixture was then added to water, and the product was extracted twice with ethyl acetate. The organic layers were combined, dried, and concentrated. The residue was purified on silica gel using a 20-50% ethyl acetate/hexane gradient to afford 12.9 mg (36%) of 2-{4-[5-(1-cyclopropyl-3-ethyl-1H-indazol-6-yl)-1H-pyrazol-1-yl]phenyl}propan-2-ol. LC/MS (EI) $t_R$ 4.30 (Method A), m/z 387.2 (M$^+$+1).

Example 66

173) 3-{5-[3-ethyl-1-(tetrahydro-2H-pyran-4-yl)-1H-pyrazolo[3,4-b]pyridin-6-yl]-1H-pyrazol-1-yl}phenol

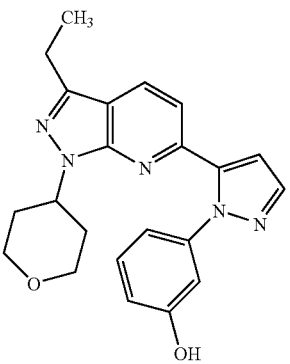

6-{1-[4-(benzyloxy)phenyl]-1H-pyrazol-5-yl}-3-ethyl-1-(tetrahydro-2H-pyran-4-yl)-1H-pyrazolo[3,4-b]pyridine (290 mg, 0.60 mmol) and ethanol (30 mL) were added to a Parr bottle. 10% Pd/C (150 mg, 0.14 mmol) was added, and the mixture was shaken under an atmosphere of hydrogen (45 psi) for 4 hours. The reaction was degassed under reduced pressure, flushed with argon for 5 minutes, filtered through Celite and concentrated to yield 0.23 g 3′-{5-[3-ethyl-1-(tetrahydro-2H-pyran-4-yl)-1H-pyrazolo[3,4-b]pyridin-6-yl]-1H-pyrazol-1-yl}phenol as an oil. LC/MS (EI) $t_R$ 2.87 (Method E), m/z 390.2 (M$^+$+1). $^1$H NMR (CDCl$_3$) δ 1.4 (t, 3H); 1.7 (m, 2H); 2.2 (m, 2H); 3.0 (q, 2H); 3.5 (t, 2H); 4.0 (m, 2H); 4.5 (m, 1H); 6.7-6.9 (m, 3H); 7.0 (s, 1H); 7.2 (m, 1H); 7.3 (d, 2H); 7.7 (s, 1H); 8.0 (m, 1H).

The following compound was prepared using a similar procedure with different starting materials:
138) 3-[5-(1-cyclopropyl-3-ethyl-1H-indazol-6-yl)-1H-pyrazol-1-yl]phenol, LC/MS (EI) $t_R$ 2.7 (Method E), m/z 345.2 (M$^+$+1)
143) 4-[5-(1-cyclopropyl-3-ethyl-1H-indazol-6-yl)-1H-pyrazol-1-yl]phenol, LC/MS (EI) $t_R$ 2.83 (Method E), m/z 345.2 (M$^+$+1)

172) 4-{5-[3-ethyl-1-(tetrahydro-2H-pyran-4-yl)-1H-pyrazolo[3,4-b]pyridin-6-yl]-1H-pyrazol-1-yl}phenol, LC/MS (EI) $t_R$ ×2.92 (Method E), m/z 390.2 (M$^+$+1).

Example 67

146) 1-cyclopropyl-3-ethyl-6-{1-[3-(2-methoxyethoxy)phenyl]-1H-pyrazol-5-yl}-1H-indazole

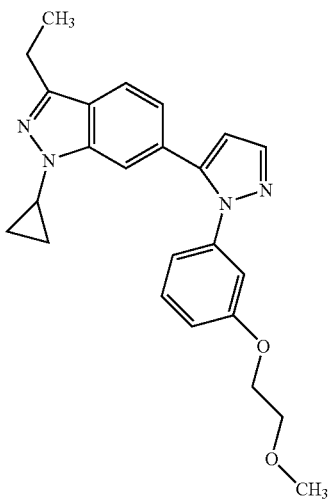

Potassium carbonate (60.2 mg, 4.36 mmol), and 1-bromo-2-methoxyethane (40.9 µl, 4.36 mmol) were added to a solution of 3-[5-(1-cyclopropyl-3-ethyl-1H-indazol-6-yl)-1H-pyrazol-1-yl]phenol (50 mg, 1.0 mmol) in N,N-dimethylformamide (3 mL), and the resulting mixture was stirred at 60° C. for 16 hours, then at 80° C. for a further 24 hours. After cooling, the reaction mixture was diluted by the addition of water/acetonitrile (1.0 mL), which was then filtered. The filtrate was purified by preparative HPLC (C18 column, 30×100 mm) using a gradient of 35-80% acetonitrile:water (with 0.1% formic acid) as the eluent at a flow rate of 45 mL/min to afford 24 mg (40%) of 1-cyclopropyl-3-ethyl-6-{1-[3-(2-methoxyethoxy)phenyl]-1H-pyrazol-5-yl}-1H-indazole. LC/MS (EI) $t_R$ 4.3 (Method E), m/z 403.2 (M$^+$+1). $^1$H NMR (CDCl$_3$) δ 1.0 (m, 4H); 1.4 (t, 3H); 3.0 (q, 2H) 3.5 (r, 4H); 3.7 (d, 2H); 4.1 (d, 2H) 6.6 (s, 1H); 6.8-6.9 (dd, 2H); 7.1 (m, 2H); 7.2 (m, 1H); 7.3 (s, 1H); 7.5 (d, 1H); 7.8 (s, 1H).

The following compounds were prepared using a similar procedure with different starting materials:

135) 1-cyclopentyl-3-ethyl-6-(1-{4-[(2-methoxyethoxy)methyl]phenyl}-1H-pyrazol-5-yl)-1H-indazole, LC/MS (EI) $t_R$ 4.56 (Method A), m/z 445.3 (M$^+$+1)

148) 1-cyclopropyl-3-ethyl-6-{1-[4-(2-methoxyethoxy)phenyl]-1H-pyrazol-5-yl}-1H-indazole, LC/MS (EI) $t_R$ 4.02 (Method E), m/z 403.2 (M$^+$+1)

174) 6-{1-[3-(2-methoxyethoxy)phenyl]-1H-pyrazol-5-yl}-3-ethyl-1-(tetrahydro-2H-pyran-4-yl)-1H-pyrazolo[3,4-b]pyridine, LC/MS (EI) $t_R$ 3.58 (Method E), m/z 448.2 (M$^+$+1)

175) 6-{1-[4-(2-methoxyethoxy)phenyl]-1H-pyrazol-5-yl}-3-ethyl-1-(tetrahydro-2H-pyran-4-yl)-1H-pyrazolo[3,4-b]pyridine, LC/MS (EI) $t_R$ 3.83 (Method E), m/z 448.2 (M$^+$+1)

176) 2-(3-{5-[3-ethyl-1-(tetrahydro-2H-pyran-4-yl)-1H-pyrazolo[3,4-b]pyridin-6-yl]-1H-pyrazol-1-yl}phenoxy)ethanol, LC/MS (EI) $t_R$ 2.74 (Method E), m/z 434.2 (M$^+$+1)

177) 2-(4-{5-[3-ethyl-1-(tetrahydro-2H-pyran-4-yl)-1H-pyrazolo[3,4-b]pyridin-6-yl]-1H-pyrazol-1-yl}phenoxy)ethanol, LC/MS (EI) $t_R$ 2.75 (Method E), m/z 434.2 (M$^+$+1).

Example 68

95) 6-[1-(1-acetylpiperidin-4-yl)-1H-pyrazol-5-yl]-1-cyclopentyl-3-ethyl-1H-indazole

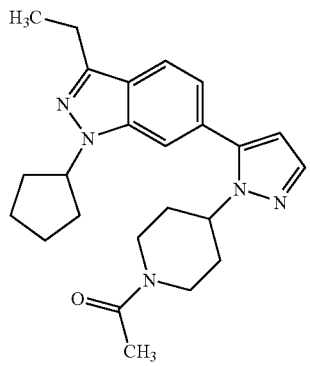

Acetyl chloride (7.8 µL, 0.11 mmol) was slowly added to a mixture of 1-cyclopentyl-3-ethyl-6-(1-piperidin-4-yl-1H-pyrazol-5-yl)-1H-indazole (20 mg, 0.055 mmol), triethylamine (15 µL, 0.11 mmol) in methylene chloride (2 mL), and the reaction was stirred for 16 hours at room temperature. Methylene chloride was added and the organic layer was washed with saturated sodium bicarbonate, water, then brine, dried, filtered and concentrated. The residue was dissolved in ethyl acetate and purified by silica gel column chromatography using 100% ethyl acetate as the eluent to afford 18 mg (81%) of 6-[1-(1-acetylpiperidin-4-yl)-1H-pyrazol-5-yl]-1-cyclopentyl-3-ethyl-1H-indazole. LC/MS (EI) $t_R$ 4.29 (Method C), m/z 406.3 (M$^+$+1).

Example 69

128) {4-[5-(1-cyclopropyl-3-ethyl-1H-indazol-6-yl)-1H-pyrazol-1-yl]phenyl}methanol

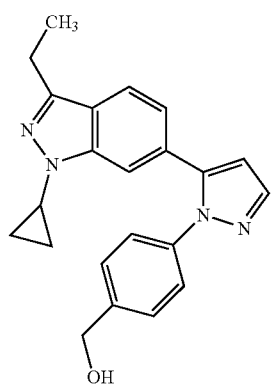

A solution of diisobutylaluminum hydride (0.19 mL, 1.5 M in toluene, 0.28 mmol) in toluene (0.19 mL) was added dropwise to a solution of methyl 4-[5-(1-cyclopropyl-3-ethyl-1H-indazol-6-yl)-1H-pyrazol-1-yl]benzoate (36 mg, 0.093 mmol) in tetrahydrofuran (5 mL) under an atmosphere of argon at −78° C. The reaction was allowed to warm to room temperature over a period of 1 hour. The mixture was then chilled to −40° C. and methanol (4 mL) was slowly added. Again, the reaction was allowed to warm slowly to room temperature, then it was poured into a mixture of ethyl acetate and water. The product was extracted (3× ethyl acetate), and the combined organics were dried and concentrated. The residue was purified by silica gel column chromatography using 50% ethyl acetate in hexanes as the eluent to afford 22.6 mg (68%) of 4-[5-(1-cyclopropyl-3-ethyl-1H-indazol-6-yl)-1H-pyrazol-1-yl]phenyl}methanol. LC/MS (EI) $t_R$ 3.19 (Method A), m/z 359.2 (M$^+$+1). $^1$H NMR (CDCl$_3$) δ 1.0 (m, 4H); 1.2 (t, 3H); 2.5 (m, 1H); 2.8 (m, 2H); 3.2 (m, 1H); 4.5 (s, 2H); 6.5 (s, 1H); 6.9 (t, 1H); 7.0-7.2 (m, 5H); 7.5 (d, 1H); 7.6 (s, 1H).

Example 70

In Vitro Measurement of Type 4 Phosphodiesterase

Enzyme Preparation:

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 µl) expressing hPDE-4D6 were combined with 50 µl of assay mix and 10 µl of inhibitors and incubated for 12 min at room temperature. Final concentrations of assay components were: 0.4 µg enzyme, 10 mM Tris-HCl (pH 7.5), 10 mM MgCl$_2$, 3 uM cAMP, 0.002 U 5'-nucleotidase, and 3×10$^4$ cpm of [3H]cAMP. The reaction was stopped by adding 100 µl of boiling 5 mM HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Packard Topcount 96 counter.

All test compounds were, dissolved in 100% DMSO and diluted into the assay such that the final concentration of DMSO is 0.1%. DMSO does not affect enzyme activity at this concentration. A decrease in adenosine concentration is indicative of inhibition of PDE activity. This procedure may be used to screen compounds of the present invention for their ability to inhibit PDE4: pIC$_{50}$ values may be determined by screening 6 to 12 concentrations of compound ranging from 0.1 nM to 10,000 nM and then plotting drug concentration versus $^3$H-adenosine concentration. Prism® may be used to estimate pIC$_{50}$ values.

Compounds of the invention show activity in the range of 10 nMv-5000 nM IC50 in the assay.

Example 71

Passive Avoidance in Rats, an In Vivo Test for Learning and Memory

The test may be performed as previously described [Zhang, H.-T., Crissman, A. M., Dorairaj, N. R., Chandler, L. J., and O'Donnell, J. M., *Neuropsychopharmacology*, 2000, 23, 198-204]. The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock may be delivered from a constant current source. All experimental groups may be first habituated to the apparatus the day before the start of the experiment. During the training, the rat (Male Spraque-Dawley (Harlan) weighing 250 to 350 g) may be placed in the illuminated compartment facing away from the closed guillotine door for 1 minute before the door was raised. The latency for entering the darkened compartment may be recorded. After the rat enters the darkened compartment, the door may be closed and a 0.5 mA electric shock was administered for 3 seconds. Twenty-four hours later, the rat may be administered 0.1 mg/kg of the test compound or saline, 30 minutes prior to the injection of saline or test compound (dosed from 0.1 to 2.5 mg/kg, i.p.), which was 30 minutes before the retention test starts. The rat may be again placed in the illuminated compartment with the guillotine door open. The latency for entering the darkened compartment may be recorded for up to 180 seconds, at which time the trial was terminated.

All data may be analyzed by analyses of variance (ANOVA); individual comparisons were made using Kewman-Keuls tests. Naïve rats required less than 30 seconds, on average, to cross from the illuminated compartment to the darkened compartment.

Example 72

Radial Arm Maze Task in Rats, an In Vivo Test for Learning and Memory

The test may be performed as previously described [Zhang, H.-T., Crissman, A. M., Dorairaj, N. R., Chandler, L. J., and —O'Donnell, J. M., *Neuropsychopharmacology*, 2000, 23, 198-204.]. Five days after initial housing, rats (male Spraque-Dawley (Harlan) weighing 250 to 350 g) may be placed in the eight-arm radial maze (each arm was 60×10×12 cm high; the maze was elevated 70 cm above the floor) for acclimation for two days. Rats may be then placed individually in the center of the maze for 5 minutes with food pellets placed close to the food wells, and then, the next day, in the wells at the end of the arms; 2 sessions a day may be conducted. Next, four randomly selected arms may be then baited with one pellet of food each. The rat may be restricted to the center platform (26 cm in diameter) for 15 seconds and then allowed to move freely throughout the maze until it collected all pellets of food or 10 minutes passed, whichever came first. Four parameters may be recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error is zero and the average reference memory error is less than one in five successive-trials, the rats may begin the drug tests. The test compound or saline may be injected 15 minutes prior to vehicle or test agent, which may be given 45 minutes before the test. Experiments are performed in a lighted room, which contained several extra-maze visual cues.

All data may be analyzed by analyses of variance (ANOVA); individual comparisons were made using Kewman-Keuls tests.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention. Upon further study of the specification, further aspects, objects and advantages of this invention will become apparent to those skilled in the art.

We claim:

1. A method for treating memory impairment in a patient comprising administering to said patient an effective amount of a compound according to Formulas III, VI, IX or X:

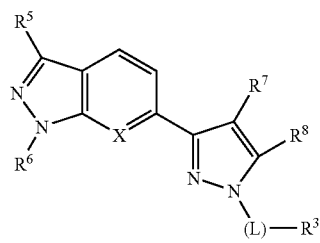

III

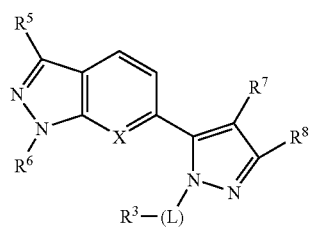

VI

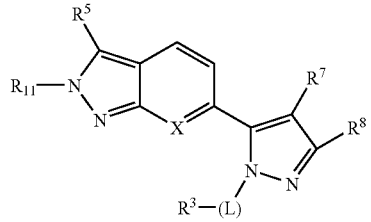

IX

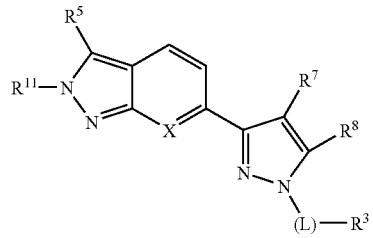

-continued

X wherein
X is CH or N;
L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen, hydroxy, cyano or combinations thereof; $(CH_2)_nCONH$; $(CH_2)_nOCONH$; $(CH_2)_nCON(C_{1-6}\text{-alkyl})$; $(CH_2)_nNHCO$; $(CH_2)_nCONHSO_2$; $(CH_2)_nSO_2NH$; $(CH_2)_nSO_2$; or $(CH_2)_nCO_2$;
n is 0 to 3;
$R^3$ is H,
  alkyl having 1 to 8 carbon atoms, which is unsubstituted or substituted one or more times by halogen, oxo, or combinations thereof wherein optionally one or more —$CH_2CH_2$— groups are replaced in each case by —CH=CH— or —C≡C— groups,
  cycloalkyl having 3 to 8 carbon atoms, which is unsubstituted or substituted one or more times by halogen, oxo, alkyl, or combinations thereof,
  aryl having 6 to 14 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, —CO—N$(R^{10})_2$, —SO$_2$—N$(R^{10})_2$, hydroxyalkyl, hydroxyalkoxy, alkoxyalkoxy, alkoxyalkoxyalkyl, carboxy, cyano, acyl, alkoxycarbonyl, alkylthio, alkylsulfinyl, alkylsulfonyl, arylsulfinyl, arylsulfonyl, aminosulfonyl, phenyl, halogenated phenyl, phenoxy, benzyloxy, acyloxy, acylamido, furanyl which is unsubstituted or substituted by halogen, $C_{1-4}$-alkyl, $C_{1-4}$-alkoxy, $C_{2-8}$-alkoxycarbonyl, and/or benzyl, pyrrolyl which is unsubstituted or substituted by halogen, $C_{1-4}$-alkyl, $C_{1-4}$-alkoxy, $C_{2-8}$-alkoxycarbonyl, and/or benzyl, pyrazolyl which is unsubstituted or substituted by halogen, $C_{1-4}$-alkyl, $C_{1-4}$-alkoxy, $C_{2-8}$-alkoxycarbonyl, and/or benzyl, isoxazolyl which is unsubstituted or substituted by halogen, $C_{1-4}$-alkyl, $C_{1-4}$-alkoxy, $C_{2-8}$-alkoxycarbonyl, and/or benzyl, imidazolyl which is unsubstituted or substituted by halogen, $C_{1-4}$-alkyl, $C_{1-4}$-alkoxy, $C_{2-8}$-alkoxycarbonyl, and/or benzyl, pyridinyl which is unsubstituted or substituted by halogen, $C_{1-4}$-alkyl, $C_{1-4}$-alkoxy, $C_{2-8}$-alkoxycarbonyl, and/or benzyl, pyrimidinyl which is unsubstituted or substituted by halogen, $C_{1-4}$-alkyl, $C_{1-4}$-alkoxy, $C_{2-8}$-alkoxycarbonyl, and/or benzyl, morpholinyl which is unsubstituted or substituted by $C_{1-4}$-alkyl, $C_{2-8}$-alkoxycarbonyl, and/or benzyl, piperadinyl which is unsubstituted or substituted by $C_{1-4}$-alkyl, $C_{2-8}$-alkoxycarbonyl, and/or benzyl, piperazinyl which is unsubstituted or substituted by $C_{1-4}$-alkyl, $C_{2-8}$-alkoxycarbonyl, and/or benzyl, tetrazolyl which is unsubstituted or substituted by $C_{1-4}$-alkyl, $C_{2-8}$-alkoxycarbonyl, and/or benzyl, alkylsulphonimide, arylsulphonimide wherein the aryl portion is optionally substituted by halogen, $C_{1-4}$-alkyl, $C_{1-4}$-alkoxy, or combinations thereof, heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, acylamido, or combinations thereof, arylalkyl having 7 to 16 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, acylamido, tetrazolyl, alkylsulphonimide, arylsulphonimide, or combinations thereof and/or substituted in the alkyl portion by halogen, oxo, cyano, or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof, cycloalkylalkyl having 4 to 16 carbon atoms, which is unsubstituted or substituted one or more times by halogen, oxo, alkyl or combinations thereof, or alkoxyalkyl having 3 to 8 carbon atoms;

$R^5$ is H, alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, or alkoxycarbonyl (—C(=O)O-alkyl) having 2 to 6 carbon atoms;

$R^6$ is H, alkyl having 1 to 6 carbon atoms, which is unsubstituted or substituted one or more times by halogen, oxo, hydroxy or combinations thereof wherein optionally one or more —$CH_2CH_2$— groups are replaced in each case by —CH=CH— or —C≡C— groups, alkoxyalkyl having 2 to 6 carbon atoms which is unsubstituted or substituted one or more times by halogen, oxo, or combinations thereof;

alkoxycarbonyl (—C(=O)O-alkyl) having 2 to 6 carbon atoms;

—CO—$NR^5R^{12}$;

cycloalkyl having 3 to 4 carbon atoms, which is unsubstituted or substituted one or more times by halogen, oxo, alkyl, or combinations thereof, cycloalkylalkyl having 4 to 16 carbon atoms, which is unsubstituted or substituted one or more times by halogen, oxo, alkyl or combinations thereof, aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido, and acyloxy, or combinations thereof, arylalkyl having 7 to 16 carbon atoms, which is unsubstituted or substituted one or more times by halogen, $CF_3$, $OCF_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido, and acyloxy, or combinations thereof, a heterocyclic group, which is saturated, partially saturated or fully unsaturated, having 5 to 10 ring atoms in which at least 1 ring atom is an N, O or S atom, which is unsubstituted or substituted one or more times by halogen, aryl, alkyl, alkoxy, alkoxycarbonyl, cyano, halogenated alkyl, nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl, carboxy, alkoxycarbonyl having 2 to 6 carbon atoms, —CO-alkyl having 2 to 6 carbon atoms, or phenyl;

$R^{10}$ is H, alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups, or alkoxy having 2 to 8 carbon atoms, which is unsubstituted or substituted one or more times by halogen;

$R^{11}$ is H, alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

R$^{12}$ is H, alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

or a pharmaceutically acceptable salt thereof.

2. A method according to claim 1, wherein L is (CH$_2$)$_n$OCONH.

3. A method according to claim 1, wherein R$^3$ is aryl having 6 to 14 carbon atoms which is substituted by at least one substituent selected from —CO—N(R$^{10}$)$_2$, aminosulfonyl, furanyl which is unsubstituted or substituted by halogen, C$_{1-4}$-alkyl, C$_{1-4}$-alkoxy, C$_{2-8}$-alkoxycarbonyl and/or benzyl, pyrrolyl which is unsubstituted or substituted by halogen, C$_{1-4}$-alkyl, C$_{1-4}$-alkoxy, C$_{2-8}$-alkoxycarbonyl, and/or benzyl, pyrazolyl which is substituted by halogen, C$_{1-4}$-alkyl, C$_{1-4}$-alkoxy, C$_{2-8}$-alkoxycarbonyl, and/or benzyl, isoxazolyl which is unsubstituted or substituted by halogen, C$_{1-4}$-alkyl, C$_{1-4}$-alkoxy, C$_{2-8}$-alkoxycarbonyl, and/or benzyl, imidazolyl which is substituted by halogen, C$_{1-4}$-alkyl, C$_{1-4}$-alkoxy, C$_{2-8}$-alkoxycarbonyl, and/or benzyl, pyridinyl which is substituted by halogen, C$_{1-4}$-alkyl, C$_{1-4}$-alkoxy, C$_{2-8}$-alkoxycarbonyl, and/or benzyl, pyrimidinyl which is unsubstituted or substituted by halogen, C$_{1-4}$-alkyl, C$_{1-4}$-alkoxy, C$_{2-8}$-alkoxycarbonyl, and/or benzyl, morpholinyl which is substituted by C$_{1-4}$-alkyl, C$_{2-8}$-alkoxycarbonyl, and/or benzyl, piperadinyl which is substituted by C$_{1-4}$-alkyl, C$_{2-8}$-alkoxycarbonyl, and/or benzyl, piperazinyl which is substituted by C$_{1-4}$-alkyl, C$_{2-8}$-alkoxycarbonyl, and/or benzyl, tetrazolyl which is unsubstituted or substituted by C$_{1-4}$-alkyl, C$_{2-8}$-alkoxycarbonyl, and/or benzyl, or arylsulphonimide wherein the aryl portion is substituted by halogen or C$_{1-4}$-alkoxy.

4. A method according to claim 1, wherein said compound is of Formula IX.

5. A method according to claim 1, wherein said compound is of Formula III.

6. A method according to claim 1, wherein said compound is of Formula VI.

7. A method according to claim 1, wherein said compound is of Formula X.

8. A method according to claim 1, wherein R$^3$ is ethyl, aryl which is substituted or unsubstituted or heteroaryl which is substituted or unsubstituted, and L is a single bond.

9. A method according to claim 1, wherein X is CH and L is a single bond.

10. A method according to claim 1, wherein R$^3$ is ethyl, aryl which is substituted or unsubstituted or heteroaryl which is substituted or unsubstituted, L is a single bond, and X is CH.

11. A method according to claim 1, wherein R$^3$ is aryl substituted at least once by —SO$_2$—N(R$^{10}$)$_2$, alkoxyalkoxy, alkoxyalkoxyalkyl or benzyloxy.

12. A method according to claim 1, wherein said compound is of Formula III or VI, and R$^6$ is alkyl having 1 to 6 carbon atoms which is substituted at least once by hydroxy; alkoxyalkyl having 2 to 6 carbon atoms which is unsubstituted or substituted one or more times by halogen, oxo, or combinations thereof; alkoxycarbonyl having 2 to 6 carbon atoms; or —CO—NR$^5$R$^{12}$.

13. A method according to claim 1, wherein said compound is of Formula III, X is CH, and L is a single bond.

14. A method according to claim 1, wherein R$^3$ is aryl having 6 to 14 carbon atoms which is unsubstituted or substituted with one or more halogen, cyano, nitro, amino, alkyl, alkoxy or carboxy.

15. A method according to claim 1, wherein R$^3$ is cyclohexyl, cyclopentyl, ethyl, CH(CH$_3$)$_2$, n-propyl, n-butyl, or t-butyl.

16. A method according to claim 1, wherein R$^3$ is thiazolyl, pyridyl or benzothiazolyl, which in each case is substituted or unsubstituted.

17. A method according to claim 1, wherein R$^3$ is benzyl, methylbenzyl, tert-butylbenzyl, methoxybenzyl, dimethoxybenzyl, carboxybenzyl, fluorobenzyl, difluorobenzyl, trifluoromethylbenzyl, trifluoromethoxybenzyl, chlorobenzyl, nitrobenzyl, methoxycarbonylbenzyl, or phenethyl, which in each case is substituted or unsubstituted.

18. A method according to claim 1, wherein R$^3$ is a heterocyclic-alkyl group, which is saturated, partially saturated or fully unsaturated, having 5 to 10 ring atoms in which at least 1 ring atom is an N, O or S atom, and which is optionally substituted one or more times in the heterocyclic portion by halogen, alkyl, hydroxy, alkoxy, halogenated alkyl, halogenated alkoxy, nitro, amino, alkylamino, dialkylamino, hydroxyalkyl, hydroxyalkoxy, carboxy, cyano, or combinations thereof and/or optionally substituted in the alkyl portion by halogen, oxo, cyano, or combinations thereof.

19. A method according to claim 1, wherein when R$^5$ is a ring substituent it is alkyl having 1 to 3 carbon atoms, and when R$^5$ is part of the —COR$^5$R$^{12}$ group it is H.

20. A method according to claim 1, wherein said compound is of Formula III or VI, and R$^6$ is cyclopropyl.

21. A method according to claim 1, wherein R$^7$ and R$^8$ are each H.

22. A method according to claim 1, wherein R$^7$ is H, and R$^8$ is H, CH$_3$, C$_2$H$_5$, CF$_3$, hydroxymethyl, 2-(2-hydroxy)propyl), carboxy, ethoxycarbonyl, CH$_3$CO, or phenyl.

23. A method according to claim 1, wherein said compound is of Formula VII or VIII, and R$^9$ is F.

24. A method according to claim 1, wherein R$^{10}$ is H or alkyl having 1 to 4 carbon atoms.

25. A method according to claim 1, wherein said compound is of Formula IX or X, and R$^{11}$ is methyl, ethyl, ethylpropyl, tetrahydro-2H-pyranylmethyl, or pyrrolidinylethyl.

26. A method according to claim 1, wherein R$^{12}$ is methyl, ethyl, ethylpropyl, or furylmethyl.

27. A method according to claim 1, wherein L is a bond, $CH_2$, $CH_2CH_2$, $CH_2CO$, $CH_2CO_2$, $CH_2CONH$, or $(CH_2)_nO$-CONH.

28. A method according to claim 1, wherein n is 0 or 2.

29. A method according to claim 1, wherein said compound is of Formula III or VI, and $R^6$ is alkyl having 1 to 6 carbon atoms, or a heterocyclic group.

30. A method according to claim 1, wherein said compound is of Formula III or VI, $R^5$ is ethyl, and $R^6$ is isopropyl, cyclopropyl, 4-tetrahydropyranyl, or 2-pyrimidinyl.

31. A method according to claim 1, wherein said compound is of Formula III or VI; $R^5$ is alkyl having 1 to 3 carbon atoms; $R^6$ is cycloalkyl having 4 carbon atoms; and $R^3$ is aryl, arylalkyl, or heterocyclic group, which in each case is substituted or unsubstituted.

32. A method according to claim 1, wherein said compound is of Formula III or VI; $R^5$ is alkyl having 1 to 3 carbon atoms; $R^6$ is cyclopropyl, isopropyl, 4-tetrahydropyranyl, 2-pyrimidinyl, or 3-tetrahydrofuranyl; and $R^3$ is aryl, arylalkyl, or heterocyclic group, which in each case is substituted or unsubstituted.

33. A method according to claim 1, wherein said compound is of Formula III or VI; $R^5$ is $CH_2CH_3$; $R^6$ is cyclopropyl; and $R^3$ is phenyl which is substituted or unsubstituted.

34. A method according to claim 1, wherein said compound is of Formula III or VI; $R^5$ is $CH_2CH_3$; $R^6$ is cyclopropyl, isopropyl, tetrahydropyranyl, or pyrimidinyl; $R^3$ is aryl, arylalkyl, or heteroaryl, which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy; and L is a single bond.

35. A method according to claim 1, wherein said compound is of Formula III or VI; $R^5$ is $CH_2CH_3$; $R^6$ is cyclopropyl, isopropyl, tetrahydropyranyl, or pyrimidinyl; and $R^3$ is phenyl which is substituted or unsubstituted.

36. A method according to claim 1, wherein said compound is of Formula III or VI; $R^5$ is $CH_2CH_3$; $R^6$ is cyclopropyl, isopropyl, tetrahydropyranyl, or pyrimidinyl; $R^3$ is phenyl which is substituted or unsubstituted; and L is a single bond.

37. A method according to claim 1, wherein said compound is of Formula IX or X; $R^5$ is alkyl having 1 to 3 carbon atoms; $R^{11}$ is alkyl having 1 to 6 carbon atoms, tetrahydro-2H-pyranylmethyl or pyrrolidinylethyl; $R^3$ is aryl, arylalkyl, or heterocyclic group, which in each case is substituted or unsubstituted; and L is a single bond.

38. A method according to claim 1, wherein said compound is selected from:
- 4-[5-(3-ethyl-2-methyl-2H-indazol-6-yl)-1H-pyrazol-1-yl]benzoic acid,
- 1,3-diethyl-6-{1-[4-(methylsulfonyl)phenyl]-1H-pyrazol-5-yl}-1H-indazole,
- 1-(cyclopropylmethyl)-3-ethyl-6-{1-[4-(methylsulfonyl)phenyl]-1H-pyrazol-5-yl}-1H-indazole,
- 3-ethyl-1-isopropyl-6-{1-[4-(methylsulfonyl)phenyl]-1H-pyrazol-5-yl}1H-indazole,
- 3-ethyl-1-(2-methoxyethyl)-6-{1-[4-(methylsulfonyl)phenyl]-1H-pyrazol-5-yl}-1H-indazole,
- 6-[1-(1-acetylpiperidin-4-yl)-1H-pyrazol-5-yl]-1-cyclopentyl-3-ethyl-1H-indazole,
- 1-(ethoxymethyl)-3-ethyl-6-{1-[4-(methylsulfonyl)phenyl]-1H-pyrazol-5-yl}-1H-indazole,
- 3-ethyl-1-(1-ethylpropyl)-6-{1-[4-(methylsulfonyl)phenyl]-1H-pyrazol-5-yl}-1H-indazole,
- 3-ethyl-2-(1-ethylpropyl)-6-{1-[4-(methylsulfonyl)phenyl]-1H-pyrazol-5-yl}-2H-indazole,
- 3-ethyl-6-{1-[4-(methylsulfonyl)phenyl]-1H-pyrazol-5-yl}-1-(tetrahydro-2H-pyran-2-ylmethyl)-1H-indazole,
- 3-ethyl-6-{1-[4-(methylsulfonyl)phenyl]-1H-pyrazol-5-yl}-2-(tetrahydro-2H-pyran-2-ylmethyl)-2H-indazole,
- 3-ethyl-6-{1-[4-(methylsulfonyl)phenyl]-1H-pyrazol-5-yl}-2-(2-pyrrolidin-1-ylethyl)-2H-indazole,
- Isopropyl 3-ethyl-6-{1-[4-(methylsulfonyl)phenyl]-1H-pyrazol-5-yl}-1H-indazole-1-carboxylate,
- 3-ethyl-6-{1-[4-(methylsulfonyl)phenyl]-1H-pyrazol-5-yl}-1-(2-pyrrolidin-1-ylethyl)-1H-indazole,
- N-(sec-butyl)-3-ethyl-6-{1-[4-(methylsulfonyl)phenyl]-1H-pyrazol-5-yl}-1H-indazole-1-carboxamide,
- 3-ethyl-6-{1-[4-(methylsulfonyl)phenyl]-1H-pyrazol-5-yl}-1-pyridin-3-yl-1H-indazole,
- N-cyclopentyl-3-ethyl-6-{1-[4-(methylsulfonyl)phenyl]-1H-pyrazol-5-yl}-1H-indazole-1-carboxamide,
- N,3-diethyl-6-{1-[4-(methylsulfonyl)phenyl]-1H-pyrazol-5-yl}-1H-indazole-1-carboxamide,
- 3-ethyl-N-(2-furylmethyl)-6-{1-[4-(methylsulfonyl)phenyl]-1H-pyrazol-5-yl}-1H-indazole-1-carboxamide,
- 3-ethyl-6-{1-[4-(methylsulfonyl)phenyl]-1H-pyrazol-5-yl}-1-pyrimidin-2-yl-1H-indazole,
- 3-ethyl-6-{1-[4-(methylsulfonyl)phenyl]-1H-pyrazol-5-yl}-1-pyrimidin-5-yl-1H-indazole,
- 1-cyclopropyl-3-ethyl-6-{1-[4-(methylsulfonyl)phenyl]-1H-pyrazol-5-yl}-1H-indazole,
- 1-(3-ethyl-6-{1-[4-(methylsulfonyl)phenyl]-1H-pyrazol-5-yl}-1H-indazol-1-yl)-2-methylpropan-2-ol,
- 3-ethyl-6-{1-[4-(methylsulfonyl)phenyl]-1H-pyrazol-5-yl}-1-(tetrahydro-2H-pyran-4-yl)-1H-indazole,
- 1-(difluoromethyl)-3-ethyl-6-{1-[4-(methylsulfonyl)phenyl]-1H-pyrazol-5-yl}-1H-indazole,
- 3-ethyl-6-{1-[4-(methylsulfonyl)phenyl]-1H-pyrazol-5-yl}-1-pyridin-2-yl-1H-indazole,
- 1-(5-cyclopropyl-1,3,4-thiadiazol-2-yl)-3-ethyl-6-{1-[4-(methylsulfonyl)phenyl]-1H-pyrazol-5-yl}-1H-indazole,
- 3-ethyl-6-{1-[4-(methylsulfonyl)phenyl]-1H-pyrazol-5-yl}-1-(tetrahydrofuran-3-yl)-1H-indazole,
- Tert-butyl 3-(3-ethyl-6-{1-[4-(methylsulfonyl)phenyl]-1H-pyrazol-5-yl}-1H-indazol-1-yl)pyrrolidine-1-carboxylate,
- 1-cyclopropyl-3-ethyl-6-(1-isopropyl-1H-pyrazol-5-yl)-1H-indazole,
- 1-cyclopropyl-3-ethyl-6-(1-methyl-1H-pyrazol-5-yl)-1H-indazole,
- 1-cyclopropyl-3-ethyl-6-(1H-pyrazol-5-yl)-1H-indazole,
- 1-cyclopropyl-3-ethyl-6-(1-ethyl-1H-pyrazol-5-yl)-1H-indazole,
- 1-cyclopropyl-3-ethyl-6-(1-pyridin-4-yl-1H-pyrazol-5-yl)-1H-indazole,
- 2-[5-(1-cyclopropyl-3-ethyl-1H-indazol-6-yl)-1H-pyrazol-1-yl]quinoxaline,
- {4-[5-(1-cyclopropyl-3-ethyl-1H-indazol-6-yl)-1H-pyrazol-1-yl]phenyl}methanol,
- 2-{4-[5-(1-cyclopropyl-3-ethyl-1H-indazol-6-yl)-1H-pyrazol-1-yl]phenyl}propan-2-ol,
- 1-{4-[5-(1-cyclopropyl-3-ethyl-1H-indazol-6-yl)-1H-pyrazol-1-yl]phenyl}-N-methylmethanesulfonamide,
- 1-cyclopropyl-3-ethyl-6-[1-(tetrahydro-2H-pyran-4-yl)-1H-pyrazol-5-yl]-1H-indazole,
- 1-cyclopropyl-3-ethyl-6-[1-(tetrahydro-2H-pyran-4-yl)-1H-pyrazol-3-yl]-1H-indazole,
- 1-cyclopropyl-6-[1-(1,1-dioxidotetrahydro-3-thienyl)-1H-pyrazol-5-yl]-3-ethyl-1H-indazole, 6-(1-cyclopentyl-1H-pyrazol-5-yl)-1-cyclopropyl-3-ethyl-1H-indazole,
1-cyclopropyl-3-ethyl-6-[1-(2,2,6,6-tetramethylpiperidin-4-yl)-1H-pyrazol-5-yl]-1H-indazole,
6-{1-[3-(benzyloxy)phenyl]-1H-pyrazol-5-yl}-1-cyclopropyl-3-ethyl-1H-indazole,
3-[5-(1-cyclopropyl-3-ethyl-1H-indazol-6-yl)-1H-pyrazol-1-yl]phenol,
3-ethyl-1-isopropyl-6-{1-[4-(methylsulfonyl)phenyl]-1H-pyrazol-5-yl}-1H-pyrazolo[3,4-b]pyridine,
2-{3-[5-(1-cyclopropyl-3-ethyl-1H-indazol-6-yl)-1H-pyrazol-1-yl]phenoxy}ethanol,
6-{1-[4-(benzyloxy)phenyl]-1H-pyrazol-5-yl}-1-cyclopropyl-3-ethyl-1H-indazole,
3-ethyl-6-{1-[4-(methylsulfonyl)phenyl]-1H-pyrazol-5-yl}-1-(tetrahydro-2H-pyran-4-yl)-1H-pyrazolo[3,4-b]pyridine,
4-[5-(1-cyclopropyl-3-ethyl-1H-indazol-6-yl)-1H-pyrazol-1-yl]phenol,
(4-{5-[3-ethyl-1-(tetrahydro-2H-pyran-4-yl)-1H-pyrazolo[3,4-b]pyridin-6-yl]-1H-pyrazol-1-yl}phenyl)methanol,
2-(4-{5-[3-ethyl-1-(tetrahydro-2H-pyran-4-yl)-1H-pyrazolo[3,4-b]pyridin-6-yl]-1H-pyrazol-1-yl}phenyl)propan-2-ol,
1-cyclopropyl-3-ethyl-6-{1-[3-(2-methoxyethoxy)phenyl]-1H-pyrazol-5-yl}-1H-indazole,
1-cyclopropyl-3-ethyl-6-[1-(3-methoxyphenyl)-1H-pyrazol-5-yl]-1H-indazole,
1-cyclopropyl-3-ethyl-6-{1-[4-(2-methoxyethoxy)phenyl]-1H-pyrazol-5-yl}-1H-indazole,
1-cyclopropyl-3-ethyl-6-[1-(4-methoxyphenyl)-1H-pyrazol-5-yl]-1H-indazole,
1-cyclopropyl-3-ethyl-6-(1-pyrimidin-2-yl-1H-pyrazol-5-yl)-1H-indazole,
3-ethyl-1-(2-methoxypyridin-4-yl)-6-(1-pyrimidin-2-yl-1H-pyrazol-5-yl)-1H-indazole,
4-[5-(3-ethyl-1-methyl-1H-indazol-6-yl)-1H-pyrazol-1-yl]benzoic acid
4-[5-(3-ethyl-1-methyl-1H-indazol-6-yl)-1H-pyrazol-1-yl]benzenesulfonamide
3-ethyl-1-methyl-6-{1-[4-(methylsulfonyl)phenyl]-1H-pyrazol-5-yl}-1H-indazole
4-[5-(3-ethyl-1-methyl-1H-indazol-6-yl)-1H-pyrazol-1-yl]benzonitrile
4-[5-(3-ethyl-2-methyl-2H-indazol-6-yl)-1H-pyrazol-1-yl]benzenesulfonamide
3-ethyl-2-methyl-6-{1-[4-(methylsulfonyl)phenyl]-1H-pyrazol-5-yl}-2H-indazole
4-[5-(3-ethyl-2-methyl-2H-indazol-6-yl)-1H-pyrazol-1-yl]benzonitrile
6-{1-[4-(difluoromethoxy)phenyl]-1H-pyrazol-5-yl}-3-ethyl1-(tetrahydro-2H-pyran-4-yl)-1H-pyrazolo[3,4-b]pyridine
3-ethyl-6-[1-(4-fluorophenyl)-1H-pyrazol-5-yl]-1-(tetrahydro-2H-pyran-4-yl)-1H-pyrazolo[3,4-b]pyridine
3-ethyl-6-(1-pyridin-4-yl-1H-pyrazol-5-yl)-1-(tetrahydro-2H-pyran-4-yl)-1H-pyrazolo[3,4-b]pyridine
3-ethyl-6-(1-phenyl-1H-pyrazol-5-yl)-1-(tetrahydro-2H-pyran-4-yl)-1H-pyrazolo[3,4-b]pyridine
3-ethyl-6-(1-pyrimidin-2-yl-1H-pyrazol-5-yl)-1-(tetrahydro-2H-pyran-4-yl)-1H-pyrazolo[3,4-b]pyridine
3-ethyl-6-[1-(3-fluorophenyl)-1H-pyrazol-5-yl]-1-(tetrahydro-2H-pyran-4-yl)-1H-pyrazolo[3,4-b]pyridine
3-ethyl-6-[1-(4-methoxyphenyl)-1H-pyrazol-5-yl]-1-(tetrahydro-2H-pyran-4-yl)-1H-pyrazolo[3,4-b]pyridine
3-ethyl-6-[1-(3-methoxyphenyl)-1H-pyrazol-5-yl]-1-(tetrahydro-2H-pyran-4-yl)-1H-pyrazolo[3,4-b]pyridine
6-{1-[4-(benzyloxy)phenyl]-1H-pyrazol-5-yl}-3-ethyl-1-(tetrahydro-2H-pyran-4-yl)-1H-pyrazolo[3,4-b]pyridine
6-{1-[3-(benzyloxy)phenyl]-1H-pyrazol-5-yl}-3-ethyl-1-(tetrahydro-2H-pyran-4-yl)-1H-pyrazolo[3,4-b]pyridine
4-{5-[3-ethyl-1-(tetrahydro-2H-pyran-4-yl)-1H-pyrazolo[3,4-b]pyridin-6-yl]-1H-pyrazol-1-yl}phenol
3-{5-[3-ethyl-1-(tetrahydro-2H-pyran-4-yl)-1H-pyrazolo[3,4-b]pyridin-6-yl]-1H-pyrazol-1-yl}phenol
and physiologically acceptable salts thereof, and
wherein said compound can be in the form of a mixture of enantiomers, a mixture of diastereomers, or in the form of a single enantiomer or a single diastereomer.

39. A method according to claim 1, wherein said compound is administered in an amount of 0.01-100 mg/kg of body weight/day.

40. A method according to claim 39, wherein said patient is a human.

41. A method according to claim 1, wherein said patient is suffering from memory impairment due to Alzheimer's disease, mild cognitive impairment due to aging, schizophrenia, Parkinson's disease, Huntington's disease, Pick's disease, Creutzfeldt-Jakob disease, depression, aging, stroke, CNS hypoxia, cerebral senility, multiinfarct dementia, HIV, cardiovascular disease, head trauma or age-related cognitive decline.

42. A method according to claim 1, wherein said patient is suffering from memory impairment due to dementia.

43. A method according to claim 1, wherein said compound is selected from:
3-ethyl-6-{1-[3-(2-methoxyethoxy)phenyl]-1H-pyrazol-5-yl}-1-(tetrahydro-2H-pyran-4-yl)-1H-indazole
3-ethyl-6-{1-[4-(2-methoxyethoxy)phenyl]-1H-pyrazol-5-yl}-1-(tetrahydro-2H-pyran-4-yl)-1H-indazole
2-(3-{5-[3-ethyl-1-(tetrahydro-2H-pyran-4-yl)-1H-indazol-6-yl]-1H-pyrazol-1-yl}phenoxy)ethanol
2-(4-{5-[3-ethyl-1-(tetrahydro-2H-pyran-4-yl)-1H-indazol-6-yl]-1H-pyrazol-1-yl}phenoxy)ethanol
and physiologically acceptable salts thereof, and
wherein said compound can be in the form of a mixture of enantiomers, a mixture of diastereomers, or in the form of a single enantiomer or a single diastereomer.

44. A method according to claim 1, wherein said compound is selected from:
6-{1-[3-(2-methoxyethoxy)phenyl]-1H-pyrazol-5-yl}-3-ethyl-1-(tetrahydro-2H-pyran-4-yl)-1H-pyrazolo[3,4-b]pyridine
6-{1-[4-(2-methoxyethoxy)phenyl]-1H-pyrazol-5-yl}-3-ethyl-1-(tetrahydro-2H-pyran-4-yl)-1H-pyrazolo[3,4-b]pyridine
2-(3-{5-[3-ethyl-1-(tetrahydro-2H-pyran-4-yl)-1H-pyrazolo[3,4-b]pyridin-6-yl]-1H-pyrazol-1-yl}phenoxy)ethanol
2-(4-{5-[3-ethyl-1-(tetrahydro-2H-pyran-4-yl)-1H-pyrazolo[3,4-b]pyridin-6-yl]-1H-pyrazol-1-yl}phenoxy)ethanol
and physiologically acceptable salts thereof, and
wherein said compound can be in the form of a mixture of enantiomers, a mixture of diastereomers, or in the form of a single enantiomer or a single diastereomer.

45. A method according to claim 1, wherein said compound is of Formula III of VI, $R^5$ is alkyl having 1 to 3 carbon atoms, $R^6$ is alkyl having 1 to 6 carbon atoms, or a heterocyclic group, and $R^3$ is aryl, arylalkyl, or heteroaryl, which in each case is substituted or unsubstituted.

46. A method according to claim 1, wherein said compound is of Formula III or Formula VI; $R^5$ is $CH_2CH_3$; $R^6$ is tetrahydropyranyl, or pyrimidinyl; $R^3$ is aryl, arylalkyl, or heteroaryl, which in each case is substituted or unsubstituted; and L is a single bond.

47. A method according to claim 46, wherein $R^3$ is phenyl, benzyl, pyridinyl, pyrimidinyl, pyrazolyl, or pyrrolyl, which in each case is substituted or unsubstituted.

48. A method according to claim 1, wherein said compound is of Formula IX or Formula X, and $R^{11}$ is alkyl having 1 to 6 carbon atoms, tetrahydro-2H-pyranylmethyl or pyrrolidinylethyl.

49. A method according to claim 1, wherein said compound is of Formula IX or Formula X; $R^5$ is $CH_2CH_3$; $R^{11}$ is methyl, tetrahydro-2H-pyranylmethyl or pyrrolidinylethyl; $R^3$ is phenyl which in each case is substituted or unsubstituted; and L is a single bond.

50. A method according to claim 10, wherein $R^5$ is alkyl having 1 to 3 carbon atoms; $R^6$ is alkyl having 1 to 6 carbon atoms, or a heterocyclic group; and $R^3$ is aryl, alkyl, or heteroaryl group, which in each case is substituted or unsubstituted.

51. A method according to claim 50, wherein $R^5$ is $CH_2CH_3$; $R^6$ is isopropyl, tetrahydropyranyl, or pyrimidinyl; and $R^3$ is phenyl, benzyl, pyridinyl, pyrimidinyl, pyrazolyl, or pyrrolyl, which in each case is substituted or unsubstituted.

52. A method according to claim 51, wherein $R^3$ is phenyl, benzyl, pyridinyl, pyrimidinyl, pyrazolyl, or pyrrolyl, which in each case is substituted or unsubstituted by alkyl, alkoxy, halogenated alkoxy, carboxy, acetyl, cyano, halogen, —CO—N($R^{10}$)$_2$, aminosulfonyl, alkylsulfonyl, tetrazolyl, alkoxyalkoxy, alkoxyalkyl, hydroxyalkyl, hydroxyalkoxy, or hydroxy.

53. A method according to claim 1, selected from:
3-ethyl-1-isopropyl-6-{1-[4-(methylsulfonyl)phenyl]-1H-pyrazol-5-yl}-1H-indazole,
3-ethyl-6-{1-[4-(methylsulfonyl)phenyl]-1H-pyrazol-5-yl}-1-pyrimidin-2-yl-1H-indazole,
3-ethyl-6-{1-[4-(methylsulfonyl)phenyl]-1H-pyrazol-5-yl}-1-(tetrahydro-2H-pyran-4-yl)-1H-pyrazolo[3,4-b]pyridine,
3-ethyl-6-(1-pyrimidin-2-yl-1H-pyrazol-5-yl)-1-(tetrahydro-2H-pyran-4-yl)-1H-pyrazolo[3,4-b]pyridine, and pharmaceutically acceptable salts thereof.

54. A method according to claim 53, wherein said compound is 3-ethyl1-isopropyl-6-{1-[4-(methylsulfonyl)phenyl]-1H-pyrazol-5-yl}-1H-indazole, or a pharmaceutically acceptable salt thereof.

55. A method according to claim 53, wherein said compound is 3-ethyl-6-{1-[4-(methylsulfonyl)phenyl]-1H-pyrazol-5-yl}-1-pyrimidin-2-yl-1H-indazole, or a pharmaceutically acceptable salt thereof.

56. A method according to claim 53, wherein said compound is 3-ethyl-6-{1-[4-(methylsulfonyl)phenyl]-1H-pyrazol-5-yl}-1-(tetrahydro-2H-pyran-4-yl)-1H-pyrazolo[3,4-b]pyridine, or a pharmaceutically acceptable salt thereof.

57. A method according to claim 53, wherein said compound is 3-ethyl-6-(1-pyrimidin-2-yl-1H-pyrazol-5-yl)-1-(tetrahydro-2H-pyran-4-yl)-1H-pyrazolo[3,4-b]pyridine, or a pharmaceutically acceptable salt thereof.

58. A method according to claim 38, wherein said compound is 3-ethyl1-isopropyl-6-{1-[4-(methylsulfonyl)phenyl]-1H-pyrazol-5-yl}-1H-indazole, or a pharmaceutically acceptable salt thereof.

59. A method according to claim 38, wherein said compound is 3-ethyl1-isopropyl-6-{1-[4-(methylsulfonyl)phenyl]-1H-pyrazol-5-yl}-1H-pyrazolo[3,4-b]pyridine, or a pharmaceutically acceptable salt thereof.

60. A method according to claim 38, wherein said compound is 3-ethyl-6-{1-[4-(methylsulfonyl)phenyl]-1H-pyrazol-5-yl}-1-(tetrahydro-2H-pyran-4-yl)-1H-pyrazolo[3,4-b]pyridine, or a pharmaceutically acceptable salt thereof.

61. A method for achieving PDE4 inhibition in a patient comprising administering to said patient an effective amount of a compound according to Formulas III, VI, IX or X:

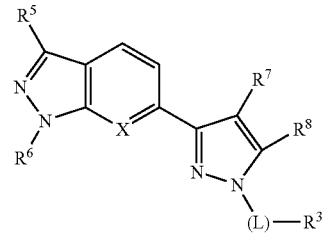

III

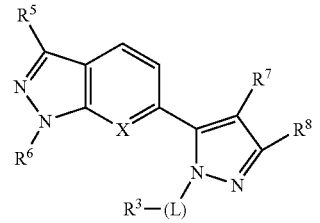

VI

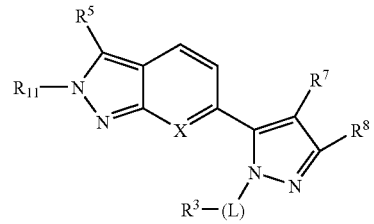

IX

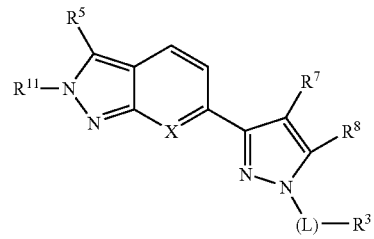

X wherein
X is CH or N;
L is a single bond; $C_1$-$C_6$ straight chain or branched alkylene, wherein a $CH_2$ group is optionally replaced by O, NH, $NR^1$, or S, which is unsubstituted or substituted one or more times by oxo, halogen, hydroxy, cyano or combinations thereof; $(CH_2)_n$CONH; $(CH_2)_n$OCONH; $(CH_2)_n$CON($C_{1-6}$-alkyl); $(CH_2)_n$NHCO; $(CH_2)_n$CONHSO$_2$; $(CH_2)_n$SO$_2$NH; $(CH_2)_n$SO$_2$; or $(CH_2)_n$CO$_2$;
n is 0 to 3;
$R^3$ is H,
alkyl having 1 to 8 carbon atoms, which is unsubstituted or substituted one or more times by halogen, oxo, or combinations thereof wherein optionally one or more —CH$_2$CH$_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, aryl having 6 to 14 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, —CO—N(R$^{10}$)$_2$, —SO$_2$—N(R$^{10}$)$_2$, hydroxyalkyl, hydroxyalkoxy, alkoxyalkoxy, alkoxyalkoxyalkyl, carboxy, cyano, acyl, alkoxycarbonyl, alkylthio, alkylsulfinyl, alkylsulfonyl, arylsulfinyl, arylsulfonyl, aminosulfonyl, phenyl, halogenated phenyl, phenoxy, benzyloxy, acyloxy, acylamido, furanyl which is unsubstituted or substituted by halogen, C$_{1-4}$-alkyl, C$_{1-4}$-alkoxy, C$_{2-8}$-alkoxycarbonyl, and/or benzyl, pyrrolyl which is unsubstituted or substituted by halogen, C$_{1-4}$-alkyl, C$_{1-4}$-alkoxy, C$_{2-8}$-alkoxycarbonyl, and/or benzyl, pyrazolyl which is unsubstituted or substituted by halogen, C$_{1-4}$-alkyl, C$_{1-4}$-alkoxy, C$_{2-8}$-alkoxycarbonyl, and/or benzyl, isoxazolyl which is unsubstituted or substituted by halogen, C$_{1-4}$-alkyl, C$_{1-4}$-alkoxy, C$_{2-8}$-alkoxycarbonyl, and/or benzyl, imidazolyl which is unsubstituted or substituted by halogen, C$_{1-4}$-alkyl, C$_{1-4}$-alkoxy, C$_{2-8}$-alkoxycarbonyl, and/or benzyl, pyridinyl which is unsubstituted or substituted by halogen, C$_{1-4}$-alkyl, C$_{1-4}$-alkoxy, C$_{2-8}$-alkoxycarbonyl, and/or benzyl, pyrimidinyl which is unsubstituted or substituted by halogen, C$_{1-4}$-alkyl, C$_{1-4}$-alkoxy, C$_{2-8}$-alkoxycarbonyl, and/or benzyl, morpholinyl which is unsubstituted or substituted by C$_{1-4}$-alkyl, C$_{2-8}$-alkoxycarbonyl, and/or benzyl, piperadinyl which is unsubstituted or substituted by C$_{1-4}$-alkyl, C$_{2-8}$-alkoxycarbonyl, and/or benzyl, piperazinyl which is unsubstituted or substituted by C$_{1-4}$-alkyl, C$_{2-8}$-alkoxycarbonyl, and/or benzyl, tetrazolyl which is unsubstituted or substituted by C$_{1-4}$-alkyl, C$_{2-8}$-alkoxycarbonyl, and/or benzyl, alkylsulphonimide, arylsulphonimide wherein the aryl portion is optionally substituted by halogen, C$_{1-4}$-alkyl, C$_{1-4}$-alkoxy, or combinations thereof, heterocyclic group, which is saturated, partially saturated or fully unsaturated, having 5 to 10 ring atoms in which at least 1 ring atom is an N, O or S atom, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, acylamido, or combinations thereof, arylalkyl having 7 to 16 carbon atoms, which is unsubstituted or substituted one or more times by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, acylamido, tetrazolyl, alkylsulphonimide, arylsulphonimide, or combinations thereof and/or substituted in the alkyl portion by halogen, oxo, cyano, or combinations thereof, a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, alkyl, hydroxy, alkoxy, halogenated alkyl, halogenated alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, arylsulfinyl, arylsulfonyl, phenyl, halogenated phenyl, phenoxy, acyloxy, tetrazolyl, alkylsulphonimide, arylsulphonimide, aryl, oxo, or combinations thereof and/or substituted in the alkyl portion by halogen, oxo, cyano, or combinations thereof, cycloalkylalkyl having 4 to 16 carbon atoms, which is unsubstituted or substituted one or more times by halogen, oxo, alkyl or combinations thereof, or alkoxyalkyl having 3 to 8 carbon atoms;

R$^5$ is H, alkyl having 1 to 6 carbon atoms, which is unsubstituted or substituted one or more times by halogen, oxo, or combinations thereof wherein optionally one or more —CH$_2$CH$_2$— groups are replaced in each case by —CH=CH— or —C≡C— groups, or alkoxycarbonyl (—C(=O)O-alkyl) having 2 to 6 carbon atoms;

R$^6$ is H, alkyl having 1 to 6 carbon atoms, which is unsubstituted or substituted one or more times by halogen, oxo, hydroxy or combinations thereof wherein optionally one or more —CH$_2$CH$_2$— groups are replaced in each case by —CH=CH— or —C≡C— groups, alkoxyalkyl having 2 to 6 carbon atoms which is unsubstituted or substituted one or more times by halogen, oxo, or combinations thereof;

alkoxycarbonyl (—C(=O)O-alkyl) having 2 to 6 carbon atoms;

—CO—NR$^5$R$^{12}$;

cycloalkyl having 3 to 4 carbon atoms, which is unsubstituted or substituted one or more times by halogen, oxo, alkyl, or combinations thereof, cycloalkylalkyl having 4 to 16 carbon atoms, which is unsubstituted or substituted one or more times by halogen, oxo, alkyl or combinations thereof, aryl having 6 to 14 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido, and acyloxy, or combinations thereof, arylalkyl having 7 to 16 carbon atoms, which is unsubstituted or substituted one or more times by halogen, CF$_3$, OCF$_3$, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, acylamido, and acyloxy, or combinations thereof, a heterocyclic group, which is saturated, partially saturated or fully unsaturated, having 5 to 10 ring atoms in which at least 1 ring atom is an N, O or S atom, which is unsubstituted or substituted one or more times by halogen, aryl, alkyl, alkoxy, alkoxycarbonyl, cyano, halogenated alkyl, nitro, oxo, amino, alkylamino, dialkylamino, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

$R^7$ is H, halogen, or alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen;

$R^8$ is H, halogen, alkyl having 1 to 6 carbon atoms wherein optionally one or more —$CH_2CH_2$— groups are replaced in each case by —CH=CH— or —C≡C— groups and wherein the alkyl is unsubstituted or substituted one or more times by halogen or hydroxyl, carboxy, alkoxycarbonyl having 2 to 6 carbon atoms, —CO-alkyl having 2 to 6 carbon atoms, or phenyl;

$R^{10}$ is H,
alkyl having 1 to 8 carbon atoms, which is unsubstituted or substituted one or more times by halogen, oxo or combinations thereof wherein optionally one or more —$CH_2CH_2$— groups are replaced in each case by —CH=CH— or —C≡C— groups, or
alkoxy having 2 to 8 carbon atoms, which is unsubstituted or substituted one or more times by halogen;

$R^{11}$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

$R^{12}$ is H,
alkyl having 1 to 6 carbon atoms, which is unsubstituted or substituted one or more times by halogen, oxo, or combinations thereof wherein optionally one or more —$CH_2CH_2$— groups are replaced in each case by —CH=CH— or —C≡C— groups, cycloalkyl having 3 to 8 carbon atoms, which is unsubstituted or substituted one or more times by halogen, oxo, alkyl, or combinations thereof, or a heterocyclic-alkyl group, which is saturated, partially saturated or fully unsaturated, having 5 to 10 ring atoms in which at least 1 ring atom is an N, O or S atom, which is unsubstituted or substituted one or more times in the heterocyclic portion by halogen, aryl, alkyl, alkoxy, cyano, halogenated alkyl, nitro, oxo, amino, alkylamino, dialkylamino, carboxy or combinations thereof and/or substituted in the alkyl portion by halogen, oxo, cyano, or combinations thereof;

or a pharmaceutically acceptable salt thereof.

* * * * *